(12) United States Patent
Jones et al.

(10) Patent No.: US 8,580,841 B2
(45) Date of Patent: Nov. 12, 2013

(54) SUBSTITUTED 1,2,3,4-TETRAHYDROCYCLOPENTA[B]INDOL-3-YL)ACETIC ACID DERIVATIVES USEFUL IN THE TREATMENT OF AUTOIMMUNE AND INFLAMMATORY DISORDERS

(75) Inventors: Robert M Jones, San Diego, CA (US); Daniel J Buzard, San Diego, CA (US); Sangdon Han, San Diego, CA (US); Sun Hee Kim, San Diego, CA (US); Juerg Lehmann, San Diego, CA (US); Brett Ullman, San Diego, CA (US); Jeanne V Moody, San Diego, CA (US); Xiuwen Zhu, San Diego, CA (US); Scott Stirn, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 226 days.

(21) Appl. No.: 13/055,333

(22) PCT Filed: Jul. 22, 2009

(86) PCT No.: PCT/US2009/004265
§ 371 (c)(1),
(2), (4) Date: Jan. 21, 2011

(87) PCT Pub. No.: WO2010/011316
PCT Pub. Date: Jan. 28, 2010

(65) Prior Publication Data
US 2011/0130409 A1    Jun. 2, 2011

Related U.S. Application Data

(60) Provisional application No. 61/135,672, filed on Jul. 23, 2008, provisional application No. 61/209,374, filed on Mar. 6, 2009.

(51) Int. Cl.
*A61K 31/403* (2006.01)
(52) U.S. Cl.
USPC ............................................ 514/411; 548/439
(58) Field of Classification Search
USPC ..................................................... 548/439
See application file for complete search history.

(56) References Cited

U.S. PATENT DOCUMENTS

| | | | |
|---|---|---|---|
| 4,057,559 A | 11/1977 | Asselin et al. |
| 4,782,076 A | 11/1988 | Mobilio et al. |
| 4,810,699 A | 3/1989 | Sabatucci et al. |
| 5,221,678 A | 6/1993 | Atkinson et al. |
| 5,776,967 A | 7/1998 | Kreft et al. |
| 5,830,911 A | 11/1998 | Failli et al. |
| 6,410,583 B1 | 6/2002 | Labelle et al. |
| 6,960,692 B2 | 11/2005 | Kohno et al. |
| 7,250,441 B2 | 7/2007 | Gopalsamy et al. |
| 8,415,484 B2 | 4/2013 | Jones et al. |
| 2003/0083269 A1 | 5/2003 | Brouillette et al. |
| 2003/0211421 A1 | 11/2003 | Hanabata et al. |
| 2004/0224941 A1 | 11/2004 | Seko et al. |
| 2004/0254222 A1 | 12/2004 | Kohno et al. |
| 2005/0004114 A1 | 1/2005 | Whitehouse et al. |
| 2005/0009786 A1 | 1/2005 | Pan et al. |
| 2005/0014724 A1 | 1/2005 | Marsilje et al. |
| 2005/0014725 A1 | 1/2005 | Mi et al. |
| 2005/0014728 A1 | 1/2005 | Pan et al. |
| 2005/0033055 A1 | 2/2005 | Bugianesi et al. |
| 2005/0239899 A1 | 10/2005 | Fecke et al. |
| 2006/0004010 A1 | 1/2006 | Habashita et al. |
| 2006/0063821 A1 | 3/2006 | Gopalsamy et al. |
| 2006/0079542 A1 | 4/2006 | Nestor |
| 2006/0122222 A1 | 6/2006 | Whitehouse et al. |
| 2006/0160771 A1 | 7/2006 | Kohno et al. |
| 2006/0211656 A1 | 9/2006 | Albert et al. |
| 2006/0223866 A1 | 10/2006 | Evindar et al. |
| 2007/0010494 A1 | 1/2007 | Ehrhardt et al. |

(Continued)

FOREIGN PATENT DOCUMENTS

| | | |
|---|---|---|
| EP | 0468785 | 1/1992 |
| EP | 1650186 A1 | 4/2006 |

(Continued)

OTHER PUBLICATIONS

English Translation of WO 2007037196, Sasaki et al., Published Apr. 5, 2007.
Actelion, Clinical Trails.gov, "Multicenter, Randomized, Double-blind, Placebo-controlled, Phase IIa Study to Evaluate the Efficacy, Safety, and Tolerability of ACT-128800, an S1P1 Receptor Agonist, Administered for 6 Weeks to Subjects With Moderate to Severe Chronic Plaque Psoriasis" http://clinicaltrials.gov/ct2/show/NCT00852670, 2009.

(Continued)

*Primary Examiner* — Brian McDowell
(74) *Attorney, Agent, or Firm* — Fish & Richardson P.C.; Lyle W. Spruce

(57) ABSTRACT

The present invention relates to certain substituted 1,2,3,4-tetrahydrocyclopenta[b]indol-3-yl)acetic acid derivatives of Formula (Ia):

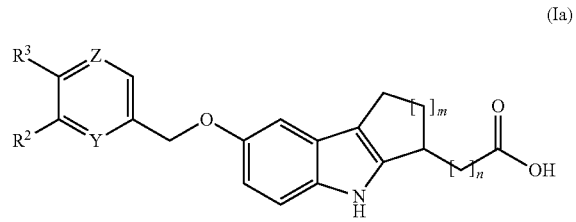

and pharmaceutically acceptable salts thereof, which exhibit useful pharmacological properties, for example, as agonists of the S1P1 receptor. Also provided by the present invention are pharmaceutical compositions containing compounds of the invention, and methods of using the compounds and compositions of the invention in the treatment of S1P1 receptor-associated disorders, for example, psoriasis, rheumatoid arthritis, Crohn's disease, transplant rejection, multiple sclerosis, systemic lupus erythematosus, ulcerative colitis, type I diabetes, acne, microbial infections or diseases and viral infections or diseases.

51 Claims, 26 Drawing Sheets

(56) References Cited

U.S. PATENT DOCUMENTS

| | | |
|---|---|---|
| 2007/0043014 A1 | 2/2007 | Doherty et al. |
| 2007/0060573 A1 | 3/2007 | Wortmann et al. |
| 2007/0149595 A1 | 6/2007 | Tanaka et al. |
| 2007/0149597 A1 | 6/2007 | Nishi et al. |
| 2007/0167425 A1 | 7/2007 | Nakade et al. |
| 2007/0173487 A1 | 7/2007 | Saha et al. |
| 2007/0173507 A1 | 7/2007 | Hirata |
| 2007/0191313 A1 | 8/2007 | Beard et al. |
| 2007/0191371 A1 | 8/2007 | Bennett et al. |
| 2007/0191468 A1 | 8/2007 | Nishi et al. |
| 2007/0244155 A1 | 10/2007 | Sharma et al. |
| 2007/0254886 A1 | 11/2007 | Habashita et al. |
| 2008/0051418 A1 | 2/2008 | Maekawa et al. |
| 2008/0153882 A1 | 6/2008 | Nishi et al. |
| 2008/0200535 A1 | 8/2008 | Ohmori et al. |
| 2008/0207584 A1 | 8/2008 | Habashita et al. |
| 2008/0319077 A1 | 12/2008 | Suzuki et al. |
| 2009/0012093 A1 | 1/2009 | Fukatsu et al. |
| 2009/0076070 A1 | 3/2009 | Harada et al. |
| 2009/0131438 A1 | 5/2009 | Ono et al. |
| 2009/0137685 A1 | 5/2009 | Kojima et al. |
| 2009/0325907 A1 | 12/2009 | Kohno et al. |
| 2010/0267778 A1 | 10/2010 | Kusuda et al. |
| 2010/0273806 A1 | 10/2010 | Jones et al. |
| 2010/0292233 A1 | 11/2010 | Jones et al. |
| 2011/0130409 A1 | 6/2011 | Jones et al. |
| 2011/0160243 A1 | 6/2011 | Jones et al. |
| 2012/0064060 A1 | 3/2012 | Habashita et al. |
| 2012/0329848 A1 | 12/2012 | Jones et al. |

FOREIGN PATENT DOCUMENTS

| | | |
|---|---|---|
| EP | 1826197 | 8/2007 |
| EP | 2003132 | 12/2008 |
| EP | 1772145 B1 | 3/2011 |
| EP | 2017263 A4 | 11/2011 |
| GB | 1436893 | 5/1976 |
| JP | 2007262009 A | 10/2007 |
| WO | 91/06537 | 5/1991 |
| WO | WO9714674 A1 | 4/1997 |
| WO | WO0064888 A1 | 11/2000 |
| WO | WO0239987 A2 | 5/2002 |
| WO | WO02064616 A2 | 8/2002 |
| WO | WO02092068 A1 | 11/2002 |
| WO | WO03029205 A1 | 4/2003 |
| WO | WO03062252 A1 | 7/2003 |
| WO | WO03061567 A3 | 12/2003 |
| WO | WO03105771 A2 | 12/2003 |
| WO | WO03074008 A3 | 2/2004 |
| WO | WO03073986 A3 | 5/2004 |
| WO | WO2004058149 A3 | 9/2004 |
| WO | WO2004074297 A1 | 9/2004 |
| WO | WO2004010949 A3 | 10/2004 |
| WO | WO2004071442 A3 | 10/2004 |
| WO | WO2004096752 A1 | 11/2004 |
| WO | WO2004103309 A2 | 12/2004 |
| WO | WO2004096757 A8 | 1/2005 |
| WO | WO2005000833 A1 | 1/2005 |
| WO | WO2004110979 A3 | 2/2005 |
| WO | WO2004103306 A3 | 3/2005 |
| WO | WO2005021503 A1 | 3/2005 |
| WO | 2005/032465 | 4/2005 |
| WO | WO2005020882 A3 | 4/2005 |
| WO | WO2004103279 A3 | 5/2005 |
| WO | WO2005041899 A2 | 5/2005 |
| WO | WO2005044780 A1 | 5/2005 |
| WO | 2005/058848 | 6/2005 |
| WO | WO2005058848 A1 | 6/2005 |
| WO | WO2005070886 A1 | 8/2005 |
| WO | WO2005079788 A1 | 9/2005 |
| WO | WO2005082089 A2 | 9/2005 |
| WO | WO2005082841 A1 | 9/2005 |
| WO | WO2005085179 A1 | 9/2005 |
| WO | WO2005097745 A1 | 10/2005 |
| WO | WO2005058295 A3 | 11/2005 |
| WO | WO2005123677 A1 | 12/2005 |
| WO | WO2006001463 A1 | 1/2006 |
| WO | WO2006009092 A1 | 1/2006 |
| WO | WO2006010379 A1 | 2/2006 |
| WO | WO2006011554 A1 | 2/2006 |
| WO | WO2006013948 A1 | 2/2006 |
| WO | WO2006020951 A1 | 2/2006 |
| WO | 2006/034337 | 3/2006 |
| WO | WO2004113330 A8 | 3/2006 |
| WO | WO2006010544 A3 | 3/2006 |
| WO | WO2006043149 A2 | 4/2006 |
| WO | 2006/047195 | 5/2006 |
| WO | WO2006064757 A1 | 6/2006 |
| WO | WO2006079406 A1 | 8/2006 |
| WO | WO2006088944 A1 | 8/2006 |
| WO | WO2006100631 A1 | 9/2006 |
| WO | WO2006100633 A1 | 9/2006 |
| WO | WO2006100635 A3 | 9/2006 |
| WO | WO2006036033 A3 | 11/2006 |
| WO | 2006/131336 | 12/2006 |
| WO | WO2006137019 A1 | 12/2006 |
| WO | WO2006137509 A1 | 12/2006 |
| WO | WO2007024922 A1 | 3/2007 |
| WO | WO2007037196 A1 | 4/2007 |
| WO | WO2007060626 A1 | 5/2007 |
| WO | WO2007080542 A1 | 7/2007 |
| WO | WO2007083089 A1 | 7/2007 |
| WO | WO2007085451 A2 | 8/2007 |
| WO | WO2007086001 A2 | 8/2007 |
| WO | WO2007091396 A1 | 8/2007 |
| WO | WO2007091501 A1 | 8/2007 |
| WO | WO2007092638 A1 | 8/2007 |
| WO | WO2007109330 A2 | 9/2007 |
| WO | 2007/116866 | 10/2007 |
| WO | WO2007095561 A3 | 10/2007 |
| WO | WO2007115820 A1 | 10/2007 |
| WO | WO2007116866 A1 | 10/2007 |
| WO | WO2007061458 A3 | 11/2007 |
| WO | WO2007092190 A3 | 11/2007 |
| WO | WO2007129473 A1 | 11/2007 |
| WO | WO2007129745 A1 | 11/2007 |
| WO | WO2007132307 A1 | 11/2007 |
| WO | WO2007100617 A3 | 1/2008 |
| WO | WO2007109334 A3 | 1/2008 |
| WO | WO2008016674 A1 | 2/2008 |
| WO | WO2008018427 A1 | 2/2008 |
| WO | WO2008019090 A2 | 2/2008 |
| WO | WO2008023783 A1 | 2/2008 |
| WO | WO2008024196 A1 | 2/2008 |
| WO | WO2008016692 A3 | 3/2008 |
| WO | WO2008028937 A1 | 3/2008 |
| WO | WO2008029371 A1 | 3/2008 |
| WO | WO2008030843 A1 | 3/2008 |
| WO | WO2008035239 A1 | 3/2008 |
| WO | WO2008029306 A3 | 5/2008 |
| WO | 2008/074821 | 6/2008 |
| WO | 2008/076356 | 6/2008 |
| WO | WO2008074820 A1 | 6/2008 |
| WO | WO2008074821 A1 | 6/2008 |
| WO | WO2008076356 A1 | 6/2008 |
| WO | WO2008079382 A1 | 7/2008 |
| WO | WO2008089015 A1 | 7/2008 |
| WO | WO2008091967 A1 | 7/2008 |
| WO | WO2008114157 A1 | 9/2008 |
| WO | 2008/128951 | 10/2008 |
| WO | WO2007098474 A8 | 11/2008 |
| WO | WO2008097819 A3 | 11/2008 |
| WO | WO2008152149 A1 | 12/2008 |
| WO | WO2009019167 A1 | 2/2009 |
| WO | WO2009019506 A1 | 2/2009 |
| WO | WO2009011850 A3 | 3/2009 |
| WO | WO2009064250 A1 | 5/2009 |
| WO | 2009/078983 | 6/2009 |
| WO | 2009/094157 | 7/2009 |
| WO | WO2009103552 A1 | 8/2009 |
| WO | 2009/151529 | 12/2009 |
| WO | 2009/151621 | 12/2009 |
| WO | 2009/151626 | 12/2009 |

(56) References Cited

FOREIGN PATENT DOCUMENTS

| WO | 2010/011316 | 1/2010 |
|---|---|---|
| WO | 2010/027431 | 3/2010 |
| WO | 2010/093704 | 8/2010 |
| WO | 2011/005290 | 1/2011 |
| WO | 2011/005295 | 1/2011 |
| WO | 2011/059784 | 5/2011 |
| WO | 2011/094008 | 8/2011 |
| WO | 2011/109471 | 9/2011 |
| WO | 2012/015758 | 2/2012 |

OTHER PUBLICATIONS

Balatoni et al., Brain Research Bulletin, 74:307-316, 2007.
Bar-Haim et al, PLoS Pathogens, 4(11):e1000211.doi:10.1371/journal.ppat.100021, 2008.
Baumruker et al., Expert Opin. Invest. Drugs, 16:283-289, 2007.
Berge et al., Journal of Pharmaceutical Sciences, 66;1-19 (1977).
Bioorganic & Medicinal Chemistry Letters Jul. 15, 2006, vol. 16, No. 14, Jul. 15, 2006, pp. 3684-3687.
Biopharmatiques, "Merging Pharma and Biotech", http://www.biopharmaceutiques.com/fr/tables/clinical_studies_709.html, 2009.
Bioreversible Carriers in Drug Design, ed. Edward B. Roche, American Pharmaceutical Association and Pergamon Press 1987 *too voluminous.
Boismenu et al., K. Leukoc Biol, 67:267-278, 2000.
Bolick et al., Arteriosler Thomb. Vasc. Biol., 25:976-981, 2005.
Brinkmann et al., J. Biol. Chem., 277:21453-21457, 2002.
Brinkmann et al., Pharmacology & Therapeutics, 115:84-105, 2007.
Brinkmann et al., Transplant Proc., 33:530-531, 2001.
Brinkmann et al., Transplantation, 72:764-769, 2001.
Brinkmann, "FTY720 (fingolimod) in Multiple Sclerosis: therapeutic effects in the immune and the central nervous system", British Journal of Pharmacology, 158: 1173-1182, 2009.
Budde et al, J. Am. Soc. Nephrol., 13:1073-1083, 2002.
Buzard, Daniel J. et al, "Recent Progress in the Development of Selective S1P1 Receptor Agonists for the Treatment of Inflammatory and Autoimmune Disorders", Expert Opinion, 1141-1159, 2008.
Buzard, Daniel J. et al., Discovery and Characterization of Potent and Selective 4-oxo-4-(5-(5-phenyl-1,2,4-oxadiazol-3-yl)indolin-1-yl)butanoic acids as S1P1 Agonists; Biiorganic & Medicinal Chemistry Letters, 6013-6018; 2011.
Buzard, Daniel J. et al., "Discovery and Characterization of Potent and Selective 4-Oxo-4-(5-(5-phenyl-1,2,4-oxadiazol-3-yl)indolin-1-yl)butanoic acids as S1P1 Receptor Agonists", Arena Pharmaceuticals, Inc., MEDI-099, ACS, Mar. 2011.
Chiba et al., Cell. Mod. Biol., 3:11-19, 2006.
Chiba, Pharmacology & Therapeutics, 108: 308-319, 2005.
Chun et al, Pharmacological Reviews, 54:265-269, 2002.
Coelho et al., J. Pharmacol. Exp. Ther., 323:626-635, 2007.
Collier et al, J. Labelled Compd. Radiopharm., 1999, 42, S264-S266.
Coste et al., Journal of Cellular and Molecular Medicine 12(3), 995-1004, 2008.
Daniel et al., J. Immunol., 178:2458-2468, 2007.
Deguchi et al., Oncology Reports, 16: 699-703, 2006.
Dev et al, Pharmacology and Therapeutics, 117:77-93, 2008.
Fu et al, Transplantation, 73:1425-1430, 2002.
Fujii et al., Am. J. Physiol. Gastrointest. Liver Phsiol., 291; G267-G274, 2006.
Fujino et al., J. Pharmacol. Exp. Ther., 305:70-77, 2003.
Fujishiro et al., J. Heart Lung Transplant, 25:825-833, 2006.
Gabriel et al, ASSAY and Drug Development Technologies, 1:291-303, 2003.
Gottlieb, et al., *J. Org. Chem.* 1997, 62, 7512-7515.
Greene, T.W. and Wuts, P.G.M., Protecting Groups in Organic Synthesis, 3$^{rd}$ Edition, 1999 [Wiley] * (too voluminous).
Griesser, "The Importance of Solvates" in *Polymorphism in the Pharmaceutical Industry*, 211-233 (Rolf Hilfiker, ed., 2006).
Groeneveld, Vascul. Pharmacol., 39:247-256, 2003.

Guillory, "Generation of Polymorphs, Hydrates, Solvates, and Amorphous Solids," in:Polymorphism in Pharmaceutical Solids, ed. Harry G.Brittan, vol. 95, Marcel Dekker, Inc. New York, 1999.
Hale et al, Bioorg. Med. Chem. Lett., 14:3351-3355, 2004.
Han, Sangdon et al., "Discovery of 2-(7-(5-phenyl-1,2,4-oxadiazol-3-yl)-1,2,3,4-tetrahydrocyclopenta[b]indol-3-yl)acetic acids: Potent and Selective Sphingosine-1-phosphate (S1P1) Receptor Agonists", Arena Pharmaceuticals, Inc., MEDI-098, ACS Poster, Mar. 2011.
Herzinger et al., Am. J. Clin. Dermatol., 8:329-336, 2007.
Hwang et al., Circulation, 100:1322-1329, 1999.
Idzko et al, J. Clin. Invest., 116:2935-2944-2006.
Ishii et al., Nature, advance online publication, Feb. 8, 2009, doi:10.1038/nature07713.
Jones, Robert M., "Discovery of Potent and Selective Sphingosine-1-Phosphate 1 (S1P1) Receptor Agonists", CHI 6$^{th}$ Annual Drug Discovery Chemistry, San Diego, CA, Apr. 12, 2011.
Jones, Robert M., "Discovery of Potent and Selective Sphingosine-1-Phosphate 1(S1P1) Receptor Agonists", CHI 6$^{th}$ Annual Discovery on Target, Boston, MA, Nov. 3, 2011.
Jung et al., Glia, 55:1656-1667, 2007.
Kaneider et al., FASEB J., 18:309-311, 2004.
Kappos et al., N. Engl. J. Med., 355:1124-1140, 2006.
Kataoka et al., Cellular & Molecular Immunology, 2:439-448, 2005.
Kaudel et al., Transplant. Proc, 39:499-502, 2007.
Kawasaki, Andrew et al., "Discovery and Characterization of 2-(7-(5-phenyl-1,2,4-oxadiazol-3-yl)-2,3-dihydro-1H-pyrrolo[1,2-a]indol-1-yl)acetic acid Derivatives as Potent & Selective Human S1P1 Receptor Agonists", Arena Pharmaceuticals, Inc., MEDI-254, ACS, Mar. 2011.
Keul et al., Arterioscler. Thromb. Vasc. Biol., 27:607-613, 2007.
Kim et al., Cell Signal, 16:89-95, 2004.
Kimura et al., Stem Cells, 25:115-124, 2007.
Kiyabayashi et al, J.Cardiovasc. Pharmacol., 35: 410-416, 2000.
Kohno et al., Biol. Pharm. Bull., 27:1392-1396, 2004.
Kohno et al., Biological & Pharmaceutical Bulletin, 28(4), 736-739, 2005.
Koreck et al., Dermatology, 206:96-105, 2003.
Kurose et al., Exp. Eye Res., 70:7-15; 2000.
LaMontagne et al., Cancer Res., 66:221-231, 2006.
Le Bas, M.D. et al, J. Labelled Compl. Radiopharm. 2001, 44, S280-S282.
Lee et al., Clin. Cancer res., 11:84588466, 2005.
Lima et al., Transplant Proc., 36:1015-1017, 2004.
Liu et al, Microsurgery, 27:300-304; 2007.
Maki et al., Transplantation, 79:1684-1686, 2002.
Maki et al., Transplantation, 79: 1051-1055, 2005.
Martini et al., Am. J. Physiol. Renal Physiol., 292: F1761-F1770, 2007.
Martini et al., Expert Opin. Investig. Drugs, 16:505-518, 2007.
Matloubian et al., Nature, 427:355-360, 2004.
Matsuura et al, Inflamm. Res., 49:404-410, 2000.
Matsuura et al., Int. J. Immunopharmacol., 22:323-331, 2000.
Miron et al, Ann. Neurol., 63:61-71, 2008.
Miyamoto et al, J. Am. Coll. Cardiol., 37: 1713-1718, 2001.
Mizushima et al, Inflamm. Bowel Dis., 10:182-192, 2004.
Morissette, et al., "High-Throughput Crystallization: Polymorphs, Salts, Co-Crystals and Solvates", *Adv. Drug Delivery Rev.*, 56:275-300 (2004).
Nakashima et al., J. Investigative Dermatology 128(12), 2833-2841, 2008.
Neurath et al., J. Exp. Med, 182:1281-1290, 1995.
Nofer et al., Circulation, 115: 501-508, 2007.
Ogawa et al, BBRC, 361: 621-628, 2007.
Okayasu et al, Gastroenterology, 98:694-702, 1990.
Okazaki et al., J. Rhematol., 29:707-716, 2002.
Oo et al., J. Biol. Chem., 282:9082-9089, 2007.
Pan et al, Chemistry & Biology, 13:1227-1234, 2006.
Premenko-Lanier et al., Nature, 454, 894, 2008.
Rausch et al., J. Magn. Reson. Imaging, 20:16-24, 2004.
Raveney et al., Arch. Ophthamol. 126(10), 1390, 2008.
Rosen et al., Immunol Rev. 195: 160-177, 2003.
Sakagawa et al., Transpl. Immunol., 13:161-168, 2004.
Sanchez et al., J. Biol. Chem., 278(47), 47281-47290, 2003.

(56) References Cited

OTHER PUBLICATIONS

Sanna et al, Nat Chem Biol., 2:434-441, 2006.
Sanna et al., J. Biol Chem., 279:13839-13848, 2004.
Sauer et al., J. Biol. Chem., 279:38471-38479, 2004.
Sawicka et al., J. Immunol., 171; 6206-6214, 2003.
Schmid et al., J. Cell Biochem., 101:259-270, 2007.
Schwab et al; Nature Immunol., 8:1295-1301, 2007.
Shimizu et al., Circulation, 111:222-229, 2005.
Stahly, Crystal Growth & Design (2007), 7(6), 1007-1026.
Storey, et al., "Automation of Solid Form Screening Procedures in the Pharmaceutical Industry—How to Avoid the Bottlenecks", *Crystallography Reviews*, 10(1):45-46 (2004).
Sturino et al: "Discovery of a potent and selective prostaglandin D2 receptor antagonist, [(3R)-4-(4-chloro-benzyl)-7-Fluoro-5-(methylsulfonyl)-1,2,3,4-tetrahydrocyclopenta[b]indol-3-yl]-acetic acid (MK-0524)", Journal of Medicinal Chemistry, Feb. 22, 2007, pp. 794-806.
Suzuki et al., J. Heart Lung Transplant, 25:302-309, 2006.
Suzuki et al., Transpl. Immunol., 4:252-255, 1996.
Taylor et al, Blood, 110:3480-3488, 2007.
Truong et al., American Journal of Transplantation, 7:2031-2038, 2007.
Villullas et al, J. Neurosci. Res, 73:215-226, 2003.
Vippagunta, et al., "Crystalline Forms", *Adv. Drug Delivery Rev.*, 48:3-26 (2001).
Webb et al., J. Neuroimmunol., 153:108-121, 2004.
Webster, Cutis, 76:4-7, 2005.
Whetzel et al., Circ. Res., 99:731-739, 2006.
Yan et al., Bioorg. & Med. Chem. Lett., 16:3679-3683, 2006.
Yanagawa et al., J. Immunol., 160:5493-5499, 1998.
Yang et al, Clinical Immunology, 107:30-35, 2003.
Zhang et al., J. Cell. Mol. Med., 11:307-314, 2007.
Zhang et al., Mini-Reviews in Medicinal Chemistry, 7:845-850, 2007.
Zhu et al, J. Org. Chem., 2002, 67, 943-948.
English Translation of Japan 2007262009, Machinaga et al., Published Oct. 11, 2007.
English Translation of WO 2007/129745, Machinaga et al., Published Nov. 15, 2007.
Higuchi and Stella, Pro-drugs as Novel Delivery Systems vol. 14 of the A.C.S. Symposium Series, 1975, 129 pages.
Remington, The Science and Practice of Pharmacy, 20th Edition, 2000, Lippincott Williams & Wilkins, (Editors: Gennaro et al) * (too voluminous).
Vachal et al., "Highly selective and potent agonists of sphinogosin-1-phosphate 1 (S1P1) receptor," Bioorganic Med Chem Lett., Jul. 2006, 16(14):3684-3687.

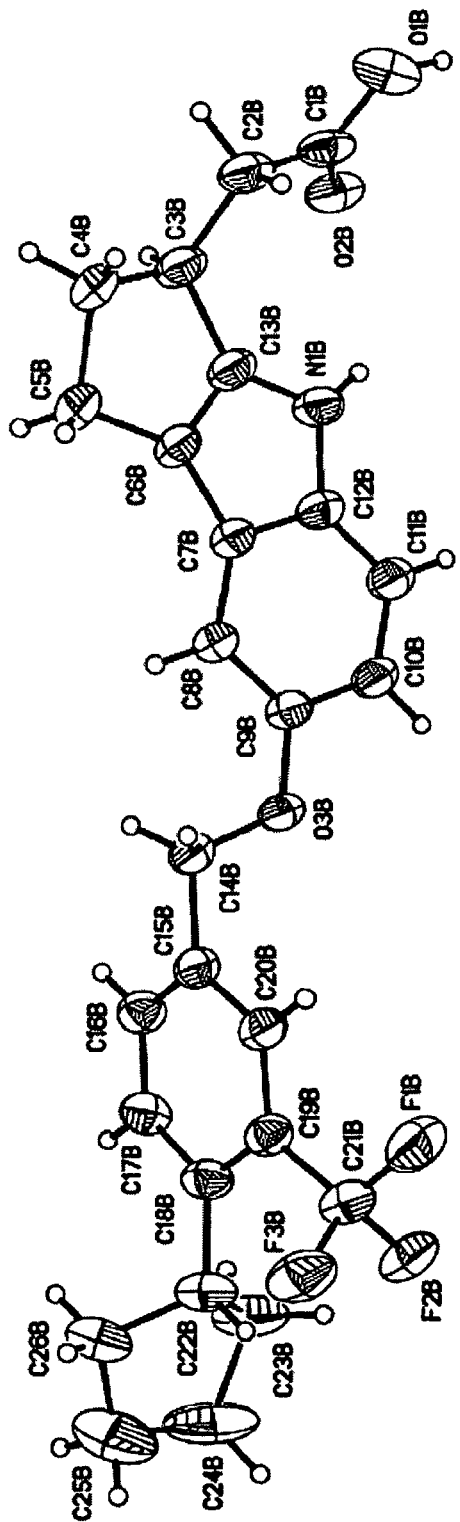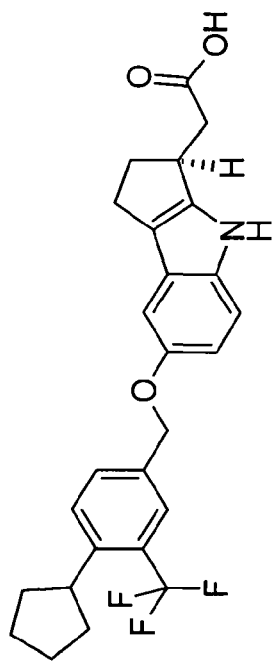
A View of a Molecule of the
1st Enantiomer of Compound 12 as described in Example 1.29
FIGURE 21

SUBSTITUTED 1,2,3,4-TETRAHYDROCYCLOPENTA[B]INDOL-3-YL)ACETIC ACID DERIVATIVES USEFUL IN THE TREATMENT OF AUTOIMMUNE AND INFLAMMATORY DISORDERS

This application is a §371 National Stage Application of International Appl. No. PCT/US2009/004265, filed Jul. 22, 2009, which claims the benefit of U.S. Provisional Appl. No. 61/135,672, filed Jul. 23, 2008, and U.S. Provisional Appl. No. 61/209,374, filed Mar. 6, 2009, each of which is incorporated herein by reference in its entirety.

FIELD OF THE INVENTION

The present invention relates to certain substituted 1,2,3,4-tetrahydrocyclopenta[b]indol-3-yl)acetic acid derivatives of Formula (Ia) and pharmaceutically acceptable salts thereof, which exhibit useful pharmacological properties, for example, as agonists of the S1P1 receptor. Also provided by the present invention are pharmaceutical compositions containing compounds of the invention, and methods of using the compounds and compositions of the invention in the treatment of S1P1 associated disorders, for example, psoriasis, rheumatoid arthritis, Crohn's disease, transplant rejection, multiple sclerosis, systemic lupus erythematosus, ulcerative colitis, type I diabetes, acne, microbial infections or diseases and viral infections or diseases.

BACKGROUND OF THE INVENTION

The present invention relates to compounds that are S1P1 receptor agonists having at least immunosuppressive, anti-inflammatory and/or hemostatic activities, e.g. by virtue of modulating leukocyte trafficking, sequestering lymphocytes in secondary lymphoid tissues, and/or enhancing vascular integrity.

The present application is in part focused on addressing an unmet need for immunosuppressive agents such as may be orally available which have therapeutic efficacy for at least autoimmune diseases and disorders, inflammatory diseases and disorders (e.g., acute and chronic inflammatory conditions), transplant rejection, cancer, and/or conditions that have an underlying defect in vascular integrity or that are associated with angiogenesis such as may be pathologic (e.g., as may occur in inflammation, tumor development and atherosclerosis) with fewer side effects such as the impairment of immune responses to systemic infection.

The sphingosine-1-phosphate (S1P) receptors 1-5 constitute a family of G protein-coupled receptors with a seven-transmembrane domain. These receptors, referred to as S1P1 to S1P5 (formerly termed endothelial differentiation gene (EDG) receptor-1, -5, -3, -6 and -8, respectively; Chun et al., *Pharmacological Reviews*, 54:265-269, 2002), are activated via binding by sphingosine-1-phosphate, which is produced by the sphingosine kinase-catalyzed phosphorylation of sphingosine. S1P1, S1P4 and S1P5 receptors activate Gi but not Gq, whereas S1P2 and S1P3 receptors activate both Gi and Gq. The S1P3 receptor, but not the S1P1 receptor, responds to an agonist with an increase in intracellular calcium.

S1P receptor agonists having agonist activity on the S1P1 receptor have been shown to rapidly and reversibly induce lymphopenia (also referred to as peripheral lymphocyte lowering (PLL); Hale et al., *Bioorg. Med. Chem. Lett.*, 14:3351-3355, 2004). This is attended by clinically useful immunosuppression by virtue of sequestering T- and B-cells in secondary lymphoid tissue (lymph nodes and Peyer's patches) and thus apart from sites of inflammation and organ grafts (Rosen et al., *Immunol. Rev.*, 195:160-177, 2003; Schwab et al., *Nature Immunol.*, 8:1295-1301, 2007). This lymphocyte sequestration, for example in lymph nodes, is thought to be a consequence of concurrent agonist-driven functional antagonism of the S1P1 receptor on T-cells (whereby the ability of S1P to mobilize T-cell egress from lymph nodes is reduced) and persistent agonism of the S1P1 receptor on lymph node endothelium (such that barrier function opposing transmigration of lymphocytes is increased) (Matloubian et al., *Nature*, 427:355-360, 2004; Baumruker et al., *Expert Opin. Investig. Drugs*, 16:283-289, 2007). It has been reported that agonism of the S1P1 receptor alone is sufficient to achieve lymphocyte sequestration (Sanna et al., *J Biol. Chem.*, 279:13839-13848, 2004) and that this occurs without impairment of immune responses to systemic infection (Brinkmann et al., *Transplantation*, 72:764-769, 2001; Brinkmann et al., *Transplant Proc.*, 33:530-531, 2001).

That agonism of endothelial S1P1 receptors has a broader role in promoting vascular integrity is supported by work implicating the S1P1 receptor in capillary integrity in mouse skin and lung (Sanna et al., *Nat Chem. Biol.*, 2:434-441, 2006). Vascular integrity can be compromised by inflammatory processes, for example as may derive from sepsis, major trauma and surgery so as to lead to acute lung injury or respiratory distress syndrome (Johan Groeneveld, *Vascul. Pharmacol.*, 39:247-256, 2003).

An exemplary S1P receptor agonist having agonist activity on the S1P1 receptor is FTY720 (fingolimod), an immunosuppressive agent currently in clinical trials (Martini et al., *Expert Opin. Investig. Drugs*, 16:505-518, 2007). FTY720 acts as a prodrug which is phosphorylated in vivo; the phosphorylated derivative is an agonist for S1P1, S1P3, S1P4 and S1P5 receptors (but not the S1P2 receptor) (Chiba, *Pharmacology & Therapeutics*, 108:308-319, 2005). FTY720 has been shown to rapidly and reversibly induce lymphopenia (also referred to as peripheral lymphocyte lowering (PLL); Hale et al., *Bioorg. Med. Chem. Lett.*, 14:3351-3355, 2004). This is attended by clinically useful immunosuppression by virtue of sequestering T- and B-cells in secondary lymphoid tissue (lymph nodes and Peyer's patches) and thus apart from sites of inflammation and organ grafts (Rosen et al., *Immunol. Rev.*, 195:160-177, 2003; Schwab et al., *Nature Immunol.*, 8:1295-1301, 2007).

In clinical trials, FTY720 elicited an adverse event (i.e., transient asymptomatic bradycardia) due to its agonism of the S1P3 receptor (Budde et al., *J. Am. Soc. Nephrol.*, 13:1073-1083, 2002; Sanna et al., *J. Biol. Chem.*, 279:13839-13848, 2004; Ogawa et al., *BBRC*, 361:621-628, 2007).

FTY720 has been reported to have therapeutic efficacy in at least: a rat model for autoimmune myocarditis and a mouse model for acute viral myocarditis (Kiyabayashi et al., *J. Cardiovasc. Pharmacol.*, 35:410-416, 2000; Miyamoto et al., *J. Am. Coll. Cardiol.*, 37:1713-1718, 2001); mouse models for inflammatory bowel disease including colitis (Mizushima et al., *Inflamm. Bowel Dis.*, 10:182-192, 2004; Deguchi et al., *Oncology Reports*, 16:699-703, 2006; Fujii et al., *Am. J. Physiol. Gastrointest. Liver Physiol.*, 291:G267-G274, 2006; Daniel et al., *J. Immunol.*, 178:2458-2468, 2007); a rat model for progressive mesangioproliferative glomerulonephritis (Martini et al., *Am. J. Physiol. Renal Physiol.*, 292:F1761-F1770, 2007); a mouse model for asthma, suggested to be primarily through the S1P1 receptor on the basis of work using the S1P1 receptor agonist SEW2871 (Idzko et al, *J. Clin. Invest.*, 116:2935-2944, 2006); a mouse model for airway inflammation and induction of bronchial hyperresponsiveness (Sawicka et al., *J. Immunol.*, 171; 6206-6214, 2003);

a mouse model for atopic dermatitis (Kohno et al., *Biol. Pharm. Bull.*, 27:1392-1396, 2004); a mouse model for ischemia-reperfusion injury (Kaudel et al., *Transplant. Proc,* 39:499-502, 2007); a mouse model for systemic lupus erythematosus (SLE) (Okazaki et al., *J. Rheumatol.,* 29:707-716, 2002; Herzinger et al, Am. J. Clin. Dermatol., 8:329-336, 2007); rat models for rheumatoid arthritis (Matsuura et al., *Int. J. Immunopharmacol.,* 22:323-331, 2000; Matsuura et al., *Inflamm. Res.,* 49:404-410, 2000); a rat model for autoimmune uveitis (Kurose et al., *Exp. Eye Res.,* 70:7-15, 2000); mouse models for type I diabetes (Fu et al, *Transplantation,* 73:1425-1430, 2002; Maki et al., *Transplantation,* 74:1684-1686, 2002; Yang et al., *Clinical Immunology,* 107:30-35, 2003; Maki et al., *Transplantation,* 79:1051-1055, 2005); mouse models for atherosclerosis (Nofer et al., *Circulation,* 115:501-508, 2007; Keul et al., *Arterioscler. Thromb. Vasc. Biol.,* 27:607-613, 2007); a rat model for brain inflammatory reaction following traumatic brain injury (TBI) (Zhang et al., *J. Cell. Mol. Med.,* 11:307-314, 2007); and mouse models for graft coronary artery disease and graft-versus-host disease (GVHD) (Hwang et al., *Circulation,* 100:1322-1329, 1999; Taylor et al., *Blood,* 110:3480-3488, 2007). In vitro results suggest that FTY720 may have therapeutic efficacy for β-amyloid-related inflammatory diseases including Alzheimer's disease (Kaneider et al., *FASEB J.,* 18:309-311, 2004). KRP-203, an S1P receptor agonist having agonist activity on the S1P1 receptor, has been reported to have therapeutic efficacy in a rat model for autoimmune myocarditis (Ogawa et al., *BBRC,* 361:621-628, 2007). Using the S1P1 receptor agonist SEW2871, it has been shown that agonism of endothelial S1P1 receptors prevents proinflammatory monocyte/ endothelial interactions in type I diabetic vascular endothelium (Whetzel et al., *Circ. Res.,* 99:731-739, 2006) and protects the vasculature against TNFα-mediated monocyte/ endothelial interactions (Bolick et al., *Arterioscler. Thromb. Vasc. Biol.,* 25:976-981, 2005).

Additionally, FTY720 has been reported to have therapeutic efficacy in experimental autoimmune encephalomyelitis (EAE) in rats and mice, a model for human multiple sclerosis (Brinkmann et al., *J. Biol. Chem.,* 277:21453-21457, 2002; Fujino et al., *J. Pharmacol. Exp. Ther.,* 305:70-77, 2003; Webb et al., *J. Neuroimmunol.,* 153:108-121, 2004; Rausch et al., *J. Magn. Reson. Imaging,* 20:16-24, 2004; Kataoka et al., *Cellular & Molecular Immunology,* 2:439-448, 2005; Brinkmann et al., *Pharmacology & Therapeutics,* 115:84-105, 2007; Baumruker et al., *Expert Opin. Investig. Drugs,* 16:283-289, 2007; Balatoni et al., *Brain Research Bulletin,* 74:307-316, 2007). Furthermore, FTY720 has been found to have therapeutic efficacy for multiple sclerosis in clinical trials. In Phase II clinical trials for relapsing-remitting multiple sclerosis, FTY720 was found to reduce the number of lesions detected by magnetic resonance imaging (MRI) and clinical disease activity in patients with multiple sclerosis (Kappos et al., *N. Engl. J. Med.,* 355:1124-1140, 2006; Martini et al., *Expert Opin. Investig. Drugs,* 16:505-518, 2007; Zhang et al., *Mini-Reviews in Medicinal Chemistry,* 7:845-850, 2007; Brinkmann, *Pharmacology & Therapeutics,* 115: 84-105, 2007). FTY720 is currently in Phase III studies of remitting-relapsing multiple sclerosis (Brinkmann, *Pharmacology & Therapeutics,* 115:84-105, 2007; Baumruker et al., *Expert. Opin. Investig. Drugs,* 16:283-289, 2007; Dev et al., *Pharmacology and Therapeutics,* 117:77-93, 2008).

Recently, FTY720 has been reported to have anti-viral activity. Specific data has been presented in the lymphocytic choriomeningitis virus (LCMV) mouse model, wherein the mice were infected with either the Armstrong or the clone 13 strain of LCMV (Premenko-Lanier et al., Nature, 454, 894, 2008).

FTY720 has been reported to impair migration of dendritic cells infected with *Francisella tularensis* to the mediastinal lymph node, thereby reducing the bacterial colonization of it. *Francisella tularensis* is associated with tularemia, ulceroglandular infection, respiratory infection and a typhoidal disease (E. Bar-Haim et al, PLoS Pathogens, 4(11): e1000211. doi:10.1371/journal.ppat.1000211, 2008).

It has also been recently reported that a short-term high dose of FTY720 rapidly reduced ocular infiltrates in experimental autoimmune uveoretinitis. When given in the early stages of ocular inflammation, FTY720 rapidly prevented retinal damage. It was reported to not only prevent infiltration of target organs, but also reduce existing infiltration (Raveney et al., Arch. Ophthalmol. 126(10), 1390, 2008).

It has been reported that treatment with FTY720 relieved ovariectomy-induced osteoporosis in mice by reducing the number of mature osteoclasts attached to the bone surface. The data provided evidence that S1P controled the migratory behaviour of osteoclast precursors, dynamically regulating bone mineral homeostasis (Ishii et al., Nature, advance online publication, 8 Feb. 2009, doi:10.1038/nature07713).

Agonism of the S1P1 receptor has been implicated in enhancement of survival of oligodendrocyte progenitor cells. Survival of oligodendrocyte progenitor cells is a required component of the remyelination process. Remyelination of multiple sclerosis lesions is considered to promote recovery from clinical relapses. (Miron et al., *Ann. Neurol.,* 63:61-71, 2008; Coelho et al., *J. Pharmacol. Exp. Ther.,* 323:626-635, 2007; Dev et al., *Pharmacology and Therapeutics,* 117:77-93, 2008). It also has been shown that the S1P1 receptor plays a role in platelet-derived growth factor (PDGF)-induced oligodendrocyte progenitor cell mitogenesis (Jung et al., *Glia,* 55:1656-1667, 2007).

Agonism of the S1P1 receptor has also been reported to mediate migration of neural stem cells toward injured areas of the central nervous system (CNS), including in a rat model of spinal cord injury (Kimura et al., *Stem Cells,* 25:115-124, 2007).

Agonism of the S1P1 receptor has been implicated in the inhibition of keratinocyte proliferation (Sauer et al., *J. Biol. Chem.,* 279:38471-38479, 2004), consistent with reports that S1P inhibits keratinocyte proliferation (Kim et al., *Cell Signal,* 16:89-95, 2004). The hyperproliferation of keratinocytes at the entrance to the hair follicle, which can then become blocked, and an associated inflammation are significant pathogenetic factors of acne (Koreck et al., *Dermatology,* 206:96-105, 2003; Webster, *Cutis,* 76:4-7, 2005).

FTY720 has been reported to have therapeutic efficacy in inhibiting pathologic angiogenesis, such as that as may occur in tumor development. Inhibition of angiogenesis by FTY720 is thought to involve agonism of the S1P1 receptor (Oo et al., *J. Biol. Chem.,* 282; 9082-9089, 2007; Schmid et al., *J. Cell Biochem.,* 101:259-270, 2007). FTY720 has been reported to have therapeutic efficacy for inhibiting primary and metastatic tumor growth in a mouse model of melanoma (LaMontagne et al., *Cancer Res.,* 66:221-231, 2006). FTY720 has been reported to have therapeutic efficacy in a mouse model for metastatic hepatocellular carcinoma (Lee et al., *Clin. Cancer Res.,* 11:84588466, 2005).

It has been reported that oral administration of FTY720 to mice potently blocked VEGF-induced vascular permeability, an important process associated with angiogenesis, inflammation, and pathological conditions such as sepsis, hypoxia, and solid tumor growth (T Sanchez et al, *J. Biol. Chem.*, 278(47), 47281-47290, 2003).

Cyclosporin A and FK506 (calcineurin inhibitors) are drugs used to prevent rejection of transplanted organs. Although they are effective in delaying or suppressing transplant rejection, classical immunosuppressants such as cyclosporin A and FK506 are known to cause several undesirable side effects including nephrotoxicity, neurotoxicity, β-cell toxicity and gastrointestinal discomfort. There is an unmet need in organ transplantation for an immunosuppressant without these side effects which is effective as a monotherapy or in combination with a classical immunosuppressant for inhibiting migration of, e.g., alloantigen-reactive T-cells to the grafted tissue, thereby prolonging graft survival.

FTY720 has been shown to have therapeutic efficacy in transplant rejection both as a monotherapy and in synergistic combination with a classical immunosuppressant, including cyclosporin A, FK506 and RAD (an mTOR inhibitor). It has been shown that, unlike the classical immunosuppressants cyclosporin A, FK506 and RAD, FTY720 has efficacy for prolonging graft survival without inducing general immunosuppression, and this difference in drug action is believed to be relevant to the synergism observed for the combination (Brinkmann et al., *Transplant Proc.,* 33:530-531, 2001; Brinkmann et al., *Transplantation,* 72:764-769, 2001).

Agonism of the S1P1 receptor has been reported to have therapeutic efficacy for prolonging allograft survival in mouse and rat skin allograft models (Lima et al., *Transplant Proc.,* 36:1015-1017, 2004; Yan et al., *Bioorg. & Med. Chem. Lett.,* 16:3679-3683, 2006). FTY720 has been reported to have therapeutic efficacy for prolonging allograft survival in a rat cardiac allograft model (Suzuki et al., *Transpl. Immunol.,* 4:252-255, 1996). FTY720 has been reported to act synergistically with cyclosporin A to prolong rat skin allograft survival (Yanagawa et al., *J. Immunol.,* 160:5493-5499, 1998), to act synergistically with cyclosporin A and with FK506 to prolong rat cardiac allograft survival, and to act synergistically with cyclosporin A to prolong canine renal allograft survival and monkey renal allograft survival (Chiba et al., *Cell Mol. Biol.,* 3:11-19, 2006). KRP-203, an S1P receptor agonist has been reported to have therapeutic efficacy for prolonging allograft survival in a rat skin allograft model and both as monotherapy and in synergistic combination with cyclosporin A in a rat cardiac allograft model (Shimizu et al., *Circulation,* 111:222-229, 2005). KRP-203 also has been reported to have therapeutic efficacy in combination with mycophenolate mofetil (MMF; a prodrug for which the active metabolite is mycophenolic acid, an inhibitor of purine biosynthesis) for prolonging allograft survival both in a rat renal allograft model and in a rat cardiac allograft model (Suzuki et al., *J. Heart Lung Transplant,* 25:302-209, 2006; Fujishiro et al., *J. Heart Lung Transplant,* 25:825-833, 2006). It has been reported that an agonist of the S1P1 receptor, AUY954, in combination with a subtherapeutic dose of RAD001 (Certican/Everolimus, an mTOR inhibitor) can prolong rat cardiac allograft survival (Pan et al., *Chemistry & Biology,* 13:1227-1234, 2006). In a rat small bowel allograft model, FTY720 has been reported to act synergistically with cyclosporin A to prolong small bowel allograft survival (Sakagawa et al., *Transpl. Immunol.,* 13:161-168, 2004). FTY720 has been reported to have therapeutic efficacy in a mouse islet graft model (Fu et al., *Transplantation,* 73:1425-1430, 2002; Liu et al., *Microsurgery,* 27:300-304; 2007) and in a study using human islet cells to evidence no detrimental effects on human islet function (Truong et al., *American Journal of Transplantation,* 7:2031-2038, 2007).

FTY720 has been reported to reduce the nociceptive behavior in the spared nerve injury model for neuropathic pain which does not depend on prostaglandin synthesis (O. Costu et al, *Journal of Cellular and Molecular Medicine* 12(3), 995-1004, 2008).

FTY720 has been reported to impair initiation of murine contact hypersensitivity (CHS). Adoptive transfer of immunized lymph node cells from mice treated with FTY720 during the sensitization phase was virtually incapable of inducing CHS response in recipients (D. Nakashima et al., *J. Investigative Dermatology* (128(12), 2833-2841, 2008).

It has been reported that prophylactic oral administration of FTY720 (1 mg/kg, three times a week), completely prevented the development of experimental autoimmune myasthenia gravis (EAMG) in C57BL/6 mice (T. Kohono et al, *Biological & Pharmaceutical Bulletin,* 28(4), 736-739, 2005).

In one embodiment, the present invention encompasses compounds which are agonists of the S1P1 receptor having selectivity over the S1P3 receptor. The S1P3 receptor, and not the S1P1 receptor, has been directly implicated in bradycardia (Sanna et al., *J. Biol. Chem.,* 279:13839-13848, 2004). An S1P1 receptor agonist selective over at least the S1P3 receptor has advantages over current therapies by virtue of an enhanced therapeutic window, allowing better tolerability with higher dosing and thus improving efficacy as therapy. The present invention encompasses compounds which are agonists of the S1P1 receptor and which exhibit no or substantially no activity for bradycardia.

S1P1 receptor agonists are useful to treat or prevent conditions where suppression of the immune system or agonism of the S1P1 receptor is in order, such as diseases and disorders mediated by lymphocytes, transplant rejection, autoimmune diseases and disorders, inflammatory diseases and disorders, and conditions that have an underlying defect in vascular integrity or that relate to angiogenesis such as may be pathologic.

In one embodiment, the present invention encompasses compounds which are agonists of the S1P1 receptor having good overall physical properties and biological activities and having an effectiveness that is substantially at least that of prior compounds with activity at the S1P1 receptor.

Citation of any reference throughout this application is not to be construed as an admission that such reference is prior art to the present application.

SUMMARY OF THE INVENTION

The present invention encompasses compounds of Formula (Ia) and pharmaceutically acceptable salts, solvates and hydrates thereof:

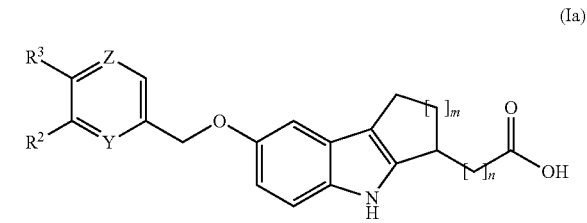

(Ia)

wherein:
m is 1 or 2;
n is 1 or 2;

Y is N or CR$^1$;
Z is N or CR$^4$; and
R$^1$, R$^2$, R$^3$ and R$^4$ are each independently selected from the group consisting of H, C$_1$-C$_6$ alkoxy, C$_1$-C$_6$ alkyl, C$_1$-C$_6$ alkylamino, C$_1$-C$_6$ alkylsulfonyl, C$_1$-C$_6$ alkylthio, carboxamide, cyano, C$_3$-C$_7$ cycloalkoxy, C$_3$-C$_7$ cycloalkyl, C$_1$-C$_6$ haloalkoxy, C$_1$-C$_6$ haloalkyl, halogen, heteroaryl and heterocyclyl, wherein said C$_1$-C$_6$ alkyl and C$_1$-C$_6$ alkoxy are each optionally substituted with one or two substituents selected from C$_3$-C$_7$ cycloalkyl and halogen.

In some embodiments, the present invention encompasses compounds of Formula (Ia) and pharmaceutically acceptable salts, solvates and hydrates thereof:

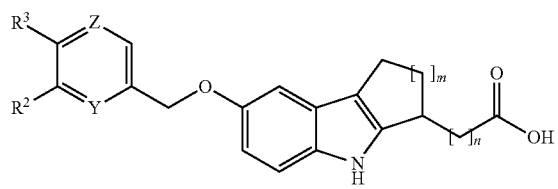

(Ia)

wherein:
m is 1 or 2;
n is 1 or 2;
Y is N or CR$^1$;
Z is N or CR$^4$; and
R$^1$, R$^2$, R$^3$ and R$^4$ are each independently selected from the group consisting of H, C$_1$-C$_6$ alkoxy, C$_1$-C$_6$ alkyl, C$_1$-C$_6$ alkylamino, C$_1$-C$_6$ alkylsulfonyl, C$_1$-C$_6$ alkylthio, carboxamide, cyano, C$_3$-C$_7$ cycloalkoxy, C$_3$-C$_7$ cycloalkyl, C$_1$-C$_6$ haloalkoxy, C$_1$-C$_6$ haloalkyl, halogen, heteroaryl and heterocyclyl, wherein said C$_1$-C$_6$ alkyl and C$_1$-C$_6$ alkoxy are each optionally substituted with one C$_3$-C$_7$ cycloalkyl group.

The present invention encompasses compounds which are S1P1 receptor agonists having at least immunosuppressive, anti-inflammatory and/or hemostatic activities, e.g. by virtue of modulating leukocyte trafficking, sequestering lymphocytes in secondary lymphoid tissues, and/or enhancing vascular integrity.

S1P1 receptor agonists are useful to treat or prevent conditions where suppression of the immune system or agonism of the S1P1 receptor is in order, such as diseases and disorders mediated by lymphocytes, transplant rejection, autoimmune diseases and disorders, inflammatory diseases and disorders (e.g., acute and chronic inflammatory conditions), cancer, and conditions that have an underlying defect in vascular integrity or that are associated with angiogenesis such as may be pathologic (e.g., as may occur in inflammation, tumor development and atherosclerosis). Such conditions where suppression of the immune system or agonism of the S1P1 receptor is in order include diseases and disorders mediated by lymphocytes, conditions that have an underlying defect in vascular integrity, autoimmune diseases and disorders, inflammatory diseases and disorders (e.g., acute and chronic inflammatory conditions), acute or chronic rejection of cells, tissue or solid organ grafts, arthritis including psoriatic arthritis and rheumatoid arthritis, diabetes including type I diabetes, demyelinating disease including multiple sclerosis, ischemia-reperfusion injury including renal and cardiac ischemia-reperfusion injury, inflammatory skin disease including psoriasis, atopic dermatitis and acne, hyperproliferative skin disease including acne, inflammatory bowel disease including Crohn's disease and ulcerative colitis, systemic lupus erythematosis, asthma, uveitis, myocarditis, allergy, atherosclerosis, brain inflammation including Alzheimer's disease and brain inflammatory reaction following traumatic brain injury, central nervous system disease including spinal cord injury or cerebral infarction, pathologic angiogenesis including as may occur in primary and metastatic tumor growth, rheumatoid arthritis, diabetic retinopathy and atherosclerosis, cancer, chronic pulmonary disease, acute lung injury, acute respiratory disease syndrome, sepsis and the like.

One aspect of the present invention pertains to pharmaceutical compositions comprising a compound of the present invention and a pharmaceutically acceptable carrier.

One aspect of the present invention pertains to pharmaceutical compositions comprising a compound of the present invention, a salt, a hydrate or solvate or a crystalline form and a pharmaceutically acceptable carrier.

One aspect of the present invention pertains to methods for treating a disorder associated with the S1P1 receptor in an individual comprising administering to the individual in need thereof a therapeutically effective amount of a compound of the present invention or a pharmaceutical composition thereof.

One aspect of the present invention pertains to methods for treating an S1P1 receptor-associated disorder in an individual comprising administering to the individual in need thereof a therapeutically effective amount of a compound of the present invention or a pharmaceutical composition thereof.

One aspect of the present invention pertains to methods for treating an S1P1 receptor-associated disorder associated with the S1P1 receptor in an individual comprising administering to the individual in need thereof a therapeutically effective amount of a compound of the present invention, a salt, a hydrate or solvate, a crystalline form, or a pharmaceutical composition thereof.

One aspect of the present invention pertains to methods for treating a disorder associated with the S1P1 receptor in an individual comprising administering to the individual in need thereof a therapeutically effective amount of a compound of the present invention or a pharmaceutical composition thereof, wherein said disorder associated with the S1P1 receptor is selected from the group consisting of: a disease or disorder mediated by lymphocytes, an autoimmune disease or disorder, an inflammatory disease or disorder, cancer, psoriasis, rheumatoid arthritis, Crohn's disease, transplant rejection, multiple sclerosis, systemic lupus erythematosus, ulcerative colitis, type I diabetes and acne.

One aspect of the present invention pertains to methods for treating a disorder associated with the S1P 1 receptor in an individual comprising administering to the individual in need thereof a therapeutically effective amount of a compound of the present invention, a salt, a hydrate or solvate, a crystalline form, or a pharmaceutical composition thereof, wherein said disorder associated with the S1P1 receptor is selected from the group consisting of: a disease or disorder mediated by lymphocytes, an autoimmune disease or disorder, an inflammatory disease or disorder, cancer, psoriasis, rheumatoid arthritis, Crohn's disease, transplant rejection, multiple sclerosis, systemic lupus erythematosus, ulcerative colitis, type I diabetes and acne.

One aspect of the present invention pertains to methods for treating a disease or disorder mediated by lymphocytes in an individual comprising administering to the individual in need thereof a therapeutically effective amount of a compound of the present invention or a pharmaceutical composition thereof.

One aspect of the present invention pertains to methods for treating an autoimmune disease or disorder in an individual comprising administering to the individual in need thereof a therapeutically effective amount of a compound of the present invention or a pharmaceutical composition thereof.

One aspect of the present invention pertains to methods for treating an inflammatory disease or disorder in an individual comprising administering to the individual in need thereof a therapeutically effective amount of a compound of the present invention or a pharmaceutical composition thereof.

One aspect of the present invention pertains to methods for treating cancer in an individual comprising administering to the individual in need thereof a therapeutically effective amount of a compound of the present invention or a pharmaceutical composition thereof.

One aspect of the present invention pertains to methods for treating a disorder in an individual comprising administering to the individual in need thereof a therapeutically effective amount of a compound of the present invention or a pharmaceutical composition thereof, wherein said disorder is selected from the group consisting of psoriasis, rheumatoid arthritis, Crohn's disease, transplant rejection, multiple sclerosis, systemic lupus erythematosus, ulcerative colitis, type I diabetes and acne.

One aspect of the present invention pertains to methods for treating psoriasis in an individual comprising administering to the individual in need thereof a therapeutically effective amount of a compound of the present invention or a pharmaceutical composition thereof.

One aspect of the present invention pertains to methods for treating rheumatoid arthritis in an individual comprising administering to the individual in need thereof a therapeutically effective amount of a compound of the present invention or a pharmaceutical composition thereof.

One aspect of the present invention pertains to methods for treating Crohn's disease in an individual comprising administering to the individual in need thereof a therapeutically effective amount of a compound of the present invention or a pharmaceutical composition thereof.

One aspect of the present invention pertains to methods for treating transplant rejection in an individual comprising administering to the individual in need thereof a therapeutically effective amount of a compound of the present invention or a pharmaceutical composition thereof.

One aspect of the present invention pertains to methods for treating multiple sclerosis in an individual comprising administering to the individual in need thereof a therapeutically effective amount of a compound of the present invention or a pharmaceutical composition thereof.

One aspect of the present invention pertains to methods for treating systemic lupus erythematosus in an individual comprising administering to the individual in need thereof a therapeutically effective amount of a compound of the present invention or a pharmaceutical composition thereof.

One aspect of the present invention pertains to methods for treating ulcerative colitis in an individual comprising administering to the individual in need thereof a therapeutically effective amount of a compound of the present invention or a pharmaceutical composition thereof.

One aspect of the present invention pertains to methods for treating type I diabetes in an individual comprising administering to the individual in need thereof a therapeutically effective amount of a compound of the present invention or a pharmaceutical composition thereof.

One aspect of the present invention pertains to methods for treating acne in an individual comprising administering to the individual in need thereof a therapeutically effective amount of a compound of the present invention or a pharmaceutical composition thereof.

One aspect of the present invention pertains to methods for treating a disorder associated with the S1P1 receptor in an individual comprising administering to the individual in need thereof a therapeutically effective amount of a compound of the present invention or a pharmaceutical composition thereof, wherein said disorder associated with the S1P 1 receptor is a microbial infection or disease or a viral infection or disease.

One aspect of the present invention pertains to methods for treating a disorder associated with the S1P1 receptor in an individual comprising administering to the individual in need thereof a therapeutically effective amount of a compound of the present invention, a salt, a hydrate or solvate, a crystalline form, or a pharmaceutical composition thereof, wherein said disorder associated with the S1P1 receptor is a microbial infection or disease or a viral infection or disease.

One aspect of the present invention pertains to methods for treating gastritis in an individual comprising administering to the individual in need thereof a therapeutically effective amount of a compound of the present invention or a pharmaceutical composition thereof.

One aspect of the present invention pertains to methods for treating polymyositis in an individual comprising administering to the individual in need thereof a therapeutically effective amount of a compound of the present invention or a pharmaceutical composition thereof.

One aspect of the present invention pertains to methods for treating thyroiditis in an individual comprising administering to the individual in need thereof a therapeutically effective amount of a compound of the present invention or a pharmaceutical composition thereof.

One aspect of the present invention pertains to methods for treating vitiligo in an individual comprising administering to the individual in need thereof a therapeutically effective amount of a compound of the present invention or a pharmaceutical composition thereof.

One aspect of the present invention pertains to methods for treating hepatitis in an individual comprising administering to the individual in need thereof a therapeutically effective amount of a compound of the present invention or a pharmaceutical composition thereof.

One aspect of the present invention pertains to methods for treating biliary cirrhosis in an individual comprising administering to the individual in need thereof a therapeutically effective amount of a compound of the present invention or a pharmaceutical composition thereof.

One aspect of the present invention pertains to the use of compounds of the present invention in the manufacture of a medicament for the treatment of an S1P1 receptor-associated disorder.

One aspect of the present invention pertains to the use of compounds of the present invention, a salt, a hydrate or solvate, a crystalline form, or a pharmaceutical composition in the manufacture of a medicament for the treatment of an S1P1 receptor-associated disorder.

One aspect of the present invention pertains to the use of compounds of the present invention in the manufacture of a medicament for the treatment of a S1P1 receptor associated disorder selected from the group consisting of: a disease or disorder mediated by lymphocytes, an autoimmune disease or disorder, an inflammatory disease or disorder, cancer, psoriasis, rheumatoid arthritis, Crohn's disease, transplant rejection, multiple sclerosis, systemic lupus erythematosus, ulcerative colitis, type I diabetes and acne.

One aspect of the present invention pertains to the use of compounds of the present invention, a salt, a hydrate or solvate, a crystalline form, or a pharmaceutical composition in the manufacture of a medicament for the treatment of a S1P1 receptor associated disorder selected from the group consisting of: a disease or disorder mediated by lymphocytes, an autoimmune disease or disorder, an inflammatory disease or disorder, cancer, psoriasis, rheumatoid arthritis, Crohn's disease, transplant rejection, multiple sclerosis, systemic lupus erythematosus, ulcerative colitis, type I diabetes and acne.

One aspect of the present invention pertains to the use of compounds of the present invention in the manufacture of a medicament for the treatment of a disease or disorder mediated by lymphocytes.

One aspect of the present invention pertains to the use of compounds of the present invention in the manufacture of a medicament for the treatment of an autoimmune disease or disorder.

One aspect of the present invention pertains to the use of compounds of the present invention in the manufacture of a medicament for the treatment of an inflammatory disease or disorder.

One aspect of the present invention pertains to the use of compounds of the present invention in the manufacture of a medicament for the treatment of cancer.

One aspect of the present invention pertains to the use of compounds of the present invention in the manufacture of a medicament for the treatment of an S1P1 receptor-associated disorder selected from the group consisting of psoriasis, rheumatoid arthritis, Crohn's disease, transplant rejection, multiple sclerosis, systemic lupus erythematosus, ulcerative colitis, type I diabetes and acne.

One aspect of the present invention pertains to the use of compounds of the present invention in the manufacture of a medicament for the treatment of psoriasis.

One aspect of the present invention pertains to the use of compounds of the present invention in the manufacture of a medicament for the treatment of rheumatoid arthritis.

One aspect of the present invention pertains to the use of compounds of the present invention in the manufacture of a medicament for the treatment of Crohn's disease.

One aspect of the present invention pertains to the use of compounds of the present invention in the manufacture of a medicament for the treatment of transplant rejection.

One aspect of the present invention pertains to the use of compounds of the present invention in the manufacture of a medicament for the treatment of multiple sclerosis.

One aspect of the present invention pertains to the use of compounds of the present invention in the manufacture of a medicament for the treatment of systemic lupus erythematosus.

One aspect of the present invention pertains to the use of compounds of the present invention in the manufacture of a medicament for the treatment of ulcerative colitis.

One aspect of the present invention pertains to the use of compounds of the present invention in the manufacture of a medicament for the treatment of type I diabetes.

One aspect of the present invention pertains to the use of compounds of the present invention in the manufacture of a medicament for the treatment of acne.

One aspect of the present invention pertains to the use of compounds of the present invention in the manufacture of a medicament for the treatment of a S1P1 receptor associated disorder wherein the S1P1 receptor associated disorder is a microbial infection or disease or a viral infection or disease.

One aspect of the present invention pertains to the use of compounds of the present invention, a salt, a hydrate or solvate, a crystalline form, or a pharmaceutical composition in the manufacture of a medicament for the treatment of a S1P1 receptor associated disorder wherein the S1P1 receptor associated disorder is a microbial infection or disease or a viral infection or disease.

One aspect of the present invention pertains to the use of compounds of the present invention in the manufacture of a medicament for the treatment of gastritis.

One aspect of the present invention pertains to the use of compounds of the present invention in the manufacture of a medicament for the treatment of polymyositis.

One aspect of the present invention pertains to the use of compounds of the present invention in the manufacture of a medicament for the treatment of thyroiditis.

One aspect of the present invention pertains to the use of compounds of the present invention in the manufacture of a medicament for the treatment of vitiligo.

One aspect of the present invention pertains to the use of compounds of the present invention in the manufacture of a medicament for the treatment of hepatitis.

One aspect of the present invention pertains to the use of compounds of the present invention in the manufacture of a medicament for the treatment of biliary cirrhosis.

One aspect of the present invention pertains to compounds of the present invention for use in a method for the treatment of the human or animal body by therapy.

One aspect of the present invention pertains to compounds of the present invention, a salt, a hydrate or solvate, a crystalline form, for use in a method for the treatment of the human or animal body by therapy.

One aspect of the present invention pertains to compounds of the present invention for use in a method for the treatment of an S1P1 receptor-associated disorder.

One aspect of the present invention pertains to compounds of the present invention, a salt, a hydrate or solvate, a crystalline form, for use in a method for the treatment of an S1P1 receptor-associated disorder.

One aspect of the present invention pertains to compounds of the present invention for use in a method for the treatment of a S1P1 receptor associated disorder selected from the group consisting of: a disease or disorder mediated by lymphocytes, an autoimmune disease or disorder, an inflammatory disease or disorder, cancer, psoriasis, rheumatoid arthritis, Crohn's disease, transplant rejection, multiple sclerosis, systemic lupus erythematosus, ulcerative colitis, type I diabetes and acne.

One aspect of the present invention pertains to compounds of the present invention, a salt, a hydrate or solvate, a crystalline form, for use in a method for the treatment of a S1P1 receptor associated disorder selected from the group consisting of: a disease or disorder mediated by lymphocytes, an autoimmune disease or disorder, an inflammatory disease or disorder, cancer, psoriasis, rheumatoid arthritis, Crohn's disease, transplant rejection, multiple sclerosis, systemic lupus erythematosus, ulcerative colitis, type I diabetes and acne.

One aspect of the present invention pertains to compounds of the present invention for use in a method for the treatment of a disease or disorder mediated by lymphocytes.

One aspect of the present invention pertains to compounds of the present invention for use in a method for the treatment of an autoimmune disease or disorder.

One aspect of the present invention pertains to compounds of the present invention for use in a method for the treatment of an inflammatory disease or disorder.

One aspect of the present invention pertains to compounds of the present invention for use in a method for the treatment of cancer.

One aspect of the present invention pertains to compounds of the present invention for use in a method for the treatment of an S1P1 receptor-associated disorder selected from the group consisting of psoriasis, rheumatoid arthritis, Crohn's disease, transplant rejection, multiple sclerosis, systemic lupus erythematosus, ulcerative colitis, type I diabetes and acne.

One aspect of the present invention pertains to compounds of the present invention for use in a method for the treatment of psoriasis.

One aspect of the present invention pertains to compounds of the present invention for use in a method for the treatment of rheumatoid arthritis.

One aspect of the present invention pertains to compounds of the present invention for use in a method for the treatment of Crohn's disease.

One aspect of the present invention pertains to compounds of the present invention for use in a method for the treatment of transplant rejection.

One aspect of the present invention pertains to compounds of the present invention for use in a method for the treatment of multiple sclerosis.

One aspect of the present invention pertains to compounds of the present invention for use in a method for the treatment of systemic lupus erythematosus.

One aspect of the present invention pertains to compounds of the present invention for use in a method for the treatment of ulcerative colitis.

One aspect of the present invention pertains to compounds of the present invention for use in a method for the treatment of type I diabetes.

One aspect of the present invention pertains to compounds of the present invention for use in a method for the treatment of acne.

One aspect of the present invention pertains to compounds of the present invention for use in a method for the treatment of a S1P1 receptor associated disorder wherein the S1P1 receptor associated disorder is a microbial infection or disease or a viral infection or disease.

One aspect of the present invention pertains to compounds of the present invention, a salt, a hydrate or solvate, a crystalline form, for use in a method for the treatment of a S1P1 receptor associated disorder wherein the S1P1 receptor associated disorder is a microbial infection or disease or a viral infection or disease.

One aspect of the present invention pertains to compounds of the present invention for use in a method for the treatment of gastritis.

One aspect of the present invention pertains to compounds of the present invention for use in a method for the treatment of polymyositis.

One aspect of the present invention pertains to compounds of the present invention for use in a method for the treatment of thyroiditis.

One aspect of the present invention pertains to compounds of the present invention for use in a method for the treatment of vitiligo.

One aspect of the present invention pertains to compounds of the present invention for use in a method for the treatment of hepatitis.

One aspect of the present invention pertains to compounds of the present invention for use in a method for the treatment of biliary cirrhosis.

One aspect of the present invention pertains to processes for preparing a composition comprising admixing a compound of the present invention and a pharmaceutically acceptable carrier.

One aspect of the present invention pertains to processes for preparing a composition comprising admixing a compound of the present invention, a salt, a hydrate or solvate, a crystalline form and a pharmaceutically acceptable carrier.

These and other aspects of the invention disclosed herein will be set forth in greater detail as the patent disclosure proceeds.

BRIEF DESCRIPTION OF THE DRAWINGS

FIG. 21 depicts a view of a molecule that appears to be the $1^{st}$ enantiomer of compound 12 (isolated after resolution of compound 12 by HPLC with a retention time of 9.1 min per the conditions reported in Example 1.29).

DETAILED DESCRIPTION OF THE INVENTION

Definitions

Figure 1:
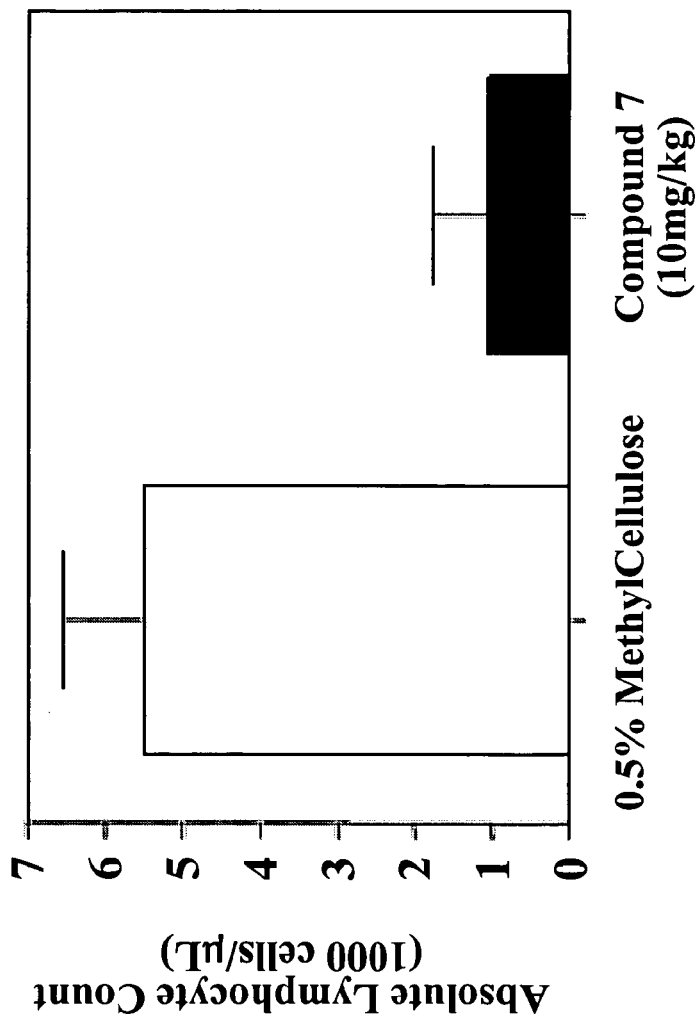
FIG. 1 shows the results of an experiment which measured the ability of Compound 7 to lower the absolute count of peripheral lymphocytes in mice compared to vehicle.

For clarity and consistency, the following definitions will be used throughout this patent document.

The term "agonist" is intended to mean a moiety that interacts with and activates a G-protein-coupled receptor, such as the S1P1 receptor, such as can thereby initiate a physiological or pharmacological response characteristic of that receptor. For example, an agonist activites an intracellular response upon binding to the receptor, or enhances GTP binding to a membrane. In certain embodiments, an agonist of the invention is an S1P1 receptor agonist that is capable of facilitating sustained S1P1 receptor internalization (see e.g., Matloubian et al., Nature, 427, 355, 2004).

The term "antagonist" is intended to mean a moiety that competitively binds to the receptor at the same site as an agonist (for example, the endogenous ligand), but which does not activate the intracellular response initiated by the active form of the receptor and can thereby inhibit the intracellular responses by an agonist or partial agonist. An antagonist does not diminish the baseline intracellular response in the absence of an agonist or partial agonist.

The term "hydrate" as used herein means a compound of the invention or a salt thereof, that further includes a stoichiometric or non-stoichiometric amount of water bound by non-covalent intermolecular forces.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "in need of treatment" and the term "in need thereof" when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

The term "individual" is intended to mean any animal, including mammals, preferably mice, rats, other rodents, rabbits, dogs, cats, swine, cattle, sheep, horses, or primates and most preferably humans.

The term "inverse agonist" is intended to mean a moiety that binds to the endogenous form of the receptor or to the constitutively activated form of the receptor and which inhibits the baseline intracellular response initiated by the active form of the receptor below the normal base level of activity which is observed in the absence of an agonist or partial agonist, or decreases GTP binding to a membrane. In some embodiments, the baseline intracellular response is inhibited in the presence of the inverse agonist by at least 30%. In some embodiments, the baseline intracellular response is inhibited in the presence of the inverse agonist by at least 50%. In some embodiments, the baseline intracellular response is inhibited in the presence of the inverse agonist by at least 75%, as compared with the baseline response in the absence of the inverse agonist.

The term "modulate or modulating" is intended to mean an increase or decrease in the amount, quality, response or effect of a particular activity, function or molecule.

The term "pharmaceutical composition" is intended to mean a composition comprising at least one active ingredient; including but not limited to, salts, solvates and hydrates of compounds of the present invention, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "therapeutically effective amount" is intended to mean the amount of active compound or pharmaceutical agent that elicits the biological or medicinal response in a tissue, system, animal, individual or human that is being sought by a researcher, veterinarian, medical doctor or other clinician, caregiver or by an individual, which includes one or more of the following:

(1) Preventing the disease, for example, preventing a disease, condition or disorder in an individual that may be predisposed to the disease, condition or disorder but does not yet experience or display the pathology or symptomatology of the disease;

(2) Inhibiting the disease, for example, inhibiting a disease, condition or disorder in an individual that is experiencing or displaying the pathology or symptomatology of the disease, condition or disorder (i.e., arresting further development of the pathology and/or symptomatology); and (3) Ameliorating the disease, for example, ameliorating a disease, condition or disorder in an individual that is experiencing or displaying the pathology or symptomatology of the disease, condition or disorder (i.e., reversing the pathology and/or symptomatology).

Chemical Group, Moiety or Radical

The term "$C_1$-$C_6$ alkoxy" is intended to mean a $C_1$-$C_6$ alkyl radical, as defined herein, attached directly to an oxygen atom. Some embodiments are 1 to 5 carbons, some embodiments are 1 to 4 carbons, some embodiments are 1 to 3 carbons and some embodiments are 1 or 2 carbons. Examples include methoxy, ethoxy, n-propoxy, isopropoxy, n-butoxy, tert-butoxy, isobutoxy, sec-butoxy and the like.

The term "$C_1$-$C_6$ alkyl" is intended to mean a straight or branched carbon radical containing 1 to 6 carbons. Some embodiments are 1 to 5 carbons, some embodiments are 1 to 4 carbons, some embodiments are 1 to 3 carbons and some embodiments are 1 or 2 carbons. Examples of an alkyl include, but are not limited to, methyl, ethyl, n-propyl, isopropyl, n-butyl, sec-butyl, isobutyl, tert-butyl, pentyl, isopentyl, tert-pentyl, neo-pentyl, 1-methylbutyl [i.e., —CH($CH_3$)$CH_2CH_2CH_3$], 2-methylbutyl [i.e., —$CH_2$CH($CH_3$)$CH_2CH_3$], n-hexyl and the like.

The term "$C_1$-$C_6$ alkylamino" is intended to mean one alkyl radical attached to an —NH-radical wherein the alkyl radical has the same meaning as described herein. Some examples include, but are not limited to, methylamino, ethylamino, n-propylamino, isopropylamino, n-butylamino, sec-butylamino, isobutylamino, tert-butylamino and the like.

The term "$C_1$-$C_6$ alkylsulfonyl" is intended to mean a $C_1$-$C_6$ alkyl radical attached to the sulfur of a sulfone radical having the formula: —S(O)$_2$— wherein the alkyl radical has the same definition as described herein. Examples include, but are not limited to, methylsulfonyl, ethylsulfonyl, n-propylsulfonyl, iso-propylsulfonyl, n-butylsulfonyl, sec-butylsulfonyl, iso-butylsulfonyl, tert-butylsulfonyl and the like.

The term "carboxamide" is intended to mean the group —CONH$_2$.

The term "carboxy" or "carboxyl" is intended to mean the group —CO$_2$H; also referred to as a carboxylic acid group.

The term "cyano" is intended to mean the group —CN.

The term "$C_3$-$C_7$ cycloalkoxy" is intended to mean a saturated ring radical containing 3 to 7 carbons directly bonded to an oxygen atom. Some examples include cyclopropyl-O—, cyclobutyl-O—, cyclopentyl-O—, cyclohexyl-O— and the like.

The term "$C_3$-$C_7$ cycloalkyl" is intended to mean a saturated ring radical containing 3 to 7 carbons. Some embodiments contain 3 to 6 carbons. Some embodiments contain 3 to 5 carbons. Some embodiments contain 5 to 7 carbons. Some embodiments contain 3 to 4 carbons. Examples include cyclopropyl, cyclobutyl, cyclopentyl, cyclohexyl, cycloheptyl and the like.

The term "$C_1$-$C_6$ haloalkoxy" is intended to mean a $C_1$-$C_6$ haloalkyl, as defined herein, which is directly attached to an oxygen atom. Examples include, but are not limited to, difluoromethoxy, trifluoromethoxy, 2,2,2-trifluoroethoxy, pentafluoroethoxy and the like.

The term "$C_1$-$C_6$ haloalkyl" is intended to mean an $C_1$-$C_6$ alkyl group, defined herein, wherein the alkyl is substituted with between one halogen up to fully substituted wherein a fully substituted $C_1$-$C_6$ haloalkyl can be represented by the formula $C_nL_{2n+1}$ wherein L is a halogen and "n" is 1, 2, 3, 4, 5 or 6. When more than one halogen is present, the halogens may be the same or different and selected from the group consisting of fluoro, chloro, bromo or iodo, preferably fluoro. Some embodiments are 1 to 5 carbons, some embodiments are 1 to 4 carbons, some embodiments are 1 to 3 carbons and some embodiments are 1 or 2 carbons. Examples of haloalkyl groups include, but are not limited to, fluoromethyl, difluoromethyl, trifluoromethyl, chlorodifluoromethyl, 2,2,2-trifluoroethyl, pentafluoroethyl and the like.

The term "halogen" or "halo" is intended to mean a fluoro, chloro, bromo or iodo group.

The term "heteroaryl" is intended to mean an aromatic ring system containing 5 to 14 aromatic ring atoms that may be a single ring, two fused rings or three fused rings, wherein at least one aromatic ring atom is a heteroatom selected from, for example, but not limited to, the group consisting of O, S and N wherein the N can be optionally substituted with H, $C_1$-$C_4$ acyl or $C_1$-$C_4$ alkyl. Some embodiments contain 5 to 6 ring atoms, for example, furanyl, thienyl, pyrrolyl, imidazolyl, oxazolyl, thiazolyl, isoxazolyl, pyrazolyl, isothiazolyl, oxadiazolyl, triazolyl, thiadiazolyl, pyridinyl, pyrazinyl, pyrimidinyl, pyridazinyl and triazinyl and the like. Some embodiments contain 8 to 14 ring atoms, for example, quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl, phenazinyl, phenothiazinyl, phenoxazinyl, benzoxazolyl, benzothiazolyl, 1H-benzimidazolyl, imidazopyridinyl, benzothienyl, benzofuranyl, and isobenzofuran and the like.

The term "heterocyclic" or "heterocyclyl" is intended to mean a non-aromatic ring containing 3 to 8 ring atoms wherein one, two or three ring atoms are heteroatoms selected from, for example, the group consisting of O, S, S(=O), S(=O)$_2$ and NH, wherein the N is optionally substituted as described herein. In some embodiments, the nitrogen is optionally substituted with $C_1$-$C_4$ acyl or $C_1$-$C_4$ alkyl. In some embodiments, ring carbon atoms are optionally substituted with oxo thus forming a carbonyl group. In some embodiments, ring sulfur atoms are optionally substituted with oxo atoms thus forming a thiocarbonyl group. The heterocyclic group can be attached/bonded to any available ring atom, for example, ring carbon, ring nitrogen and the like. In some embodiments the heterocyclic group is a 3-, 4-, 5-, 6- or 7-membered ring. Examples of a heterocyclic group include, but are not limited to, aziridin-1-yl, aziridin-2-yl, azetidin-1-yl, azetidin-2-yl, azetidin-3-yl, piperidin-1-yl, piperidin-2-yl, piperidin-3-yl, piperidin-4-yl, morpholin-2-yl, morpholin-3-yl, morpholin-4-yl, piperzin-1-yl, piperzin-2-yl, piperzin-3-yl, piperzin-4-yl, pyrrolidin-1-yl, pyrrolidin-2-yl, pyrrolidin-3-yl, [1,3]-dioxolan-2-yl, thiomorpholin-4-yl, [1,4]oxazepan-4-yl, 1,1-dioxothiomorpholin-4-yl, azepan-1-yl, azepan-2-yl, azepan-3-yl, azepan-4-yl, tetrahydrofuran-2-yl, tetrahydrofuran-3-yl and the like.

Compounds of the Invention:

One aspect of the present invention pertains to certain compounds of Formula (Ia) and pharmaceutically acceptable salts, solvates and hydrates thereof:

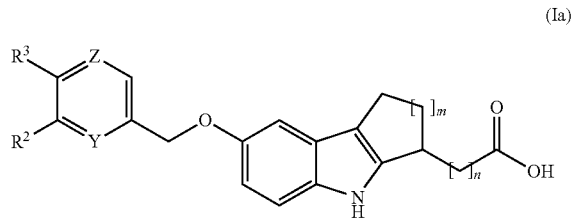

(Ia)

wherein:
m, n, $R^2$, $R^3$, Y and Z have the same definitions as described herein, supra and infra.

It is understood that the present invention embraces compounds, solvates and/or hydrates of compounds, pharmaceutically acceptable salts of compounds, and solvates and/or hydrates of pharmaceutically acceptable salts of compounds, wherein the compounds are as described herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., m, n, $R^1$, $R^2$, $R^3$, Y and Z) contained within the generic chemical formulae described herein, for example, (Ia), (Ic), (Ie), (Ig), (Ii), (Ik), (Im) are specifically embraced by the present invention just as if each and every combination was individually explicitly recited, to the extent that such combinations embrace stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein.

As used herein, "substituted" indicates that at least one hydrogen atom of the chemical group is replaced by a non-hydrogen substituent or group. The non-hydrogen substituent or group can be monovalent or divalent. When the substituent or group is divalent, then it is understood that this group is further substituted with another substituent or group. When a chemical group herein is "substituted" it may have up to the full valence of substitution, for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents and the like. Likewise, "substituted with one or more substituents" refers to the substitution of a group with one substituent up to the total number of substituents physically allowed by the group. Further, when a group is substituted with more than one substituent, the substituents can be identical or they can be different.

Compounds of the invention also include tautomeric forms, such as keto-enol tautomers and the like. Tautomeric forms can be in equilibrium or sterically locked into one form by appropriate substitution. It is understood that the various tautomeric forms are within the scope of the compounds of the present invention.

Compounds of the invention also include all isotopes of atoms occurring in the intermediates and/or final compounds. Isotopes include those atoms having the same atomic number but different mass numbers. For example, isotopes of hydrogen include deuterium and tritium.

It is understood and appreciated that compounds of Formula (Ia) and formulae related thereto may have one or more chiral centers and therefore can exist as enantiomers and/or diastereomers. The invention is understood to extend to and embrace all such enantiomers, diastereomers and mixtures thereof, including but not limited to racemates. It is understood that Formula (Ia) and formulae used throughout this disclosure are intended to represent all individual enantiomers and mixtures thereof, unless stated or shown otherwise.

The Variable "n"

In some embodiments, n is 1.

In some embodiments, compounds of the present invention are represented by Formula (Ic) as illustrated below:

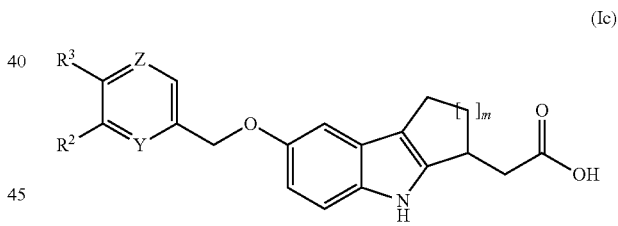

(Ic)

wherein each variable in Formula (Ic) has the same meaning as described herein, supra and infra.

In some embodiments, n is 2.

In some embodiments, compounds of the present invention are represented by Formula (Ie) as illustrated below:

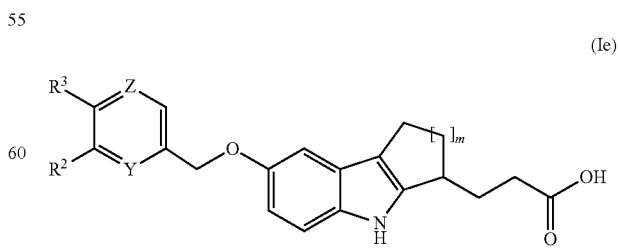

(Ie)

wherein each variable in Formula (Ie) has the same meaning as described herein, supra and infra.

The Variable "m"

In some embodiments, m is 1.

In some embodiments, compounds of the present invention are represented by Formula (Ig) as illustrated below:

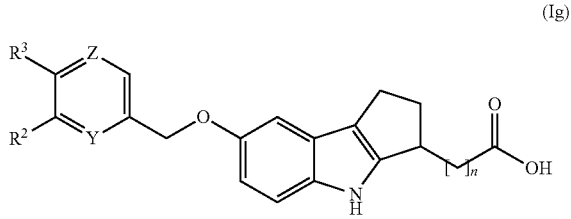

(Ig)

wherein each variable in Formula (Ig) has the same meaning as described herein, supra and infra.

In some embodiments, m is 2.

In some embodiments, compounds of the present invention are represented by Formula (Ii) as illustrated below:

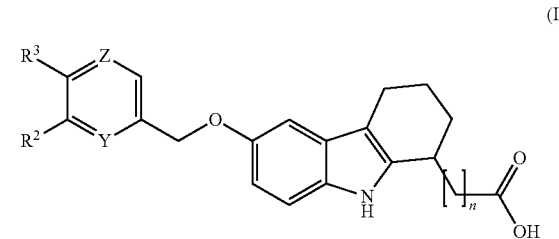

(Ii)

wherein each variable in Formula (Ii) has the same meaning as described herein, supra and infra.

The Variables Y and Z

In some embodiments, Y is N or $CR^1$ and Z is N or $CR^4$.
In some embodiments, Y is N and Z is N.
In some embodiments, Y is N and Z is $CR^4$.
In some embodiments, Y is $CR^1$ and Z is N.
In some embodiments, Y is $CR^1$ and Z is $CR^4$.
In some embodiments, Y is N.
In some embodiments, Y is $CR^1$.
In some embodiments, Z is N.
In some embodiments, Z is $CR^4$.

The Group $R^1$

In some embodiments, $R^1$ is selected from the group consisting of H, $C_1$-$C_6$ alkoxy, $C_1$-$C_6$ alkyl, $C_1$-$C_6$ alkylamino, $C_1$-$C_6$ alkylsulfonyl, $C_1$-$C_6$ alkylthio, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl and heterocyclyl, wherein said $C_1$-$C_6$ alkyl and $C_1$-$C_6$ alkoxy are each optionally substituted with one or two substituents selected from $C_3$-$C_7$ cycloalkyl and halogen.

In some embodiments, $R^1$ is selected from the group consisting of H, $C_1$-$C_6$ alkoxy, $C_1$-$C_6$ alkyl, $C_1$-$C_6$ alkylamino, $C_1$-$C_6$ alkylsulfonyl, $C_1$-$C_6$ alkylthio, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl and heterocyclyl, wherein said $C_1$-$C_6$ alkyl and $C_1$-$C_6$ alkoxy are each optionally substituted with one $C_3$-$C_7$ cycloalkyl group.

In some embodiments, $R^1$ is H or $C_1$-$C_6$ haloalkyl.
In some embodiments, $R^1$ is H.
In some embodiments, $R^1$ is trifluoromethyl.

The Group $R^2$

In some embodiments, $R^2$ is selected from the group consisting of H, $C_1$-$C_6$ alkoxy, $C_1$-$C_6$ alkyl, $C_1$-$C_6$ alkylamino, $C_1$-$C_6$ alkylsulfonyl, $C_1$-$C_6$ alkylthio, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl and heterocyclyl, wherein said $C_1$-$C_6$ alkyl and $C_1$-$C_6$ alkoxy are each optionally substituted with one or two substituents selected from $C_3$-$C_7$ cycloalkyl and halogen.

In some embodiments, $R^2$ is selected from the group consisting of H, $C_1$-$C_6$ alkoxy, $C_1$-$C_6$ alkyl, $C_1$-$C_6$ alkylamino, $C_1$-$C_6$ alkylsulfonyl, $C_1$-$C_6$ alkylthio, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl and heterocyclyl, wherein said $C_1$-$C_6$ alkyl and $C_1$-$C_6$ alkoxy are each optionally substituted with one $C_3$-$C_7$ cycloalkyl group.

In some embodiments, $R^2$ is selected from the group consisting of H, cyano, $C_1$-$C_6$ haloalkoxy and $C_1$-$C_6$ haloalkyl.

In some embodiments, $R^2$ is selected from the group consisting of H, cyano, trifluoromethoxy and trifluoromethyl.

In some embodiments, $R^2$ is H.
In some embodiments, $R^2$ is cyano.
In some embodiments, $R^2$ is trifluoromethoxy.
In some embodiments, $R^2$ is trifluoromethyl.

The Group $R^3$

In some embodiments, $R^3$ is selected from the group consisting of H, $C_1$-$C_6$ alkoxy, $C_1$-$C_6$ alkyl, $C_1$-$C_6$ alkylamino, $C_1$-$C_6$ alkylsulfonyl, $C_1$-$C_6$ alkylthio, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl and heterocyclyl, wherein said $C_1$-$C_6$ alkyl and $C_1$-$C_6$ alkoxy are each optionally substituted with one or two substituents selected from $C_3$-$C_7$ cycloalkyl and halogen.

In some embodiments, $R^3$ is selected from the group consisting of H, $C_1$-$C_6$ alkoxy, $C_1$-$C_6$ alkyl, $C_1$-$C_6$ alkylamino, $C_1$-$C_6$ alkylsulfonyl, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl and heterocyclyl, wherein said $C_1$-$C_6$ alkyl and $C_1$-$C_6$ alkoxy are each optionally substituted with one or two substituents selected from $C_3$-$C_7$ cycloalkyl and halogen In some embodiments, $R^3$ is selected from the group consisting of H, $C_1$-$C_6$ alkoxy, $C_1$-$C_6$ alkyl, $C_1$-$C_6$ alkylamino, $C_1$-$C_6$ alkylsulfonyl, $C_1$-$C_6$ alkylthio, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl and heterocyclyl, wherein said $C_1$-$C_6$ alkyl and $C_1$-$C_6$ alkoxy are each optionally substituted with one $C_3$-$C_7$ cycloalkyl group.

In some embodiments, $R^3$ is selected from the group consisting of H, $C_1$-$C_6$ alkoxy, $C_1$-$C_6$ alkyl, $C_3$-$C_7$ cycloalkyl, $C_1$-$C_6$ haloalkoxy, $C_1$-$C_6$ haloalkyl, halogen and heterocyclyl.

In some embodiments, $R^3$ is selected from the group consisting of selected from the group consisting of H, carboxamide, chloro, cyano, cyclobutyl, cyclohexyl, cyclopentyl, cyclopentyloxy, cyclopropyl, cyclopropylmethoxy, cyclohexylmethyl, 3,3-difluoropyrrolidin-1-yl, ethylamino, isobutyl, isopropoxy, methylsulfonyl, neopentyl, propyl, pyrrolidin-1-yl, 1,2,3-thiadiazol-4-yl, trifluoromethoxy and trifluoromethyl.

In some embodiments, $R^3$ is selected from the group consisting of H, chloro, cyclobutyl, cyclohexyl, cyclopentyl, cyclopropyl, 3,3-difluoropyrrolidin-1-yl, isobutyl, isopropoxy, neopentyl, propyl, pyrrolidin-1-yl, trifluoromethoxy and trifluoromethyl.

In some embodiments, $R^3$ is H.
In some embodiments, $R^3$ is chloro.

In some embodiments, $R^3$ is cyclobutyl.
In some embodiments, $R^3$ is cyclohexyl.
In some embodiments, $R^3$ is cyclopentyl.
In some embodiments, $R^3$ is cyclopropyl.
In some embodiments, $R^3$ is 3,3-difluoropyrrolidin-1-yl.
In some embodiments, $R^3$ is isobutyl.
In some embodiments, $R^3$ is isopropoxy.
In some embodiments, $R^3$ is neopentyl.
In some embodiments, $R^3$ is propyl.
In some embodiments, $R^3$ is pyrrolidin-1-yl.
In some embodiments, $R^3$ is trifluoromethoxy.
In some embodiments, $R^3$ is trifluoromethyl.
In some embodiments, $R^3$ is carboxamide.
In some embodiments, $R^3$ is cyano.
In some embodiments, $R^3$ is cyclopentyloxy.
In some embodiments, $R^3$ is cyclopropylmethoxy.
In some embodiments, $R^3$ is cyclohexylmethyl.
In some embodiments, $R^3$ is ethylamino.
In some embodiments, $R^3$ is methylsulfonyl.
In some embodiments, $R^3$ is 1,2,3-thiadiazol-4-yl.

The Group $R^4$

In some embodiments, $R^4$ is selected from the group consisting of H, $C_1$-$C_6$ alkoxy, $C_1$-$C_6$ alkyl, $C_1$-$C_6$ alkylamino, $C_1$-$C_6$ alkylsulfonyl, $C_1$-$C_6$ alkylthio, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl and heterocyclyl, wherein said $C_1$-$C_6$ alkyl and $C_1$-$C_6$ alkoxy are each optionally substituted with one or two substituents selected from $C_3$-$C_7$ cycloalkyl and halogen.

In some embodiments, $R^4$ is selected from the group consisting of H, $C_1$-$C_6$ alkoxy, $C_1$-$C_6$ alkyl, $C_1$-$C_6$ alkylamino, $C_1$-$C_6$ alkylsulfonyl, $C_1$-$C_6$ alkylthio, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl and heterocyclyl, wherein said $C_1$-$C_6$ alkyl and $C_1$-$C_6$ alkoxy are each optionally substituted with one $C_3$-$C_7$ cycloalkyl group.

In some embodiments, $R^4$ is selected from the group consisting of H, cyano, $C_1$-$C_6$ haloalkoxy and $C_1$-$C_6$ haloalkyl.

In some embodiments, $R^4$ is selected from the group consisting of H, cyano and $C_1$-$C_6$ haloalkyl.

In some embodiments, $R^4$ is selected from the group consisting of H, cyano, trifluoromethoxy and trifluoromethyl.

In some embodiments, $R^4$ is selected from the group consisting of H, cyano and trifluoromethyl.

In some embodiments, $R^4$ is H.
In some embodiments, $R^4$ is cyano.
In some embodiments, $R^4$ is trifluoromethyl.
In some embodiments, $R^4$ is trifluoromethoxy.

Certain Combinations

Some embodiments of the present invention pertain to compounds selected from compounds of Formula (Ia) and pharmaceutically acceptable salts, solvates and hydrates thereof, wherein:
  m is 1 or 2;
  n is 1 or 2;
  Y is N or $CR^1$;
  Z is N or $CR^4$;
  $R^1$ is H or $C_1$-$C_6$ haloalkyl;
  $R^2$ is selected from the group consisting of H, cyano, $C_1$-$C_6$ haloalkoxy and $C_1$-$C_6$ haloalkyl;
  $R^3$ is selected from the group consisting of H, $C_1$-$C_6$ alkoxy, $C_1$-$C_6$ alkyl, $C_3$-$C_7$ cycloalkyl, $C_1$-$C_6$ haloalkoxy, $C_1$-$C_6$ haloalkyl, halogen and heterocyclyl; and
  $R^4$ is selected from the group consisting of H, cyano and $C_1$-$C_6$ haloalkyl.

Some embodiments of the present invention pertain to compounds selected from compounds of Formula (Ia) and pharmaceutically acceptable salts, solvates and hydrates thereof, wherein:
  m is 1 or 2;
  n is 1 or 2;
  Y is N or $CR^1$;
  Z is N or $CR^4$;
  $R^1$ is H or trifluoromethyl;
  $R^2$ is selected from the group consisting of H, cyano, trifluoromethoxy and trifluoromethyl;
  $R^3$ is selected from the group consisting of H, chloro, cyclobutyl, cyclohexyl, cyclopentyl, cyclopropyl, 3,3-difluoropyrrolidin-1-yl, isobutyl, isopropoxy, neopentyl, propyl, pyrrolidin-1-yl, trifluoromethoxy and trifluoromethyl; and
  $R^4$ is selected from the group consisting of H, cyano and trifluoromethyl.

Some embodiments of the present invention pertain to compounds selected from compounds of Formula (Ik) and pharmaceutically acceptable salts, solvates and hydrates thereof:

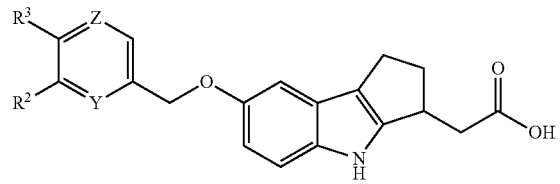

(Ik)

wherein:
  Y is N or $CR^1$;
  Z is N or $CR^4$;
  $R^1$ is H or $C_1$-$C_6$ haloalkyl;
  $R^2$ is selected from the group consisting of H, cyano, $C_1$-$C_6$ haloalkoxy and $C_1$-$C_6$ haloalkyl;
  $R^3$ is selected from the group consisting of H, $C_1$-$C_6$ alkoxy, $C_1$-$C_6$ alkyl, $C_1$-$C_6$ alkylamino, $C_1$-$C_6$ alkylsulfonyl, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl and heterocyclyl, wherein said $C_1$-$C_6$ alkyl and $C_1$-$C_6$ alkoxy are each optionally substituted with one or two substituents selected from $C_3$-$C_7$ cycloalkyl and halogen; and
  $R^4$ is selected from the group consisting of H, cyano, $C_1$-$C_6$ haloalkoxy and $C_1$-$C_6$ haloalkyl.

Some embodiments of the present invention pertain to compounds selected from compounds of Formula (Ik) and pharmaceutically acceptable salts, solvates and hydrates thereof:

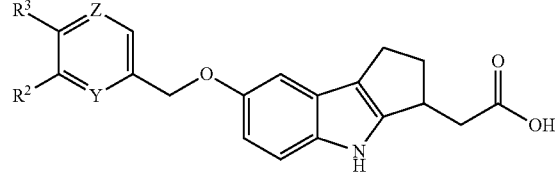

(Ik)

wherein:

Y is N or CR$^1$;

Z is N or CR$^4$;

R$^1$ is H or C$_1$-C$_6$ haloalkyl;

R$^2$ is selected from the group consisting of H, cyano, C$_1$-C$_6$ haloalkoxy and C$_1$-C$_6$ haloalkyl;

R$^3$ is selected from the group consisting of H, C$_1$-C$_6$ alkoxy, C$_1$-C$_6$ alkyl, C$_3$-C$_7$ cycloalkyl, C$_1$-C$_6$ haloalkoxy, C$_1$-C$_6$ haloalkyl, halogen and heterocyclyl; and R$^4$ is selected from the group consisting of H, cyano and C$_1$-C$_6$ haloalkyl.

Some embodiments of the present invention pertain to compounds selected from compounds of Formula (Ik) and pharmaceutically acceptable salts, solvates and hydrates thereof:

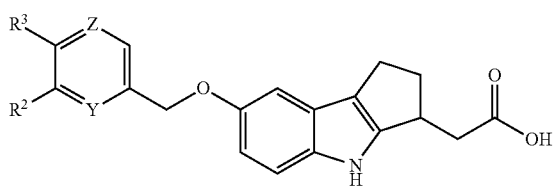
(Ik)

wherein:

Y is N or CR$^1$;

Z is N or CR$^4$;

R$^1$ is H or trifluoromethyl;

R$^2$ is selected from the group consisting of H, cyano, trifluoromethoxy and trifluoromethyl;

R$^3$ is selected from the group consisting of H, carboxamide, chloro, cyano, cyclobutyl, cyclohexyl, cyclopentyl, cyclopentyloxy, cyclopropyl, cyclopropylmethoxy, cyclohexylmethyl, 3,3-difluoropyrrolidin-1-yl, ethylamino, isobutyl, isopropoxy, methylsulfonyl, neopentyl, propyl, pyrrolidin-1-yl, 1,2,3-thiadiazol-4-yl, trifluoromethoxy and trifluoromethyl; and R$^4$ is selected from the group consisting of H, cyano, trifluoromethoxy and trifluoromethyl.

Some embodiments of the present invention pertain to compounds selected from compounds of Formula (Ik) and pharmaceutically acceptable salts, solvates and hydrates thereof, wherein:

Y is N or CR$^1$;

Z is N or CR$^4$;

R$^1$ is H or trifluoromethyl;

R$^2$ is selected from the group consisting of H, cyano, trifluoromethoxy and trifluoromethyl;

R$^3$ is selected from the group consisting of H, chloro, cyclobutyl, cyclohexyl, cyclopentyl, cyclopropyl, 3,3-difluoropyrrolidin-1-yl, isobutyl, isopropoxy, neopentyl, propyl, pyrrolidin-1-yl, trifluoromethoxy and trifluoromethyl; and R$^4$ is selected from the group consisting of H, cyano and trifluoromethyl.

Some embodiments of the present invention pertain to compounds selected from compounds of Formula (Im) and pharmaceutically acceptable salts, solvates and hydrates thereof:

(Im)

wherein:

R$^2$ is selected from the group consisting of H, cyano, C$_1$-C$_6$ haloalkoxy and C$_1$-C$_6$ haloalkyl; and R$^3$ is selected from the group consisting of H, C$_1$-C$_6$ alkoxy, C$_1$-C$_6$ alkyl, C$_1$-C$_6$ alkylamino, C$_1$-C$_6$ alkylsulfonyl, carboxamide, cyano, C$_3$-C$_7$ cycloalkoxy, C$_3$-C$_7$ cycloalkyl, C$_1$-C$_6$ haloalkoxy, C$_1$-C$_6$ haloalkyl, halogen, heteroaryl and heterocyclyl, wherein said C$_1$-C$_6$ alkyl and C$_1$-C$_6$ alkoxy are each optionally substituted with one or two substituents selected from C$_3$-C$_7$ cycloalkyl and halogen.

Some embodiments of the present invention pertain to compounds selected from compounds of Formula (Im) and pharmaceutically acceptable salts, solvates and hydrates thereof:

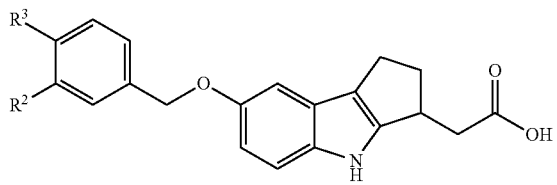
(Im)

wherein:

R$^2$ is selected from the group consisting of H, cyano, C$_1$-C$_6$ haloalkoxy and C$_1$-C$_6$ haloalkyl; and R$^3$ is selected from the group consisting of H, C$_1$-C$_6$ alkoxy, C$_1$-C$_6$ alkyl, C$_3$-C$_7$ cycloalkyl, C$_1$-C$_6$ haloalkoxy, C$_1$-C$_6$ haloalkyl, halogen and heterocyclyl.

Some embodiments of the present invention pertain to compounds selected from compounds of Formula (Im) and pharmaceutically acceptable salts, solvates and hydrates thereof:

(Im)

wherein:

R$^2$ is selected from the group consisting of H, cyano, trifluoromethoxy and trifluoromethyl; and R$^3$ is selected from the group consisting of H, carboxamide, chloro, cyano, cyclobutyl, cyclohexyl, cyclopentyl, cyclopentyloxy, cyclopropyl, cyclopropylmethoxy, cyclohexylmethyl, 3,3-difluoropyrrolidin-1-yl, ethylamino, isobutyl, isopropoxy, methylsulfonyl, neopentyl, propyl, pyrrolidin-1-yl, 1,2,3-thiadiazol-4-yl, trifluoromethoxy and trifluoromethyl.

Some embodiments of the present invention pertain to compounds selected from compounds of Formula (Im) and pharmaceutically acceptable salts, solvates and hydrates thereof, wherein:

$R^2$ is selected from the group consisting of H, cyano, trifluoromethoxy and trifluoromethyl; and $R^3$ is selected from the group consisting of H, chloro, cyclobutyl, cyclohexyl, cyclopentyl, cyclopropyl, 3,3-difluoropyrrolidin-1-yl, isobutyl, isopropoxy, neopentyl, propyl, pyrrolidin-1-yl, trifluoromethoxy and trifluoromethyl.

Esters and Prodrugs

One aspect of the present invention pertains to compounds of Formula (IIa) as synthetic intermediates useful in the preparation of compounds of Formula (Ia) and/or prodrugs useful for the delivery of compounds of Formula (Ia):

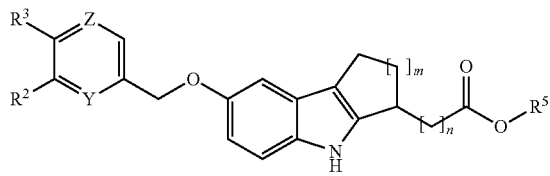

(IIa)

m, n, $R^2$, $R^3$, Y, Z and W have the same definitions as described herein, supra and infra, and $R^6$ is $C_1$-$C_6$ alkyl.

One aspect of the present invention pertains to compounds of Formula (IIa).

In some embodiments, $R^5$ is ethyl.

In some embodiments, $R^5$ is tert-butyl.

For brevity, it is appreciated that all of the embodiments described herein, supra and infra, that relate to the common variables shared between Compounds of Formula (Ia) and (IIa) namely, m, n, $R^2$, $R^3$, Y, Z and W, apply to Compounds of Formula (IIa) just as if they were each individually disclosed herewith specific reference to Formula (IIa).

One aspect of the present invention pertains to compounds of Formula (IIa) as synthetic intermediates useful in the preparation of compounds of Formula (Ia).

One aspect of the present invention pertains to compounds of Formula (IIa) as esters of compounds, described and shown herein, such as compounds in Table A, where $R^5$ is ethyl.

One aspect of the present invention pertains to compounds of Formula (IIa) as esters of compounds, described and shown herein, such as compounds in Table A, where $R^5$ is tert-butyl.

One aspect of the present invention pertains to compounds of Formula (IIa) as prodrugs useful for the delivery of compounds of Formula (Ia).

One aspect of the present invention pertains to compounds of Formula (IIa) useful as prodrugs of compounds of Formula (Ia).

Some embodiments of the present invention include every combination of one or more compounds selected from the following group shown in Table A.

TABLE A

| Cmpd No. | Chemical Structure | Chemical Name |
|---|---|---|
| 1 | 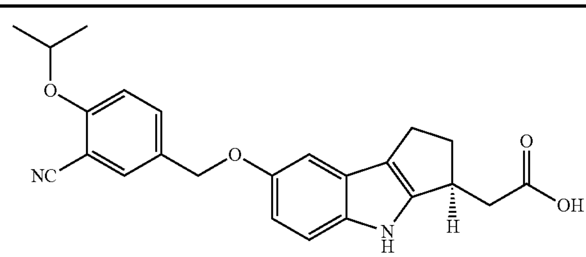 | (S)-2-(7-(3-cyano-4-isopropoxybenzyloxy)-1,2,3,4-tetrahydrocyclopenta[b]indol-3-yl)acetic acid |
| 2 | 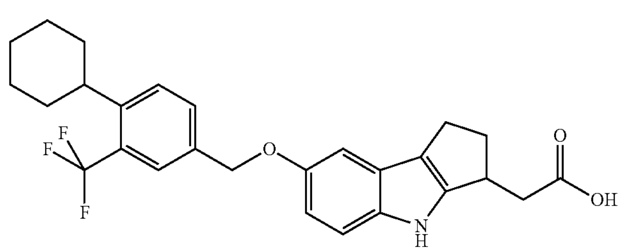 [SMILES: O=C(O)CC1CCc2c1[nH]c1ccc(OCc3ccc(C4CCCCC4)c(C(F)(F)F)c3)cc21] | 2-(7-(4-cyclohexyl-3-(trifluoromethyl)benzyloxy)-1,2,3,4-tetrahydrocyclopenta[b]indol-3-yl)acetic acid |
| 3 | 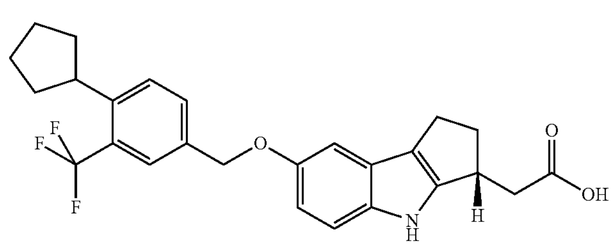 [SMILES: O=C(O)C[C@H]1CCc2c1[nH]c1ccc(OCc3ccc(C4CCCC4)c(C(F)(F)F)c3)cc21] | (R)-2-(7-(4-cyclopentyl-3-(trifluoromethyl)benzyloxy)-1,2,3,4-tetrahydrocyclopenta[b]indol-3-yl)acetic acid |

TABLE A-continued

| Cmpd No. | Chemical Structure | Chemical Name |
|---|---|---|
| 4 | 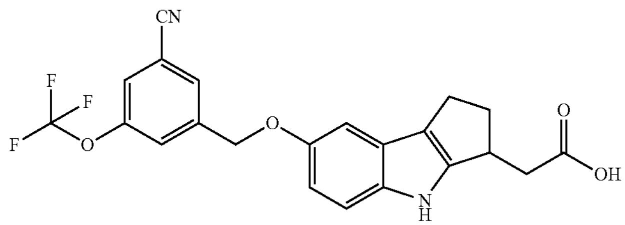 [SMILES: N#Cc1cc(COc2ccc3[nH]c4c(c3c2)CCC4CC(=O)O)cc(OC(F)(F)F)c1] | 2-(7-(3-cyano-5-(trifluoromethoxy)benzyloxy)-1,2,3,4-tetrahydrocyclopenta[b]indol-3-yl)acetic acid |
| 5 | 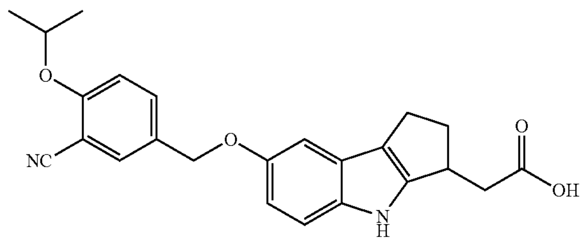 [SMILES: CC(C)Oc1ccc(COc2ccc3[nH]c4c(c3c2)CCC4CC(=O)O)cc1C#N] | 2-(7-(3-cyano-4-isopropoxybenzyloxy)-1,2,3,4-tetrahydrocyclopenta[b]indol-3-yl)acetic acid |
| 6 | 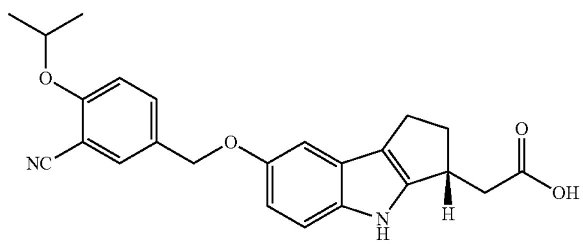 [SMILES: CC(C)Oc1ccc(COc2ccc3[nH]c4c(c3c2)CC[C@@H]4CC(=O)O)cc1C#N] | (R)-2-(7-(3-cyano-4-isopropoxybenzyloxy)-1,2,3,4-tetrahydrocyclopenta[b]indol-3-yl)acetic acid |
| 7 | 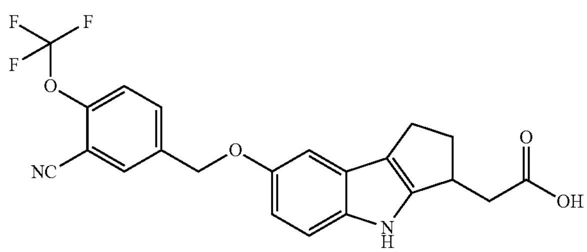 [SMILES: N#Cc1cc(COc2ccc3[nH]c4c(c3c2)CCC4CC(=O)O)ccc1OC(F)(F)F] | 2-(7-(3-cyano-4-(trifluoromethoxy)benzyloxy)-1,2,3,4-tetrahydrocyclopenta[b]indol-3-yl)acetic acid |
| 8 | 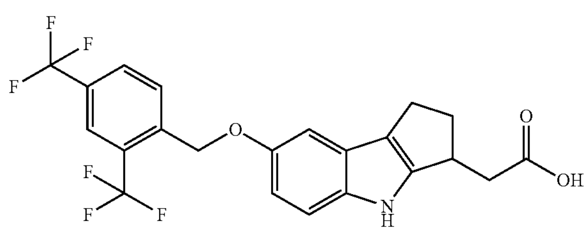 [SMILES: O=C(O)CC1CCc2c1[nH]c1ccc(OCc3ccc(C(F)(F)F)cc3C(F)(F)F)cc21] | 2-(7-(2,4-bis(trifluoromethyl)benzyloxy)-1,2,3,4-tetrahydrocyclopenta[b]indol-3-yl)acetic acid |
| 9 | 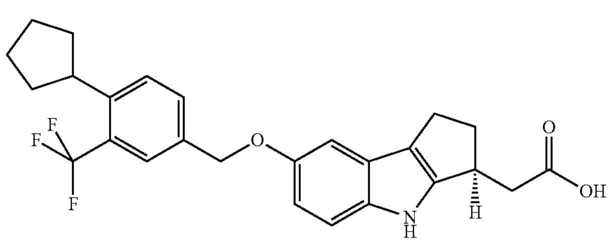 [SMILES: O=C(O)C[C@@H]1CCc2c1[nH]c1ccc(OCc3ccc(C4CCCC4)c(C(F)(F)F)c3)cc21] | (S)-2-(7-(4-cyclopentyl-3-(trifluoromethyl)benzyloxy)-1,2,3,4-tetrahydrocyclopenta[b]indol-3-yl)acetic acid |

TABLE A-continued

| Cmpd No. | Chemical Structure | Chemical Name |
|---|---|---|
| 10 | 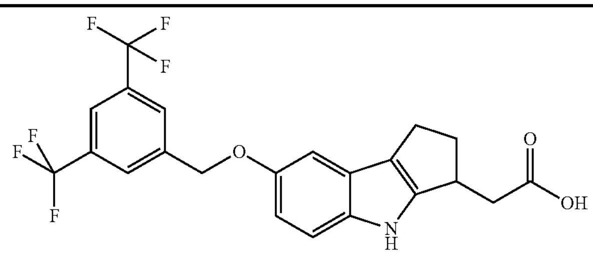 | 2-(7-(3,5-bis(trifluoromethyl)benzyloxy)-1,2,3,4-tetrahydrocyclopenta[b]indol-3-yl)acetic acid |
| 11 | 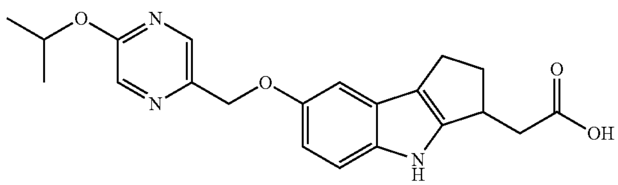 [SMILES: CC(C)Oc1cnc(COc2ccc3[nH]c4c(c3c2)CCC4CC(=O)O)cn1] | 2-(7-((5-isopropoxypyrazin-2-yl)methoxy)-1,2,3,4-tetrahydrocyclopenta[b]indol-3-yl)acetic acid |
| 12 | 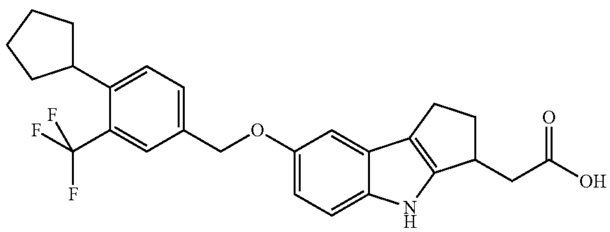 [SMILES: O=C(O)CC1CCc2c1[nH]c1ccc(OCc3ccc(C4CCCC4)c(C(F)(F)F)c3)cc21] | 2-(7-(4-cyclopentyl-3-(trifluoromethyl)benzyloxy)-1,2,3,4-tetrahydrocyclopenta[b]indol-3-yl)acetic acid |
| 13 | 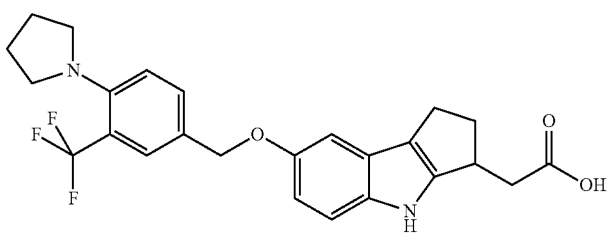 [SMILES: O=C(O)CC1CCc2c1[nH]c1ccc(OCc3ccc(N4CCCC4)c(C(F)(F)F)c3)cc21] | 2-(7-(4-(pyrrolidin-1-yl)-3-(trifluoromethyl)benzyloxy)-1,2,3,4-tetrahydrocyclopenta[b]indol-3-yl)acetic acid |
| 14 | 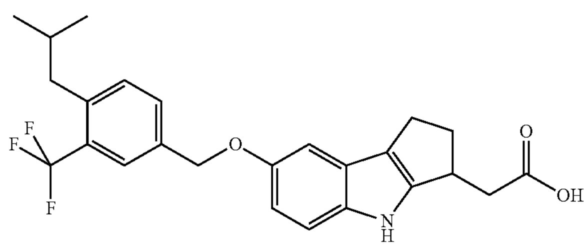 [SMILES: CC(C)Cc1ccc(COc2ccc3[nH]c4c(c3c2)CCC4CC(=O)O)cc1C(F)(F)F] | 2-(7-(4-isobutyl-3-(trifluoromethyl)benzyloxy)-1,2,3,4-tetrahydrocyclopenta[b]indol-3-yl)acetic acid |
| 15 | 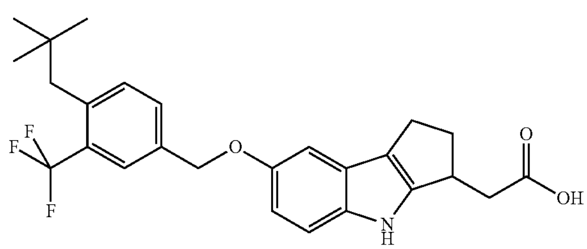 [SMILES: CC(C)(C)Cc1ccc(COc2ccc3[nH]c4c(c3c2)CCC4CC(=O)O)cc1C(F)(F)F] | 2-(7-(4-neopentyl-3-(trifluoromethyl)benzyloxy)-1,2,3,4-tetrahydrocyclopenta[b]indol-3-yl)acetic acid |
| 16 | 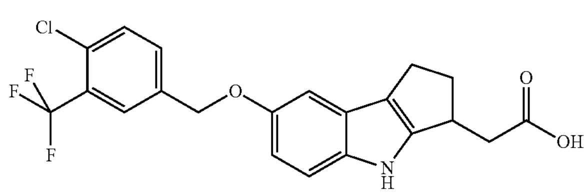 [SMILES: O=C(O)CC1CCc2c1[nH]c1ccc(OCc3ccc(Cl)c(C(F)(F)F)c3)cc21] | 2-(7-(4-chloro-3-(trifluoromethyl)benzyloxy)-1,2,3,4-tetrahydrocyclopenta[b]indol-3-yl)acetic acid |

TABLE A-continued

| Cmpd No. | Chemical Structure | Chemical Name |
|---|---|---|
| 17 | 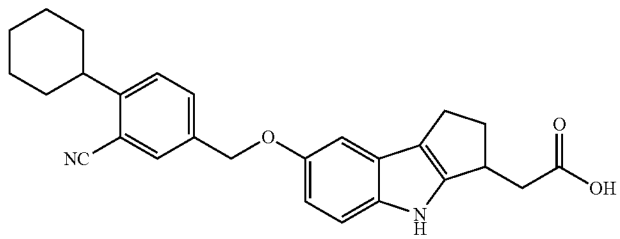 [SMILES: N#Cc1cc(COc2ccc3[nH]c4c(c3c2)CCC4CC(=O)O)ccc1C1CCCCC1] | 2-(7-(3-cyano-4-cyclohexylbenzyloxy)-1,2,3,4-tetrahydrocyclopenta[b]indol-3-yl)acetic acid |
| 18 | 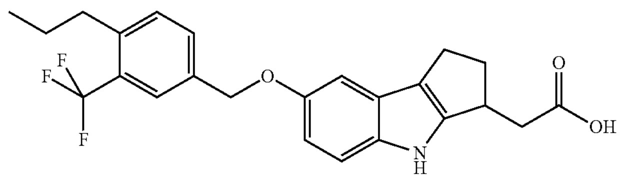 [SMILES: CCCc1ccc(COc2ccc3[nH]c4c(c3c2)CCC4CC(=O)O)cc1C(F)(F)F] | 2-(7-(4-propyl-3-(trifluoromethyl)benzyloxy)-1,2,3,4-tetrahydrocyclopenta[b]indol-3-yl)acetic acid |
| 19 | 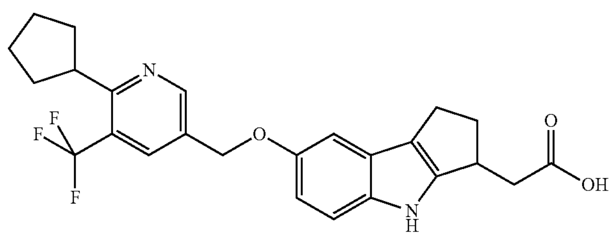 [SMILES: O=C(O)CC1CCc2c1[nH]c1ccc(OCc3cnc(C4CCCC4)c(C(F)(F)F)c3)cc21] | 2-(7-((6-cyclopentyl-5-(trifluoromethyl)pyridin-3-yl)methoxy)-1,2,3,4-tetrahydrocyclopenta[b]indol-3-yl)acetic acid |
| 20 | 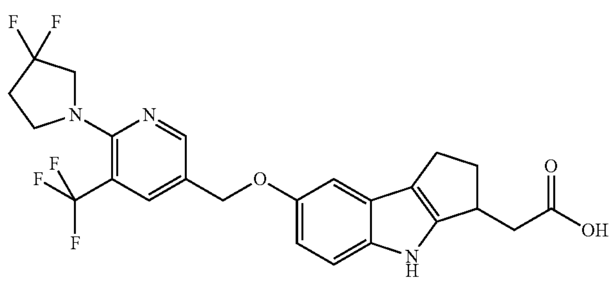 [SMILES: O=C(O)CC1CCc2c1[nH]c1ccc(OCc3cnc(N4CCC(F)(F)C4)c(C(F)(F)F)c3)cc21] | 2-(7-((6-(3,3-difluoropyrrolidin-1-yl)-5-(trifluoromethyl)pyridin-3-yl)methoxy)-1,2,3,4-tetrahydrocyclopenta[b]indol-3-yl)acetic acid |
| 21 | 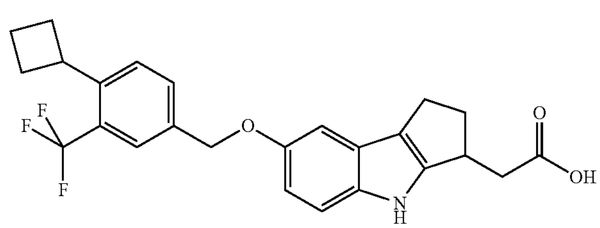 [SMILES: O=C(O)CC1CCc2c1[nH]c1ccc(OCc3ccc(C4CCC4)c(C(F)(F)F)c3)cc21] | 2-(7-(4-cyclobutyl-3-(trifluoromethyl)benzyloxy)-1,2,3,4-tetrahydrocyclopenta[b]indol-3-yl)acetic acid |
| 22 | 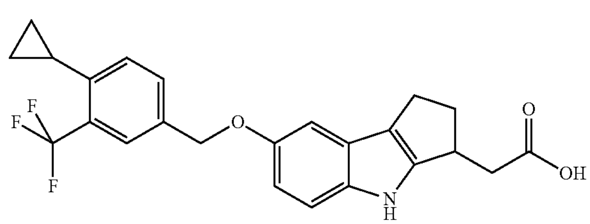 [SMILES: O=C(O)CC1CCc2c1[nH]c1ccc(OCc3ccc(C4CC4)c(C(F)(F)F)c3)cc21] | 2-(7-(4-cyclopropyl-3-(trifluoromethyl)benzyloxy)-1,2,3,4-tetrahydrocyclopenta[b]indol-3-yl)acetic acid |

TABLE A-continued

| Cmpd No. | Chemical Structure | Chemical Name |
|---|---|---|
| 23 | 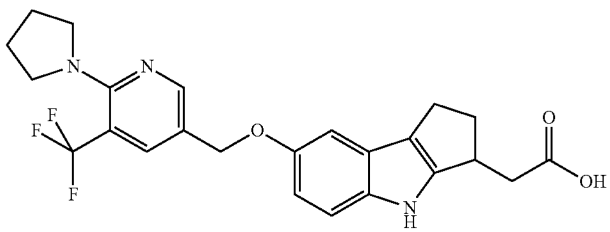 [SMILES: O=C(O)CC1CCc2c1[nH]c1ccc(OCc3cnc(N4CCCC4)c(C(F)(F)F)c3)cc21] | 2-(7-((6-(pyrrolidin-1-yl)-5-(trifluoromethyl)pyridin-3-yl)methoxy)-1,2,3,4-tetrahydrocyclopenta[b]indol-3-yl)acetic acid |
| 24 | 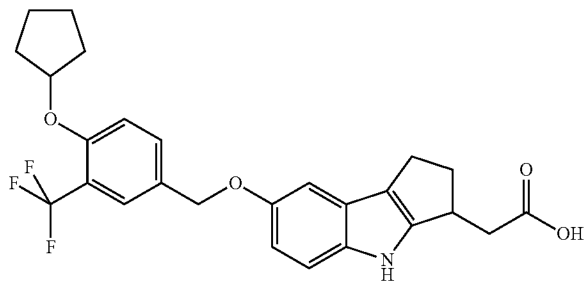 [SMILES: O=C(O)CC1CCc2c1[nH]c1ccc(OCc3ccc(OC4CCCC4)c(C(F)(F)F)c3)cc21] | 2-(7-(4-(cyclopentyloxy)-3-(trifluoromethyl)benzyloxy)-1,2,3,4-tetrahydrocyclopenta[b]indol-3-yl)acetic acid |
| 25 | 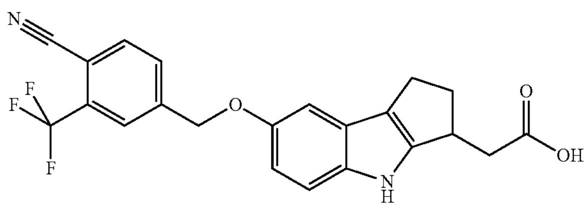 [SMILES: N#Cc1ccc(COc2ccc3[nH]c4c(c3c2)CCC4CC(=O)O)cc1C(F)(F)F] | 2-(7-(4-cyano-3-(trifluoromethyl)benzyloxy)-1,2,3,4-tetrahydrocyclopenta[b]indol-3-yl)acetic acid |
| 26 | 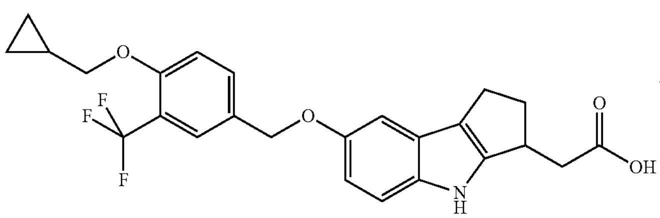 [SMILES: O=C(O)CC1CCc2c1[nH]c1ccc(OCc3ccc(OCC4CC4)c(C(F)(F)F)c3)cc21] | 2-(7-(4-(cyclopropylmethoxy)-3-(trifluoromethyl)benzyloxy)-1,2,3,4-tetrahydrocyclopenta[b]indol-3-yl)acetic acid |
| 27 | 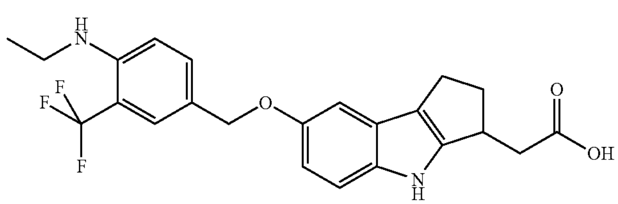 [SMILES: CCNc1ccc(COc2ccc3[nH]c4c(c3c2)CCC4CC(=O)O)cc1C(F)(F)F] | 2-(7-(4-(ethylamino)-3-(trifluoromethyl)benzyloxy)-1,2,3,4-tetrahydrocyclopenta[b]indol-3-yl)acetic acid |
| 28 | 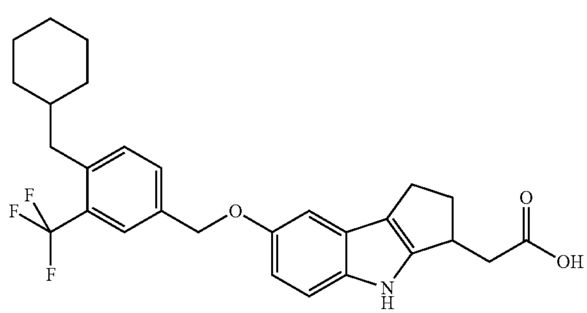 [SMILES: O=C(O)CC1CCc2c1[nH]c1ccc(OCc3ccc(CC4CCCCC4)c(C(F)(F)F)c3)cc21] | 2-(7-(4-(cyclohexylmethyl)-3-(trifluoromethyl)benzyloxy)-1,2,3,4-tetrahydrocyclopenta[b]indol-3-yl)acetic acid |

TABLE A-continued

| Cmpd No. | Chemical Structure | Chemical Name |
| --- | --- | --- |
| 29 | 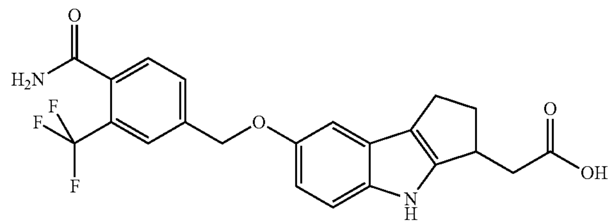 [SMILES: NC(=O)c1ccc(COc2ccc3[nH]c4c(c3c2)CCC4CC(=O)O)cc1C(F)(F)F] | 2-(7-(4-carbamoyl-3-(trifluoromethyl)benzyloxy)-1,2,3,4-tetrahydrocyclopenta[b]indol-3-yl)acetic acid |
| 30 | 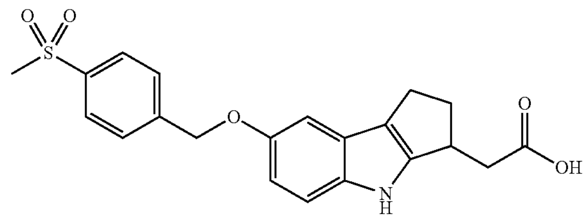 [SMILES: CS(=O)(=O)c1ccc(COc2ccc3[nH]c4c(c3c2)CCC4CC(=O)O)cc1] | 2-(7-(4-(methylsulfonyl)benzyloxy)-1,2,3,4-tetrahydrocyclopenta[b]indol-3-yl)acetic acid |
| 31 | 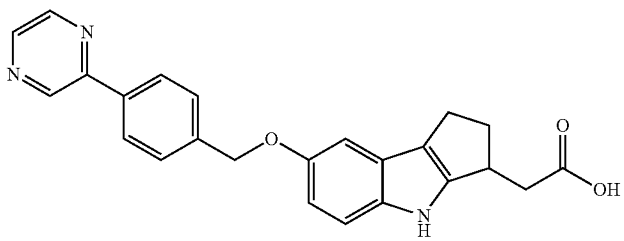 [SMILES: O=C(O)CC1CCc2c1[nH]c1ccc(OCc3ccc(-c4cnccn4)cc3)cc21] | 2-(7-(4-(pyrazin-2-yl)benzyloxy)-1,2,3,4-tetrahydrocyclopenta[b]indol-3-yl)acetic acid |
| 32 | 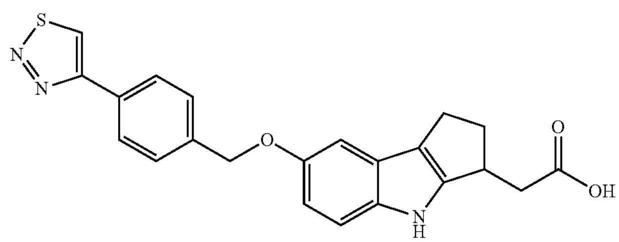 [SMILES: O=C(O)CC1CCc2c1[nH]c1ccc(OCc3ccc(-c4csnn4)cc3)cc21] | 2-(7-(4-(1,2,3-thiadiazol-4-yl)benzyloxy)-1,2,3,4-tetrahydrocyclopenta[b]indol-3-yl)acetic acid |

Additionally, individual compounds and chemical genera of the present invention, for example, those compounds found in Table A including diastereomers and enantiomers thereof, encompass all pharmaceutically acceptable salts, solvates and hydrates, thereof.

It is understood that the present invention embraces each diastereomer, each enantiomer and mixtures thereof of each compound and generic formulae disclosed herein just as if they were each individually disclosed with the specific stereochemical designation for each chiral carbon. Separation of the individual isomers (such as, by chiral HPLC, recrystallization of diastereomeric mixtures and the like) or selective synthesis (such as, by enantiomeric selective syntheses and the like) of the individual isomers is accomplished by application of various methods which are well known to practitioners in the art.

The compounds of the Formula (Ia) of the present invention may be prepared according to relevant published literature procedures that are used by one skilled in the art. Exemplary reagents and procedures for these reactions appear hereinafter in the working examples. Protection and deprotection may be carried out by procedures generally known in the art (see, for example, Greene, T. W. and Wuts, P. G. M., *Protecting Groups in Organic Synthesis*, 3$^{rd}$ Edition, 1999 [Wiley]; incorporated herein by reference in its entirety).

The embodiments of the present invention include every combination of one or more salts selected from the following group and pharmaceutically acceptable solvates and hydrates thereof:

Calcium salt of (R)-2-(7-(4-cyclopentyl-3-(trifluoromethyl)benzyloxy)-1,2,3,4-tetrahydrocyclopenta[b]indol-3-yl)acetic acid; and L-Arginine salt of (R)-2-(7-(4-cyclopentyl-3-(trifluoromethyl)benzyloxy)-1,2,3,4-tetrahydrocyclopenta[b]indol-3-yl)acetic acid.

Pharmaceutical Compositions

A further aspect of the present invention pertains to pharmaceutical compositions comprising one or more compounds as described herein and one or more pharmaceutically acceptable carriers. Some embodiments pertain to pharmaceutical compositions comprising a compound of the present invention and a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before filling and sealing an appropriate vial or ampule. These are just a few examples of the many appropriate methods well known in the art for preparing dosage forms.

A compound of the present invention can be formulated into pharmaceutical compositions using techniques well known to those in the art. Suitable pharmaceutically acceptable carriers, outside those mentioned herein, are known in the art; for example, see Remington, *The Science and Practice of Pharmacy*, 20$^{th}$ Edition, 2000, Lippincott Williams & Wilkins, (Editors: Gennaro et al.)

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt, solvate, hydrate or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation, insufflation or by a transdermal patch. Transdermal patches dispense a drug at a controlled rate by presenting the drug for absorption in an efficient mariner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use; in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or suspensions, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a salt, solvate, hydrate or physiologically functional derivative thereof can be used as active ingredients in pharmaceutical compositions, specifically as S1P1 receptor modulators. The term "active ingredient" is defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits and as is customary and known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but are not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate by the patient's physician or caregiver it may be necessary to deviate upward or downward from the doses described herein.

The amount of active ingredient or an active salt, solvate or hydrate derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in one model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, whether an acute or chronic disease state is being treated or prophylaxis is conducted or whether further active compounds are administered in addition to the compounds of the present invention and as part of a drug combination. The dosage regimen for treating a disease condition with the compounds and/or compositions of this invention is selected in accordance with a variety factors including those cited above. Thus, the actual dosage regimen employed may vary widely and therefore may deviate from a preferred dosage regimen and one skilled in the art will recognize that dosage and dosage regimens outside these typical ranges can be tested and, where appropriate, may be used in the methods of this invention.

The desired dose may conveniently be presented in a single dose or as divided doses administered at appropriate intervals, for example, as 2, 3, 4 or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

For preparing pharmaceutical compositions from the compounds of the present invention, the suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or encapsulating materials.

In powders, the carrier is a finely divided solid which is in a mixture with the finely divided active component.

In tablets, the active component is mixed with the carrier having the necessary binding capacity in suitable proportions and compacted to the desired shape and size.

The powders and tablets may contain varying percentage amounts of the active compound. A representative amount in a powder or tablet may be from 0.5 to about 90 percent of the active compound. However, an artisan would know when amounts outside of this range are necessary. Suitable carriers for powders and tablets include magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein (e.g., by stirring). The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising the active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols (e.g., nasal aerosols, by inhalation), this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well known to the person skilled in the art. Solutions or dispersions of the compounds of the present invention or a pharmaceutically acceptable salt, solvate, hydrate or derivative thereof in water, water/alcohol mixtures or suitable saline solutions, for example, can be employed using customary additives (e.g., benzyl alcohol or other suitable preservatives), absorption enhancers for increasing the bioavailability, solubilizers, dispersants and others and, if appropriate, customary propellants (e.g., carbon dioxide, CFCs, such as, dichlorodifluoromethane, trichlorofluoromethane, dichlorotetrafluoroethane and the like). The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder (e.g., a powder mix of the compound in a suitable powder base such as lactose, starch, starch derivatives such as hydroxypropylmethyl cellulose and polyvinylpyrrolidone (PVP)). Conveniently the powder carrier will form a gel in the nasal cavity. The powder composition may be presented in unit dose form (e.g., capsules, cartridges) as for gelatin or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

In some embodiments, the compositions are tablets or capsules for oral administration.

In some embodiments, the compositions are liquids for intravenous administration.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as those pharmaceutically acceptable salts listed by Berge et al., *Journal of Pharmaceutical Sciences*, 66:1-19 (1977), incorporated herein by reference in its entirety.

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and that when administered into an individual undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A. C. S. Symposium Series; and in *Bioreversible Carriers in Drug Design*, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when S1P1 receptor agonists are utilized as active ingredients in a pharmaceutical composition, these are not intended for use only in humans, but in other non-human mammals as well. Indeed, recent advances in the area of animal health-care mandate that consideration be given for the use of active agents, such as S1P1 receptor agonists, for the treatment of an S1P1 receptor-associated disease or disorder in companionship animals (e.g., cats, dogs, etc.) and in livestock animals (e.g., cows, chickens, fish, etc.). Those of ordinary skill in the art are readily credited with understanding the utility of such compounds in such settings.

Hydrates and Solvates

It is understood that when the phrase "pharmaceutically acceptable salts, solvates and hydrates" is used in reference to a particular formula herein, it is intended to embrace solvates and/or hydrates of compounds of the particular formula, pharmaceutically acceptable salts of compounds of the particular formula as well as solvates and/or hydrates of pharmaceutically acceptable salts of compounds of the particular formula. It is also understood by a person of ordinary skill in the art that hydrates are a subgenus of solvates.

The compounds of the present invention can be administrated in a wide variety of oral and parenteral dosage forms. It will be apparent to those skilled in the art that the following dosage forms may comprise, as the active component, either a compound of the invention or a pharmaceutically acceptable salt or as a solvate or hydrate thereof. Moreover, various hydrates and solvates of the compounds of the invention and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in:

*Polymorphism in Pharmaceutical Solids*, ed. Harry G. Brittan, Vol. 95, Marcel Dekker, Inc., New York, 1999, incorporated herein by reference in its entirety. Accordingly, one aspect of the present invention pertains to hydrates and solvates of compounds of the present invention and/or their pharmaceutical acceptable salts, as described herein, that can be isolated and characterized by methods known in the art, such as, thermogravimetric analysis (TGA), TGA-mass spectroscopy, TGA-Infrared spectroscopy, powder X-ray diffraction (PXRD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

The embodiments of the present invention include every combination of one or more solvate or hydrate selected from the following group:

D-Lysine salt of (S)-2-(7-(4-cyclopentyl-3-(trifluoromethyl) benzyloxy)-1,2,3,4-tetrahydrocyclopenta[b]indol-3-yl) acetic acid hydrate; and (R)-1-Phenethylamine salt of (S)-2-(7-(4-cyclopentyl-3-(trifluoromethyl)benzyloxy)-1,2,3,4-tetrahydrocyclopenta [b]indol-3-yl)acetic acid acetonitrile solvate.

In some embodiments, the crystalline form is (S)-2-(7-(4-cyclopentyl-3-(trifluoromethyl)benzyloxy)-1,2,3,4-tetrahydrocyclopenta[b]indol-3-yl)acetic acid hydrate.

Figure 12:
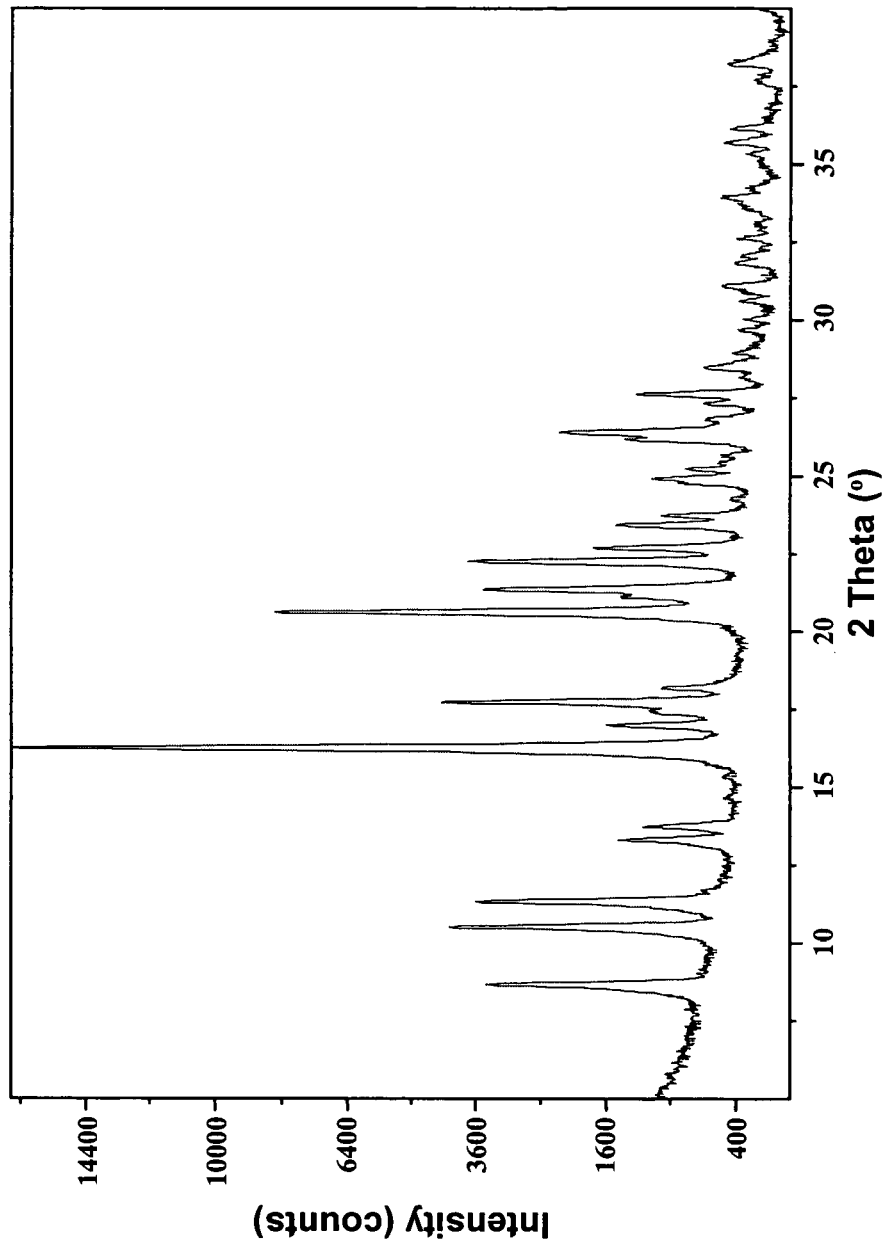
FIG. 12 depicts a powder X-ray diffraction (PXRD) pattern for a crystal form of the $2^{nd}$ enantiomer of compound 12 (isolated after resolution of compound 12 by HPLC with a retention time of 13.9 min per the conditions reported in Example 1.29).

In some embodiments, the crystalline form of (S)-2-(7-(4-cyclopentyl-3-(trifluoromethyl)benzyloxy)-1,2,3,4-tetrahydrocyclopenta[b]indol-3-yl)acetic acid hydrate has an X-ray powder diffraction pattern substantially as shown in FIG. 12, wherein by "substantially" is meant that the reported peaks can vary by about ±0.2° 2θ.

Figure 13:
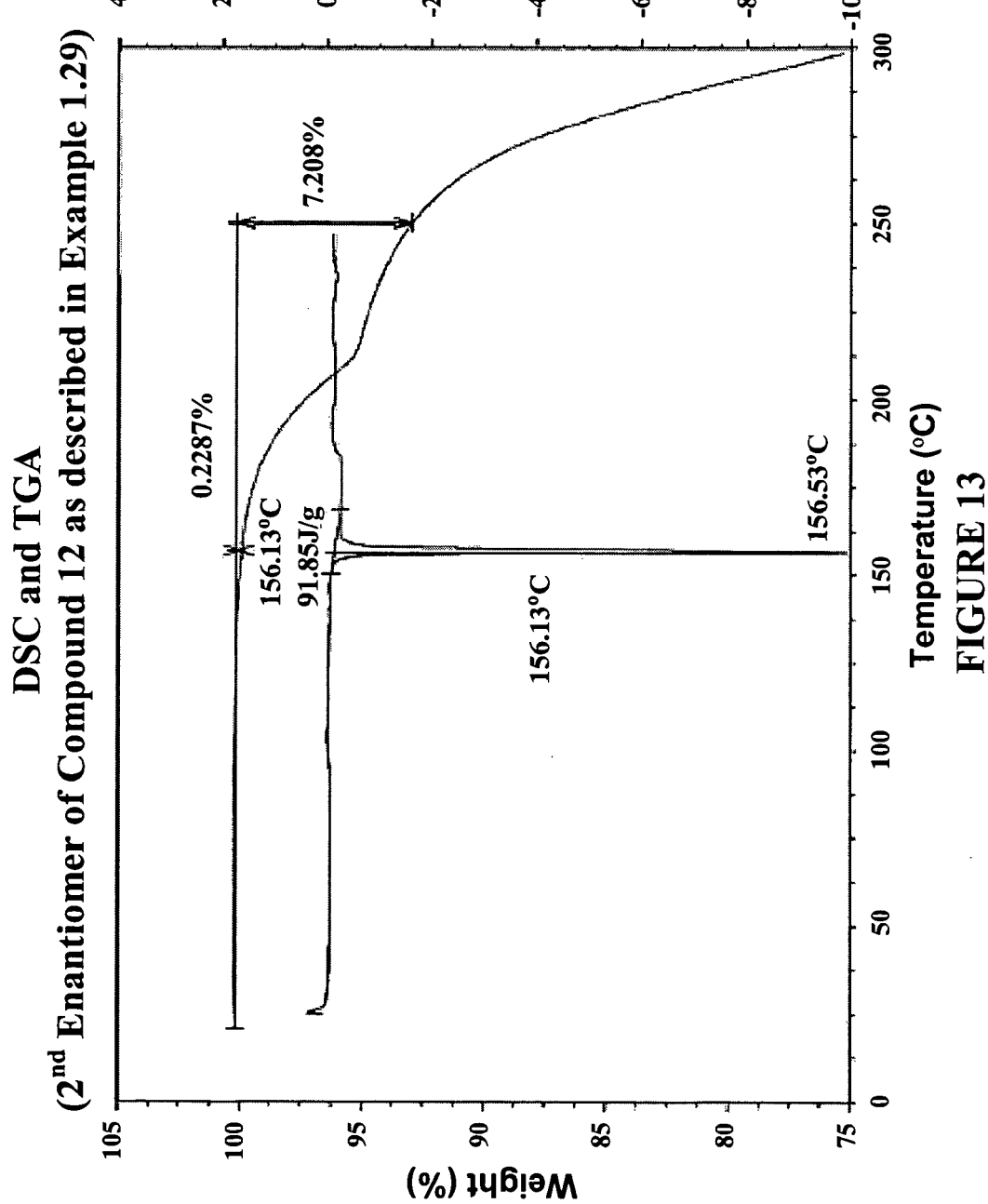
FIG. 13 depicts a differential scanning calorimetry (DSC) thermogram and a thermogravimetric analysis (TGA) thermogram for the $2^{nd}$ enantiomer of compound 12 (isolated after resolution of compound 12 by HPLC, with a retention time of 13.9 min per the conditions reported in Example 1.29).

In some embodiments, the crystalline form of (S)-2-(7-(4-cyclopentyl-3-(trifluoromethyl)benzyloxy)-1,2,3,4-tetrahydrocyclopenta[b]indol-3-yl)acetic acid hydrate has a differential scanning calorimetry thermogram substantially as shown in FIG. 13, wherein by "substantially" is meant that the reported DSC features can vary by about ±4° C.

In some embodiments, the crystalline form of (S)-2-(7-(4-cyclopentyl-3-(trifluoromethyl)benzyloxy)-1,2,3,4-tetrahydrocyclopenta[b]indol-3-yl)acetic acid hydrate has a thermogravimetric analysis thermogram substantially as shown in FIG. 13.

Figure 14:
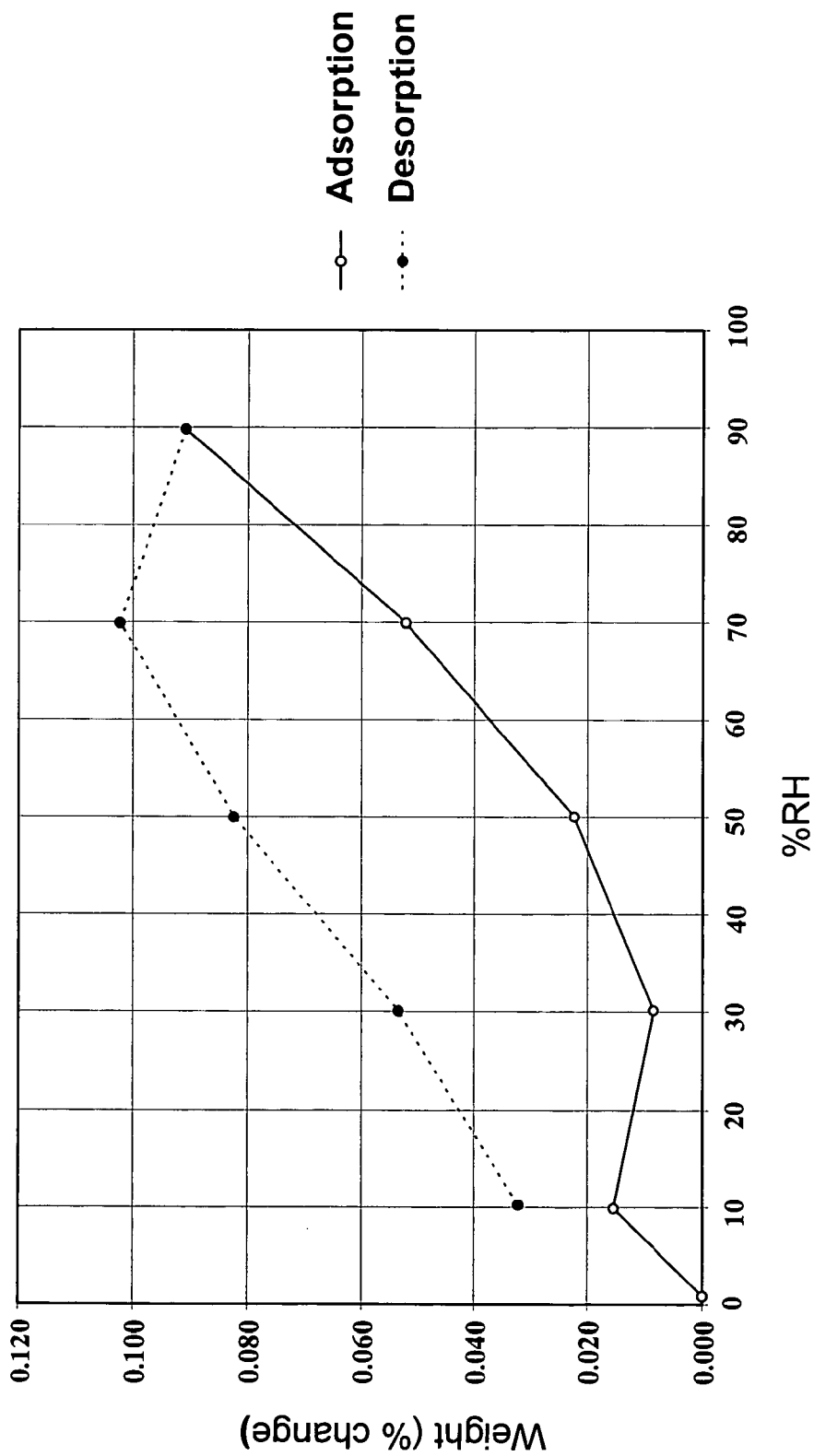
FIG. 14 depicts a moisture sorption analysis for the $2^{nd}$ enantiomer of compound 12 (isolated after resolution of compound 12 by HPLC, with a retention time of 13.9 min per the conditions reported in Example 1.29).
Figure 15:
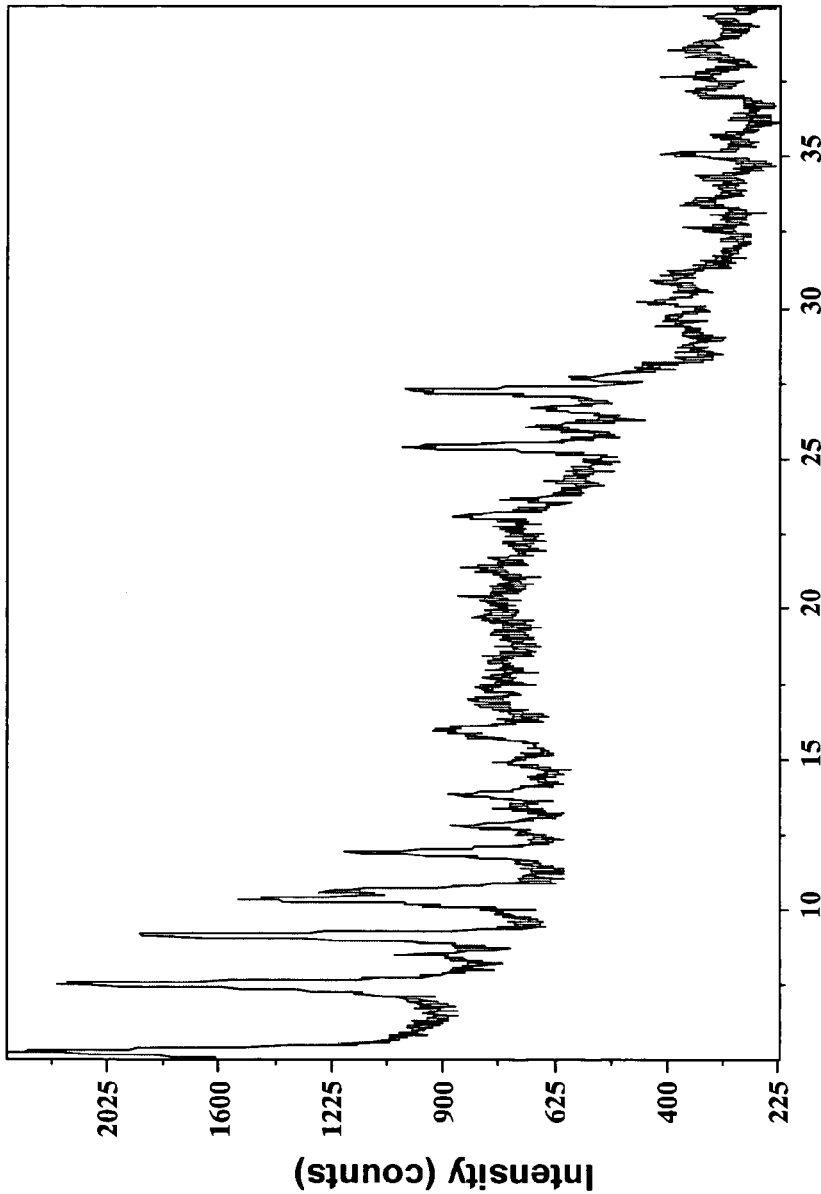
FIG. 15 depicts a powder X-ray diffraction (PXRD) pattern for a crystal form of the Ca salt of the $2^{nd}$ enantiomer of compound 12 (as described in Example 1.32).
Figure 16:
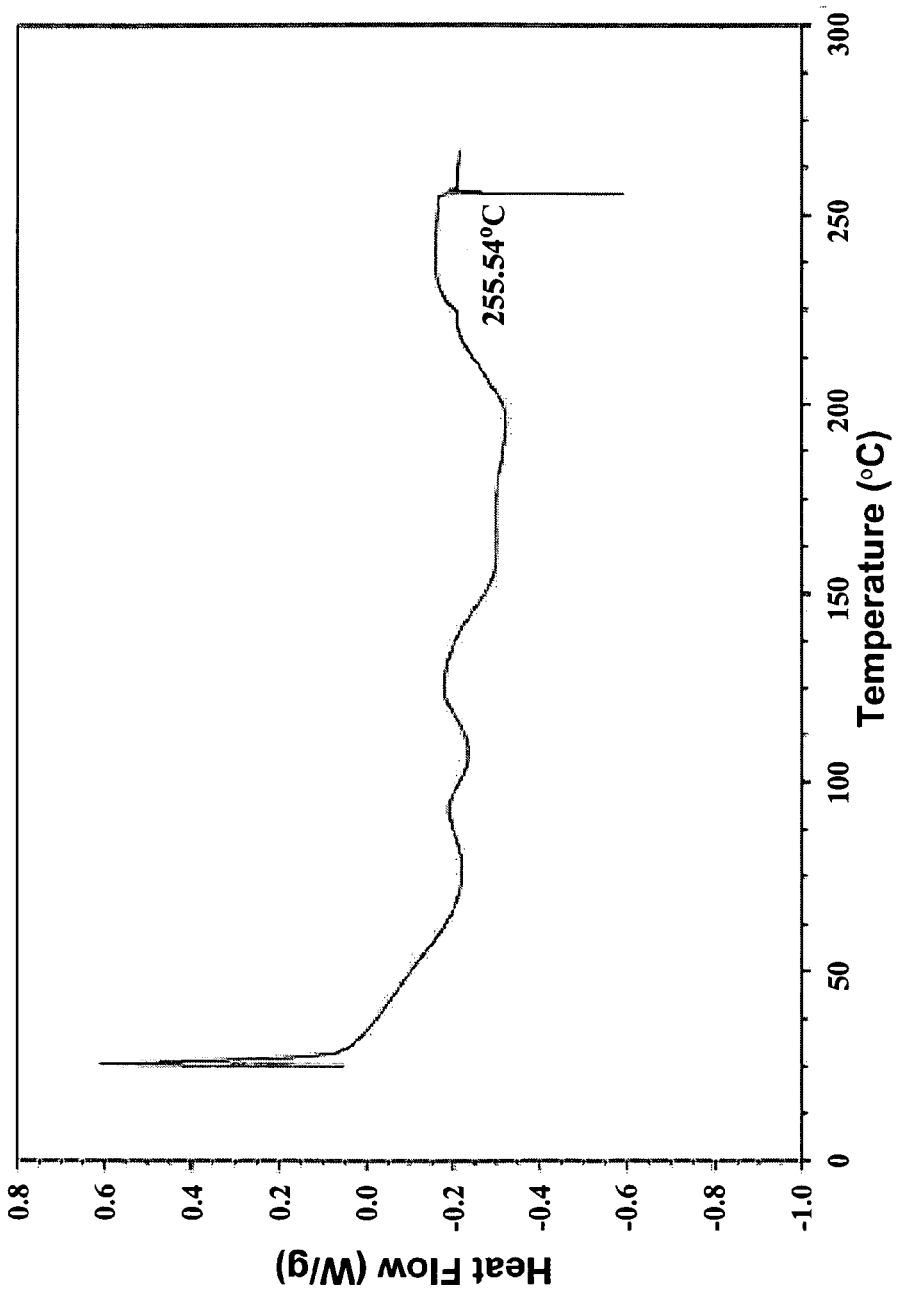
FIG. 16 depicts a differential scanning calorimetry (DSC) thermogram for the Ca salt of the $2^{nd}$ enantiomer of compound 12 (as described in Example 1.32).
Figure 17:
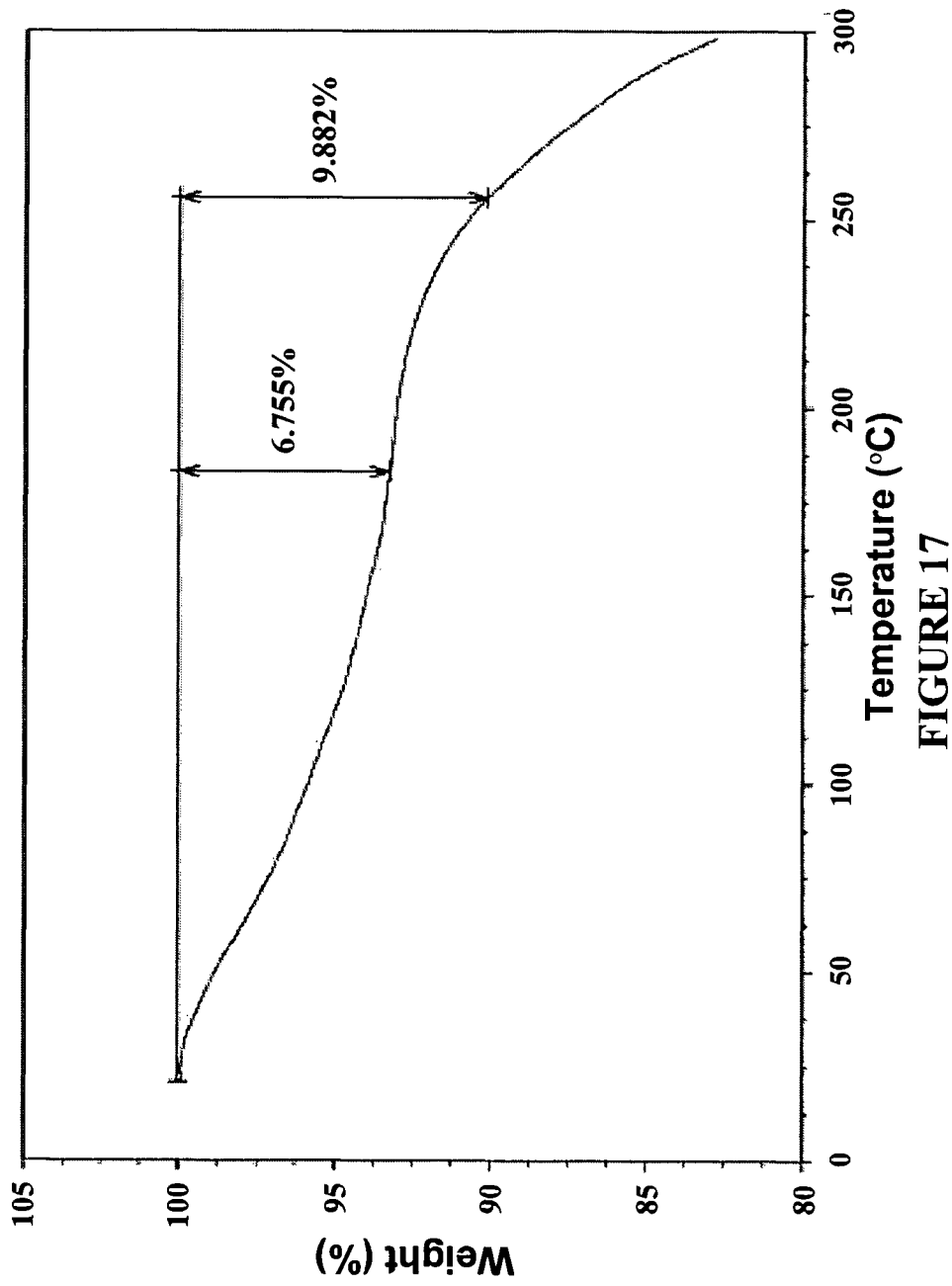
FIG. 17 depicts a thermogravimetric analysis (TGA) thermogram for the Ca salt of the $2^{nd}$ enantiomer of compound 12 (as described in Example 1.32).
Figure 18:
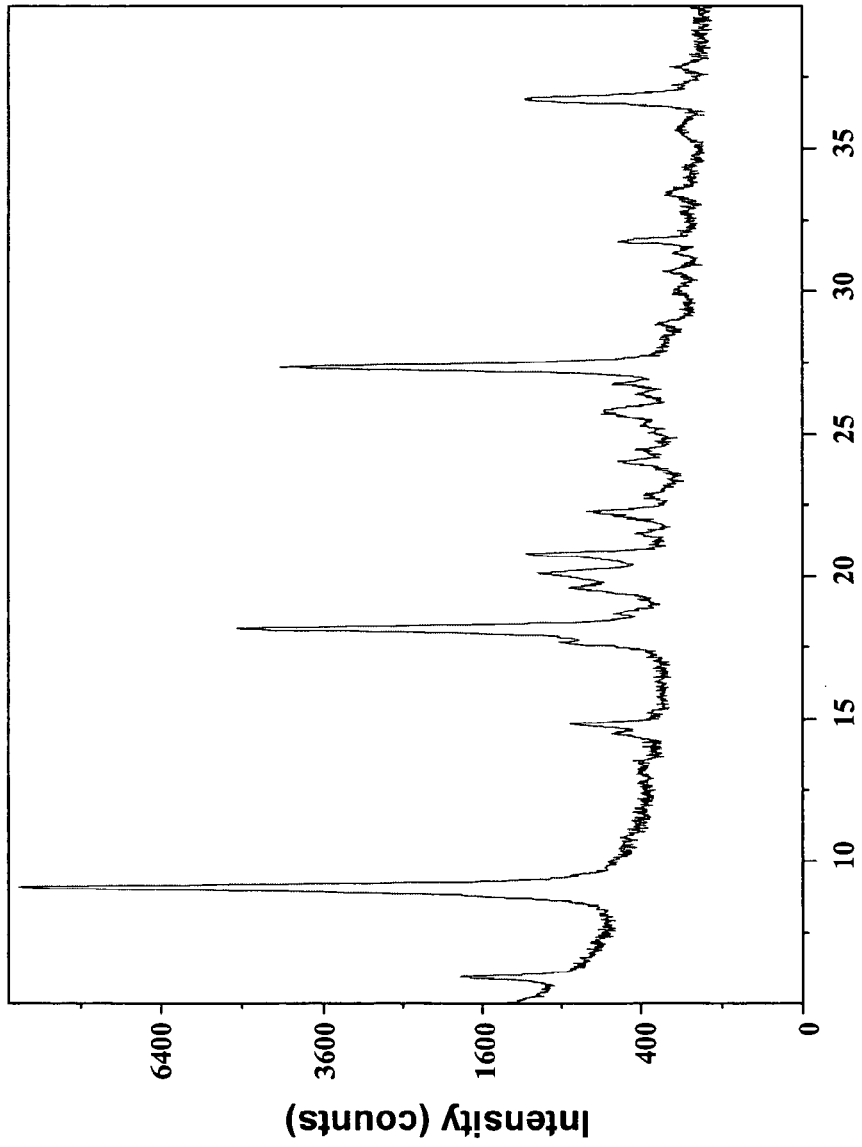
FIG. 18 depicts a powder X-ray diffraction (PXRD) pattern for a crystal form of the D-Lysine salt of the $1^{st}$ enantiomer of compound 12 (as described in Example 1.34).
Figure 19:
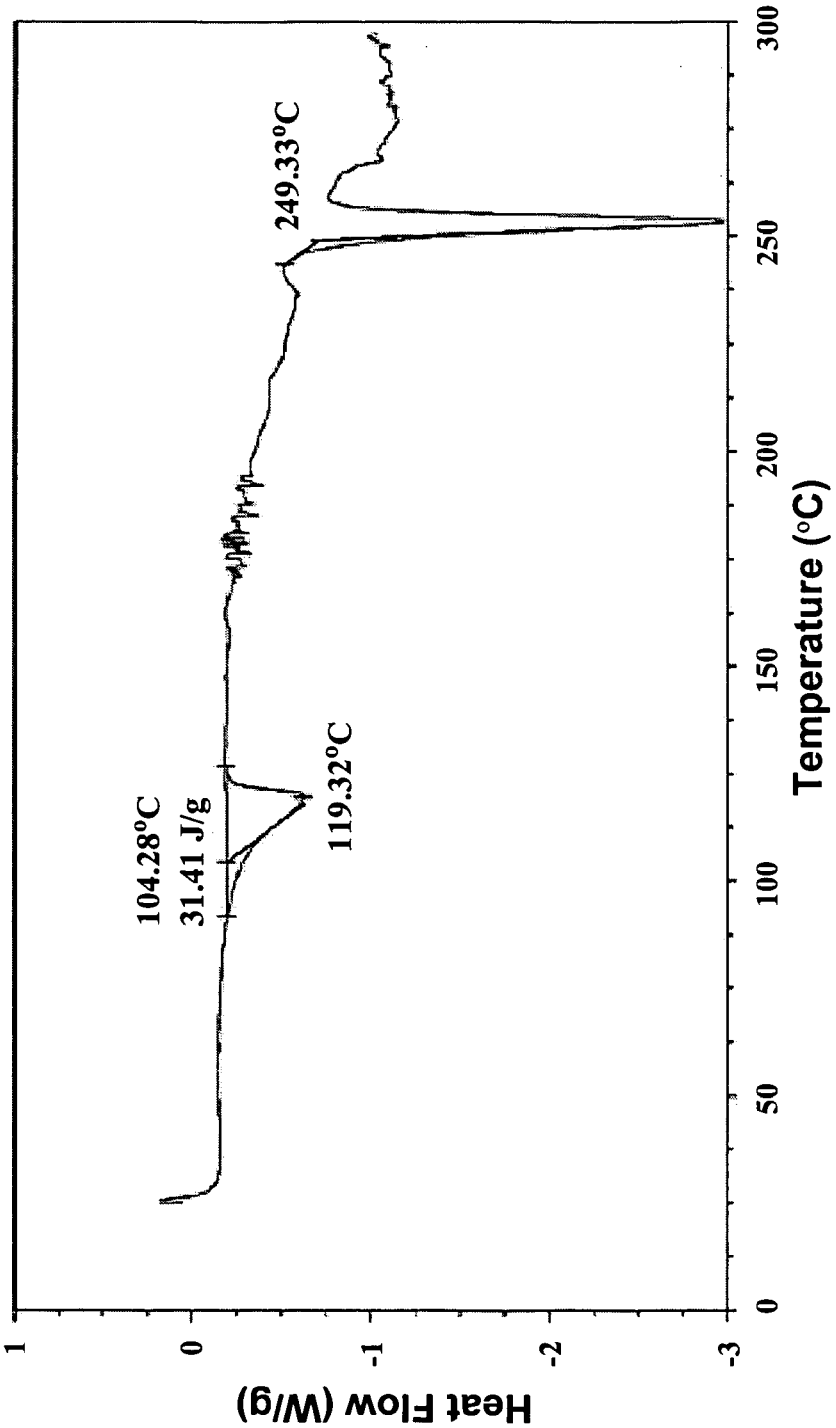
FIG. 19 depicts a differential scanning calorimetry (DSC) thermogram for the D-Lysine salt of the $1^{st}$ enantiomer of compound 12 (as described in Example 1.34).
Figure 20:
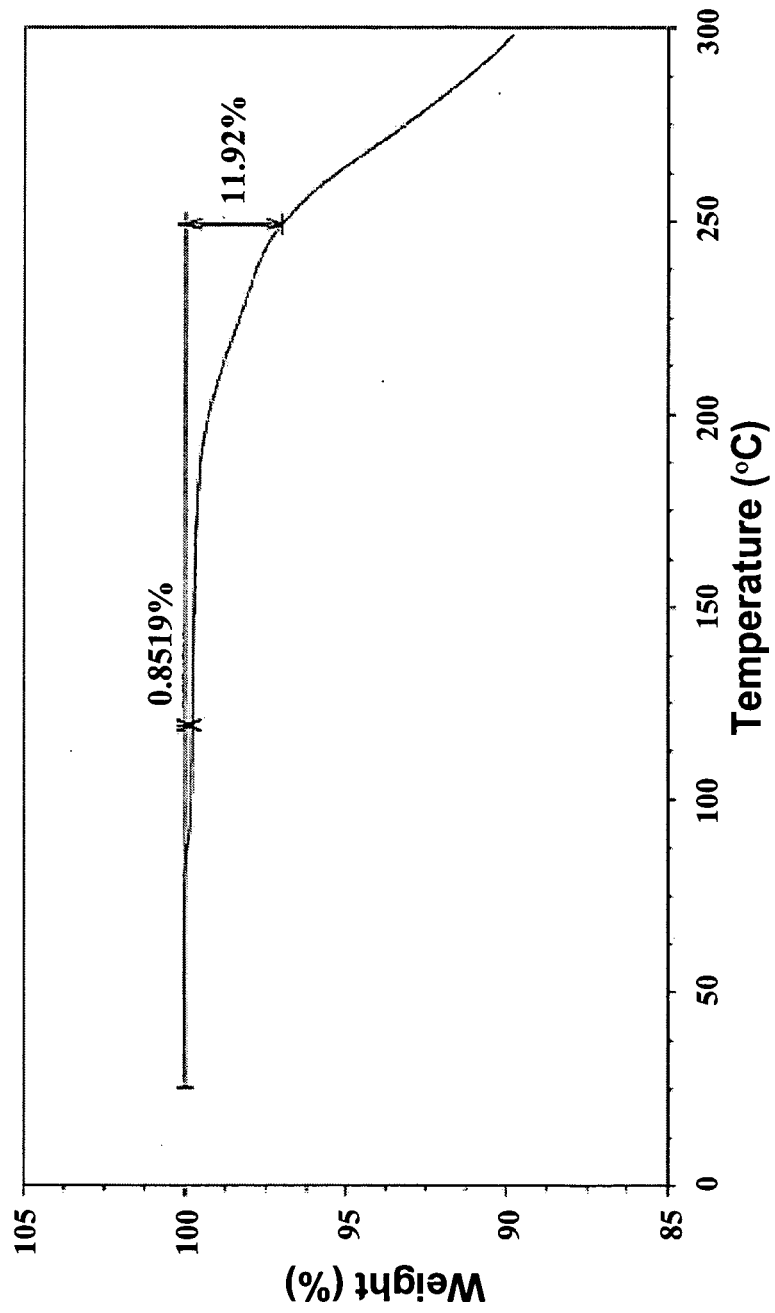
FIG. 20 depicts a thermogravimetric analysis (TGA) thermogram for the D-Lysine salt of the $1^{st}$ enantiomer of compound 12 (as described in Example 1.34).
Figure 22:
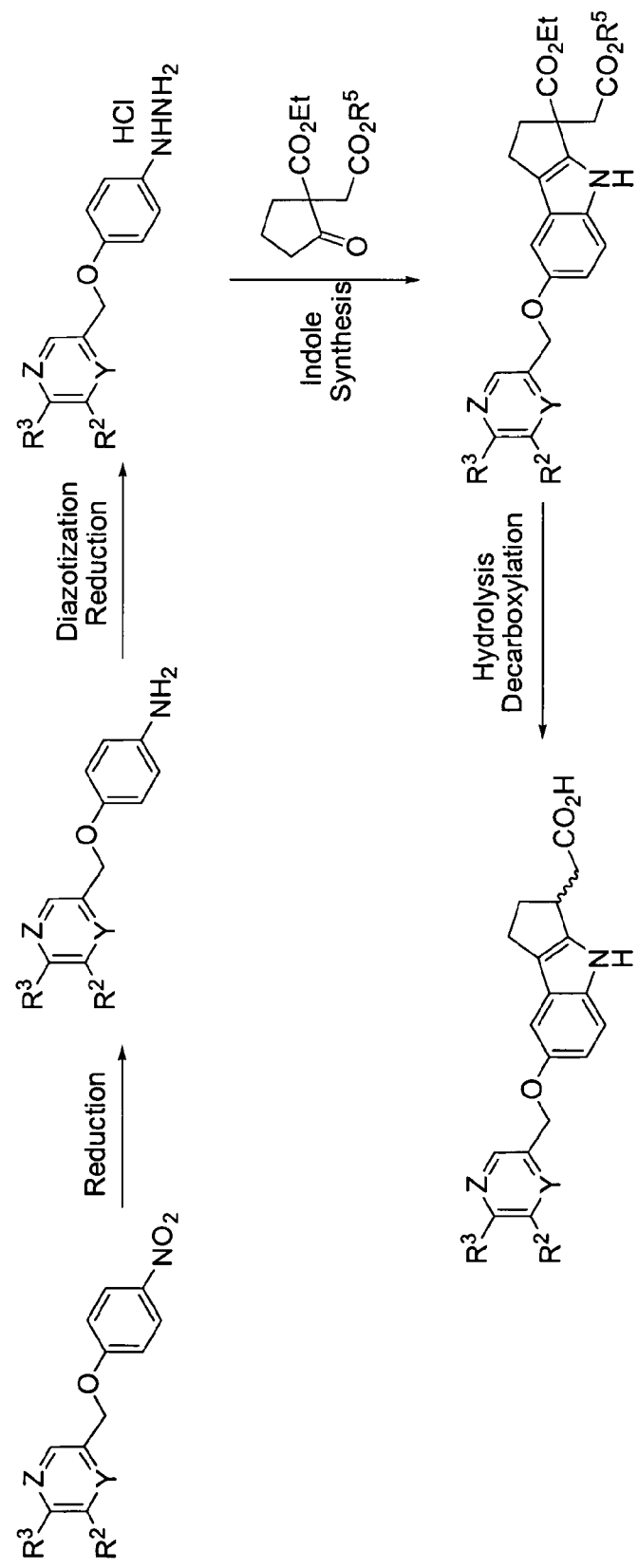
FIG. 22 shows a general synthetic scheme for the preparation of 1,2,3,4-tetrahydrocyclopenta[b]indol-3-yl)acetic acid derivatives, via the Fisher indole synthesis. Subsequent hydrolysis and decarboxylation affords compounds of Formula (Ia) wherein "m" is 1 and "n" is 1.
Figure 23:
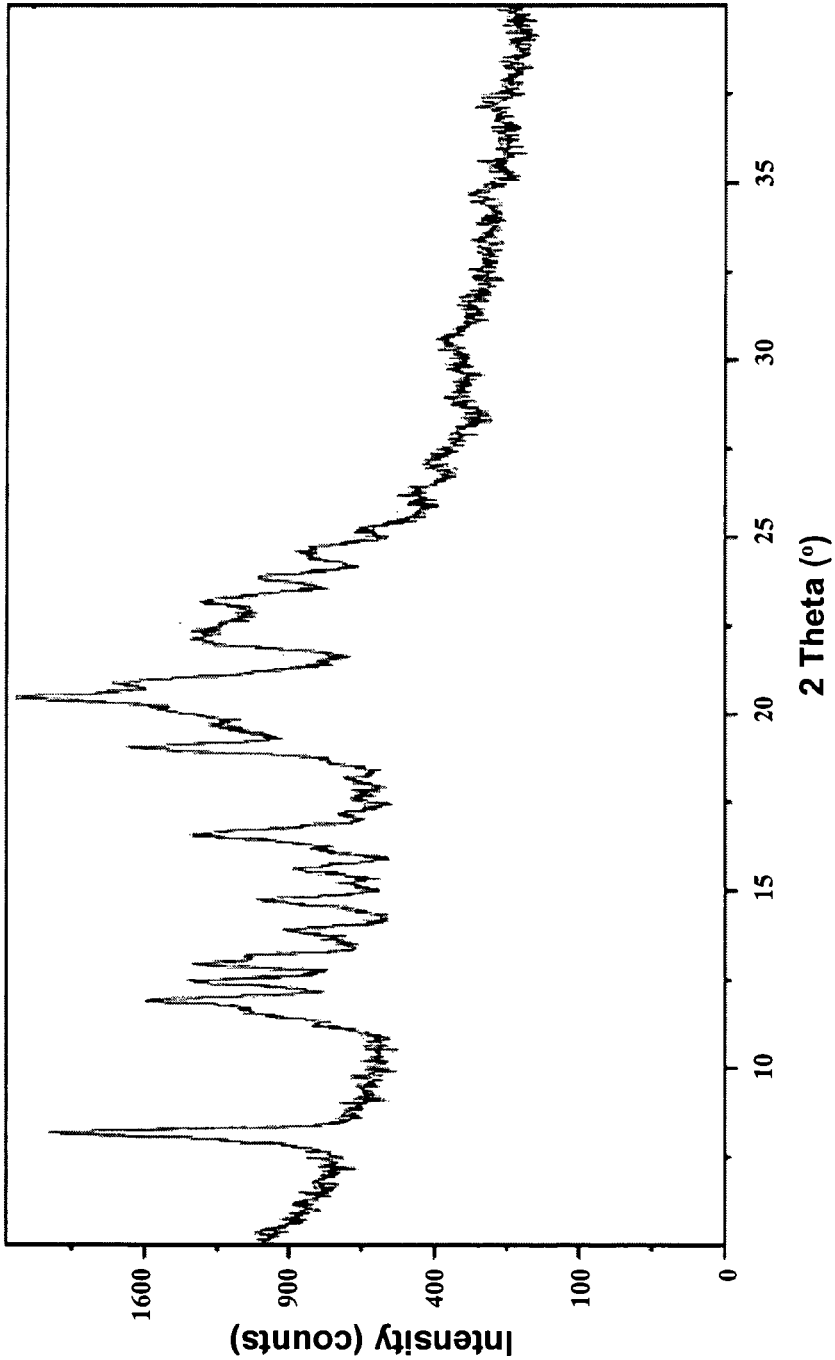
FIG. 23 depicts a powder X-ray diffraction (PXRD) pattern for a crystal form of the L-Arginine salt of the $2^{nd}$ enantiomer of compound 12 (as described in Example 1.33).
Figure 24:
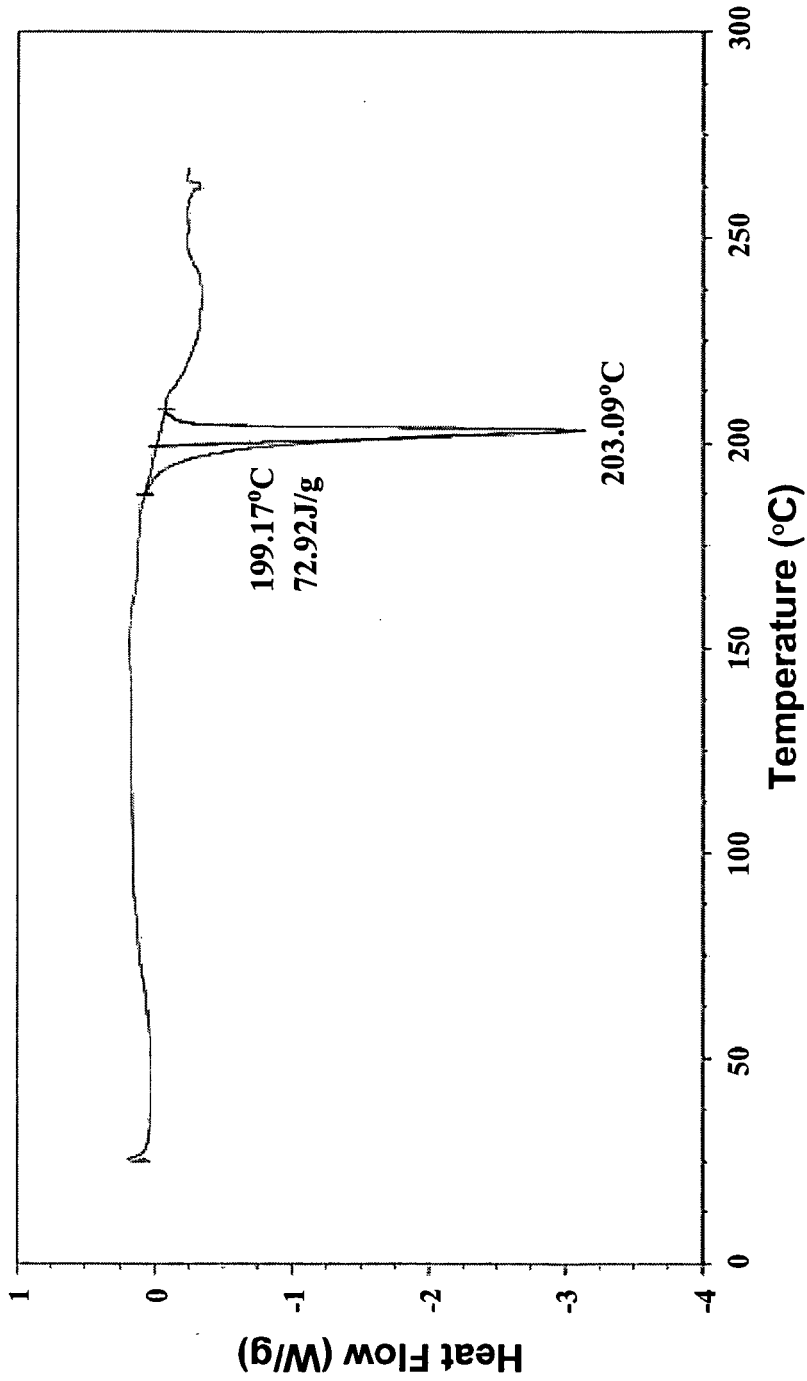
FIG. 24 depicts a differential scanning calorimetry (DSC) thermogram for the L-Arginine salt of the $2^{nd}$ enantiomer of compound 12 (as described in Example 1.33).
Figure 25:
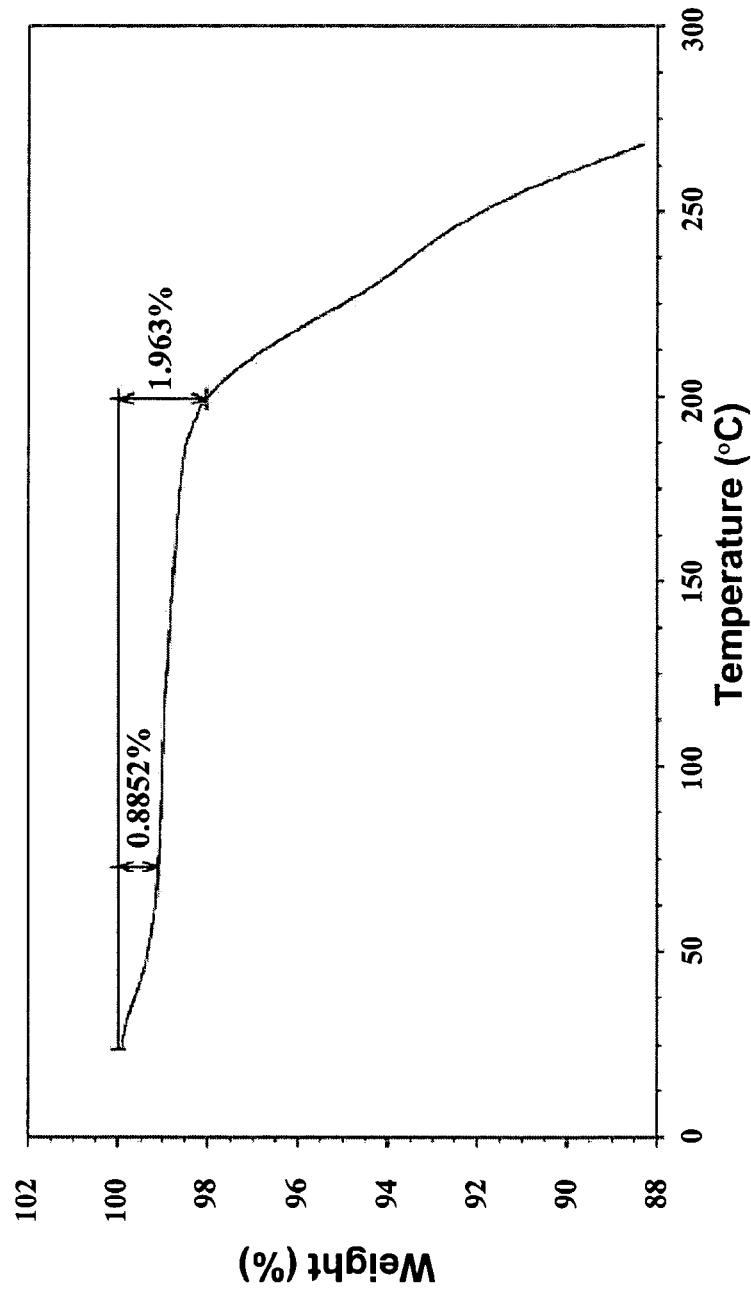
FIG. 25 depicts a thermogravimetric analysis (TGA) thermogram for the L-Arginine salt of the $2^{nd}$ enantiomer of compound 12 (as described in Example 1.33).
Figure 26:
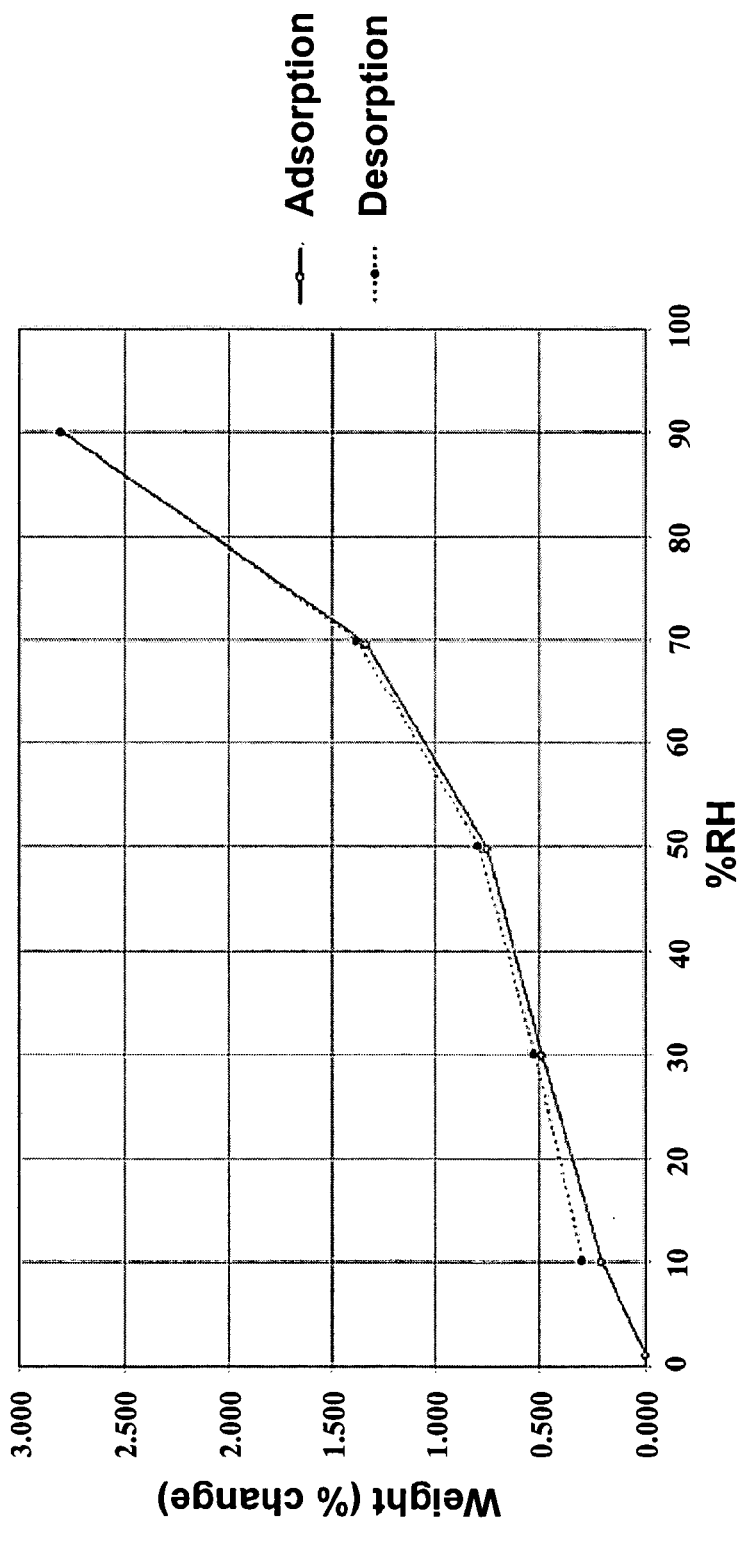
FIG. 26 depicts a moisture sorption analysis for the L-Arginine salt of the $2^{nd}$ enantiomer of compound 12 (as described in Example 1.33).

In some embodiments, the crystalline form of (S)-2-(7-(4-cyclopentyl-3-(trifluoromethyl)benzyloxy)-1,2,3,4-tetrahydrocyclopenta[b]indol-3-yl)acetic acid hydrate has a moisture-sorption analysis substantially as shown in FIG. 14, wherein by "substantially" is meant that the reported moisture-sorption analysis features can vary by about ±5% relative humidity.

Other Utilities

Another object of the present invention relates to radiolabeled compounds of the present invention that are useful not only in radio-imaging but also in assays, both in vitro and in vivo, for localizing and quantitating the S1P1 receptor in tissue samples, including human and for identifying S1P1 receptor ligands by inhibition binding of a radiolabeled compound. It is a further object of this invention to develop novel S1P1 receptor assays which comprise such radiolabeled compounds.

The present invention embraces isotopically-labeled compounds of the present invention. Isotopically or radiolabeled compounds are those which are identical to compounds disclosed herein, but for the fact that one or more atoms are replaced or substituted by an atom having an atomic mass or mass number different from the atomic mass or mass number most commonly found in nature. Suitable radionuclides that may be incorporated in compounds of the present invention include, but are not limited, to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{75}$Br, $^{76}$Br, $^{77}$Br, $^{82}$Br, $^{123}$I, $^{124}$I, $^{125}$I and $^{131}$I. The radionuclide that is incorporated in the instant radiolabeled compounds will depend on the specific application of that radiolabeled compound. For example, for in vitro S1P1 receptor labeling and competition assays, compounds that incorporate $^3$H, $^{14}$C, $^{82}$Br, $^{125}$I, $^{131}$I or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radiolabeled" or "labeled compound" is a compound of Formula (Ia), (Ic), (Ie), (Ig), (Ii), (Ik) or (Im) containing at least one radionuclide. In some embodiments the radionuclide is selected from the group consisting of $^3$H, $^{14}$C, $^{125}$I, $^{35}$S and $^{82}$Br.

Certain isotopically-labeled compounds of the present invention are useful in compound and/or substrate tissue distribution assays. In some embodiments the radionuclide $^3$H and/or $^{14}$C isotopes are useful in these studies. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in FIGS. 3 to 6 and examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or a scarcer radio-isotope or nonradioactive isotope.

Synthetic methods for incorporating radio-isotopes into organic compounds are applicable to compounds of the invention and are well known in the art. Certain synthetic methods, for example, for incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^3$H]: This procedure is rather inexpensive and requires precursors containing reducible functional groups such as aldehydes, ketones, lactones, esters and the like.

C. Reduction with Lithium Aluminum Hydride [$^3$H]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [$^3$H]: This procedure is usually employed to prepare O-methyl or N-methyl [$^3$H] products by treating appropriate precursors with high specific activity methyl iodide [$^3$H]. This method in general allows for higher specific activity, such as for example, about 70-90 Ci/mmol.

Synthetic methods for incorporating activity levels of $^{125}$I into target molecules include:

A. Sandmeyer and like reactions: This procedure transforms an aryl amine or a heteroaryl amine into a diazonium salt, such as a diazonium tetrafluoroborate salt and subsequently to $^{125}$I labeled compound using Na$^{125}$I. A represented procedure was reported by Zhu, G-D. and co-workers in *J. Org. Chem.*, 2002, 67, 943-948.

B. Ortho $^{125}$Iodination of phenols: This procedure allows for the incorporation of $^{125}$I at the ortho position of a phenol as reported by Collier, T. L. and co-workers in *J. Labelled Compd. Radiopharm.*, 1999, 42, S264-S266.

C. Aryl and heteroaryl bromide exchange with $^{125}$I: This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A representative procedure was reported by Le Bas, M.-D. and co-workers in *J. Labelled Compd. Radiopharm.* 2001, 44, S280-S282.

A radiolabeled S1P1 receptor compound of Formula (Ia) can be used in a screening assay to identify/evaluate compounds. In general terms, a newly synthesized or identified compound (i.e., test compound) can be evaluated for its ability to reduce binding of the "radiolabeled compound of Formula (Ia)" to the S1P1 receptor. Accordingly, the ability of a test compound to compete with the "radiolabeled compound of Formula (Ia)" for the binding to the S1P1 receptor directly correlates to its binding affinity.

The labeled compounds of the present invention bind to the S1P1 receptor. In one embodiment the labeled compound has an IC$_{50}$ less than about 500 µM, in another embodiment the labeled compound has an IC$_{50}$ less than about 100 µM, in yet another embodiment the labeled compound has an IC$_{50}$ less than about 10 µM, in yet another embodiment the labeled compound has an IC$_{50}$ less than about 1 µM and in still yet another embodiment the labeled inhibitor has an IC$_{50}$ less than about 0.1 µM.

Other uses of the disclosed receptors and methods will become apparent to those of skill in the art based upon, inter alia, a review of this disclosure.

As will be recognized, the steps of the methods of the present invention need not be performed any particular number of times or in any particular sequence. Additional objects, advantages and novel features of this invention will become apparent to those skilled in the art upon examination of the following examples thereof, which are intended to be illustrative and not intended to be limiting.

EXAMPLES

Example 1

Syntheses of Compounds of the Present Invention

Illustrated syntheses for compounds of the present invention are shown in FIGS. 3 through 6 where the variables have the same definitions as used throughout this disclosure.

The compounds of the invention and their syntheses are further illustrated by the following examples. The following examples are provided to further define the invention without, however, limiting the invention to the particulars of these examples. The compounds described herein, supra and infra, are named according to the AutoNom version 2.2, CS Chem-Draw Ultra Version 9.0.7. In certain instances common names are used and it is understood that these common names would be recognized by those skilled in the art.

Chemistry: Proton nuclear magnetic resonance ($^1$H NMR) spectra were recorded on a Bruker Avance-400 equipped with a QNP (Quad Nucleus Probe) or a BBI (Broad Band Inverse) and z-gradient. Proton nuclear magnetic resonance ($^1$H NMR) spectra were also recorded on a Bruker Avance-500 equipped a BBI (Broad Band Inverse) and z-gradient. Chemical shifts are given in parts per million (ppm) with the residual solvent signal used as reference. NMR abbreviations are used as follows: s=singlet, d=doublet, dd=doublet of doublets, t=triplet, q=quartet, m=multiplet, bs=broad singlet. Microwave irradiations were carried out using a Smith Synthesizer™ or an Emrys Optimizer™ (Biotage). Thin-layer chromatography (TLC) was performed on silica gel 60 F$_{254}$ (Merck), preparatory thin-layer chromatography (prep TLC) was preformed on PK6F silica gel 60 A 1 mm plates (Whatman) and column chromatography was carried out on a silica gel column using Kieselgel 60, 0.063-0.200 mm (Merck). Evaporation was done under reduced pressure on a Büchi rotary evaporator. Celite® 545 was used for filtration of palladium.

LCMS spec: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2.

Example 1.1

Preparation of 2-(7-(3-Cyano-5-(trifluoromethoxy) benzyloxy)-1,2,3,4-tetrahydrocyclopenta[b]indol-3-yl)acetic Acid (Compound 4)

Step A: Preparation of Ethyl 1-(2-Ethoxy-2-oxoethyl)-2-oxocyclopentanecarboxylate.

To a solution of ethyl 2-oxocyclopentanecarboxylate (93.27 g, 597 mmol) and ethyl 2-bromoacetate (144.64 g, 866 mmol) in acetone (1.2 L) was added K$_2$CO$_3$ (165 g, 1194 mmol). The mixture was heated at 56° C. for 24 h. The solid was filtered off and the filtering cake was washed with acetone (3×100 mL). The filtrate was concentrated and the resultant liquid was purified by a silica gel plug to give the title compound as light yellow liquid (54.7 g). LCMS m/z=243.3 [M+H]$^+$; $^1$H NMR (400 MHz, CDCl$_3$) δ ppm 1.23 (t, J=7.14 Hz, 3H), 1.24 (t, J=7.14 Hz, 3H), 1.95-2.03 (m, 1H), 2.06-2.15 (m, 2H), 2.35-2.50 (m, 2H), 2.55-2.60 (m, 1H), 2.80 (dd, J=15.2, 2.09 Hz, 1H), 2.95 (dd, J=15.2, 2.09 Hz, 1H), 4.09 (q, J=7.14 Hz, 2H), 4.12 (q, J=7.14 Hz, 2H).

Step B: Preparation of 2-(2-Oxocyclopentyl)acetic Acid.

A solution of ethyl 1-(2-ethoxy-2-oxoethyl)-2-oxocyclopentanecarboxylate (50.0 g, 206 mmol) in HOAc (500 mL) and 6 M HCl (250 mL) was heated at 100° C. for 6 h. The solvent was removed under reduced pressure and the residue was partitioned between EtOAc (500 mL) and H$_2$O (200 mL). Aqueous layer was separated and extracted with EtOAc (2×250 mL). The combined organic layers were washed with H$_2$O (300 mL), brine (300 mL), dried over Na$_2$SO$_4$, decanted and concentrated to yield the title compound as a white solid (22 g). $^1$H NMR (400 MHz, CDCl$_3$) δ ppm 1.59-1.72 (m, 1H), 1.75-1.90 (m, 1H), 2.03-2.10 (m, 1H), 2.20 (dd, J=10.9, 8.9 Hz, 1H), 2.30-2.40 (m, 2H), 2.40-2.50 (m, 2H), 2.80 (dd, J=15.7, 7.2 Hz, 1H), 11.5 (s, 1H).

Step C: Preparation of Ethyl 2-(2-Oxocyclopentyl)acetate.

To a solution of 2-(2-oxocyclopentyl)acetic acid (23.6 g, 166 mmol) in absolute ethanol (400 mL) was added H$_2$SO$_4$ (16.28 g, 166 mmol). The resultant solution was heated under reflux overnight. The reaction mixture was concentrated and the liquid residue was added into ice-water (200 mL). The aqueous mixture was extracted with DCM (3×200 mL). The combined organic layers were washed with H$_2$O (300 mL), brine (300 mL), dried over Na$_2$SO$_4$, decanted, concentrated and dried under vacuum to afford the title compound as a light yellow liquid (27.2 g). LCMS m/z=171.3 [M+H]$^+$; $^1$H NMR (400 MHz, CDCl$_3$) δ ppm 1.19 (t, J=7.14 Hz, 3 H), 1.50-1.62 (m, 1 H), 1.65-1.80 (m, 1 H), 1.92-2.02 (m, 1 H), 2.12 (dd, J=16.7, 8.86 Hz, 1 H), 2.19-2.29 (m, 2 H), 2.30-2.44 (m, 2 H), 2.65 (dd, J=15.12, 2.6 Hz, 1H), 4.07 (q, J=7.14 Hz, 2H).

Step D: Preparation of Ethyl 2-(7-Hydroxy-1,2,3,4-tetrahydrocyclopenta[b]indol-3-yl)acetate.

2-Iodo-4-methoxyaniline (2.0 g, 8.03 mmol) and ethyl 2-(2-oxocyclopentyl)acetate (2.05 g, 12.1 mmol) were dissolved in DMF (30 mL) and tetraethyl orthosilicate (2.12 g, 10.4 mmol) and pyridinum p-toluenesulfonate (PPTS) (0.081 g, 0.321 mmol) were added. The reaction mixture was heated and stirred at 135° C. for 4 h. After cooling to 120° C., DIEA (3.11 g, 24.09 mmol) and palladium (II) acetate (0.054 g, 0.241 mmol) were added. The reaction mixture was stirred for 3 h and then partitioned between ethyl acetate and water. The aqueous layer was extracted twice with ethyl acetate. The combined organic extracts were dried over sodium sulfate, filtered and concentrated under reduced pressure. The resultant solution was diluted with 50% ethyl acetate in hexanes and filtered through a pad of silica gel. The filtrate was concentrated and purified by silica gel column chromatography to give 1.9 g of ethyl 2-(7-methoxy-1,2,3,4-tetrahydrocyclopenta[b]indol-3-yl)acetate containing residual ethyl 2-(2-oxocyclopentyl)acetate. The mixture was dissolved in DCM (80 mL) and cooled to 0° C. Boron tribromide (21.0 mL, 21.0 mmol, 1.0 M in DCM) was added and the reaction was stirred for 1.5 h. Ice water was added and the reaction mixture was allowed to reach room temperature. The aqueous mixture was extracted three times with DCM. The combined organics were dried over sodium sulfate, filtered and concentrated under reduced pressure. The residue was purified by silica gel column chromatography to give the title compound (650 mg). LCMS m/z=260.3 [M+H]$^+$; $^1$H NMR (400 MHz, CDCl$_3$) δ ppm 1.29 (t, J=7.2 Hz, 3H), 2.05-2.14 (m, 1H), 2.50 (dd, J=16.8, 11.2 Hz, 1H), 2.68-2.86 (m, 4H), 3.48-3.58 (m, 1H), 4.16-4.24 (m, 2H), 6.66 (dd, J=8.6, 2.4 Hz, 1H), 6.85 (d, J=2.4 Hz, 1H), 7.15 (d, J=8.7 Hz, 1H), 8.4 (s, 1H).

Step E: Preparation of 3-Cyano-5-(trifluoromethoxy)benzoyl Chloride.

Oxalyl chloride (2.0 M in DCM, 0.636 mL, 1.272 mmol) was added to neat 3-cyano-5-(trifluoromethoxy)benzoic acid (98 mg, 0.424 mmol) and one drop of DMF was added. The reaction mixture was stirred at room temperature for 30 min and then concentrated under reduced pressure.

Step F: Preparation of 3-(Hydroxymethyl)-5-(trifluoromethoxy)benzonitrile.

3-Cyano-5-(trifluoromethoxy)benzoyl chloride (844 mg, 3.38 mmol) was dissolved in THF (10 mL) and cooled to 0° C. Sodium borohydride (320 mg, 8.45 mmol) was added, followed by methanol (2 mL) and the reaction was stirred for 20 min at 0° C. before it was allowed to warm to room temperature. After 2 h, the reaction mixture was acidified to pH 3 with 1.0 M HCl. The aqueous mixture was extracted with ethyl acetate and the combined extracts were dried over sodium sulfate, filtered and concentrated under reduced pressure. The residue was purified by silica gel column chromatography to give the title compound (440 mg). LCMS m/z=218.3 [M+H]$^+$.

Step G: Preparation of 2-(7-(3-Cyano-5-(trifluoromethoxy)benzyloxy)-1,2,3,4-tetrahydrocyclopenta[b]indol-3-yl)acetic Acid.

Ethyl 2-(7-hydroxy-1,2,3,4-tetrahydrocyclopenta[b]indol-3-yl)acetate (100 mg, 0.386 mmol) and 3-(hydroxymethyl)-5-(trifluoromethoxy)benzonitrile (84 mg, 0.386 mmol) were dissolved in THF (3.0 mL) and cooled to 0° C. Triphenylphosphine (202 mg, 0.771 mmol) and diisopropylazodicarboxylate (DIAD) (0.15 mL, 0.771 mmol) were added. The mixture was warmed to room temperature and stirred for 1 h. Additional DIAD (0.15 mL, 0.771 mmol) and triphenylphosphine (202 mg, 0.771 mmol) were added and the reaction mixture was stirred for 1 h. The reaction mixture was diluted with water and extracted three times with ethyl acetate. The combined organics were dried over sodium sulfate, filtered and concentrated under reduced pressure. The residue was purified by silica gel column chromatography to give 50.8 mg of impure ethyl 2-(7-(3-cyano-5-(trifluoromethoxy)benzyloxy)-1,2,3,4-tetrahydrocyclopenta[b]indol-3-yl)acetate. The material was dissolved in dioxane (1.3 mL) and 1.0 M aqueous LiOH (0.33 mL, 0.33 mmol) was added. The reaction was monitored by HPLC until judged complete and then acidified to pH 2 with 1.0 M HCL. The aqueous mixture was extracted three times with ethyl acetate. The combined organics were dried over sodium sulfate, filtered and concentrated under reduced pressure. The residue was purified by silica gel column chromatography followed by HPLC to give the title compound (1.1 mg). LCMS m/z=431.2 [M+H]$^+$; $^1$H NMR (400 MHz, CD$_3$OD) δ ppm 2.11-2.20 (m, 1H), 2.50 (dd, J=15.8, 8.0 Hz, 1H), 2.66-2.84 (m, 4H), 3.51-3.60 (m, 1H), 5.18 (s, 2H), 6.78 (dd, J=8.8, 2.5 Hz, 1H), 6.95 (d, J=2.4 Hz, 1H), 7.20 (d, J=8.9 Hz, 1H), 7.64 (s, 1H), 7.73 (s, 1H), 7.84 (s, 1H).

Example 1.2

Preparation of 2-(7-(3,5-Bis(trifluoromethyl)benzyloxy)-1,2,3,4-tetrahydrocyclopenta[b]indol-3-yl) acetic Acid (Compound 10)

Step A: Preparation of Ethyl 2-(7-(3,5-Bis(trifluoromethyl)benzyloxy)-1,2,3,4-tetrahydrocyclopenta[b]indol-3-yl)acetate.

Ethyl 2-(7-hydroxy-1,2,3,4-tetrahydrocyclopenta[b]indol-3-yl)acetate (61 mg, 0.235 mmol), was dissolved in DMF (1.0 mL) and cesium carbonate (77 mg, 0.235 mmol) and 1-(bromomethyl)-3,5-bis(trifluoromethyl)benzene (72 mg, 0.235 mmol) were added. The reaction mixture was stirred at room temperature for 16 h and then filtered through a pad of Celite®. The filtrate was diluted with water and extracted three times with ethyl acetate. The combined organics were dried over sodium sulfate, filtered and concentrated under reduced pressure. The residue was purified by silica gel column chromatography to give the title compound (28.6 mg). LCMS m/z=486.4 [M+H]$^+$.

Step B: Preparation of 2-(7-(3,5-Bis(trifluoromethyl)benzyloxy)-1,2,3,4-tetrahydrocyclopenta[b]indol-3-yl)acetic Acid.

Ethyl 2-(7-(3,5-bis(trifluoromethyl)benzyloxy)-1,2,3,4-tetrahydrocyclopenta[b]indol-3-yl)acetate (28.6 mg, 0.059 mmol) was dissolved in dioxane (1.0 mL) and 1.0 M aqueous LiOH (0.166 mL, 0.166 mmol) was added. The solution was stirred at room temperature for 3 h before it was acidified to pH 3 with 1.0 M HCl and extracted twice with ethyl acetate. The combined extracts were dried over sodium sulfate, filtered and concentrated under reduced pressure to give the title compound (23 mg). LCMS m/z=458.3 [M+H]$^+$; $^1$H NMR (400 MHz, CDCl$_3$) δ ppm 2.12-2.24 (m, 1H), 2.61 (dd, J=17.0, 10.7 Hz, 1H), 2.73-2.89 (m, 4H), 3.53-3.63 (m, 1H), 5.19 (s, 2H), 6.86 (dd, J=8.6, 2.5 Hz, 1H), 7.0 (d, J=2.5 Hz, 1H), 7.24 (d, J=8.8 Hz, 1H), 7.82 (s, 1H), 7.94 (s, 2H), 8.33 (s, 1H).

Example 1.3

Preparation of 2-(7-(3-Cyano-4-isopropoxybenzyloxy)-1,2,3,4-tetrahydrocyclopenta[b]indol-3-yl)acetic Acid (Compound 5)

Step A: Preparation of 5-(Hydroxymethyl)-2-isopropoxybenzonitrile.

From 3-cyano-4-isopropoxybenzoic acid, in a similar manner to the one described in Example 1.1, Step E and F, the title compound was obtained. $^1$H NMR (400 MHz, CDCl$_3$) δ ppm 1.40 (d, J=6.2 Hz, 6H), 1.72 (t, J=5.6 Hz, 1H), 4.6-4.69 (m, 3H), 6.95 (d, J=8.8 Hz, 1H), 7.50 (dd, J=8.6, 2.0 Hz, 1H), 7.55 (d, J=2.3 Hz, 1H).

Step B: Preparation of 5-(Chloromethyl)-2-isopropoxybenzonitrile.

5-(Hydroxymethyl)-2-isopropoxybenzonitrile (5.96 g, 31.2 mmol) was dissolved in toluene (90 mL) and thionyl chloride (13.65 mL, 187 mmol) was added. The reaction mixture was warmed to 75° C. and stirred for 20 min. The reaction mixture was diluted with hexanes and washed with water and saturated aqueous sodium bicarbonate. The hexane solution was dried over sodium sulfate, filtered and concentrated under reduced pressure to give the title compound (5.6 g). $^1$H NMR (400 MHz, CDCl$_3$) δ ppm 1.41 (d, J=6.1 Hz, 6H), 4.52 (s, 2H), 4.66 (septet, J=6.1 Hz, 1H), 6.95 (d, J=8.6 Hz, 1H), 7.51 (dd, J=8.7, 2.4 Hz, 1H), 7.57 (d, J=2.3 Hz, 1H).

Step C: Preparation of Ethyl 2-(7-(3-Cyano-4-isopropoxybenzyloxy)-1,2,3,4-tetrahydrocyclopenta[b]indol-3-yl)acetate.

Ethyl 2-(7-hydroxy-1,2,3,4-tetrahydrocyclopenta[b]indol-3-yl)acetate (1.237 g, 4.77 mmol) was dissolved in DMF (12 mL) and cesium carbonate (1.554 g, 4.77 mmol) was added. The reaction mixture was stirred at room temperature for 10 min and 5-(chloromethyl)-2-isopropoxybenzonitrile (1.0 g, 4.77 mmol) was added. The reaction mixture was stirred at 40° C. for 2 h before it was cooled to room temperature. The heterogenous mixture was filtered through Celite® and the filtrate was concentrated under reduced pressure. The residue was purified by silica gel column chromatography to give the title compound (1.32 g). LCMS m/z=433.5 [M+H]$^+$; $^1$H NMR (400 MHz, CDCl$_3$) δ ppm 1.29 (t, J=7.2 Hz, 3H), 1.40 (d, J=6.1 Hz, 6H), 2.05-2.16 (m, 1H), 2.50 (dd, J=16.7, 11.1 Hz, 1H), 2.69-2.88 (m, 4H), 3.50-3.59 (m, 1H), 4.16-4.26 (m, 2H), 4.65 (septet, J=6.1 Hz, 1H), 5.00 (s, 2H), 6.80 (dd, J=8.7, 2.5 Hz, 1H), 6.94-6.97 (m, 2H), 7.20 (d, J=8.8 Hz, 1H), 7.58 (dd, J=8.7, 2.3 Hz, 1H), 7.64 (d, J=2.0 Hz, 1H), 8.45 (s, 1H).

Step D: Preparation of 2-(7-(3-Cyano-4-isopropoxybenzyloxy)-1,2,3,4-tetrahydrocyclopenta[b]indol-3-yl)acetic Acid.

Ethyl 2-(7-(3-cyano-4-isopropoxybenzyloxy)-1,2,3,4-tetrahydrocyclopenta[b]indol-3-yl)acetate (1.32 g, 3.05 mmol) was dissolved in dioxane (34 mL) and 1.0 M aqueous LiOH (9.16 mL, 9.16 mmol) was added. The reaction was stirred at room temperature for 6 h and then warmed to 35° C. and stirred for one additional hour. After cooling to room temperature, the reaction was acidified to pH 3 with 1.0 M HCl and partitioned between water and ethyl acetate. The organics were removed and the aqueous layer was extracted twice with ethyl acetate. The combined extracts were dried over sodium sulfate, filtered and concentrated to give the title compound (1.23 g). LCMS m/z=405.6 [M+H]$^+$; $^1$H NMR (400 MHz, DMSO-d$_6$) δ ppm 1.32 (d, J=5.9 Hz, 6H), 2.03-2.13 (m, 1H), 2.35 (dd, J=15.9, 9.0 Hz, 1H), 2.58-2.77 (m, 4H), 3.41-3.51 (m, 1H), 4.79 (septet, J=5.9 Hz, 1H), 5.01 (s, 2H), 6.69 (dd, J=8.8, 2.4 Hz, 1H), 6.91 (d, J=2.4 Hz, 1H), 7.19 (d, J=8.6 Hz, 1H), 7.28 (d, J=8.8 Hz, 1H), 7.70 (dd, J=8.8, 2.3 Hz, 1H), 7.76 (d, J=2.1 Hz, 1H), 10.45 (s, 1H), 12.1 (bs, 1H).

Resolution via Chiral HPLC.
Column: normal phase preparative ChiralCel OD, 50×500 mm ID, 20 μm particle size
Eluent: 75% Hexane/25% Isopropanol, with 0.05% trifluoroacetic acid
Gradient: Isocratic
Flow: 60 mL/min
Detector: 254 nm
Retention Times: 1$^{st}$ enantiomer: 33 min; 2$^{nd}$ enantiomer: 40 min.

Example 1.4

Preparation of 2-(7-(4-Cyclopentyl-3-(trifluoromethyl)benzyloxy)-1,2,3,4-tetrahydrocyclopenta[b]indol-3-yl)acetic Acid (Compound 12)

Step A: Preparation of Methyl 4-Chloro-3-(trifluoromethyl)benzoate.

To a solution of 4-chloro-3-(trifluoromethyl)benzoic acid (10.37 g, 46.2 mmol) in methanol (100 mL) was added concentrated sulfuric acid (0.51 mL, 9.24 mmol). The mixture was heated under reflux overnight. The mixture was allowed to cool to room temperature and concentrated under reduced pressure to form a solid. The solid was filtered and washed with water. The solid was then stirred with saturated aqueous sodium bicarbonate solution to remove any residual sulfuric acid, filtered and dried under vacuum to give the title compound as a white solid (10.18 g). $^1$H NMR (400 MHz, CDCl$_3$) δ ppm 3.96 (s, 3H), 7.60 (d, J=8.34 Hz, 1H), 8.14 (dd, J=8.34, 2.02 Hz, 1H), 8.37 (d, J=2.02 Hz, 1H).

Step B: Preparation of Methyl 4-Cyclopentyl-3-(trifluoromethyl)benzoate.

To zinc(II) chloride (0.5 M solution in tetrahydrofuran, 88.0 mL, 44.0 mmol) was added cyclopentylmagnesium chloride (2 M solution in ether, 20.5 mL, 41.1 mmol). The resulting suspension was stirred at room temperature for 1 h. To the above suspension was added methyl 4-chloro-3-(trifluoromethyl)benzoate (7.00 g, 29.3 mmol) and bis(tri-tert-butylphosphine)palladium (1.35 g, 2.64 mmol) at room temperature. The mixture was heated under reflux for 2 h. The mixture was allowed to cool to room temperature, quenched with saturated aqueous sodium bicarbonate solution and filtered. The filtrate was extracted with ethyl acetate. The organic layer was dried over anhydrous sodium sulfate, concentrated under reduced pressure and purified by silica gel column chromatography to give the title compound as an oil (7.64 g). LCMS m/z=273.2 [M+H]$^+$; $^1$H NMR (400 MHz, CDCl$_3$) δ ppm 1.57-1.66 (m, 2H), 1.68-1.82 (m, 2H), 1.82-1.94 (m, 2H), 2.04-2.21 (m, 2H), 3.33-3.49 (m, 1H), 3.93 (s, 3H), 7.54 (d, J=8.21 Hz, 1H), 8.13 (dd, J=8.34, 1.77 Hz, 1H), 8.27 (s, 1H).

Step C: Preparation of (4-Cyclopentyl-3-(trifluoromethyl)phenyl)methanol.

To a solution of methyl 4-cyclopentyl-3-(trifluoromethyl)benzoate (8.16 g, 30.0 mmol) in 1,4-dioxane (200 mL) was added lithium borohydride solution (2 M in tetrahydrofuran, 30.0 mL, 59.9 mmol). The mixture was heated under reflux for 2.5 h. The mixture was allowed to cool to room temperature and carefully quenched with 1 N aqueous HCl solution to pH 5. The organic layer was separated and the aqueous layer was extracted with ethyl acetate. The combined organic layers were dried over anhydrous sodium sulfate, concentrated under reduced pressure and purified by silica gel column chromatograhy to give the title compound as a colorless oil (1.21 g). $^1$H NMR (400 MHz, CDCl$_3$) δ ppm 1.56-1.63 (m, 2H), 1.66-1.77 (m, 2H), 1.81-1.91 (m, 2H), 2.03-2.15 (m, 2H), 3.37 (quintet, J=8.00 Hz, 1H), 4.71 (d, J=4.29 Hz, 2H), 7.45-7.47 (m, 1H), 7.49 (d, J=1.14 Hz, 1H), 7.60 (s, 1H).

Step D: Preparation of 4-(Chloromethyl)-1-cyclopentyl-2-(trifluoromethyl)benzene.

To (4-cyclopentyl-3-(trifluoromethyl)phenyl)methanol (1.21 g, 4.95 mmol) was added thionyl chloride (5.5 mL, 74.2 mmol). The mixture was heated at 50° C. for 2 h before it was allowed to cool to room temperature and stirred at room temperature overnight. The mixture was poured into an ice and stirred for 5 min before it was extracted with dichloromethane. The organic extract was washed with saturated aqueous sodium bicarbonate solution, dried over anhydrous sodium sulfate and concentrated under reduced pressure to give the title compound as an oil (1.16 g). $^1$H NMR (400 MHz, CDCl$_3$) δ ppm 1.55-1.63 (m, 2H), 1.69-1.77 (m, 2H), 1.82-1.90 (m, 2H), 2.05-2.13 (m, 2H), 3.37 (quintet, J=8.59 Hz, 1H), 4.58 (s, 2H), 7.46 (d, J=8.00 Hz, 1H), 7.52 (d, J=8.00 Hz, 1H), 7.61 (d, J=1.52 Hz, 1H).

Step E: Preparation of Ethyl 2-(7-(4-Cyclopentyl-3-(trifluoromethyl)benzyloxy)-1,2,3,4-tetrahydrocyclopenta[b]indol-3-yl)acetate.

To a solution of ethyl 2-(7-hydroxy-1,2,3,4-tetrahydrocyclopenta[b]indol-3-yl)acetate (50.0 mg, 0.193 mmol) and 4-(chloromethyl)-1-cyclopentyl-2-(trifluoromethyl)benzene (152.0 mg, 0.578 mmol) in DMF (3 mL) was added cesium carbonate (75.0 mg, 0.231 mmol). The mixture was stirred at room temperature overnight, filtered through Celite®, and concentrated under reduced pressure. The residue was purified by HPLC to give the title compound as a light pink oil (38.7 mg). LCMS m/z=486.5 [M+H]$^+$.

Step F: Preparation of 2-(7-(4-Cyclopentyl-3-(trifluoromethyl)benzyloxy)-1,2,3,4-tetrahydrocyclopenta[b]indol-3-yl)acetic Acid.

To a solution of ethyl 2-(7-(4-cyclopentyl-3-(trifluoromethyl)benzyloxy)-1,2,3,4-tetrahydrocyclopenta[b]indol-3-yl)acetate (38.7 mg, 0.080 mmol) in a mixed solvent of methanol (1.5 mL), tetrahydrofuran (0.5 mL), and water (0.5 mL) was added LiOH hydrate (11.7 mg, 0.279 mmol). The mixture was stirred at room temperature overnight before the mixture was acidified to pH 4 with 1 N aqueous HCl solution and extracted with ethyl acetate. The organic layer was dried over anhydrous sodium sulfate, concentrated under reduced pressure and dried under vacuum. The foam was triturated with water to give a solid. The solid was filtered to give the title compound as a light pink solid (25.7 mg). LCMS m/z=458.4[M+H]$^+$; $^1$H NMR (400 MHz, DMSO-d$_6$) δ ppm 1.56-1.70 (m, 4H), 1.80-1.87 (m, 2H), 1.95-2.11 (m, 3H), 2.34 (dd, J=16.04, 8.97 Hz, 1H), 2.59-2.74 (m, 4H), 3.21-3.25 (m, 1H), 3.41-3.49 (m, 1H), 5.11 (s, 2H), 6.70 (dd, J=8.72, 2.40 Hz, 1H), 6.92 (d, J=2.27 Hz, 1H), 7.19 (d, J=8.72 Hz, 1H), 7.61 (d, J=8.00 Hz, 1H), 7.68 (d, J=8.00 Hz, 1H), 7.70 (s, 1H), 10.45 (s, 1H), 12.18 (bs, 1H).

Resolution via Chiral HPLC.
Column: normal phase preparative ChiralCel OD, 50×500 mm ID, 20 µm particle size
Eluent: IPA containing 0.05% TFA/hexanes containing 0.05% TFA (8/92)
Gradient: Isocratic
Flow: 60 mL/min
Detector: 220 nm
Retention Times: 1$^{st}$ enantiomer: 38.9 min; 2$^{nd}$ enantiomer: 48.4 min.

Example 1.5

Preparation of 2-(7-((5-Isopropoxypyrazin-2-yl)methoxy)-1,2,3,4-tetrahydrocyclopenta[b]indol-3-yl)acetic Acid (Compound 11)

Step A: Preparation of 2-Isopropoxy-5-methylpyrazine.

To a solution of 2-bromo-5-methylpyrazine (3 g, 17.34 mmol) in 2-propanol (14 mL) was added sodium propan-2-olate (3.56 g, 43.3 mmol) and heated under microwave irradiation at 115° C. for 1.1 h. The organic solvent was evaporated before water was added to the residue. The mixture was extracted with dichloromethane (2×75 mL). The organic phase was dried over sodium sulfate, filtered and concentrated. The residue was purified by silica gel column chromatography to give the title compound as a brown oil (1.0 g). LCMS m/z=153.4 [M+H]$^+$; $^1$H NMR (400 MHz, CDCl$_3$) δ ppm 1.27 (d, J=6.19 Hz, 6H), 2.39 (s, 3H), 5.10-5.20 (m, 1H), 7.84 (s, 1H), 7.99 (s, 1H).

Step B: Preparation of 2-Isopropoxy-5-methylpyrazine.

A mixture of 2-isopropoxy-5-methylpyrazine (0.250 g, 1.65 mmol), NBS (0.293 g, 1.65 mmol) and AIBN (0.270 g, 1.65 mmol) in toluene (5 mL) was refluxed for 1 h after which 1.0 eq of NBS was added. The reaction mixture was heated under reflux for 20 min before it was cooled to room temperature. The solids were removed by filtration and the filtrate was concentrated under vacuum. The residue was purified by silica gel column chromatography to give the title compound as a brown oil (35 mg).

Step C: Preparation of 2-(7-((5-Isopropoxypyrazin-2-yl)methoxy)-1,2,3,4-tetrahydrocyclopenta[b]indol-3-yl)acetic Acid.

Ethyl 2-(7-hydroxy-1,2,3,4-tetrahydrocyclopenta[b]indol-3-yl)acetate (0.035 g, 0.135 mmol) and cesium carbonate (0.048 g, 0.148 mmol) were dissolved in DMF (0.5 mL) and stirred at room temperature for 5 min. To this mixture at 0° C. was added a solution of 2-(bromomethyl)-5-isopropoxypyrazine (0.034 g, 0.148 mmol) in DMF (0.20 mL) and was stirred at room temperature for 60 h. The solids were removed by filtration. The filtrate was purified by HPLC to give ethyl 2-(7-((5-isopropoxypyrazin-2-yl)methoxy)-1,2,3,4-tetrahydrocyclopenta[b]indol-3-yl)acetate (11 mg). To the ester dissolved in dioxane (288 µL) was added aqueous LiOH (1 N, 72 µL). The mixture was stirred at room temperature for 16 h; before more aqueous LiOH (1 N, 200 µL) was added. Stirring was continued for 1 h. To the reaction mixture was added water (1.5 mL) and the reaction mixture was acidified to pH 3 with 1 N HCl. The mixture was purified by HPLC to give the title compound as a yellow solid (7 mg). LCMS m/z=382.4 [M+H]$^+$; $^1$H NMR (500 MHz, CDCl$_3$) δ ppm 1.32 (d, J=6.31 Hz, 6H), 1.95-2.18 (m, 1H), 2.28-2.41 (m, 1H), 2.56-2.79 (m, 4H), 3.36-3.56 (m, 1H), 5.09 (s, 2H), 5.15-5.33 (m, 1H), 6.71 (d, J=8.83 Hz, 1H), 6.94 (s, 1H), 7.20 (d, J=8.83 Hz, 1H), 8.20 (s, 1H), 8.30 (s, 1H), 10.37 (s, 1H).

Example 1.6

Preparation of 2-(7-(3-Cyano-4-(trifluoromethoxy)benzyloxy)-1,2,3,4-tetrahydrocyclopenta[b]indol-3-yl)acetic Acid (Compound 7)

Step A: Preparation of 3-Bromo-4-(trifluoromethoxy)benzoic Acid.

4-(Trifluoromethoxy)benzoic acid (2 g, 9.70 mmol) and iron(III) chloride (1.574 g, 9.70 mmol) were suspended in nitromethane (20 mL). To this mixture was added bromine (0.497 mL, 9.70 mmol) at 0° C. The solution was heated under microwave irradiation at 110° C. for 2 h. The reaction mixture was added to cold water (100 mL) and extracted with ethylacetate (2×100 mL). The organic phase was washed with an aqueous solution of sodium thiosulfate pentahydrate and brine. The organic layer was concentrated and the residue was purified by HPLC to give the title compound as a white solid (1.5 g). LCMS m/z=287.0 [M+H]$^+$; $^1$H NMR (400 MHz, DMSO-d$_6$) δ ppm 7.67 (d, 1H), 8.06 (d, 1H), 8.29 (s, 1H), 13.47 (s, 1H).

Step B: Preparation of 3-Cyano-4-(trifluoromethoxy)benzoic Acid.

3-Bromo-4-(trifluoromethoxy)benzoic acid (1.4 g, 4.91 mmol) and cyanocopper (0.572 g, 6.39 mmol) were mixed in N-methyl-2-pyrrolidinone (NMP) (14 mL). The mixture was heated in a microwave at 200° C. for 2 h. The reaction was diluted with dichloromethane (150 mL). Celite® was added and the mixture was stirred vigorously for 10 min. The solids were removed by filtration. The organic layer was washed with water (125 mL) and concentrated. The residue was purified by HPLC to give the title compound as an off-white solid (0.979 g). LCMS m/z=232.3 [M+H]$^+$.

Step C: Preparation of 5-(Hydroxymethyl)-2-(trifluoromethoxy)benzonitrile.

From 3-cyano-4-(trifluoromethoxy)benzoic acid, in a similar manner to the one described in Example 1.3, Step A, the title compound was obtained as a clear oil. LCMS m/z=218.2 [M+H]$^+$. $^1$H NMR (400 MHz, CDCl$_3$) δ ppm 4.81 (s, 2H), 7.40-7.44 (m, 1H), 7.67-7.71 (m, 2H), 7.78 (s, 1H).

Step D: Preparation of 5-(Chloromethyl)-2-(trifluoromethoxy)benzonitrile.

5-(Hydroxymethyl)-2-(trifluoromethoxy)benzonitrile (0.150 g, 0.691 mmol) was taken up in toluene (2 mL) and thionyl chloride (0.303 mL, 4.14 mmol) was added. The mixture was heated at 75° C. for 15 min. Water was added and the mixture was extracted with hexanes (2×75 mL). The organics were treated with aqueous NaHCO$_3$. The organic layer was separated, dried over magnesium sulfate, filtered and concentrated to give the title compound as a colorless oil (120 mg). LCMS m/z=236.2 [M+H]$^+$. $^1$H NMR (500 MHz, CDCl$_3$) δ ppm 1.98 (s, 1H), 4.52 (s, 2H), 7.32-7.34 (m, 1H), 7.59-7.62 (m, 1H), 7.68 (s, 1H).

Step E: Preparation of 2-(7-(3-Cyano-4-(trifluoromethoxy)benzyloxy)-1,2,3,4-tetrahydrocyclopenta[b]indol-3-yl)acetic Acid.

Ethyl 2-(7-hydroxy-1,2,3,4-tetrahydrocyclopenta[b]indol-3-yl)acetate (0.100 g, 0.386 mmol) and cesium carbonate (0.138 g, 0.424 mmol) were dissolved in DMF (1.0 mL), stirred at room temperature for 10 min, followed by addition of 5-(chloromethyl)-2-(trifluoromethoxy)benzonitrile (0.100 g, 0.424 mmol) in DMF (0.300 mL) at 0° C. This mixture was stirred at room temperature for 3 h. The reaction mixture was quenched with water and extracted with ethylacetate (2×50 mL). The organic phase was washed with brine and concentrated. The residue was taken up in dioxane (4 mL) before aqueous 1 N LiOH (1.3 mL) was added. The mixture was stirred at room temperature for 2.5 h before it was quenched with water and acidified to pH 3 using aqueous 3 N HCl. The mixture was purified by HPLC to give the title compound (0.040 g). LCMS m/z=431.2 [M+H]$^+$, $^1$H NMR (500 MHz, DMSO-d$_6$) δ ppm 2.00-2.20 (m, 1H), 2.01-2.21 (m, 1H), 2.23-2.43 (m, 1H), 2.55-2.83 (m, 4H), 3.33-3.57 (m, 1H), 5.16 (s, 2H), 6.73 (dd, J=8.83, 2.52 Hz, 1H), 6.94 (s, 1H), 7.21 (d, J=8.83 Hz, 1H), 7.69 (dd, J=8.67, 1.42 Hz, 1H), 7.94 (dd, J=8.67, 2.05 Hz, 1H), 8.09 (s, 1H), 10.40 (s, 1H).

Example 1.7

Preparation of 2-(7-(2,4-Bis(trifluoromethyl)benzyloxy)-1,2,3,4-tetrahydrocyclopenta[b]indol-3-yl) acetic Acid (Compound 8)

Step A: Preparation of Ethyl 2-(7-(2,4-Bis(trifluoromethyl)benzyloxy)-1,2,3,4-tetrahydrocyclopenta[b]indol-3-yl)acetate.

To a mixture of ethyl 2-(7-hydroxy-1,2,3,4-tetrahydrocyclopenta[b]indol-3-yl)acetate (0.130 g, 0.5 mmol) and K$_2$CO$_3$ (0.069 g, 0.500 mmol) in DMF (1 mL) was added 1-(bromomethyl)-2,4-bis(trifluoromethyl)benzene (0.154 g, 0.500 mmol). The mixture was heated at 70° C. overnight, taken up in EtOAc, washed with water (thrice) and brine. The organics were dried over MgSO$_4$ and concentrated. The residue was purified by silica gel column chromatography to give the title compound an orange solid (0.195 g). LCMS m/z=486.3 [M+H]$^+$.

Step B: Preparation of 2-(7-(2,4-Bis(trifluoromethyl)benzyloxy)-1,2,3,4-tetrahydrocyclopenta[b]indol-3-yl)acetic Acid.

To a solution of ethyl 2-(7-(2,4-bis(trifluoromethyl)benzyloxy)-1,2,3,4-tetrahydrocyclopenta[b]indol-3-yl)acetate (0.191 g, 0.393 mmol) in dioxane (1.312 mL) and water (0.656 mL) was added NaOH (0.826 mL, 0.826 mmol). The mixture was heated under reflux for 2 h, cooled to room temperature and diluted with water. After washing with DCM, the aqueous layer was acidified with 1 M HCl and extracted with EtOAc (thrice). The combined extracts were washed with brine, dried over MgSO$_4$ and concentrated to give the title compound as a magenta solid (19.9 mg). LCMS m/z=458.1 [M+H]$^+$, $^1$H NMR (400 MHz, DMSO-d$_6$) δ ppm 2.03-2.13 (m, 1H), 2.35 (dd, J=15.98, 9.03 Hz, 1H), 2.58-2.78 (m, 4H), 3.41-3.52 (m, 1H), 5.31 (s, 2H), 6.72 (dd, J=8.78, 2.46 Hz, 1H), 6.92 (d, J=2.40 Hz, 1H), 7.23 (d, J=8.72 Hz, 1H), 7.99-8.19 (m, 3H), 10.52 (s, 1H), 12.19 (s, 1H).

Example 1.8

Preparation of 2-(7-(4-Cyclohexyl-3-(trifluoromethyl)benzyloxy)-1,2,3,4-tetrahydrocyclopenta[b] indol-3-yl)acetic Acid (Compound 2)

Step A: Preparation of 1-Chloro-4-(chloromethyl)-2-(trifluoromethyl)benzene.

(4-Chloro-3-(trifluoromethyl)phenyl)methanol (5.1 g, 24.22 mmol) was added in small portions to thionyl chloride (20 mL, 275 mmol). The reaction mixture was stirred at 50° C. for 18 h and heated under reflux for 23 h. The mixture was concentrated and dried under high vacuum to give the title compound as a colorless liquid (5.41 g). $^1$H NMR (400 MHz, CDCl$_3$) δ ppm 4.58 (s, 2H), 7.50-7.51 (m, 2H), 7.71 (s, 1H).

Step B: Preparation of Ethyl 2-(7-(4-Chloro-3-(trifluoromethyl)benzyloxy)-1,2,3,4-tetrahydrocyclopenta[b]indol-3-yl)acetate.

A mixture of ethyl 2-(7-hydroxy-1,2,3,4-tetrahydrocyclopenta[b]indol-3-yl)acetate (222 mg, 0.856 mmol), 1-chloro-4-(chloromethyl)-2-(trifluoromethyl)benzene (240 mg, 1.048 mmol), and cesium carbonate (165 mg, 0.856 mmol) in DMF (5 mL) was stirred at room temperature. After 3 days, more cesium carbonate (165 mg, 0.856 mmol) was added. After stirring for an additional 2 d, the mixture was extracted with water and CH$_2$Cl$_2$. The organics were dried over MgSO$_4$, filtered and concentrated. The residue was purified by silica gel column chromatography to give the title compound as a white solid (258 mg). LCMS m/z=452.1 [M+H]$^+$;

¹H NMR (400 MHz, CDCl₃) δ ppm 1.29 (t, J=7.2 Hz, 3H), 2.06-2.14 (m, 1H), 2.47-2.54 (m, 1H), 2.71-2.86 (m, 4H), 3.51-3.57 (m, 1H), 4.17-4.25 (m, 2H), 5.10 (s, 2H), 6.82 (dd, J=8.8, 2.5, 1H), 6.96 (d, J=2.5 Hz, 1H), 7.21 (dd, J=8.8, 0.32 Hz, 1H), 7.49-7.52 (m, 1H), 7.58 (dd, J=8.2, 2.6 Hz, 1H), 7.80 (d, J=1.92 Hz, 1H), 8.48 (s, 1H).

Step C: Preparation of 2-(7-(4-Cyclohexyl-3-(trifluoromethyl)benzyloxy)-1,2,3,4-tetrahydrocyclopenta[b]indol-3-yl)acetic Acid.

A mixture of ethyl 2-(7-(4-chloro-3-(trifluoromethyl)benzyloxy)-1,2,3,4-tetrahydrocyclopenta[b]indol-3-yl)acetate (50 mg, 0.111 mmol), 0.5 M cyclohexylzinc(II) bromide (0.5 M in THF, 3 mL, 1.5 mmol), and bis(tri-t-butylphosphine)palladium (3 mg, 5.87 µmol) were stirred under reflux for 18 h. The mixture was allowed to cool to room temperature before water (1 mL), MeOH (1 mL) and LiOH hydrate (70 mg, 1.668 mmol) were added. The mixture was stirred at room temperature for 2 h. The mixture was purified by HPLC. Fractions containing product were basified with 1 M NaHCO₃ and partially concentrated. The residue was extracted with 0.5 M citric acid and CH₂Cl₂. The organics were dried over MgSO₄, filtered and concentrated to give the title compound as a tanned sticky solid (14.4 mg). LCMS m/z=472.2 [M+H]⁺; ¹H NMR (400 MHz, CDCl₃) δ ppm 1.38-1.50 (m, 4H), 1.76-1.85 (m, 6H), 2.11-2.17 (m, 1H), 2.58-2.65 (m, 1H), 2.75-2.93 (m, 5H), 3.56-3.60 (m, 1H), 5.07 (s, 2H), 6.84 (dd, J=8.8, 2.5 Hz, 1H), 7.00 (d, J=2.4 Hz, 1H), 7.21 (d, J=8.8 Hz, 1H), 7.46 (d, J=8.1 Hz, 1H), 7.59 (d, J=8.1 Hz, 1H), 7.70 (d, J=1.2 Hz, 1H), 8.27 (s, 1H).

Example 1.9

Preparation of 2-(7-(4-(Pyrrolidin-1-yl)-3-(trifluoromethyl)benzyloxy)-1,2,3,4-tetrahydrocyclopenta[b]indol-3-yl)acetic Acid (Compound 13)

Step A: Preparation of Ethyl 2-(7-(4-(Pyrrolidin-1-yl)-3-(trifluoromethyl)benzyloxy)-1,2,3,4-tetrahydrocyclopenta[b]indol-3-yl)acetate.

A mixture of ethyl 2-(7-(4-chloro-3-(trifluoromethyl)benzyloxy)-1,2,3,4-tetrahydrocyclopenta[b]indol-3-yl)acetate (50.9 mg, 0.113 mmol), pyrrolidine (0.047 mL, 0.563 mmol), diacetoxypalladium (1.264 mg, 5.63 µmol), biphenyl-2-yl-di-tert-butylphosphine (3.36 mg, 11.0 µmol) and sodium 2-methylpropan-2-olate (27.1 mg, 0.282 mmol) in dioxane (3 mL) was heated under microwave irradiation at 120° C. for 2 h. The mixture was purified by HPLC. Fractions containing product were basified with 1 M NaHCO₃ and concentrated. The residue was extracted with 0.5 M citric acid and CH₂Cl₂. The organics were dried over MgSO₄, filtered, and concentrated to give the title compound as a white solid (17.8 mg). LCMS m/z=487.4 [M+H]⁺.

Step B: Preparation of 2-(7-(4-(Pyrrolidin-1-yl)-3-(trifluoromethyl)benzyloxy)-1,2,3,4-tetrahydrocyclopenta[b]indol-3-yl)acetic Acid.

To a solution of ethyl 2-(7-(4-(pyrrolidin-1-yl)-3-(trifluoromethyl)benzyloxy)-1,2,3,4-tetrahydrocyclopenta[b]indol-3-yl)acetate (17.8 mg, 0.037 mmol) in 5 mL (THF/water/MeOH 3:1:1), LiOH hydrate (7.68 mg, 0.183 mmol) was added. After stirring at room temperature for 2 h, the mixture was partially concentrated and the residue was extracted with 0.5 M citric acid and CH₂Cl₂. The organics were dried over MgSO₄, filtered and concentrated to give the title compound as a brownish sticky solid (16.3 mg). LCMS m/z=459.4 [M+H]⁺; ¹H NMR (400 MHz, CDCl₃) δ ppm 1.83-1.95 (m, 4H), 2.09-2.16 (m, 1H), 2.57-2.64 (m, 1H), 2.73-2.90 (m, 4H), 3.27-3.35 (m, 4H), 3.53-3.59 (m, 1H), 4.99 (s, 2H), 6.82 (dd, J=8.8, 2.4 Hz, 1H), 6.96-7.01 (m, 2H), 7.19 (d, J=8.7 Hz, 1H), 7.45 (dd, J=8.6 Hz, 2.0 Hz, 1H), 7.66 (d, J=2.0 Hz, 1H), 8.27 (s, 1H).

Example 1.10

Preparation of 2-(7-(4-Isobutyl-3-(trifluoromethyl)benzyloxy)-1,2,3,4-tetrahydrocyclopenta[b]indol-3-yl)acetic Acid (Compound 14)

Ethyl 2-(7-(4-chloro-3-(trifluoromethyl)benzyloxy)-1,2,3,4-tetrahydrocyclopenta[b]indol-3-yl)acetate (200 mg, 0.443 mmol) was dissolved in THF (7 mL) and isobutylzinc(II) bromide (2.66 mL, 1.328 mmol) and bis(tri-t-butylphosphine)palladium(0) (0.011 g, 0.022 mmol) were added. The reaction was stirred at room temperature for 16 h and warmed to 50° C. After stirring for 24 h, isobutylzinc(II) bromide (4 mL) was added and the mixture was heated to 90° C. The reaction was cooled to room temperature, and 1.0 M LiOH (5 mL) and dioxane (5 mL) were added. The reaction was stirred at room temperature for 24 h and then acidified to pH 3 with 1 M HCl. The aqueous mixture was extracted three times with EtOAc. The combined extracts were dried over sodium sulfate, filtered and concentrated under reduced pressure. The residue was purified by silica gel column chromatography to provide the title compound (33 mg). LCMS m/z=446.7 [M+H]⁺; ¹H NMR (400 MHz, DMSO-d₆) δ ppm 0.89 (d, J=6.6 Hz, 6H), 1.87-1.98 (m, 1H), 2.03-2.13 (m, 1H), 2.35 (dd, J=15.9, 9.0 Hz, 1H), 2.60-2.76 (m, 6H), 3.42-3.50 (m, 1H), 5.12 (s, 2H), 6.71 (dd, J=8.6, 2.4 Hz, 1H), 6.93 (d, J=2.4 Hz, 1H), 7.20 (d, J=8.7 Hz, 1H), 7.47 (d, J=8.0 Hz, 1H), 7.67 (d, J=8.2 Hz, 1H), 7.75 (d, J=1.4 Hz, 1H), 10.47 (bs, 1H).

Example 1.11

Preparation of 2-(7-(4-Neopentyl-3-(trifluoromethyl)benzyloxy)-1,2,3,4-tetrahydrocyclopenta[b]indol-3-yl)acetic Acid (Compound 15)

Ethyl 2-(7-(4-chloro-3-(trifluoromethyl)benzyloxy)-1,2,3,4-tetrahydrocyclopenta[b]indol-3-yl)acetate (200 mg, 0.443 mmol) was dissolved in THF (7.0 mL) and neopentylzinc(II) iodide (2.66 mL of a 0.5 M solution in THF) and bis(tri-t-butylphosphine)palladium(0) (0.011 g, 0.022 mmol) were added. The reaction mixture was stirred at room temperature for 16 h and then warmed to 50° C. After stirring for 24 h, neopentylzinc(II) iodide (5.0 mL of a 0.5 M solution in THF) was added and the reaction mixture was heated to 90° C. The reaction vessel was cooled to room temperature before 1.0 M LiOH (5 mL) and dioxane (5.0 mL) were added. After stirring for 24 h, the reaction was acidified with 1.0 M HCl to pH 3 and extracted three times with EtOAc. The combined extracts were dried over sodium sulfate, filtered and concentrated under reduced pressure. The residue was purified by HPLC. The purified fractions were neutralized with sodium bicarbonate and then acidified to pH 5 with 1.0 M citric acid. The aqueous mixture was extracted with EtOAc and the organic layer was washed two times with water. The EtOAc layer was dried over sodium sulfate, filtered and concentrated under reduced pressure to provide the title compound (12.3 mg). LCMS m/z=460.6 [M+H]⁺; ¹H NMR (400 MHz, CDCl₃) δ ppm 0.96 (s, 9H), 2.08-2.19 (m, 1H), 2.61 (dd, J=17.0, 10.9 Hz, 1H), 2.73-2.90 (m, 6H), 3.54-3.63 (m, 1H), 5.09 (s, 2H), 6.85 (dd, J=8.8, 2.5 Hz, 1H), 7.0 (d, J=2.5 Hz, 1H), 7.22 (d, J=9.0 Hz, 1H), 7.36 (d, J=8.0 Hz, 1H), 7.55 (d, J=8.1 Hz, 1H), 7.74 (d, J=1.1 Hz, 1H), 8.29 (bs, 1H).

Example 1.12

Preparation of 2-(7-(4-Chloro-3-(trifluoromethyl) benzyloxy)-1,2,3,4-tetrahydrocyclopenta[b]indol-3-yl)acetic Acid (Compound 16)

The title compound was isolated as a by-product from Example 1.11. LCMS m/z=424.2 [M+H]$^+$; $^1$H NMR (400 MHz, CDCl$_3$) δ ppm 2.09-2.19 (m, 1H), 2.61 (dd, J=17.3, 11.0 Hz, 1H), 2.72-2.89 (m, 4H), 3.53-3.63 (m, 1H), 5.10 (s, 2H), 6.83 (dd, J=8.7, 2.4 Hz, 1H), 6.97 (d, J=2.4 Hz, 1H), 7.22 (d, J=8.6 Hz, 1H), 7.50 (d, J=8.2 Hz, 1H), 7.57 (dd, J=8.2, 1.6 Hz, 1H), 7.80 (d, J=1.8 Hz, 1H), 8.33 (bs, 1H).

Example 1.13

Preparation of 2-(7-(3-Cyano-4-cyclohexylbenzyloxy)-1,2,3,4-tetrahydrocyclopenta[b]indol-3-yl) acetic Acid (Compound 17)

Step A: Preparation of Methyl 3-cyano-4-hydroxybenzoate.

To a mixture of methyl 3-bromo-4-hydroxybenzoate (1.78 g, 7.70 mmol) and copper(I) cyanide (0.897 g, 10.02 mmol) was added NMP (10 mL). The mixture was heated to 200° C. for 2 h under microwave irradiation. The mixture was diluted with ethyl acetate and quenched with 1 N aqueous HCl solution. After the addition of brine, the organic layer was separated and the aqueous layer was extracted with ethyl acetate. The combined organic layers were dried over anhydrous sodium sulfate, concentrated under reduced pressure and purified by silica gel column chromatography. The combined fractions were concentrated under reduced pressure and triturated with cold water to provide the title compound as an off-white solid (0.63 g). LCMS m/z=178.2 [M+H]$^+$; $^1$H NMR (400 MHz, CDCl$_3$) δ ppm 3.92 (s, 3H), 6.55 (bs, 1H), 7.04 (d, J=8.72 Hz, 1H), 8.15 (dd, J=8.72, 2.15 Hz, 1H), 8.23 (d, J=1.89 Hz, 1H).

Step B: Preparation of Methyl 3-Cyano-4-(trifluoromethylsulfonyloxy)benzoate.

To a suspension of methyl 3-cyano-4-hydroxybenzoate (1.24 g, 7.0 mmol) in dichloromethane (35 mL) was added trifluoromethanesulfonic anhydride (1.8 mL, 10.7 mmol), diisopropylethylamine (1.8 mL, 10.3 mmol), and N,N-dimethylaminopyridine (0.21 g, 1.75 mmol) at 0° C. The mixture was stirred at room temperature overnight. The reaction was quenched with 1 N aqueous HCl solution. The organic layer was separated and the aqueous layer was extracted with dichloromethane. The combined organic layers were dried over anhydrous magnesium sulfate, concentrated under reduced pressure and purified by silica gel column chromatography to provide the title compound as a brown oil (1.44 g). $^1$H NMR (400 MHz, CDCl$_3$) δ ppm 3.99 (s, 3H), 7.59 (d, J=8.84 Hz, 1H), 8.37 (dd, J=8.84, 2.15 Hz, 1H), 8.44 (d, J=2.02 Hz, 1H).

Step C: Preparation of Methyl 3-Cyano-4-cyclohexylbenzoate.

To a solution of methyl 3-cyano-4-(trifluoromethylsulfonyloxy)benzoate (0.7 g, 2.26 mmol) in tetrahydrofuran (30 mL) was added 0.5 M cyclohexylzinc(II) bromide solution in tetrahydrofuran (13.6 mL, 6.8 mmol) and bis(tri-tert-butylphosphine)palladium (0.058 g, 0.113 mmol) at room temperature. The mixture was heated under reflux for 2 h. The mixture was allowed to cool to room temperature, quenched with saturated aqueous sodium bicarbonate solution and filtered through Celite®. The filtrate was extracted with ethyl acetate. The organic layer was dried over anhydrous sodium sulfate, concentrated under reduced pressure and purified by silica gel column chromatography to provide the title compound as an oil (0.24 g). $^1$H NMR (400 MHz, CDCl$_3$) δ ppm 1.24-1.33 (m, 1H), 1.42-1.53 (m, 4H), 1.77-1.84 (m, 1H), 1.86-1.95 (m, 4H), 2.99-3.08 (m, 1H), 3.93 (s, 3H), 7.45 (d, J=8.34 Hz, 1H), 8.17 (dd, J=8.15, 1.71 Hz, 1H), 8.27 (d, J=1.52 Hz, 1H).

Step D: Preparation of 2-Cyclohexyl-5-(hydroxymethyl)benzonitrile.

To a solution of methyl 3-cyano-4-cyclohexylbenzoate (299.0 mg, 1.229 mmol) in 1,4-dioxane (30 mL) was added 2 M lithium borohydride solution in tetrahydrofuran (1.23 mL, 2.46 mmol). The mixture was heated under reflux for 2.5 h. The mixture was cooled to 0° C. and quenched with 1 N aqueous HCl solution slowly to pH 5. After the addition of brine solution, the mixture was extracted with ethyl acetate. The organic layer was dried over anhydrous sodium sulfate, concentrated under reduced pressure and purified by silica gel column chromatography to provide the title compound as a white solid (190.5 mg). LCMS m/z=216.5 [M+H]$^+$; $^1$H NMR (400 MHz, CDCl$_3$) δ ppm 1.23-1.33 (m, 1H), 1.41-1.52 (m, 4H), 1.76-1.83 (m, 1H), 1.84-1.92 (m, 4H), 2.90-3.05 (m, 1H), 4.70 (d, J=5.81 Hz, 2H), 7.36 (d, J=8.21 Hz, 1H), 7.53 (dd, J=8.27, 1.71 Hz, 1H), 7.61 (d, J=1.39 Hz, 1H).

Step E: Preparation of 5-(Chloromethyl)-2-cyclohexylbenzonitrile.

To 2-cyclohexyl-5-(hydroxymethyl)benzonitrile (190.5 mg, 0.885 mmol) was added thionyl chloride (5.0 mL, 68.1 mmol). The mixture was heated at 50° C. for 2 h and then room temperature overnight. The mixture was poured into an ice and stirred for 5 min. The mixture was extracted with dichloromethane. The organic layer was washed with saturated aqueous sodium bicarbonate solution, dried over anhydrous sodium sulfate and concentrated under reduced pressure to provide the title compound as a white solid (184.9 mg). LCMS m/z=234.1 [M+H]$^+$; $^1$H NMR (400 MHz, CDCl$_3$) δ ppm 1.23-1.31 (m, 1H), 1.40-1.52 (m, 4H), 1.76-1.82 (m, 1H), 1.83-1.92 (m, 4H), 2.93-3.03 (m, 1H), 4.55 (s, 2H), 7.37 (d, J=8.08 Hz, 1H), 7.55 (dd, J=8.02, 1.83 Hz, 1H), 7.62 (d, J=1.64 Hz, 1H).

Step F: Preparation of Ethyl 2-(7-(3-Cyano-4-cyclohexylbenzyloxy)-1,2,3,4-tetrahydrocyclopenta[b]indol-3-yl)acetate.

To a solution of ethyl 2-(7-hydroxy-1,2,3,4-tetrahydrocyclopenta[b]indol-3-yl)acetate (166.0 mg, 0.641 mmol) and 5-(chloromethyl)-2-cyclohexylbenzonitrile (147.0 mg, 0.629 mmol) in N,N-dimethylformamide (15 mL) was added cesium carbonate (246.0 mg, 0.755 mmol). The mixture was stirred at room temperature for 41 h. The mixture was diluted with ethyl acetate, filtered through Celite®, concentrated under reduced pressure and purified by silica gel column chromatography to provide the title compound as a yellow foam (185.3 mg). LCMS m/z=457.5 [M+H]$^+$; $^1$H NMR (400 MHz, CDCl$_3$) δ ppm 1.18-1.28 (m, 1H), 1.30 (t, J=7.20 Hz, 3H), 1.41-1.52 (m, 4H), 1.79 (dd, J=12.82, 1.33 Hz, 1H), 1.85-1.93 (m, 4H), 2.06-2.15 (m, 1H), 2.50 (dd, J=16.80, 11.24 Hz, 1H), 2.68-2.86 (m, 4H), 2.94-3.04 (m, 1H), 3.49-3.61 (m, 1H), 4.16-4.25 (m, 2H), 5.06 (s, 2H), 6.82 (dd, J=8.78, 2.46 Hz, 1H), 6.97 (d, J=2.53 Hz, 1H), 7.21 (d, J=8.72 Hz, 1H), 7.37 (d, J=8.21 Hz, 1H), 7.62 (dd, J=8.15, 1.71 Hz, 1H), 7.71 (d, J=1.52 Hz, 1H), 8.47 (bs, 1H).

Step G: Preparation of 2-(7-(3-Cyano-4-cyclohexylbenzyloxy)-1,2,3,4-tetrahydrocyclopenta[b]indol-3-yl)acetic Acid.

To a solution of ethyl 2-(7-(3-cyano-4-cyclohexylbenzyloxy)-1,2,3,4-tetrahydrocyclopenta[b]indol-3-yl)acetate (185.3 mg, 0.406 mmol) in 1,4-dioxane (5.0 mL) was added 1 M aqueous LiOH solution (1.22 mL, 1.22 mmol). The mixture was stirred at room temperature for 5 h. The mixture was concentrated under reduced pressure. The residue was dissolved in ethyl acetate and then acidified with 1 N aqueous HCl acid solution to pH 4. The organic layer was separated, dried over anhydrous sodium sulfate and concentrated under reduced pressure. The concentrate was triturated with dichloromethane to provide the title compound as a pink solid (98.9 mg). LCMS m/z=429.6 [M+H]$^+$; $^1$H NMR (400 MHz, DMSO-$d_6$) δ ppm 1.21-1.31 (m, 1H), 1.33-1.54 (m, 4H), 1.68-1.74 (m, 1H), 1.74-1.88 (m, 4H), 2.08 (dd, J=4.93, 3.54 Hz, 1H), 2.34 (dd, J=16.04, 8.97 Hz, 1H), 2.61-2.76 (m, 4H), 2.81-2.89 (m, 1H), 3.45 (bs, 1H), 5.07 (s, 2H), 6.70 (dd, J=8.78, 2.46 Hz, 1H), 6.91 (d, J=2.40 Hz, 1H), 7.19 (d, J=8.72 Hz, 1H), 7.52 (d, J=8.08 Hz, 1H), 7.72 (dd, J=8.15, 1.71 Hz, 1H), 7.81 (d, J=1.52 Hz, 1H), 10.46 (s, 1H), 12.18 (bs, 1H).

Example 1.14

Preparation of 2-(7-(4-Propyl-3-(trifluoromethyl) benzyloxy)-1,2,3,4-tetrahydrocyclopenta[b]indol-3-yl)acetic Acid (Compound 18)

Step A: Preparation of 2-(7-(4-Propyl-3-(trifluoromethyl) benzyloxy)-1,2,3,4-tetrahydrocyclopenta[b]indol-3-yl)acetate.

To a solution of ethyl 2-(7-(4-chloro-3-(trifluoromethyl) benzyloxy)-1,2,3,4-tetrahydrocyclopenta[b]indol-3-yl)acetate (213.8 mg, 0.473 mmol) in tetrahydrofuran (5 mL) was added 0.5 M propylzinc bromide solution in tetrahydrofuran (4.7 mL, 2.4 mmol) and bis(tri-tert-butylphosphine)palladium (24.7 mg, 0.047 mmol). The mixture was heated at 90° C. for 64 h. The mixture was allowed to cool to room temperature, quenched with saturated aqueous sodium bicarbonate solution and filtered. The filtrate was extracted with ethyl acetate. The organic layer was dried over anhydrous sodium sulfate, concentrated under reduced pressure and purified by silica gel column chromatography to provide the title compound as a yellow foam (69.1 mg). LCMS m/z=460.5 [M+H]$^+$.

Step B: Preparation of 2-(7-(3-Cyano-4-cyclohexylbenzyloxy)-1,2,3,4-tetrahydrocyclopenta[b]indol-3-yl)acetic Acid.

To a solution of ethyl 2-(7-(4-propyl-3-(trifluoromethyl) benzyloxy)-1,2,3,4-tetrahydrocyclopenta[b]indol-3-yl)acetate (75.8 mg, 0.165 mmol) in 1,4-dioxane (2 mL) was added 1 M aqueous LiOH solution (0.495 mL, 0.495 mmol). The mixture was stirred at room temperature for 5 h. The mixture was then quenched with 1 N aqueous HCl solution to pH 5. After the addition of brine solution, the mixture was extracted with ethyl acetate, dried over anhydrous sodium sulfate, concentrated under reduced pressure and purified by silica gel column chromatography to provide the title compound as a purple foam (9.7 mg). LCMS m/z=432.5 [M+H]$^+$; $^1$H NMR (400 MHz, CD$_3$CN) δ ppm 0.98 (t, J=7.33 Hz, 3H), 1.57-1.71 (m, 2H), 2.04-2.18 (m, 1H), 2.60 (d, J=7.45 Hz, 2H), 2.66-2.83 (m, 5H), 3.46-3.57 (m, 1H), 5.10 (s, 2H), 6.76 (dd, J=8.78, 2.46 Hz, 1H), 6.96 (d, J=2.40 Hz, 1H), 7.23 (d, J=8.84 Hz, 1H), 7.44 (d, J=7.96 Hz, 1H), 7.62 (d, J=7.96 Hz, 1H), 7.73 (s, 1H), 8.86 (bs, 1H).

Example 1.15

Preparation of 2-(7-(4-Cyclobutyl-3-(trifluoromethyl)benzyloxy)-1,2,3,4-tetrahydrocyclopenta[b]indol-3-yl)acetic Acid (Compound 21)

To a solution of ethyl 2-(7-(4-chloro-3-(trifluoromethyl) benzyloxy)-1,2,3,4-tetrahydrocyclopenta[b]indol-3-yl)acetate (202.8 mg, 0.449 mmol) in tetrahydrofuran (1 mL) was added 0.5 M cyclobutylzinc(II) bromide solution in tetrahydrofuran (8.98 mL, 4.49 mmol) and bis(tri-t-butylphosphine) palladium (46.8 mg, 0.090 mmol) at room temperature. The mixture was heated at 90° C. for 63 h. The mixture was then quenched with 1 N aqueous HCl solution and filtered through Celite®. The filtrate was extracted with ethyl acetate. The organic layer was washed with brine solution to remove excess HCl and concentrated under reduced pressure. The residue was purified by HPLC. The combined fractions were triturated with saturated aqueous sodium bicarbonate solution to basic solution and concentrated under reduced pressure. The residue was dissolved in ethyl acetate and acidified to pH 4. The organic layer was washed with water until the aqueous layer was neutral. The organic layer was dried over anhydrous sodium sulfate and concentrated under reduced pressure to provide the title compound as a pink solid (32.3 mg). LCMS m/z=444.6 [M+H]$^+$; $^1$H NMR (400 MHz, DMSO-$d_6$) δ ppm 1.78-1.87 (m, 1H), 1.93-2.02 (m, 1H), 2.03-2.12 (m, 1H), 2.16-2.28 (m, 4H), 2.34 (dd, J=15.98, 9.03 Hz, 1H), 2.60-2.75 (m, 4H), 3.41-3.51 (m, 1H), 3.74-3.84 (m, 1H), 5.12 (s, 2H), 6.70 (dd, J=8.78, 2.46 Hz, 1H), 6.92 (d, J=2.40 Hz, 1H), 7.19 (d, J=8.84 Hz, 1H), 7.66-7.78 (m, 3H), 10.46 (s, 1H), 12.20 (bs, 1H).

Example 1.16

Preparation of 2-(7-(4-Cyclopropyl-3-(trifluoromethyl)benzyloxy)-1,2,3,4-tetrahydrocyclopenta[b]indol-3-yl)acetic Acid (Compound 22)

To a solution of ethyl 2-(7-(4-chloro-3-(trifluoromethyl) benzyloxy)-1,2,3,4-tetrahydrocyclopenta[b]indol-3-yl)acetate (200.5 mg, 0.444 mmol) in tetrahydrofuran (1 mL) was added 0.5 M cyclopropylzinc(II) bromide solution in tetrahydrofuran (8.87 mL, 4.44 mmol) and bis(tri-t-butylphosphine) palladium (46.3 mg, 0.089 mmol) at room temperature. The mixture was heated at 90° C. for 63 h. The mixture was then quenched with 1 N aqueous HCl solution and filtered through Celite®. The filtrate was extracted with ethyl acetate. The organic layer was washed with brine solution to remove excess HCl and concentrated under reduced pressure. The residue was purified by HPLC. The combined fractions were triturated with saturated aqueous sodium bicarbonate solution to basic solution and concentrated under reduced pressure. The residue was dissolved in ethyl acetate and acidified to pH 4. The organic layer was washed with water until the aqueous layer was neutral. The organic layer was dried over anhydrous sodium sulfate and concentrated under reduced pressure to provide the title compound as a light brown solid (36.6 mg). LCMS m/z=430.5 [M+H]$^+$; $^1$H NMR (400 MHz, DMSO-$d_6$) δ ppm 0.74-0.88 (m, 2H), 0.98-1.07 (m, 2H), 2.02-2.12 (m, 2H), 2.34 (dd, J=15.98, 9.03 Hz, 1H), 2.59-2.76 (m, 4H), 3.39-3.52 (m, 1H), 5.10 (s, 2H), 6.69 (dd, J=8.72, 2.53 Hz, 1H), 6.91 (d, J=2.40 Hz, 1H), 7.10-7.26 (m, 2H), 7.61 (d, J=8.34 Hz, 1H), 7.72 (d, J=1.14 Hz, 1H), 10.45 (s, 1H), 12.20 (bs, 1H).

Example 1.17

Preparation of 2-(7-((6-Cyclopentyl-5-(trifluoromethyl)pyridin-3-yl)methoxy)-1,2,3,4-tetrahydrocyclopenta[b]indol-3-yl)acetic Acid (Compound 19)

Step A: Preparation of 2-Chloro-5-(chloromethyl)-3-(trifluoromethyl)pyridine.

To a cold solution of 5-(chloromethyl)-2-methoxy-3-(trifluoromethyl)pyridine (0.3 g, 1.33 mmol) in DMF (0.6 mL) was added dropwise POCl$_3$ (1.02 g, 6.65 mmol). The reaction was stirred for 1 h at 100° C. in a sealed tube. The reaction was cooled to room temperature, and poured onto ice water (10 mL). The reaction was extracted with DCM (thrice) and the combined organic layer was washed with water and brine, dried with MgSO$_4$ and concentrated. The residue was purified by silica gel column chromatography to provide the title compound (0.20 g). LCMS m/z=230.1 [M+H]$^+$. $^1$H NMR (400 MHz, CDCl$_3$) δ ppm 4.62 (s, 2H), 8.06 (d, J=2.3 Hz, 1H), 8.57 (d, J=2.3 Hz, 1H).

Step B: Preparation of Ethyl 2-[7-{(6-Chloro-5-trifluoromethyl)pyridine-3-yl}methoxy-1,2,3,4-tetrahydrocyclopenta[b]indol-3-yl]acetate.

From ethyl 2-(7-hydroxy-1,2,3,4-tetrahydrocyclopenta[b]indol-3-yl)acetate and 2-chloro-5-(chloromethyl)-3-(trifluoromethyl)pyridine, in a similar manner to the one described in Example 1.4, Step E, the title compound was obtained. LCMS m/z=453.4 [M+H]$^+$. $^1$H NMR (400 MHz, CDCl$_3$) δ ppm 1.29 (t, J=7.1 Hz, 3H), 2.06-2.14 (m, 1H), 2.50 (dd, J=16.9, 11.2 Hz, 1H), 2.71-2.86 (m, 4H), 3.50-3.58 (m, 1H), 4.16-4.24 (m, 2H), 5.14 (s, 2H), 6.81 (dd, J=8.7 and 2.4 Hz, 1H), 6.97 (d, J=2.4 Hz, 1H), 7.22 (d, J=8.6 Hz, 1H), 8.14 (d, J=2.1 Hz, 1H), 8.52 (bs, 1H), 8.63 (d, J=2.1 Hz, 1H).

Step C: Preparation of ethyl 2-[7-{(6-Cyclopentyl-5-trifluoromethyl)pyridine-3-yl}methoxy-1,2,3,4-tetrahydrocyclopenta[b]indol-3-yl]acetate.

From ethyl 2-[7-{(6-chloro-5-trifluoromethyl)pyridine-3-yl}methoxy-1,2,3,4-tetrahydrocyclopenta[b]indol-3-yl]acetate and cyclopentylzinc(II) bromide, in a similar manner to the one described in Example 1.8, Step C, the title compound was obtained. LCMS m/z=487.4 [M+H]$^+$.

Step D: Preparation of 2-[7-{(6-Cyclopentyl-5-trifluoromethyl)pyridine-3-yl}methoxy-1,2,3,4-tetrahydrocyclopenta[b]indol-3-yl]acetic Acid.

The title compound was obtained from ethyl 2-[7-{(6-cyclopentyl-5-trifluoromethyl)pyridine-3-yl}methoxy-1,2,3,4-tetrahydrocyclopenta[b]indol-3-yl]acetate, in a similar manner to the one described in Example 1.4 Step F. LCMS m/z=459.5 [M+H]$^+$. $^1$H NMR (400 MHz, CDCl$_3$) δ ppm 1.68-1.75 (m, 2H), 1.87-1.95 (m, 4H), 1.98-2.05 (m, 2H), 2.10-2.19 (m, 1H), 2.62 (dd, J=17.1 and 10.8 Hz, 1H), 2.72-2.88 (m, 4H), 3.44-3.50 (m, 1H), 3.55-3.62 (m, 1H), 5.11 (s, 2H), 6.83 (dd, J=8.8 and 2.4 Hz, 1H), 7.01 (d, J=2.4 Hz, 1H), 7.22 (d, J=8.7 Hz, 1H), 8.00 (d, J=1.8 Hz, 1H), 8.35 (bs, 1H), 8.80 (d, J=1.8 Hz, 1H).

Example 1.18

Preparation of 2-(7-((6-(Pyrrolidin-1-yl)-5-(trifluoromethyl)pyridin-3-yl)methoxy)-1,2,3,4-tetrahydrocyclopenta[b]indol-3-yl)acetic Acid (Compound 23)

Step A: Preparation of ethyl 2-[7-{(6-Pyrrolidin-1-yl)-5-(trifluoromethyl)pyridine-3-yl}methoxy-1,2,3,4-tetrahydrocyclopenta[b]indol-3-yl]acetate.

Ethyl 2-[7-{(6-chloro-5-trifluoromethyl)pyridine-3-yl}methoxy-1,2,3,4-tetrahydrocyclopenta[b]indol-3-yl]acetate (60 mg, 0.132 mmol), pyrrolidine (47 mg, 0.66 mmol), Et$_3$N (67 mg, 0.66 mmol), and IPA (0.7 mL) in a heavy welled tube was heated under microwave irradiation at 180° C. for 2 h. The mixture was purified by HPLC to provide the title compound (20 mg). LCMS m/z=488.5 [M+H]$^+$.

Step B: Preparation of 2-[7-{(6-Pyrrolidin-1-yl)-5-(trifluoromethyl)pyridine-3-yl}methoxy-1,2,3,4-tetrahydrocyclopenta[b]indol-3-yl]acetic Acid.

From ethyl 2-[7-{(6-pyrrolidin-1-yl)-5-(trifluoromethyl)pyridine-3-yl}methoxy-1,2,3,4-tetrahydrocyclopenta[b]indol-3-yl]acetate, in a similar manner to the one described in Example 1.4, Step F, the title compound was obtained. LCMS m/z=460.6 [M+H]$^+$. $^1$H NMR (400 MHz, CDCl$_3$) δ ppm 1.92-1.96 (m, 4H), 2.10-2.17 (m, 1H), 2.60 (dd, J=17.1, 10.6 Hz, 1H), 2.74-2.87 (m, 4H), 3.55-3.62 (m, 5H), 4.97 (s, 2H), 6.80 (dd, J=8.7, 2.4 Hz, 1H), 7.00 (d, J=2.4 Hz, 1H), 7.19 (d, J=8.6 Hz, 1H), 7.91 (d, J=2.2 Hz, 1H), 8.30 (bs, 1H), 8.34 (d, J=2.2 Hz, 1H).

Example 1.19

Preparation of 2-(7-((6-(3,3-Difluoropyrrolidin-1-yl)-5-(trifluoromethyl)pyridin-3-yl)methoxy)-1,2,3,4-tetrahydrocyclopenta[b]indol-3-yl)acetic Acid (Compound 20)

Step A: Preparation of Ethyl 2-(7-((6-(3,3-Difluoropyrrolidin-1-yl)-5-(trifluoromethyl)pyridin-3-yl)methoxy)-1,2,3,4-tetrahydrocyclopenta[b]indol-3-yl)acetate.

From ethyl 2-[7-{(6-chloro-5-trifluoromethyl)pyridine-3-yl}methoxy-1,2,3,4-tetrahydrocyclopenta[b]indol-3-yl]acetate and 3,3-difluoropyrrolidine hydrochloride, in a similar manner to the one described in Example 1.18, Step A, the title compound was obtained. LCMS m/z=524.4 [M+H]$^+$.

Step B: Preparation of 2-[7-{(6-(3,3-Difluoropyrrolidin-1-yl)-5-(trifluoromethyl)pyridine-3-yl}methoxy-1,2,3,4-tetrahydrocyclopenta[b]indol-3-yl]acetic Acid.

Ethyl 2-[7-{(6-(3,3-difluoropyrrolidin-1-yl)-5-(trifluoromethyl)pyridine-3-yl}methoxy-1,2,3,4-tetrahydrocyclopenta[b]indol-3-yl]acetate was hydrolysized with 1 N LiOH in a similar manner to the one described in Example 1.4, Step F to provide the title compound. LCMS m/z=496.4 [M+H]$^+$. $^1$H NMR (400 MHz, CDCl$_3$) δ ppm 2.09-2.18 (m, 1H), 2.35-2.46 (m, 2H), 2.60 (dd, J=17.1, 10.8 Hz, 1H), 2.74-2.88 (m, 4H), 3.54-3.61 (m, 1H), 3.84 (t, J=7.3 Hz, 2H), 3.94 (t, J=13.4 Hz, 2H), 5.00 (s, 2H), 6.80 (dd, J=8.6, 2.4 Hz, 1H), 6.99 (d, J=2.5 Hz, 1H), 7.20 (d, J=8.7 Hz, 1H), 7.96 (d, J=2.2 Hz, 1H), 8.32 (bs, 1H), 8.39 (d, J=2.2 Hz, 1H).

Example 1.20

Preparation of 2-(7-(4-(Methylsulfonyl)benzyloxy)-1,2,3,4-tetrahydrocyclopenta[b]indol-3-yl)acetic acid (Compound 30)

Step A: Preparation of Ethyl 2-(7-(4-(Methylsulfonyl)benzyloxy)-1,2,3,4-tetrahydrocyclopenta[b]indol-3-yl)acetate.

To a stirred mixture of ethyl 2-(7-hydroxy-1,2,3,4-tetrahydrocyclopenta[b]indol-3-yl)acetate (50 mg, 0.19 mmol) and cesium carbonate (94 mg, 0.29 mmol) in DMF (1.5 mL) was added 1-(bromomethyl)-4-(methylsulfonyl)benzene (72 mg, 0.29 mmol). The reaction mixture was stirred at room temperature for 1 h, the solid was filtered. The filtrate was concentrated, and the residue was purified by preparative TLC to give the title compound (40 mg) as an off-white solid. LCMS m/z=428.3 [M+H]$^+$. $^1$H NMR (400 MHz, CDCl$_3$) δ 1.30 (t, J=7.2 Hz, 3H), 2.07-2.15 (m, 1H), 2.50 (dd, J=16.7 and 11.2 Hz, 1H), 2.70-2.86 (m, 4H), 3.05 (s, 3H), 3.52-3.58 (m, 1H), 4.17-4.25 (m, 2H), 5.20 (s, 2H), 6.84 (dd, J=8.8 and 2.4 Hz, 1H), 6.96 (d, J=2.1 Hz, 1H), 7.21 (d, J=8.8 Hz, 1H), 7.68 (d, J=8.1 Hz, 2H), 7.95 (d, J=8.3 Hz, 2H), 8.49 (s, 1H).

Step B: Preparation of 2-(7-(4-(Methylsulfonyl)benzyloxy)-1,2,3,4-tetrahydrocyclopenta[b]indol-3-yl)acetic Acid.

To the stirred solution of ethyl 2-(7-(4-(methylsulfonyl)benzyloxy)-1,2,3,4-tetrahydrocyclopenta[b]indol-3-yl)acetate (40 mg, 0.094 mmol) in dioxane was added 1M LiOH aqueous solution (0.47 mL, 0.47 mmol). The reaction mixture was stirred at room temperature for 24 h. The solvent was partly removed, diluted with water, and acidified with HCl solution. The pinkish solid was collected and dried to give the title compound (26 mg). LCMS m/z=400.4 [M+H]$^+$. $^1$H NMR (400 MHz, DMSO-d$_6$) δ 2.04-2.08 (m, 1H), 2.35 (dd, J=16.0 and 9.0 Hz, 1H), 2.63-2.75 (m, 4H), 3.20 (s, 3H), 3.45-3.50 (m, 1H), 5.21 (s, 2H), 6.73 (dd, J=8.7 and 2.4 Hz, 1H), 6.92 (d, J=2.4 Hz, 1H), 7.20 (d, J=8.7 Hz, 1H), 7.71 (d, J=8.3 Hz, 2H), 7.92 (d, J=8.3 Hz, 2H), 10.47 (s, 1H), 12.18 (s, 1H).

Example 1.21

Preparation of 2-(7-(4-(Cyclohexylmethyl)-3-(trifluoromethyl)benzyloxy)-1,2,3,4-tetrahydrocyclopenta[b]indol-3-yl)acetic acid (Compound 28)

Step A: Preparation of Methyl 4-(Cyclohexylmethyl)-3-(trifluoromethyl)benzoate.

To a stirred solution of methyl 4-chloro-3-(trifluoromethyl)benzoate (238 mg, 1.0 mmol) and bis(tri-t-butylphosphine)palladium (0) (51 mg, 0.10 mmol) in THF (2 mL) was added (cyclohexylmethyl)zinc(II) bromide (6 mL, 3.00 mmol) at room temperature. The reaction mixture was heated at reflux for 2 h, quenched with saturated NaHCO$_3$ solution, filtered through Celite. The filtrate was extracted with ethyl acetate. The combined organics were dried and concentrated, and the residue was purified by column chromatography to give the title compound (280 mg) as colorless oil. LCMS m/z=301.4 [M+H]$^+$. $^1$H NMR (400 MHz, CDCl$_3$) δ 0.96-1.06 (m, 2H), 1.14-1.22 (m, 3H), 1.62-1.72 (m, 6H), 2.71 (d, J=6.7 Hz, 2H), 3.94 (s, 3H), 7.39 (d, J=8.1 Hz, 1H), 8.10 (dd, J=8.0 and 1.5 Hz, 1H), 8.30 (d, J=1.4 Hz, 1H).

Step B: Preparation of (4-(Cyclohexylmethyl)-3-(trifluoromethyl)phenyl)methanol.

To a stirred solution of methyl 4-(cyclohexylmethyl)-3-(trifluoromethyl)benzoate (280 mg, 0.93 mmol) in dioxane (8 mL) was added 2 M lithium borohydride in THF solution (0.93 mL, 1.86 mmol). The reaction mixture was heated at 80° C. for 2 h, cooled down, poured into water, acidified with HCl solution to pH 4, and extracted with ethyl acetate. The combined organics were washed with saturated NaHCO$_3$ solution and water, dried and concentrated. The residue was purified by silica gel column chromatography to give the title compound (190 mg) as a colorless oil. $^1$H NMR (400 MHz, CDCl$_3$) δ 0.96-1.06 (m, 2H), 1.14-1.22 (m, 3H), 1.62-1.72 (m, 6H), 2.67 (d, J=6.7 Hz, 2H), 4.71 (d, J=5.7 Hz, 2H), 7.29 (d, J=7.9 Hz, 1H), 7.45 (dd, J=8.0 and 1.6 Hz, 1H), 7.62 (d, J=1.6 Hz, 1H).

Step C: Preparation of 4-(Bromomethyl)-1-(cyclohexylmethyl)-2-(trifluoromethyl)benzene.

To a stirred solution of (4-(cyclohexylmethyl)-3-(trifluoromethyl)phenyl)methanol (80 mg, 0.29 mmol) in dry DCM (1 mL) was added tribromophosphine (11 μL, 0.12 mmol) at 0° C. The reaction mixture was slowly warmed to room temperature and stirred for 1 h, poured into water, extracted with DCM. The combined organics were washed with saturated NaHCO$_3$ solution and brine, dried and concentrated. The residue was purified by column chromatography to give the title compound (80 mg) as a colorless oil. $^1$H NMR (400 MHz, CDCl$_3$) δ 0.96-1.06 (m, 2H), 1.14-1.22 (m, 3H), 1.55-1.72 (m, 6H), 2.65 (d, J=6.5 Hz, 2H), 4.49 (s, 2H), 7.28 (d, J=8.0 Hz, 1H), 7.47 (dd, J=8.0 and 1.7 Hz, 1H), 7.63 (d, J=1.6 Hz, 1H).

Step D: Preparation of Ethyl 2-(7-(4-(Cyclohexylmethyl)-3-(trifluoromethyl)benzyloxy)-1,2,3,4-tetrahydrocyclopenta[b]indol-3-yl)acetate.

To a stirred reaction mixture of ethyl 2-(7-hydroxy-1,2,3,4-tetrahydrocyclopenta[b]indol-3-yl)acetate (40 mg, 0.15 mmol) and cesium carbonate (75 mg, 0.23 mmol) in DMF (1 mL) was added 4-(bromomethyl)-1-(cyclohexylmethyl)-2-(trifluoromethyl)benzene (78 mg, 0.23 mmol). The reaction mixture was stirred at room temperature for 1 h. The solid was filtered and washed with ethyl acetate. The combined filtrate was concentrated, and the residue was purified by preparative TLC to give the title compound (40 mg) as an oil. LCMS m/z=514.5 [M+H]$^+$. $^1$H NMR (400 MHz, CDCl$_3$) δ 0.96-1.06 (m, 2H), 1.14-1.22 (m, 3H), 1.30 (t, J=7.2 Hz, 3H), 1.55-1.72 (m, 6H), 2.07-2.15 (m, 1H), 2.50 (dd, J=16.7 and 11.2 Hz, 1H), 2.66 (d, J=6.8 Hz, 2H), 2.70-2.86 (m, 4H), 3.52-3.58 (m, 1H), 4.18-4.25 (m, 2H), 5.08 (s, 2H), 6.85 (dd, J=8.8 and 2.4 Hz, 1H), 7.00 (d, J=2.4 Hz, 1H), 7.21 (d, J=8.8 Hz, 1H), 7.31 (d, J=7.9 Hz and 1.6 Hz, 1H), 7.55 (d, J=7.8 Hz, 1H), 7.72 (d, J=1.6 Hz, 1H), 8.46 (s, 1H).

Step E: Preparation of 2-(7-(4-(Cyclohexylmethyl)-3-(trifluoromethyl)benzyloxy)-1,2,3,4-tetrahydrocyclopenta[b]indol-3-yl)acetic Acid.

To a stirred solution of ethyl 2-(7-(4-(cyclohexylmethyl)-3-(trifluoromethyl)benzyloxy)-1,2,3,4-tetrahydrocyclopenta[b]indol-3-yl)acetate (40 mg, 0.078 mmol) in dioxane was added 1 M LiOH aqueous solution (0.39 mL, 0.39 mmol). The reaction mixture was stirred at room temperature for 5 h. The solvent was partly removed, then diluted with water, acidified with HCl solution. The pinkish solid was collect and dried to give the title compound (19.5 mg). LCMS m/z=486.3 [M+H]$^+$. $^1$H NMR (400 MHz, DMSO-d$_6$) δ 0.96-1.06 (m, 2H), 1.14-1.22 (m, 3H), 1.55-1.70 (m, 6H), 2.05-2.10 (m, 1H), 2.40 (dd, J=16.0 and 9.0 Hz, 1H), 2.62-2.75 (m, 6H), 3.42-3.50 (m, 1H), 5.12 (s, 2H), 6.72 (dd, J=8.7 and 2.4 Hz, 1H), 6.94 (d, J=2.4 Hz, 1H), 7.21 (d, J=8.8 Hz, 1H), 7.45 (d, J=8.0 Hz, 1H), 7.66 (d, J=7.8 Hz, 1H), 7.75 (s, 1H), 10.48 (s, 1H), 12.20 (br, 1H).

Example 1.22

Preparation of 2-(7-(4-(Ethylamino)-3-(trifluoromethyl)benzyloxy)-1,2,3,4-tetrahydrocyclopenta[b]indol-3-yl)acetic acid (Compound 27)

To a mixture of ethyl 2-(7-(4-chloro-3-(trifluoromethyl)benzyloxy)-1,2,3,4-tetrahydrocyclopenta[b]indol-3-yl)acetate (50 mg, 0.11 mmol) in dioxane was added 2-dicyclohexylphosphino-2'-(N,N-dimethylamino)biphenyl (4.4 mg, 0.011 mmol), Pd$_2$dba$_3$ (5 mg, 5.5 μmol), 2 M ethanamine in THF (0.28 mL, 0.55 mmol) and sodium tert-butoxide (21 mg, 0.22 mmol). The reaction mixture was heated at 120° C. for 2 h under microwave irradiation, quenched by saturated NH$_4$Cl solution and extracted with ethyl acetate. The combined organics were dried and concentrated. The residue was purified first by preparative TLC followed by preparative HPLC to give the title compound (7 mg) as a white solid. LCMS m/z=433.5 [M+H]$^+$. $^1$H NMR (400 MHz, CDCl$_3$) δ 1.30 (t, J=7.1 Hz, 3H), 2.10-2.17 (m, 1H), 2.62 (dd, J=17.0 and 10.9 Hz, 1H), 2.75-2.86 (m, 4H), 3.23 (q, J=7.1 Hz, 2H), 3.54-3.62 (m, 1H), 4.96 (s, 2H), 6.73 (d, J=8.6 Hz, 1H), 6.83 (dd, J=8.8 and 2.4 Hz, 1H), 7.00 (d, J=2.4 Hz, 1H), 7.19 (d, J=8.8 Hz, 1H), 7.46 (dd, J=8.5 and 1.7 Hz, 1H), 7.53 (d, J=1.7 Hz, 1H), 8.28 (s, 1H).

Example 1.23

Preparation of 2-(7-(4-(Cyclopropylmethoxy)-3-(trifluoromethyl)benzyloxy)-1,2,3,4-tetrahydrocyclopenta[b]indol-3-yl)acetic acid (Compound 26)

Step A: Preparation of Cyclopropylmethyl 4-(Cyclopropylmethoxy)-3-(trifluoromethyl)benzoate.

To a solution of 4-hydroxy-3-(trifluoromethyl)benzoic acid (0.483 g, 2.343 mmol) in DMF (10 mL) was added Cs$_2$CO$_3$ (2.29 g, 7.03 mmol), followed by (bromomethyl)cyclopropane (0.568 mL, 5.86 mmol). The reaction was stirred at 80° C. for 16 h. The mixture was filtered. The filtrate was concentrated under vacuum and taken up in EtOAc. The organic solution was washed with water (thrice), dried over MgSO$_4$ and concentrated. The residue was purified by silica gel column chromatography to give the title compound as an oil (0.643 g). LCMS m/z=315.3 [M+H]$^+$. $^1$H NMR (400 MHz, CDCl$_3$) δ ppm 0.33-0.44 (m, 4H), 0.59-0.69 (m, 4H), 1.21-1.34 (m, 2H), 4.01 (d, J=6.57 Hz, 2H), 4.15 (d, J=7.20 Hz, 2H), 6.99 (d, J=8.84 Hz, 1H), 8.18 (dd, J=8.72, 2.15 Hz, 1H), 8.28 (d, J=2.02 Hz, 1H).

Step B: Preparation of 4-(Cyclopropylmethoxy)-3-(trifluoromethyl)benzoic Acid

To a solution of cyclopropylmethyl 4-(cyclopropylmethoxy)-3-(trifluoromethyl)benzoate (0.642 g, 2.043 mmol) in THF:MeOH (1:1, 10 mL) was added LiOH (1M, aq) (12.26 mmol). The reaction was stirred overnight, quenched with HCl (1M, aq) and extracted with EtOAc (twice). The combined extracts were dried over MgSO$_4$ and concentrated to give the title compound as a white solid (0.502 g). LCMS m/z=261.1 [M+H]$^+$. $^1$H NMR (400 MHz, CDCl$_3$) δ ppm 0.39-0.46 (m, 2H), 0.62-0.71 (m, 2H), 1.23-1.38 (m, 1H), 4.03 (d, J=6.57 Hz, 2H), 7.02 (d, J=8.72 Hz, 1H), 8.23 (dd, J=8.72, 2.15 Hz, 1H), 8.34 (d, J=2.02 Hz, 1H).

Step C: Preparation of (4-(Cyclopropylmethoxy)-3-(trifluoromethyl)phenyl)methanol.

To a solution of 4-(cyclopropylmethoxy)-3-(trifluoromethyl)benzoic acid in THF (7 mL) at 0° C. was slowly added BH$_3$DMS (2.0 M in THF) (1.592 mL, 3.18 mmol). After stirring for 0.5 h at 0° C., the reaction was allowed to return to room temperature and stirred overnight. The reaction mixture was slowly added to a saturated solution of NaHCO$_3$ at 0° C. and extracted with EtOAc (thrice). The combined extracts were dried over MgSO$_4$ and purified by silica gel column chromatography to give the title compound as a solid (0.358 g). $^1$H NMR (400 MHz, CDCl$_3$) δ ppm 0.34-0.43 (m, 2H), 0.57-0.67 (m, 2H), 1.22-1.32 (m, 1H), 3.94 (d, J=6.57 Hz, 2H), 4.66 (s, 2H), 6.96 (d, J=8.46 Hz, 1H), 7.46 (dd, J=8.46, 2.02 Hz, 1H), 7.57 (s, 1H).

Step D: Preparation of 4-(Chloromethyl)-1-(cyclopropylmethoxy)-2-(trifluoromethyl)benzene.

To a solution of (4-(cyclopropylmethoxy)-3-(trifluoromethyl)phenyl)methanol (0.258 g, 1.454 mmol) in toluene (4 mL) was added thionyl chloride (0.637 mL, 8.72 mmol). The reaction was stirred at 75° C. for 1.5 h. The reaction mixture was poured into ice water and extracted with hexanes (twice). The combined extracts were washed with NaHCO$_3$ (thrice), dried over MgSO$_4$ and concentrated to give the title compound as a white solid (0.275 g). $^1$H NMR (400 MHz, CDCl$_3$) δ ppm 0.36-0.43 (m, 2H), 0.59-0.67 (m, 2H), 1.21-1.34 (m, 1H), 3.95 (d, J=6.44 Hz, 2H), 4.56 (s, 2H), 6.95 (d, J=8.59 Hz, 1H), 7.48 (dd, J=8.53, 2.34 Hz, 1H), 7.58 (d, J=2.15 Hz, 1H).

Step E: Preparation of Ethyl 2-(7-(4-(Cyclopropylmethoxy)-3-(trifluoromethyl)benzyloxy)-1,2,3,4-tetrahydrocyclopenta[b]indol-3-yl)acetate.

To a solution of ethyl 2-(7-hydroxy-1,2,3,4-tetrahydrocyclopenta[b]indol-3-yl)acetate (0.069 g, 0.264 mmol) in DMF (1 mL) was added Cs$_2$CO$_3$ (0.086 g, 0.264 mmol) followed by 4-(chloromethyl)-1-(cyclopropylmethoxy)-2-(trifluoromethyl)benzene (0.070 g, 0.264 mmol). The reaction mixture was stirred for 16 h and filtered. The filtrate was concentrated under vacuum and purified by silica gel column chromatography to give the title compound as a light yellow oil (0.023 g). LCMS m/z=488.2 [M+H]$^+$. $^1$H NMR (400 MHz, CDCl$_3$) δ ppm 0.35-0.44 (m, 2H), 0.58-0.67 (m, 2H), 1.24-1.34 (m, 4H), 2.04-2.16 (m, 1H), 2.51 (dd, J=16.74, 11.05 Hz, 1H), 2.68-2.90 (m, 4H), 3.49-3.61 (m, 1H), 3.94 (d, J=6.44 Hz, 2H), 4.15-4.27 (m, 2H), 5.03 (s, 2H), 6.82 (dd, J=8.72, 2.40 Hz, 1H), 6.93-7.02 (m, 2H), 7.20 (d, J=8.84 Hz, 1H), 7.56 (dd, J=8.53, 1.96 Hz, 1H), 7.67 (d, J=1.89 Hz, 1H), 8.45 (bs, 1H).

Step F: Preparation of 2-(7-(4-(Cyclopropylmethoxy)-3-(trifluoromethyl)benzyloxy)-1,2,3,4-tetrahydrocyclopenta[b]indol-3-yl)acetic acid.

To a solution of ethyl 2-(7-(4-(cyclopropylmethoxy)-3-(trifluoromethyl)benzyloxy)-1,2,3,4-tetrahydrocyclopenta[b]indol-3-yl)acetate (22.9 mg, 0.047 mmol) in dioxane was added 1M LiOH (0.188 mL, 0.188 mmol). The reaction mixture was stirred 3 h, taken up in EtOAc and washed with 1 M HCl. The EtOAc extract was dried over MgSO$_4$ and concentrated. The residue was purified by preparative HPLC/MS to give the title compound as a solid. LCMS m/z=460.3 [M+H]$^+$. $^1$H NMR (400 MHz, DMSO-d$_6$) δ ppm 0.30-0.38 (m, 2H), 0.52-0.59 (m, 2H), 1.17-1.27 (m, 1H), 2.03-2.13 (m, 1H), 2.35 (dd, J=15.98, 8.91 Hz, 1H), 2.59-2.76 (m, 4H), 3.99 (d, J=6.69 Hz, 2H), 5.05 (s, 2H), 6.69 (dd, J=8.84, 2.40 Hz, 1H), 6.91 (d, J=2.53 Hz, 1H), 7.19 (d, J=8.72 Hz, 1H), 7.24 (d, J=8.46 Hz, 1H), 7.62-7.71 (m, 2H), 10.45 (s, 1H).

Example 1.24

Preparation of 2-(7-(4-(Cyclopentyloxy)-3-(trifluoromethyl)benzyloxy)-1,2,3,4-tetrahydrocyclopenta[b]indol-3-yl)acetic acid (Compound 24)

Step A: Preparation of Cyclopentyl 4-(Cyclopentyloxy)-3-(trifluoromethyl)benzoate.

From bromocyclopropane, the title compound was prepared using a similar method as described in Example 1.23, Step A to give an oil. LCMS m/z=343.4 [M+H]$^+$. $^1$H NMR (400 MHz, CDCl$_3$) δ ppm 1.58-1.72 (m, 4H), 1.75-1.88 (m, 6H), 1.88-2.02 (m, 6H), 4.87-4.99 (m, 1H), 5.32-5.45 (m, 1H), 7.00 (d, J=8.72 Hz, 1H), 8.12 (dd, J=8.72, 2.02 Hz, 1H), 8.20 (d, J=1.89 Hz, 1H).

Step B: Preparation of 4-(Cyclopentyloxy)-3-(trifluoromethyl)benzoic Acid.

From cyclopentyl 4-(cyclopentyloxy)-3-(trifluoromethyl)benzoate, the title compound was prepared using a similar method as described in Example 1.23, Step B to give a white solid. LCMS m/z=275.4 [M+H]$^+$.

Step C: Preparation of (4-(Cyclopentyloxy)-3-(trifluoromethyl)phenyl)methanol.

From 4-(cyclopentyloxy)-3-(trifluoromethyl)benzoic acid, the title compound was prepared using a similar method as described in Example 1.23, Step C to give an oil. $^1$H NMR (400 MHz, CDCl$_3$) δ ppm 1.61-1.68 (m, 2H), 1.76-1.86 (m, 2H), 1.86-1.96 (m, 4H), 4.64 (s, 2H), 4.84-4.91 (m, 1H), 6.98 (d, J=8.59 Hz, 1H), 7.45 (dd, J=8.59, 2.15 Hz, 1H), 7.55 (d, J=1.89 Hz, 1H).

Step D: Preparation of 4-(Chloromethyl)-1-(cyclopentyloxy)-2-(trifluoromethyl)benzene.

From (4-(cyclopentyloxy)-3-(trifluoromethyl)phenyl)methanol, the title compound was prepared using a similar method as described in Example 1.23, Step D to give an oil. $^1$H NMR (400 MHz, CDCl$_3$) δ ppm 1.58-1.70 (m, 2H), 1.76-1.86 (m, 2H), 1.86-1.95 (m, 4H), 4.56 (s, 2H), 4.84-4.90 (m, 1H), 6.96 (d, J=8.59 Hz, 1H), 7.47 (dd, J=8.53, 2.34 Hz, 1H), 7.57 (d, J=2.15 Hz, 1H).

Step E: Preparation of Ethyl 2-(7-(4-(Cyclopentyloxy)-3-(trifluoromethyl)benzyloxy)-1,2,3,4-tetrahydrocyclopenta[b]indol-3-yl)acetate.

From 4-(chloromethyl)-1-(cyclopentyloxy)-2-(trifluoromethyl)benzene, the title compound was prepared using a similar method as described in Example 1.23, Step E to give an oil. LCMS m/z=502.4 [M+H]⁺. $^1$H NMR (400 MHz, CDCl$_3$) δ ppm 1.30 (t, J=7.14 Hz, 3H), 1.57-1.69 (m, 2H), 1.76-1.97 (m, 6H), 2.05-2.16 (m, 1H), 2.51 (dd, J=16.74, 11.18 Hz, 1H), 2.68-2.89 (m, 4H), 3.49-3.61 (m, 1H), 4.14-4.28 (m, 2H), 4.84-4.91 (m, 1H), 5.02 (s, 2H), 6.83 (dd, J=8.78, 2.46 Hz, 1H), 6.94-7.04 (m, 2H), 7.21 (d, J=8.72 Hz, 1H), 7.55 (dd, J=8.59, 2.02 Hz, 1H), 7.65 (d, J=2.02 Hz, 1H), 8.45 (bs, 1H).

Step F: Preparation of 2-(7-(4-(Cyclopentyloxy)-3-(trifluoromethyl)benzyloxy)-1,2,3,4-tetrahydrocyclopenta[b]indol-3-yl)acetic acid.

The title compound was prepared using a similar method as described in Example 1.23, Step F to give a solid. LCMS m/z=474.4 [M+H]⁺. $^1$H NMR (400 MHz, DMSO-d$_6$) δ ppm 1.53-1.79 (m, 6H), 1.82-1.97 (m, 2H), 2.00-2.15 (m, 1H), 2.35 (dd, J=15.92, 8.97 Hz, 1H), 2.58-2.79 (m, 4H), 3.41-3.51 (m, 1H), 4.94-5.08 (m, 3H), 6.69 (dd, J=8.78, 2.46 Hz, 1H), 6.92 (d, J=2.40 Hz, 1H), 7.19 (d, J=8.72 Hz, 1H), 7.25 (d, J=9.22 Hz, 1H), 7.61-7.72 (m, 2H), 10.45 (s, 1H), 12.18 (bs, 1H)

Example 1.25

Preparation of 2-(7-(4-Cyano-3-(trifluoromethyl) benzyloxy)-1,2,3,4-tetrahydrocyclopenta[b]indol-3-yl)acetic acid (Compound 25)

Step A: Preparation of 4-(Hydroxymethyl)-2-(trifluoromethyl)benzonitrile.

To a solution of (4-chloro-3-(trifluoromethyl)phenyl) methanol (0.300 g, 1.425 mmol) in DMA was added dicyanozinc (0.335 g, 2.85 mmol) and tetrakis(triphenylphosphine) palladium (0) (0.165 g, 0.142 mmol). The reaction flask was degassed and charged with nitrogen, then heated at 150° C. for 6 h under microwave irradiation. The reaction mixture was poured into water and extracted with EtOAc. The EtOAc extract was washed with brine, dried over MgSO$_4$ and purified by silica gel column chromatography to give the title compound as a white solid (0.105 g). LCMS m/z=202.1 [M+H]⁺. $^1$H NMR (400 MHz, CDCl$_3$) δ ppm 1.98 (bs, 1H), 4.87 (s, 2H), 7.69 (d, J=0.88 Hz, 1H), 7.77-7.88 (m, 2H)

Step B: Preparation of 4-(chloromethyl)-2-(trifluoromethyl)benzonitrile

From 4-(hydroxymethyl)-2-(trifluoromethyl)benzonitrile, the title compound was prepared using a similar method as described in Example 1.23, Step D to give an oil. LCMS m/z=220.2 [M+H]⁺. $^1$H NMR (400 MHz, DMSO-d$_6$) δ ppm 4.65 (s, 2H), 7.73 (d, J=1.39 Hz, 1H), 7.84 (d, J=7.71 Hz, 2H).

Step C: Preparation of Ethyl 2-(7-(4-Cyano-3-(trifluoromethyl)benzyloxy)-1,2,3,4-tetrahydrocyclopenta[b]indol-3-yl)acetate.

From 4-(chloromethyl)-2-(trifluoromethyl)benzonitrile, the title compound was prepared using a similar method as described in Example 1.23 Step E to give an oil. LCMS m/z=443.3 [M+H]⁺. $^1$H NMR (400 MHz, CDCl$_3$) δ ppm 1.30 (t, J=7.14 Hz, 3H), 2.03-2.18 (m, 1H), 2.50 (dd, J=16.80, 11.24 Hz, 1H), 2.68-2.91 (m, 4H), 3.48-3.63 (m, 1H), 4.13-4.28 (m, 2H), 5.21 (s, 2H), 6.83 (dd, J=8.72, 2.53 Hz, 1H), 6.96 (d, J=2.40 Hz, 1H), 7.23 (d, J=8.72 Hz, 1H), 7.73-7.81 (m, 1H), 7.81-7.88 (m, 1H), 7.91 (s, 1H), 8.52 (bs, 1H).

Step D: Preparation of 2-(7-(4-cyano-3-(trifluoromethyl) benzyloxy)-1,2,3,4-tetrahydrocyclopenta[b]indol-3-yl)acetic acid.

The title compound was prepared using a similar method as described in Example 1.23, Step F to give a solid. LCMS m/z=415.4 [M+H]⁺. $^1$H NMR (400 MHz, DMSO-d$_6$) δ ppm 2.01-2.14 (m, 1H), 2.35 (dd, J=15.98, 9.03 Hz, 1H), 2.57-2.78 (m, 4H), 3.38-3.53 (m, 1H), 5.29 (s, 2H), 6.75 (dd, J=8.78, 2.46 Hz, 1H), 6.94 (d, J=2.53 Hz, 1H), 7.22 (d, J=8.72 Hz, 1H), 7.97 (s, 1H), 8.07 (s, 1H), 8.19 (d, J=7.96 Hz, 1H), 10.50 (s, 1H), 12.18 (bs, 1H)

Example 1.26

Preparation of 2-(7-(4-Carbamoyl-3-(trifluoromethyl)benzyloxy)-1,2,3,4-tetrahydrocyclopenta[b] indol-3-yl)acetic acid (Compound 29)

To a solution of 2-(7-(4-cyano-3-(trifluoromethyl)benzyloxy)-1,2,3,4-tetrahydrocyclopenta[b]indol-3-yl)acetic acid (9.0 mg, 0.022 mmol) in dioxane (1 mL) was added 1M LiOH (aq) (3.0 mL). The reaction was stirred at 50° C. for 48 h. 1M HCl (aq) was added to adjust pH to 3. The mixture was extracted with EtOAc. The EtOAc extract was dried over MgSO$_4$ and the residue was purified by preparative HPLC/MS to give the title compound as a solid (2.1 mg). LCMS m/z=433.2 [M+H]⁺. $^1$H NMR (400 MHz, DMSO-d$_6$) δ ppm 2.01-2.14 (m, 1H), 2.32-2.42 (m, 1H), 2.57-2.78 (m, 4H), 5.20 (s, 2H), 6.72 (d, J=11.37 Hz, 1H), 6.93 (d, J=2.40 Hz, 1H), 7.20 (d, J=8.72 Hz, 1H), 7.50-7.59 (m, 2H), 7.76 (d, J=7.58 Hz, 1H), 7.82 (s, 1H), 7.91 (s, 1H), 10.47 (s, 1H), 12.17 (bs, 1H).

Example 1.27

Preparation of 2-(7-(4-(Pyrazin-2-yl)benzyloxy)-1,2, 3,4-tetrahydrocyclopenta[b]indol-3-yl)acetic acid (Compound 31)

Step A: Preparation of (4-(Pyrazin-2-yl)phenyl)methanol.

A mixture of 2-chloropyrazine (0.230 ml, 2.62 mmol), 4-(hydroxymethyl)phenylboronic acid (517 mg, 3.41 mmol), tetrakis(triphenylphosphine)palladium (0) (303 mg, 0.262 mmol) and 2 M potassium phosphate aqueous solution (2.62 ml, 5.24 mmol) in dioxane (10 mL) was heated at 80° C. overnight under nitrogen. The mixture was cooled down, poured into water and extracted with ethyl acetate. The combined organic layers were dried and concentrated. The residue was purified by preparative HPLC to give the title compound (350 mg) as an off-white solid. LCMS m/z=187.0 [M+H]⁺. $^1$H NMR (400 MHz, CDCl$_3$) δ 4.79 (s, 2H), 7.52 (d, J=8.1 Hz, 2H), 8.02 (d, J=8.1 Hz, 2H), 8.51 (d, J=2.5 Hz, 1H), 8.63 (dd, J=2.4 and 1.6 Hz, 1H), 9.03 (d, J=1.6 Hz, 1H).

Step B: Preparation of 4-(Pyrazin-2-yl)benzyl methanesulfonate.

To a stirred solution of (4-(pyrazin-2-yl)phenyl)methanol (40 mg, 0.22 mmol) and DIEA (56 μL, 0.32 mmol) in DCM (1 mL) was added methanesulfonyl chloride (29.5 mg, 0.258 mmol) at 0° C. The reaction mixture was stirred at that temperature for 1 h, poured into water, and extracted with DCM. The combined organics were dried and concentrated to give the title compound (50 mg) without further purification. LCMS m/z=265.1 [M+H]⁺.

Step C: Preparation of Ethyl 2-(7-(4-(Pyrazin-2-yl)benzyloxy)-1,2,3,4-tetrahydrocyclopenta[b]indol-3-yl)acetate.

To a mixture of ethyl 2-(7-hydroxy-1,2,3,4-tetrahydrocyclopenta[b]indol-3-yl)acetate (20 mg, 0.077 mmol) and cesium carbonate (38 mg, 0.12 mmol) in DMF (1 mL) was added 4-(pyrazin-2-yl)benzyl methanesulfonate (41 mg, 0.15 mmol). The reaction mixture was stirred at room temperature overnight. The solid was filtered, and the filtrate was concentrated. The residue was purified by preparative TLC to give the title compound (15 mg). LCMS m/z=428.3 [M+H]⁺. $^1$H NMR (400 MHz, CDCl$_3$) δ 1.30 (t, J=7.1 Hz, 3H), 2.07-2.14

(m, 1H), 2.50 (dd, J=16.7 and 11.2 Hz, 1H), 2.70-2.87 (m, 4H), 3.50-3.57 (m, 1H), 4.18-4.24 (m, 2H), 5.18 (s, 2H), 6.87 (dd, J=8.8 and 2.4 Hz, 1H), 7.01 (d, J=2.3 Hz, 1H), 7.21 (d, J=8.7 Hz, 1H), 7.62 (d, J=8.2 Hz, 2H), 8.03 (d, J=8.3 Hz, 2H), 8.46 (s, 1H), 8.51 (d, J=2.5 Hz, 1H), 8.64 (dd, J=2.3 and 1.6 Hz, 1H), 9.04 (d, J=1.4 Hz, 1H).

Step D: Preparation of 2-(7-(4-(Pyrazin-2-yl)benzyloxy)-1,2,3,4-tetrahydrocyclopenta[b]indol-3-yl)acetic Acid.

To a stirred solution of ethyl 2-(7-(4-(pyrazin-2-yl)benzyloxy)-1,2,3,4-tetrahydrocyclopenta[b]indol-3-yl)acetate (15 mg, 0.035 mmol) in dioxane (1 mL) was added 1 M lithium hydroxide solution (0.175 mL, 0.175 mmol). The reaction mixture was stirred at room temperature for 5 h and acidified with HCl solution. The mixture was purified by HPLC to give the title compound (8 mg) as a pinkish solid. LCMS m/z=400.4 [M+H]$^+$. $^1$H NMR (400 MHz, DMSO-d$_6$) δ 2.04-2.12 (m, 1H), 2.35 (dd, J=16.0 and 9.0 Hz, 1H), 2.62-2.75 (m, 4H), 3.44-3.50 (m, 1H), 5.17 (s, 2H), 6.74 (dd, J=8.7 and 2.4 Hz, 1H), 6.95 (d, J=2.4 Hz, 1H), 7.21 (d, J=8.7 Hz, 1H), 7.62 (d, J=8.2 Hz, 2H), 8.15 (d, J=8.3 Hz, 2H), 8.61 (d, J=2.5 Hz, 1H), 8.72 (dd, J=2.3 and 1.6 Hz, 1H), 9.26 (d, J=1.5 Hz, 1H), 10.47 (s, 1H), 12.20 (s, 1H).

Example 1.28

Preparation of 2-(7-(4-(1,2,3-Thiadiazol-4-yl)benzyloxy)-1,2,3,4-tetrahydrocyclopenta[b]indol-3-yl) acetic acid (Compound 32)

Step A: Preparation of Ethyl 2-(7-(4-(1,2,3-Thiadiazol-4-yl)benzyloxy)-1,2,3,4-tetrahydrocyclopenta[b]indol-3-yl)acetate.

In a 4 mL vial were placed ethyl 2-(7-hydroxy-1,2,3,4-tetrahydrocyclopenta[b]indol-3-yl)acetate (64.8 mg, 0.250 mmol), cesium carbonate (81 mg, 0.250 mmol), and 4-(4-(bromomethyl)phenyl)-1,2,3-thiadiazole (63.8 mg, 0.250 mmol). DMA (1 mL) was added and the reaction was stirred at room temperature overnight. The solid was removed by filtration and rinsed with EtOAc. The filtrate was concentrated under reduced pressure and the residue was purified by silica gel column chromatography to give the title compound (42.7 mg). LCMS m/z=434.2 [M+H]$^+$.

Step B: Preparation of 2-(7-(4-(1,2,3-Thiadiazol-4-yl)benzyloxy)-1,2,3,4-tetrahydrocyclopenta[b]indol-3-yl)acetic Acid.

To a solution of ethyl 2-(7-(4-(1,2,3-thiadiazol-4-yl)benzyloxy)-1,2,3,4-tetrahydrocyclopenta[b]indol-3-yl)acetate (42.7 mg, 0.030 mmol) in dioxane was added 1M LiOH (0.394 mL, 0.394 mmol). The reaction was stirred overnight. The reaction mixture was taken up in EtOAc and washed with 1 M HCl. The EtOAc extract was dried over MgSO$_4$ and concentrated. The residue was purified by silica gel column chromatography to give the title compound as a solid. LCMS m/z=406.4 [M+H]$^+$. $^1$H NMR (400 MHz, DMSO-d$_6$) δ ppm 2.03-2.12 (m, 1H), 2.36 (dd, J=16.04, 8.97 Hz, 1H), 2.58-2.79 (m, 4H), 3.41-3.51 (m, 1H), 5.16 (s, 2H), 6.74 (dd, J=8.78, 2.46 Hz, 1H), 6.95 (d, J=2.40 Hz, 1H), 7.21 (d, J=8.72 Hz, 1H), 7.63 (d, J=8.21 Hz, 2H), 8.15 (d, J=8.21 Hz, 2H), 9.61 (s, 1H), 10.46 (s, 1H), 12.19 (bs, 1H).

Example 1.29

Preparation of 2-(7-(4-Cyclopentyl-3-(trifluoromethyl)benzyloxy)-1,2,3,4-tetrahydrocyclopenta[b]indol-3-yl)acetic Acid (Compound 12)

Step A: Preparation of Methyl 4-Chloro-3-(trifluoromethyl)benzoate.

To a solution of 4-chloro-3-(trifluoromethyl)benzoic acid (200 g, 891 mmol) in MeOH (600 mL, 14.8 mol), sulfuric acid (27 mL, 445 mmol) was added. The mixture was stirred at reflux for 6 h, allowed to cool and the solvent evaporated under reduce pressure. The resulting liquid residue (~250 mL) was poured onto ice water whereby a white suspension formed. The solid was filtered and washed with 0.05 N NaOH (3×200 mL) followed by H$_2$O (3×200 mL). The solid was dried under vacuum for 16 h followed by 4 h at 40° C. to give the title compound as an off-white solid (197.0 g). $^1$H NMR (400 MHz, CDCl$_3$) δ ppm, 3.98 (s, 3H), 7.62 (d, J=8.4 Hz, 1H), 8.16 (dd, J=8.8 Hz, 2.0 Hz, 1H), 8.39 (d, J=2.0 Hz, 1H).

Step B: Preparation of Methyl 4-Cyclopentyl-3-(trifluoromethyl)benzoate.

To a solution of 4-chloro-3-(trifluoromethyl)benzoate (196.7 g, 824 mmol) in THF (100 mL), cyclopentylzinc(II) bromide (1979 mL, 989 mmol) was added dropwise at 7.8° C. The temperature at the end of the addition rose to 22° C. bis(Tri-t-butylphosphine)palladium (21.07 g, 41.2 mmol) was added to the dark brown solution at the same temperature, and the resulting mixture was stirred at 70° C. for 8 h. The mixture was added to saturated aqueous NaHCO$_3$ (100 mL) at 0° C., stirred at the same temperature for 30 min and then at 22° C. for 2 h. The resulting suspension was filtered through Celite and the filtrate concentrated under vacuum. The solids were washed with EtOAc (3×300 mL), the filtrate was combined with the previous concentrate and the combined organics were washed with H$_2$O (2×600 mL), brine (2×500 mL), dried (Na$_2$SO$_4$), decanted and concentrated under reduced pressure to give the title compound as an orange oil (227 g) without further purification. LCMS m/z=273.4 [M+H]$^+$; $^1$H NMR (400 MHz, CDCl$_3$) δ ppm 1.71-1.60 (m, 2H), 1.83-1.75 (m, 2H), 1.95-1.87 (m, 2H), 2.21-2.11 (m, 2H), 3.46 (quintet, J=8.8 Hz, 1H), 3.97 (s, 3H), 7.58 (d, J=8.4 Hz, 1H), 8.18 (dd, J=8.0 Hz, 1.6 Hz, 1H), 8.31 (d, J=1.6 Hz, 1H).

Step C: Preparation of (4-Cyclopentyl-3-(trifluoromethyl)phenyl)methanol.

To a solution of 4-cyclopentyl-3-(trifluoromethyl)benzoate (224 g, 823 mmol) in 1,4-dioxane (600 mL), LiBH$_4$ (494 mL, 987 mmol, 2 M solution in THF) was added dropwise at 22° C. The resulting suspension was stirred at 85.5° C. for 5.5 h. The dark brown solution was cooled to 0° C. and the pH adjusted to 5 by slowly adding 6 N HCl (130 mL). The layers were separated and to the aqueous phase H$_2$O (250 mL) and NaCl (20 g) added. The combined aqueous were extracted with EtOAc (2×250 mL). The EtOAc layer was added to the previously separated organic phase and the combined organics were concentrated under reduced pressure. The resulting suspension was filtered through a pad of Celite/Na$_2$SO$_4$ and the solids were washed with EtOAc (3×400 mL). The combined organics were rotary evaporated and the dark brown oily residue was subjected to chromatography on silica to give the title compound as colorless liquid (110 g). LCMS m/z=243.3 [M−H]$^+$; $^1$H NMR (400 MHz, CDCl$_3$) δ ppm 1.67-1.55 (m, 2H), 1.82-1.69 (m, 2H), 1.95-1.83 (m, 2H), 2.19-2.04 (m, 2H), 3.39 (quintet, J=8.0 Hz, 1H), 4.72 (s, 2H), 7.55-7.46 (m, 2H), 7.62 (s, 1H).

Step D: Preparation of 4-(Chloromethyl)-1-cyclopentyl-2-(trifluoromethyl)benzene.

To (4-cyclopentyl-3-(trifluoromethyl)phenyl)methanol (110 g, 113 mmol), thionyl chloride (329 mL, 4.50 mol) was added dropwise at such a rate as to maintain the internal temperature between 10-25° C. (cooled with ice-water). The resulting mixture was stirred at 50° C. for 3.5 h followed by 6 h at 25° C. The mixture was concentrated under reduced pressure and the resulting oily residue poured into ice-water (450 mL) under vigorous stirring. The layers were separated and the aqueous phase extracted with CH$_2$Cl$_2$ (3×400 mL). The combined organic layers were washed with saturated NaHCO$_3$ (400 mL), brine (2×400 mL), dried (Na$_2$SO$_4$), filtered over fresh Na$_2$SO$_4$, and concentrated in vacuo to give the title compound as a pale yellow oil (113.3 g). $^1$H NMR (400 MHz, CDCl$_3$) δ ppm 1.67-1.57 (m, 2H), 1.81-1.71 (m, 2H), 1.94-1.84 (m, 2H), 2.16-2.07 (m, 2H), 3.39 (quintet, J=8.6 Hz, 1H), 4.61 (s, 2H), 7.49 (d, J=8.4 Hz, 1H), 7.54 (dd, J=8.4 Hz, 1.6 Hz, 1H), 7.63 (d, J=1.6 Hz, 1H).

Step E: Preparation of Ethyl 2-(7-Methoxy-1,2,3,4-tetrahydrocyclopenta[b]indol-3-yl)acetate.

To a solution of 2-iodo-4-methoxyaniline (20.0 g, 80 mmol), ethyl-2-(2-oxocyclopentyl)acetate (20.5 g, 120 mmol, 1.5 eq) and tetraethyl orthosilicate (21.7 g, 104 mmol, 1.3 eq) in anhydrous DMF (100 mL), was added pyridine p-toluenesulfonate (0.807 g, 3.21 mmol, 0.04 eq). The dark brown solution was stirred at 135° C. for 5 h under N$_2$, allowed to cool to 100° C. and then added DIPEA (31.1 g, 241 mmol, 3 eq) followed by Pd(OAc)$_2$ (0.541 g, 2.41 mmol, 0.03 eq). The resulting mixture was stirred at 120° C. for 22 h under N$_2$, concentrated under reduced pressure. The residue was taken up in DCM, filtered through a plug of silica and the solvent was evaporated under reduced pressure. The residue was purified by silica gel column chromatography to give the title compound. LCMS m/z=274.4 [M+H]$^+$.

Step F: Preparation of Ethyl 2-(7-Hydroxy-1,2,3,4-tetrahydrocyclopenta[b]indol-3-yl)acetate.

DCM (305 mL) was transferred to a 1 L 3-necked round-bottomed flask and cooled to −11° C. (internal) (ice acetone bath). BBr$_3$ (72.0 mL, 761 mmol) was added to the DCM with stirring. A solution of ethyl 2-(7-methoxy-1,2,3,4-tetrahydrocyclopenta[b]indol-3-yl)acetate (41.62 g, 152 mmol) in DCM (145 mL) was added in drops maintaining the internal temperature at between −5 to 0° C. After the addition the reaction was stirred for 1 h below 0° C. The reaction mixture was slowly poured into mixture of ice (400 mL) and saturated K$_2$CO$_3$ (400 mL) and stirred well (pH maintained at 9-7). The organic layer was separated, washed with brine (1×100 mL), dried over MgSO$_4$, filtered and concentrated under reduced pressure. The residual brown oil was purified by a pad of silica gel to give the title compound (8.03 g). LCMS m/z=260.2.

Step G: Preparation of Ethyl 2-(7-(4-Cyclopentyl-3-(trifluoromethyl)benzyloxy)-1,2,3,4-tetrahydrocyclopenta[b]indol-3-yl)acetate.

In a 2 L, 3-necked, round-bottomed flask under nitrogen atmosphere were placed ethyl 2-(7-hydroxy-1,2,3,4-tetrahydrocyclopenta[b]indol-3-yl)acetate (55.85 g, 215 mmol), cesium carbonate (84.2 g, 258 mmol), 4-(chloromethyl)-1-cyclopentyl-2-(trifluoromethyl)benzene (68 g, 259 mmol) in DMA (670 mL). The mixture was stirred 15 minutes at room temperature and heated at 50° C. overnight. The mixture was cooled down to room temperature and filtered. The filtrate was concentrated under vacuum. The residue was added hexanes (400 mL) and heated to 40° C. to give a dark solution. The solution was cooled down to room temperature over the weekend. The mixture was concentrated in vacuo and dried under vacuum to give the title compound (129.7 g). LCMS m/z=486.2.

Step H: Preparation of 2-(7-(4-Cyclopentyl-3-(trifluoromethyl)benzyloxy)-1,2,3,4-tetrahydrocyclopenta[b]indol-3-yl)acetic Acid.

In a 3 L, 3-necked, round-bottomed flask was placed ethyl 2-(7-(4-cyclopentyl-3-(trifluoromethyl)benzyloxy)-1,2,3,4-tetrahydrocyclopenta[b]indol-3-yl)acetate (139.4 g, 287 mmol) in dioxane (1.8 L). The mixture was added 2N lithium hydroxide (0.431 L, 861 mmol) and heated to 45-55° C. for 3 h. The mixture was concentrated in vacuo. The residue was added MTBE/water and acidified with concentrated HCl (until pH3) while keeping the temperature under 20° C. with an ice bath. The aqueous layer was separated and extracted with MTBE. The combined organic layers were washed several times with water until pH3 at the end of the washes. Acetonitrile and water were added to the MTBE solution and the mixture was concentrated in vacuo to give the title compound (130 g) without further purification. LCMS m/z=458.4.

Resolution via Chiral HPLC (conducted by Chiral Technologies Inc)
Column: normal phase preparative ChiralCel® OJH®
Eluent: CO$_2$/MeOH (75-25%)
Gradient: Isocratic
Flow: 400 mL/min
Detector: 254 nm
Retention Times: 1$^{st}$ enantiomer: 9.1 min (appears to correspond to the 2$^{nd}$ enantiomer purified under chiral HPLC conditions described in Example 1.4); 2$^{nd}$ enantiomer: 13.9 min (appears to correspond to the 1$^{st}$ enantiomer purified under chiral HPLC conditions described in Example 1.4).

After chiral resolution, the respective purified fractions were concentrated to dryness.

To a solution of the 1$^{st}$ enantiomer of Compound 12 as described in Example 1.29 in acetonitrile and ethanol was added (S)-1-phenethylamine (1 equivalent). The mixture was heated briefly and allowed to concentrate by slow evaporation. A precipitate was formed, filtered and dried. Single crystals of the 1$^{st}$ enantiomer of Compound 12 (as described in Example 1.29) were obtained and subjected to X-ray crystallography analysis. They were observed to be as depicted in FIG. 21.

Example 1.30

Preparation of 2-(7-(4-Cyclopentyl-3-(trifluoromethyl)benzyloxy)-1,2,3,4-tetrahydrocyclopenta[b]indol-3-yl)acetic Acid (Compound 12)

Step A: Preparation of 1-(2-(Trifluoromethyl)phenyl)cyclopentanol.

A solution of 1-bromo-2-(trifluoromethyl)benzene (0.5 g, 2.222 mmol) in anhydrous THF (10 mL) was cooled to −78° C. (dry ice IPA bath) under argon atmosphere. BuLi (2.5 M in hexanes, 1.068 mL, 2.67 mmol) was added in drops with efficient stirring. The reaction mixture was stirred at −78° C. for 40 min. A solution of cyclopentanone (0.243 g, 2.89 mmol) in anhydrous THF (1.5 mL) was added slowly (in drops) at −78° C. The reaction mixture was stirred at −78° C. for 30 min, gradually brought to room temperature, and stirred for 1 h. The reaction mixture was cooled by an ice bath, quenched with water, and acidified to pH 4-5 by addition of concentrated HCl. The solvent was removed under reduced pressure. The residue was dissolved in methylene chloride, washed with water (2 times), dried over Na$_2$SO$_4$, filtered and concentrated under reduced pressure. The residue was purified by silica gel chromatography to give the title compound as an oil (250 mg). LCMS m/z=213.1 [M−H$_2$O+H]$^+$.

Step B: Preparation of 1-Cyclopentyl-2-(trifluoromethyl)benzene.

To a solution of 1-(2-(trifluoromethyl)phenyl)cyclopentanol (5.1 g, 22.15 mmol) in ethanol (32 mL) was added 10% Pd—C (500 mg; Degussa; wet) and the mixture was hydrogenated overnight with a hydrogen balloon. The reaction mixture was filtered through celite. The filtrate was poured into ice-water (100 mL) and extracted with CH$_2$Cl$_2$ (2×70 mL). The combined CH$_2$Cl$_2$ layer was washed with water (1×75 mL), dried over Na$_2$SO$_4$ and the solvent was removed under reduced pressure to give the title compound (4.3 g). $^1$H NMR (400 MHz, CDCl$_3$) δ ppm 1.58-1.67 (m, 4H), 1.81-1.90 (m, 2H), 2.06-2.15 (m, 2H), 3.32-3.43 (m, 1H), 7.22-7.26 (m, 1H), 7.45-7.51 (m, 2H), 7.58 (d, J=8 Hz, 1H).

Step C: Preparation of 4-Bromo-1-cyclopentyl-2-(trifluoromethyl)benzene.

To a solution of 1-cyclopentyl-2-(trifluoromethyl)benzene (0.5 g, 2.334 mmol) in acetic acid (2.5 mL) was added bromine (1.202 mL, 23.34 mmol). The mixture was stirred well, added concentrated H$_2$SO$_4$ (2.5 mL), and stirred at 40° C. for 1.5 h. The reaction mixture was poured into ice-water and extracted with CH$_2$Cl$_2$. The CH$_2$Cl$_2$ layer was washed with water, followed by a solution of sodium thiosulfate, then with water. The organic layer was dried over Na$_2$SO$_4$ and the solvent was removed under reduced pressure. The residue was purified by silica gel chromatography to give the title compound (250 mg). $^1$H NMR (400 MHz, DMSO-d$_6$) δ ppm 1.52-1.75 (m, 4H), 1.78-1.88 (m, 2H), 1.95-2.04 (m, 2H), 3.16-3.26 (m, 1H), 7.57 (d, J=8.4 Hz, 1H), 7.76 (d, J=2 Hz, 1H), 7.81 (dd, J=8.4 Hz, 2 Hz, 1H).

Step D: Preparation of 4-Cyclopentyl-3-(trifluoromethyl) benzaldehyde.

In a 15 mL round-bottomed flask were placed 4-Bromo-1-cyclopentyl-2-(trifluoromethyl)benzene (0.186 g, 0.635 mmol) and anhydrous THF (1.86 mL) under argon atmosphere. The solution was stirred well and cooled to −78° C. (dry ice IPA bath). BuLi (2.5 M in hexanes, 0.281 mL, 0.703 mmol) was added in drops (slowly) and the reaction mixture was stirred at low temperature for 25 min. Anhydrous DMF (0.1 mL, 0.766 mmol) was added in drops at −78° C. (slowly). The mixture was stirred at −78° C. for 20 min then in room temperature for 30 min. The reaction was quenched with water, acidified with 2M HCl and extracted with EtOAc. The EtOAc layer was washed with water, dried over Na$_2$SO$_4$, and concentrated in vacuo to give the title compound as an oil (60 mg). LCMS m/z=243.3 [M+H]$^+$. $^1$H NMR (400 MHz, DMSO-d$_6$) δ ppm 1.55-1.7 (m, 4H), 1.79-1.94 (m, 2H), 1.95-2.09 (m, 2H), 3.29-3.37 (m, 1H), 7.86 (d, J=8 Hz, 1H), 8.12 (d, J=8 Hz, 1H), 8.16 (d, J=1.2 Hz, 1H), 10.46 (s, 1H).

Step E: Preparation of (4-Cyclopentyl-3-(trifluoromethyl) phenyl)methanol.

To a solution of 4-cyclopentyl-3-(trifluoromethyl)benzaldehyde (0.25 g, 1.032 mmol) in ethanol (2.5 mL) was added sodium borohydride (0.047 g, 1.238 mmol) and the mixture was stirred in room temperature for 2 h. The mixture was quenched with water, acidified with 6N HCl, diluted with more water and extracted with CH$_2$Cl$_2$. The CH$_2$Cl$_2$ layer was washed with water, dried over Na$_2$SO$_4$, filtered and concentrated in vacuo to give the title compound (0.22 g). LCMS m/z=227.5 [M−H$_2$O+H]$^+$. $^1$H NMR (400 MHz, DMSO-d$_6$) δ ppm 1.54-1.72 (m, 4H), −1.77-1.89 (m, 2H), 1.93-2.05 (m, 2H), 3.19-3.28 (m, 1H), 4.52 (d, J=6 Hz, 2H), 5.28 (t, J=5.6 Hz, 1H), 7.52-7.6 (m, 3H).

Step F: Preparation of 4-(Chloromethyl)-1-cyclopentyl-2-(trifluoromethyl)benzene.

To (4-cyclopentyl-3-(trifluoromethyl)phenyl)methanol (110 g, 113 mmol) thionyl chloride (329 mL, 4.50 mol, 10 eq) was added dropwise at such a rate as to maintain the internal temperature between 10-25° C. (cooled with ice-water). The resulting mixture was stirred at 50° C. for 3.5 h followed by 6 h at 25° C. The mixture was concentrated under reduced pressure and the resulting oily residue poured into ice-water (450 mL) under vigorous stirring. The layers were separated and the aqueous phase extracted with CH$_2$Cl$_2$ (3×400 mL). The combined organic layers were washed with saturated NaHCO$_3$ (400 mL), brine (2×400 mL), dried (Na$_2$SO$_4$), filtered over fresh Na$_2$SO$_4$, and concentrated in vacuo to afford 4-(chloromethyl)-1-cyclopentyl-2-(trifluoromethyl)benzene as a pale yellow oil (113.3 g, 96%). $^1$H NMR (400 MHz, CDCl$_3$) δ ppm 1.67-1.57 (m, 2H), 1.81-1.71 (m, 2H), 1.94-1.84 (m, 2H), 2.16-2.07 (m, 2H), 3.39 (quintet, J=8.6 Hz, 1H), 4.61 (s, 2H), 7.49 (d, 0.1=8.4 Hz, 1H), 7.54 (dd, J=8.4 Hz, 1.6 Hz, 1H), 7.63 (d, J=1.6 Hz, 1H).

Step G: Preparation of Ethyl 3-(2-Ethoxy-2-oxoethyl)-7-methoxy-1,2,3,4-tetrahydrocyclopenta[β]indole-3-carboxylate.

To a suspension of (4-methoxyphenyl)hydrazine hydrochloride (379.5 g, 2.17 mol) and ethyl 1-(2-ethoxy-2-oxoethyl)-2-oxocyclopentanecarboxylate (526 g, 2.17 mol) in EtOH (2.0 L), AcOH (131 g, 124 mL, 2.17 mol) was added and the mixture was stirred at 75° C. for 18 h under N$_2$. The fine dark brown suspension was allowed to cool and neutralized with saturated aqueous NaHCO$_3$. The solvent was evaporated under reduced pressure. The brown oily residue was taken up in EtOAc (2 L), filtered and the organics were washed with water (3×500 mL) and brine (2×500 mL). The combined aqueous layers were re-extracted with EtOAc. The combined organics were dried (MgSO$_4$) and the solvent was evaporated under reduced pressure to give the title compound (703.4 g) as a thick dark brown oil. LCMS m/z=346.2 [M+H]$^+$; $^1$H NMR (400 MHz, DMSO-d$_6$) δ ppm 1.15 (t, J=7.2 Hz, 3H), 1.17 (t, J=7.2 Hz, 3H), 2.48-2.42 (m, 1H), 2.81 (d, J=16.6 Hz, 1H), 2.82-2.70 (m, 2H), 3.05-2.99 (m, 1H), 3.18 (d, J=16.6 Hz, 1H), 3.73 (s, 3H), 4.12-4.00 (m, 4H), 6.67 (dd, J=8.8, 2.5 Hz, 1H), 6.85 (d, J=2.4 Hz, 1H), 7.21 (d, J=8.7 Hz, 1H), 10.57 (s, 1H).

Step H: Preparation of 3-(Carboxymethyl)-7-methoxy-1,2,3,4-tetrahydrocyclopenta[β]indole-3-carboxylic Acid.

A 50 wt % aqueous solution of NaOH (346 g, 4.32 mol, 4 equiv.) was slowly added to a solution of ethyl 3-(2-ethoxy-2-oxoethyl)-7-methoxy-1,2,3,4-tetrahydrocyclopenta[β]indole-3-carboxylate (373 g, 1.08 mol) in EtOH (2.0 L) and the resulting mixture was stirred at 60° C. for 18 h under N$_2$. The brown suspension was neutralized at 0° C. with 6 N HCl and the solvent was evaporated. The brown residue was partitioned between H$_2$O (2 L) and EtOAc (1 L) and the layers separated. The aqueous layer was further washed with EtOAc (3×500 mL) and the pH of the aqueous phase was adjusted to 3-4 with 6 N HCl. The precipitate was collected and dried under vacuum at ambient temperature overnight to give the title compound (191.4 g) as a brown solid. LCMS m/z=290.4 [M+H]$^+$; $^1$H NMR (400 MHz, DMSO-d$_6$) δ ppm 2.43-2.36 (m, 1H), 2.68 (d, J=16.9 Hz, 1H), 2.82-2.69 (m, 2H), 3.07-3.01 (m, 1H), 3.12 (d, J=16.9 Hz, 1H), 3.72 (s, 3H), 6.66 (dd, J=8.7, 2.4 Hz, 1H), 6.84 (d, J=2.4 Hz, 1H), 7.20 (d, J=8.6 Hz, 1H), 10.55 (s, 1H), 12.30 (s, 2H).

Step I: Preparation of 2-(7-Methoxy-1,2,3,4-tetrahydrocyclopenta[β]indol-3-yl)acetic Acid.

A solution of 3-(carboxymethyl)-7-methoxy-1,2,3,4-tetrahydrocyclopenta[β]indole-3-carboxylic acid (191 g, 0.66 mol) in AcOH (1.0 L) was stirred at 60° C. for 4.5 h under N$_2$. The dark brown solution was concentrated. The precipitate was collected, washed with H$_2$O (3×500 mL) and dried at 40° C. under vacuum overnight to give the title compound (126.4 g) as a brown solid. LCMS m/z=246.1 [M+H]$^+$; $^1$H NMR (400 MHz, DMSO-d$_6$) δ ppm 2.12-2.04 (m, 1H), 2.35 (dd, J=16.0, 9.1 Hz, 1H), 2.77-2.60 (m, 4H), 3.50-3.43 (m, 1H), 3.72 (s, 3H), 6.62 (dd, J=8.8, 2.5 Hz, 1H), 6.81 (d, J=2.3 Hz, 1H), 7.18 (d, J=8.7 Hz, 1H), 10.42 (s, 1H), 12.16 (s, 1H).

Step J: Preparation of Ethyl 2-(7-Hydroxy-1,2,3,4-tetrahydrocyclopenta[β]indol-3-yl)acetate.

To a solution of BBr$_3$ (115 g, 43.3 mL, 458 mmol, 3 equiv.) in CH$_2$Cl$_2$ (70 mL) a suspension of 2-(7-methoxy-1,2,3,4- tetrahydrocyclopenta[b]indol-3-yl)acetic acid (37.44 g, 153 mmol) in CH$_2$Cl$_2$ (300 mL) was added slowly while maintaining the reaction temperature between −5° C. to 0° C. The resulting dark brown suspension was stirred at −5 to 0° C. for an additional 1 h. EtOH (187 mL) was added dropwise to the reaction mixture while maintaining the temperature between 0-10° C. The resulting solution was heated at 40° C. for 30 min. The solution was cooled and the pH adjusted to 8 by adding 10 N NaOH (142.9 mL, 1.43 mol) slowly while maintaining the temperature between 0-3° C. The solvent was removed under reduced pressure until about 200 mL of concentrate remained. The pH was adjusted to about 7 with concentrated HCl, the suspension filtered, the solids washed with H$_2$O (3×200 mL) and dried under vacuum at ambient temperature overnight. The light brown material was dissolved in EtOAc (200 mL), and filtered washing the solids with EtOAc. The combined organics were washed with saturated aqueous NaHCO$_3$ (2×200 mL), brine (200 mL), dried (Na$_2$SO$_4$) and the solvent rotary evaporated to give the title compound (35.2 g) as a light brown solid. LCMS m/z=260.1 [M+H]$^+$; $^1$H NMR (400 MHz, DMSO-d$_6$) δ ppm 1.20 (t, J=7.1 Hz, 3H), 2.11-2.03 (m, 1H), 2.42 (dd, J=15.7, 8.9 Hz, 1H), 2.71-2.55 (m, 3H), 2.76 (dd, J=15.7, 5.5 Hz, 1H), 3.49-3.42 (m, 1H), 4.11 (q, J=7.1 Hz, 2H), 6.49 (dd, J=8.6, 2.3 Hz, 1H), 6.62 (d, J=2.1 Hz, 1H), 7.07 (d, J=8.6 Hz, 1H), 8.47 (s, 1H), 10.25 (s, 1H).

Step K: Preparation of Ethyl 2-(7-(4-Cyclopentyl-3-(trifluoromethyl)benzyloxy)-1,2,3,4-tetrahydrocyclopenta[b]indol-3-yl)acetate.

To a solution of 4-(chloromethyl)-1-cyclopentyl-2-(trifluoromethyl)benzene (46.2 g, 176 mmol, 1.2 eq) in DMF (400 mL) ethyl 2-(7-hydroxy-1,2,3,4-tetrahydrocyclopenta[β]indol-3-yl)acetate (38.0 g, 147 mmol) was added in one portion followed by Cs$_2$CO$_3$ (71.6 g, 220 mmol, 1.5 eq). An exotherm was observed over the first 15 min (temperature increased to 72.8° C.) after which the mixture was further stirred at 50° C. under N$_2$ for 13.5 h. The reaction mixture was allowed to cool, filtered under suction washing the solids with EtOAc and the filtrate evaporated under reduced pressure. The dark brown oily residue was taken up in EtOAc, washed with H$_2$O (3×300 mL) and the aqueous phase re-extracted with EtOAc. The combined organics were dried (MgSO$_4$), filtered and rotary evaporated to give the title compound (77 g) as a thick dark brown oil which was used in the next step without further purification. LCMS m/z=486.4 [M+H]$^+$; $^1$H NMR (400 MHz, DMSO-d$_6$) δ ppm 1.19 (t, J=7.2 Hz, 3H), 1.73-1.54 (m, 4H), 1.89-1.77 (m, 2H), 2.12-1.94 (m, 3H), 2.44 (dd, J=17.2, 8.4 Hz, 1H), 2.81-2.60 (m, 4H), 3.30-3.20 (m, 1H), 3.54-3.44 (m, 1H), 4.12 (q, J=7.2 Hz, 2H), 5.12 (s, 2H), 6.72 (dd, J=8.8, 2.4 Hz, 1H), 6.94 (d, J=2.4 Hz, 1H), 7.20 (d, J=8.8 Hz, 1H), 7.62 (d, J=7.8 Hz, 1H), 7.73-7.67 (m, 2H), 10.47 (s, 1H), Step L: Preparation of 2-(7-(4-Cyclopentyl-3-(trifluoromethyl)benzyloxy)-1,2,3,4-tetrahydrocyclopenta[b]indol-3-yl)acetic Acid.

To a solution of ethyl 2-(7-(4-cyclopentyl-3-(trifluoromethyl)benzyloxy)-1,2,3,4-tetrahydrocyclopenta[b]indol-3-yl)acetate (71.2 g, 147 mmol) in 1,4-dioxane (400 mL) an aqueous solution of LiOH.H$_2$O (220 mL, 2 M, 3 eq) was added. The resulting two phase mixture was stirred at 50° C. under N$_2$ for 5 h. The reaction mixture was allowed to cool and the pH adjusted to 3-4 with 6 N HCl. The solvent was rotary evaporated and to the two phase aqueous/product mixture CH$_2$Cl$_2$ added. The layers were separated and the organics washed with H$_2$O (2×300 mL). The combined aqueous phases were re-extracted with CH$_2$Cl$_2$. The combined organic layers were dried (MgSO$_4$), filtered and rotary evaporated. The dark brown oily residue was taken up in MeOH and the solvent evaporated under reduced pressure. The dark brown residue was taken up again in a minimum amount of MeOH and left in the fridge over 16 h. The precipitate was collected under suction, washing the solids with hexanes, and dried under high vacuum to afford the product (34.5 g, 51%) as an off-white solid. The filtrate containing product was concentrated to dryness to give a dark brown fluffy solid (33.6 g) which was processed further separately. LCMS m/z=458.2 [M+H]$^+$; $^1$H NMR (400 MHz, DMSO-d$_6$) δ ppm 1.76-1.57 (m, 4H), 1.93-1.81 (m, 2H), 2.16-1.97 (m, 3H), 2.38 (dd, J=15.2, 8.8 Hz, 1H), 2.80-2.62 (m, 4H), 3.32-3.23 (m, 1 H), 3.54-3.44 (m, 1H), 5.15 (s, 2H), 6.74 (dd, J=8.8, 2.4 Hz, 1H), 6.96 (d, J=2.4 Hz, 1H), 7.23 (d, J=8.8 Hz, 1H), 7.65 (d, J=8.4 Hz, 1H), 7.76-7.70 (m, 2H), 10.48 (s, 1H), 12.20 (s, 1H).

Example 1.31

Preparation of 2-(7-(4-Cyclopentyl-3-(trifluoromethyl)benzyloxy)-1,2,3,4-tetrahydrocyclopenta[b]indol-3-yl)acetic Acid Step A: Preparation of 1-Cyclopentyl-2-(trifluoromethyl)benzene.

In a 5 L 3-necked, round-bottomed flask fitted with a mechanical stirrer, a temperature probe, a dry nitrogen inlet, a condenser and an addition funnel was placed anhydrous THF (750 mL) and magnesium (40.5 g, 1667 mmol) under N$_2$. The slurry was cooled to 10° C. in an ice bath. A solution of FeCl$_3$ (18.02 g, 111 mmol) in anhydrous THF (80 mL) (Note: dissolution of FeCl$_3$ in THF was exothermic) was added dropwise to the magnesium slurry via a syringe. N1,N1,N2,N2-tetramethylethane-1,2-diamine (201 mL, 1333 mmol) was added to the reaction mixture via a 500 mL addition funnel at 15° C. causing the temperature to go up to 22.5° C. The reaction mixture was cooled to 18° C. and stirred at that temperature for 1 h and 45 min. It was then heated to 44-45° C., stirred for 1 h, cooled to 5-10° C., and added a mixture of 1-bromo-2-(trifluoromethyl)benzene (150 mL, 1111 mmol) and bromocyclopentane (143 mL, 1333 mmol) dropwise while keeping internal temperature under 30° C. (temperature was maintained between 22 to 30° C.). After addition was complete, the reaction mixture was cooled to 17-18° C. and stirred overnight at room temperature. This main reaction mixture was cooled to 10° C. and added magnesium (15 g). Meanwhile, in a separate 1 L round-bottomed flask under N$_2$, Mg (20 g, 0.5 eq) in THF (300 mL) was added a solution of FeCl$_3$ (9 g, 0.5 eq) in anhydrous THF (30 mL) like described above. The obtained mixture was stirred at room temperature for 30 min, heated to 45° C. for 1 h, cooled to room temperature, and added dropwise into the main reaction mixture via an addition funnel (remaining magnesium was transferred by a spatula) while keeping the internal temperature under 30° C. The reaction was continued at room temperature for 1 h, cooled to 5° C. (ice bath) and quenched slowly with saturated NH$_4$Cl solution (150 mL) (quench was exothermic satd. NH4Cl was added slowly with efficient stirring). Celite was added after quenching the reaction and stirred well. The mixture was filtered through a 3 L sintered funnel. The filter cake was washed with THF. The filtrate was concentrated under reduced pressure at 37° C. (bath temperature)/155 Torr to obtain a brown oil. The oil was cooled by ice bath and 6N HCl (500 mL) was poured into it slowly with efficient stirring (addition of HCl was exothermic initially, then the exotherm subsided). The mixture was extracted with hexane (2×400 mL). The hexane layer was separated out and filtered through a pad of celite. The filtrate (hexane layer) was washed with water (3×300 mL), dried (Na₂SO₄) and silica (550 g) added; slurried well. The slurry was filtered and the filtrate (light yellow in color) was concentrated under reduced pressure (rotavapor; bath temp. 37 C at 185-188 Torr) to give the title compound as a light orange oil, (190 g, 91.4% purity by LC at 214 nm). $^1$H NMR (400 MHz, DMSO-d₆) δ 1.56-1.71 (m, 4H), 1.80-1.88 (m, 2H), 1.96-2.05 (m, 2H), 3.22-3.29 (m, 1H), 7.35-7.40 (m, 1H), 7.16-7.65 (m, 2H).

Step B: Preparation of 4-(Chloromethyl)-1-cyclopentyl-2-(trifluoromethyl)benzene.

In a 1 L, 3-necked reaction flask fitted with a mechanical stirrer, a temperature probe, an addition funnel and a dry nitrogen inlet was placed 1-cyclopentyl-2-(trifluoromethyl) benzene (50 g, 233 mmol). The material was stirred and cooled to −12° C. (dry ice/IPA bath). Concentrated sulfuric acid (100 mL, 1877 mmol) was added dropwise so that the temperature was maintained between −12° C. to −10° C. The mixture was cooled to −15° C. and s-trioxane (27.3 g, 303 mmol) was added in 3 batches (9.1 g each batch) while the temperature was maintained at between −15° C. to −10° C. The mixture was stirred at −10° C. and almost immediately sulfurochloridic acid (28.1 mL, 420 mmol) was added slowly maintaining the temperature at between −10° C. to −5° C. The mixture was stirred for 20 min at −5° C. and 3 h between −2 to −3° C. The reaction mixture was slowly poured (with efficient stirring) into ice-water (1 L). MTBE (700 mL) was added and the mixture was stirred well. Celite (300 g) was added and stirred well. The celite slurry was filtered and the celite bed was washed with MTBE. The aqueous layer of the filtrate was separated and extracted with MTBE (1×700 mL). The combined MTBE layer was washed with water (1×500 mL) followed by saturated NaHCO₃ (2×350 mL). The MTBE layer was then washed with water (2×500 mL), dried (Na₂SO₄) and filtered. The filtrate was concentrated (at 38° C., bath temperature; 200 Torr) to give a yellow oil. The oil was taken up in hexane (500 mL) and filtered through a bed of silica; then the silica bed was washed with hexane. The filtrate was concentrated under reduced pressure (38° C., bath temperature; at 200 Torr) to give the title compound as a light yellow oil (36.2 g; 89% purity by LC at 214 nm). $^1$H NMR (400 MHz, DMSO-d₆) δ 1.55-1.72 (m, 4H), 1.78-1.89 (m, 2H), 1.94-2.04 (m, 2H), 3.19-3.28 (m, 1H), 4.82 (s, 2H), 7.62-7.72 (m, 3H).

Step C: Preparation of 1-Cyclopentyl-4-((4-nitrophenoxy) methyl)-2-(trifluoromethyl)benzene.

In a 1 L flask equipped with a stirrer, thermocouple, condenser and a nitrogen inlet, was placed nitrophenol (28 g, 201 mmol) in DMA (150 mL) and potassium carbonate powder (28.7 g, 207 mmol). 4-(Chloromethyl)-1-cyclopentyl-2-(trifluoromethyl)benzene (45.4 g, 173 mmol) was added and washed in with DMA (120 mL). The reaction was heated at 80° C. (bath, internal 77° C.) overnight. The mixture was cooled and poured into ice water (1 L). The solids formed were allowed to settle with stirring for 4 h and collected by filtration. The solid collected was stirred in sodium bicarbonate solution (300 mL), filtered, washed with water, and air dried. The pale yellow residue was washed with hexanes (250 mL) and the solids were dried in vacuum oven overnight to give the title compound (41.4 g, ~85% pure by LC). LCMS m/z=366.2 [M+H]⁺.

Step D: Preparation of 4-(4-Cyclopentyl-3-(trifluoromethyl)benzyloxy)aniline hydrochloride.

In a 2 L flask equipped with stirrer and thermocouple, was placed 1-cyclopentyl-4-((4-nitrophenoxy)methyl)-2-(trifluoromethyl)benzene (40 g, 109 mmol) in ACN (520 mL). Ammonium chloride (3M, 520 mL) was added and the mixture was stirred and cooled to 2.5° C. Zinc (35.8 g, 547 mmol) was added in portions keeping temperature below 5° C. After addition was completed, the reaction mixture was allowed to warm to room temperature and stirred overnight. The mixture was filtered through a bed of celite (50 g) and the filter bed was washed with ACN (150 mL). The aqueous layer of the filtrate was separated and back extracted with isopropyl acetate (200 mL). The combined organic layers were dried over sodium sulfate (50 g), filtered and concentrated. The residue was dissolved in ethanol (120 mL), added HCl (1.25 M in EtOH, 140 mL), and stirred at ambient for 2.5 hours. After removal of the solvent, the residual solids was triturated with ACN (120 mL), filtered, washed with ACN (2×50 mL), and dried under vacuum to give the title compound (29.8 g).

Step E: Preparation of (4-(4-Cyclopentyl-3-(trifluoromethyl)benzyloxy)phenyl)hydrazine Hydrochloride.

4-(4-Cyclopentyl-3-(trifluoromethyl)benzyloxy)aniline hydrochloride (30 g, 81 mmol) was suspended in water (285 mL), and concentrated HCl (18 mL) was added. The suspension was stirred efficiently and cooled in ice/IPA bath to −0° C. Sodium nitrite (5.57 g, 81 mmol) in water (12 mL) was added. After addition, the reaction was stirred at 2° C. for 40 minutes. Some solids on the side were washed with ACN (10 mL). The mixture was cooled to −1° C. and tin (II)chloride (45.9 g, 242 mmol) dissolved in concentrated HCl (30 mL) was added slowly. A thick precipitate was formed and stirring was continued for 30 minutes. The mixture was warmed to room temperature and stirred for 3 h. The mixture was filtered, washed with HCl (0.1 M) and the solid was dried under vacuum to give the title compound (40.6 g).

Step F: Preparation of Ethyl 7-(4-Cyclopentyl-3-(trifluoromethyl)benzyloxy)-3-(2-ethoxy-2-oxoethyl)-1,2,3,4-tetrahydrocyclopenta[b]indole-3-carboxylate.

In a 1 L flask was placed EtOH (500 mL). Sulfuric acid (2.4 g, 23.98 mmol) was added at 40° C., followed by ethyl 1-(2-ethoxy-2-oxoethyl)-2-oxocyclopentanecarboxylate (15.2 g, 62.7 mmol). (4-(4-Cyclopentyl-3-(trifluoromethyl)benzyloxy)phenyl)hydrazine hydrochloride (24.0 g, 62.0 mmol) was added and the solution became light yellow and homogenous. The reaction mixture was refluxed overnight with a Dean-Starks condenser attached. The mixture was cooled and extracted in ethyl acetate (3×100 mL). The organics were washed with water (200 mL), sodium bicarbonate solution (2×70 mL), water (100 mL), dried over magnesium sulfate, and concentrated. The residue was dissolved in hexanes/ethyl acetate (80:20, 300 mL), added silica gel (30 g) and stirred for 35 minutes. The slurry was filtered, washed with the same elution solvent (100 mL) and the filtrate was concentrated to give the title compound (26.7 g). LCMS m/z=558.5 [M+H]⁺.

Step G: Preparation of Sodium 3-(Carboxylatomethyl)-7-(4-cyclopentyl-3-(trifluoromethyl)benzyloxy)-1,2,3,4-tetrahydrocyclopenta[b]indole-3-carboxylate.

In a 500 mL flask was placed ethyl 7-(4-cyclopentyl-3-(trifluoromethyl)benzyloxy)-3-(2-ethoxy-2-oxoethyl)-1,2,3,4-tetrahydrocyclopenta[b]indole-3-carboxylate (24.1 g, 43.2 mmol) in isopropanol (275 mL). Sodium hydroxide solution (20%, 129.5 mL, 130 mmol) was added and the mixture was heated at 100° C. (bath) for 2.5 h. The mixture was cooled, filtered, washed with isopropanol, and dried overnight under vacuum at 40° C. to give the title compound (17.5 g). LCMS m/z=502.6 [M−2Na+3H]⁺.

Step H: Preparation of 2-(7-(4-Cyclopentyl-3-(trifluoromethyl)benzyloxy)-1,2,3,4-tetrahydrocyclopenta[b]indol-3-yl)acetic Acid.

To a stirred solution of sodium 3-(carboxylatomethyl)-7-(4-cyclopentyl-3-(trifluoromethyl)benzyloxy)-1,2,3,4-tetrahydrocyclopenta[b]indole-3-carboxylate (16.5 g, 30.2 mmol) in water at 40° C. was added ammonium chloride solution (9.71%, 100 mL). The reaction was heated at 92° C. (bath) for 4.4 h. The mixture was refrigerated overnight, decanted and triturated with ice cold 6N HCl (100 mL). The solid was collected by filtration, washed with diluted HCl (100 mL) and dried overnight in a vacuum oven at 40° C. to give the title compound (8.5 g). LCMS m/z=458.3 [M+H]$^+$.

Example 1.32

Preparation of the Ca salt of the 2$^{nd}$ Enantiomer of Compound 12

Prior to use, the 2$^{nd}$ enantiomer of Compound 12, as described in Example 1.29, was slurried in acetonitrile overnight, filtered and dried to produce a crystalline form. To the crystalline form (40 mg) was added acetonitrile (1 mL) and the mixture was warmed to 60° C. The counterion was added by adding 20 µL of calcium acetate solution (2 M) and 20 µL of water then seeding with crystalline salt and allowing to slowly cool to room temperature. The resulting solid was filtered and dried to give a white solid.

Example 1.33

Preparation of L-Arginine Salt of the 2$^{nd}$ Enantiomer of Compound 12

The 2$^{nd}$ enantiomer of Compound 12 as described in Example 1.29 (174.7 mg, 0.381 mmol) was dissolved in IPA (1.57 mL) and L-arginine (66.4 mg, 0.381 mmol) was added as a solution in water (263 µL). The homogeneous solution was warmed to 40° C. After 15 min. at this temperature, a precipitate had formed. The reaction mixture was warmed to 70° C. causing the precipitate to dissolve. The heat bath was turned off. A precipitate began to form at 40° C. and the reaction was allowed to cool to 28° C. before collecting the solids by filtration. The solids were washed with 14% water in IPA to give the L-arginine salt of the title compound (130 mg).

Example 1.34

Preparation of the D-Lysine salt of the 1$^{st}$ Enantiomer of Compound 12

To the 1$^{st}$ enantiomer of Compound 12 as described in Example 1.29 in acetonitrile with 3% water was added D-lysine (1 M aqueous solution). After stirring overnight at ambient temperature, the resulting solid was filtered and dried.

Example 1.35

Preparation of the (R)-1-phenethylamine salt acetonitrile solvate of the 2$^{nd}$ Enantiomer of Compound 12

To a solution of the 2$^{nd}$ enantiomer of Compound 12 as described in Example 1.29 in acetonitrile was added (R)-1-phenethylamine (1 equivalent). The mixture was heated briefly and allowed to cool down. A precipitate was formed, filtered and dried. Single crystals of the (R)-1-phenylethanamine salt of the 2$^{nd}$ enantiomer of Compound 12 (as described in Example 1.29) were recrystallized by slow evaporation from acetonitrile and acetone and subjected to X-ray crystallography analysis. An acetonitrile solvate was observed in the ratio of 4 salt moieties to 1 acetonitrile molecule.

Example 2

Homogeneous Time-Resolved Fluorescence (HTRF®) Assay for Direct cAMP Measurement Compounds were screened for agonists of the S1P1 receptor (e.g., human S1P1 receptor) using the HTRF® assay for direct cAMP measurement (Gabriel et al., Assay and Drug Development Technologies, 1:291-303, 2003) and recombinant CHO-K1 cells stably transfected with S1P1 receptors. CHO-K1 cells were obtained from ATCC® (Manassas, Va.; Catalog #CCL-61). An agonist of the S1P1 receptor was detected in the HTRF® assay for direct cAMP measurement as a compound which decreased cAMP concentration. HTRF® assay also was used to determine EC$_{50}$ values for S1P1 receptor agonists.

Principle of the assay: HTRF® assay kit was purchased from Cisbio-US, Inc. (Bedford, Mass.; Catalog #62AM4PEC). The HTRF® assay supported by the kit is a competitive immunoassay between endogenous cAMP produced by the CHO-K1 cells and tracer cAMP labeled with the dye d2. The tracer binding is visualized by a monoclonal anti-cAMP antibody labeled with Cryptate. The specific signal (i.e., fluorescence resonance energy transfer, FRET) is inversely proportional to the concentration of unlabeled cAMP in the standard or sample.

Standard curve: The fluorescence ratio (665 nm/620 nm) of the standards (0.17 to 712 nM cAMP) included in the assay was calculated and used to generate a cAMP standard curve according to the kit manufacturer's instructions. The fluorescence ratio of the samples (test compound or compound buffer) was calculated and used to deduce respective cAMP concentrations by reference to the cAMP standard curve.

Setup of the assay: The HTRF® assay was carried out using a two-step protocol essentially according to the kit manufacturer's instructions, in 20 µL total volume per well in 384-well plate format (ProxiPlates; PerkinElmer, Fremont, Calif.; catalog #6008280). To each of the experimental wells was transferred 1500 recombinant CHO-K1 cells in 5 µL phosphate buffered saline containing calcium chloride and magnesium chloride ("PBS+"; Invitrogen, Carlsbad, Calif.; catalog #14040) supplemented with IBMX (250 µM) and rolipram (20 µM) (phosphodiesterase inhibitors; Sigma-Aldrich, St. Louis, Mo.; catalog #15879 and catalog #R6520, respectively), followed by test compound in 5 µL compound buffer (PBS+ supplemented with 10 µL NKH477 (water-soluble forskolin derivative; SignaGen Laboratories, Gaithersburg, Md.; catalog #PKI-NKH477-010)) or 5 µL compound buffer. The plate was then incubated at room temperature for 1 h. To each well was then added 5 µL cAMP-d2 conjugate in lysis buffer and 5 µL Cryptate conjugate in lysis buffer according to the kit manufacturer's instructions. The plate was then further incubated at room temperature for 1 hour, after which the assay plate was read.

Assay readout: HTRF® readout was accomplished using a PHERAstar (BMG LABTECH Inc., Durham, N.C.) or EnVision™ (PerkinElmer, Fremont Calif.) microplate reader.

Certain compounds of the present invention and their corresponding activity values are shown in Table B.

TABLE B

| Compound No. | EC$_{50}$ S1P1 (HTRF) |
|---|---|
| 4 | 16 nM |
| 8 | 9 nM |
| 10 | 26 nM |

Certain other compounds of the invention had activity values ranging from about 35 pm to about 362 nM in this assay.

Example 3

Cellular/Functional $Ca^{2+}$ Assay for Agonist Activity on S1P3 Receptor

A compound of the invention can be shown to have no or substantially no agonist activity on the S1P3 receptor by using in assay a human neuroblastoma cell line which endogenously expresses S1P3 (predominantly), S1P2 and S1P5 receptors, but not S1P1 or S1P4 receptors, based on mRNA analysis (Villullas et al., *J. Neurosci. Res.*, 73:215-226, 2003). Of these, S1P3 and S1P2 receptors respond to agonists, such as S1P, with an intracellular calcium increase. No or substantially no increase of intracellular calcium in response to a test compound is indicative of the test compound exhibiting no or substantially no agonist activity on the S1P3 receptor. Such an assay can be performed commercially, e.g. by Caliper LifeSciences (Hopkinton, Mass.).

Assay: The human neuroblastoma cells are washed and resuspended in physiological buffer. The cells are then loaded with dye that measures intracellular calcium. S1P is used as a reference agonist. After addition of S1P or a test compound, fluorescence is measured at 485 nm excitation/525 nm emission every 2 s for at least 60 s. Calcium ionophore A23187 is then added as an internal positive control Example 4

Effect of Compounds in Peripheral Lymphocyte Lowering (PLL) Assay

Figure 2:
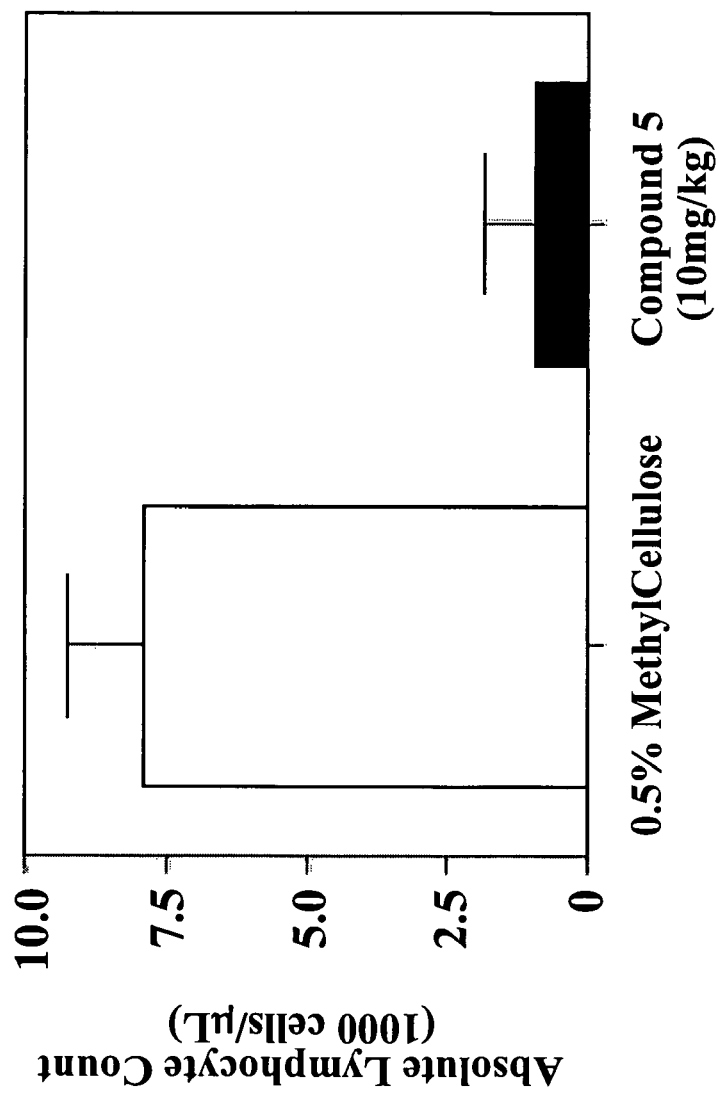
FIG. 2 shows the results of an experiment which measured the ability of Compound 5 to lower the absolute count of peripheral lymphocytes in mice compared to vehicle.
Figure 3:
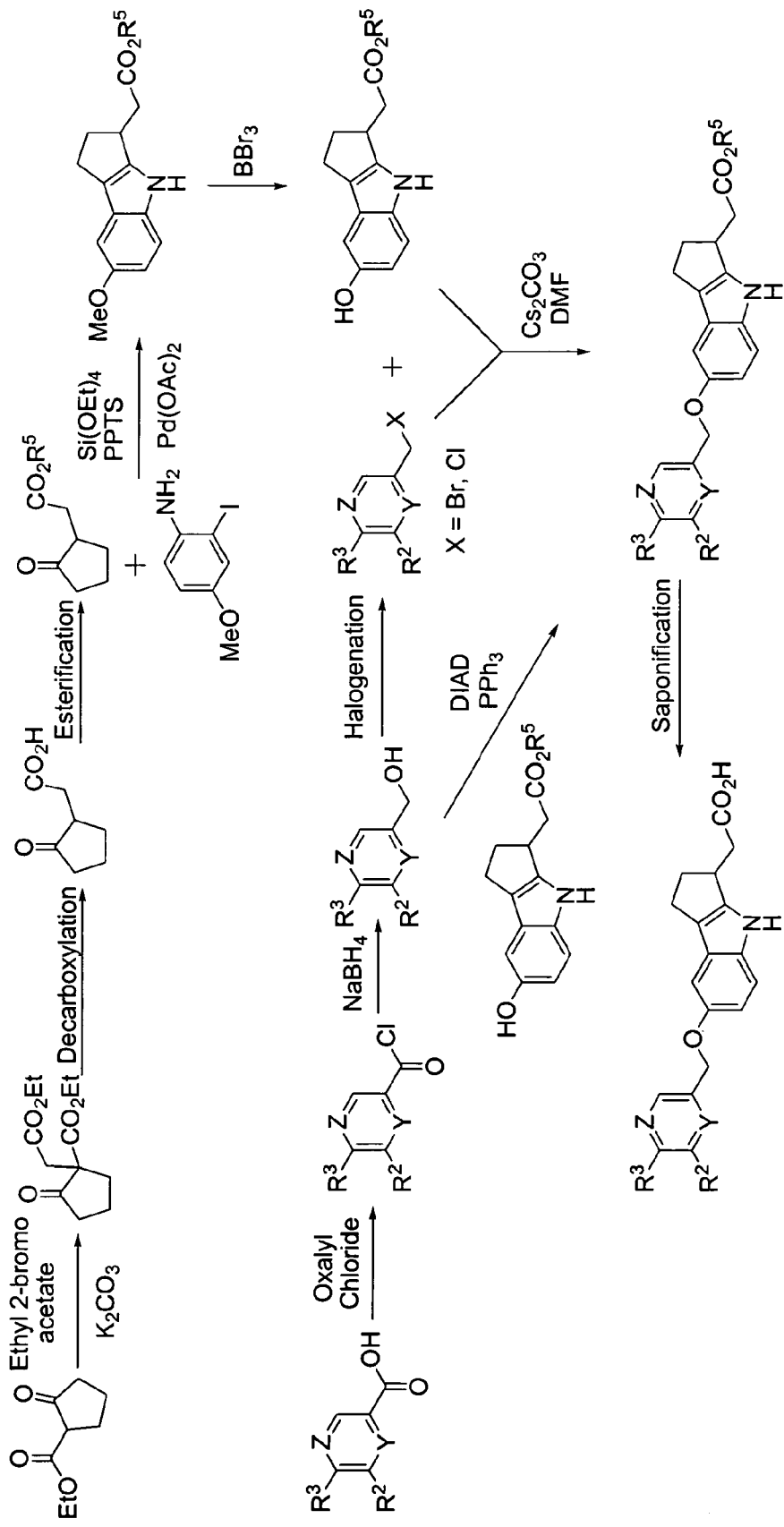
FIG. 3 shows a general synthetic scheme for the preparation of 1,2,3,4-tetrahydrocyclopenta[b]indol-3-yl)acetic acid derivatives, via coupling of the aryl methyl halides or alcohols with ethyl 2-(7-hydroxy-1,2,3,4-tetrahydrocyclopenta[b]indol-3-yl)acetate. Subsequent hydrolysis of the ester functionality affords compounds of Formula (Ia) wherein "m" is 1 and "n" is 1.
Figure 4:
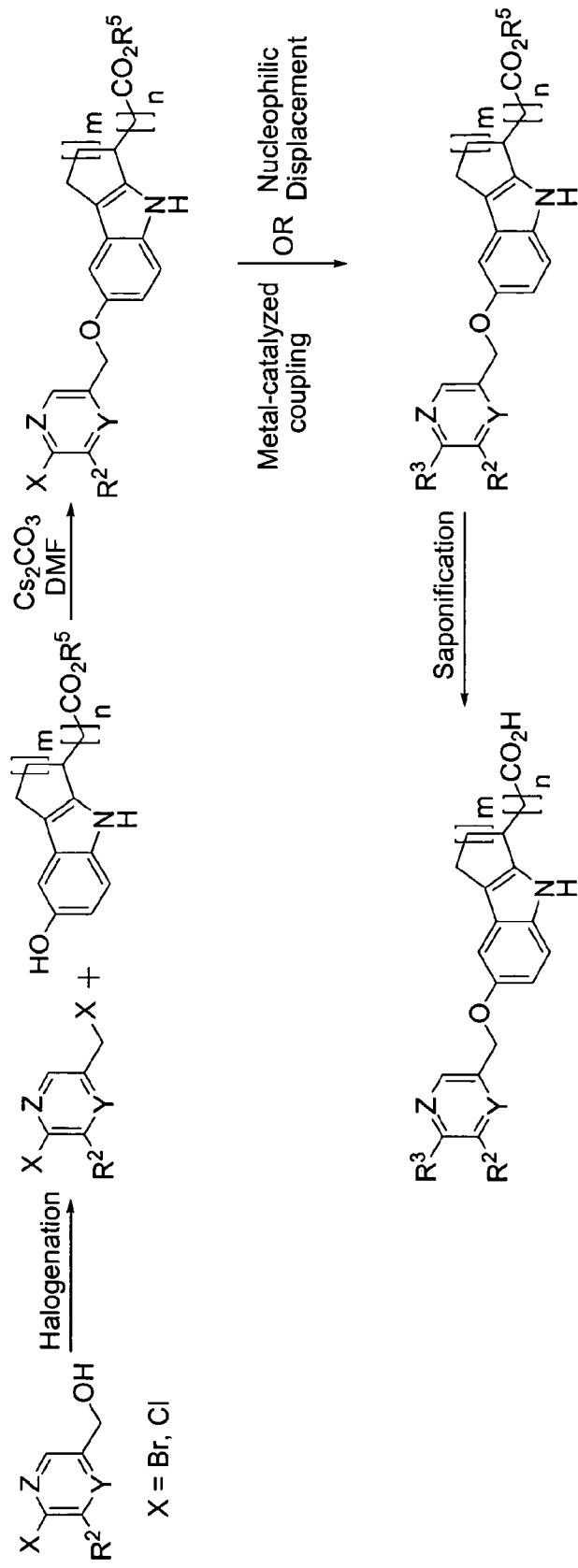
FIG. 4 shows a general synthetic scheme for the preparation of an halogenated 1,2,3,4-tetrahydrocyclopenta[b]indol-3-yl)acetic acid intermediate, via coupling of the aryl methyl halides with ethyl 2-(7-hydroxy-1,2,3,4-tetrahydrocyclopenta[b]indol-3-yl)acetate. Subsequent functionalization at the aromatic halogen and hydrolysis of the ester functionality afford compounds of Formula (Ia) wherein "m" is 1 and "n" is 1.
Figure 5:
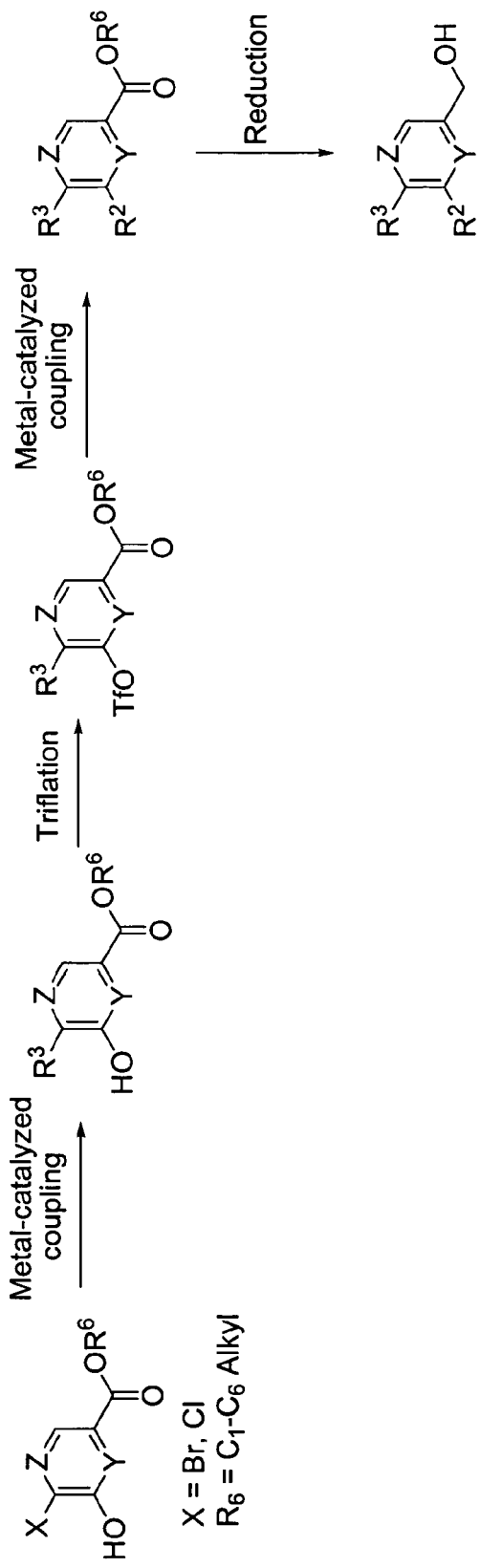
FIG. 5 shows a general synthetic scheme for the preparation of alcohol intermediates used in the preparation of compounds of Formula (Ia). The synthetic scheme shows the functionalization at the aromatic halogen by metal-catalyzed coupling, followed by conversion of the hydroxyl group to a triflate moiety. Subsequent replacement of the triflate with a variety of functional groups by metal-catalyzed coupling reactions and reduction of the ester moiety afforded alcohol intermediates.
Figure 6:
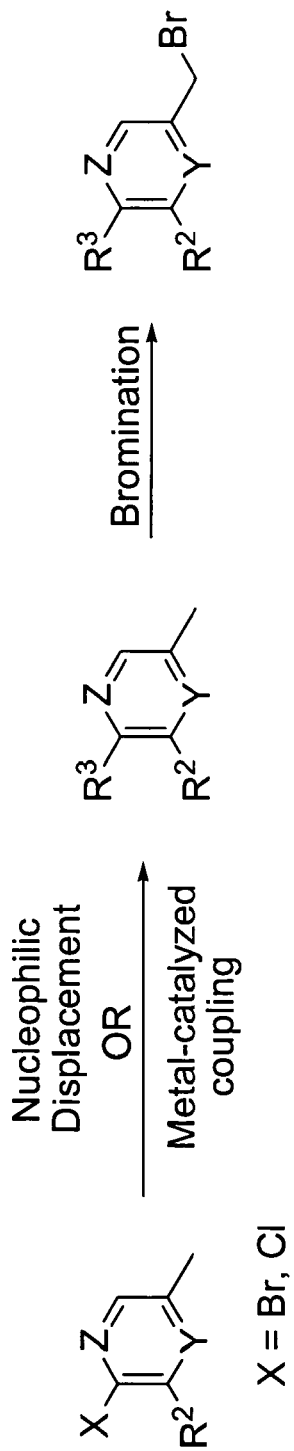
FIG. 6 shows a general synthetic scheme for the preparation of bromide intermediates used in the preparation of compounds of Formula (Ia). The synthetic scheme shows the functionalization at the aromatic halogen by metal-catalyzed coupling or nucleophilic displacement. Subsequent bromination of the methyl group affords bromide intermediates.
Figure 7:
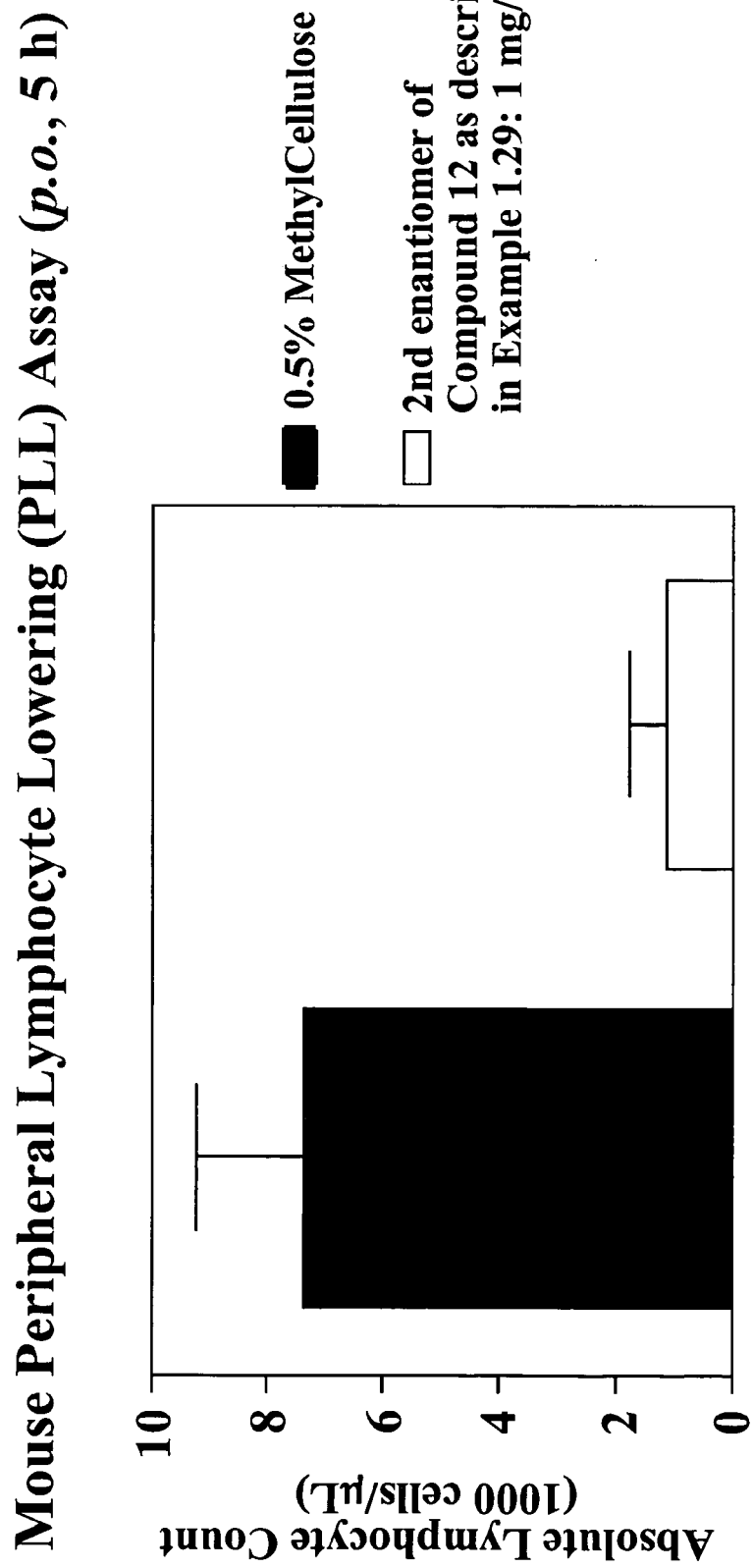
FIG. 7 shows the results of an experiment which measured the ability of the $2^{nd}$ enantiomer of compound 12 (isolated after resolution of compound 12 by HPLC with a retention time of 13.9 min per the conditions reported in Example 1.29) to lower the absolute count of peripheral lymphocytes in mice compared to vehicle.
Figure 8:
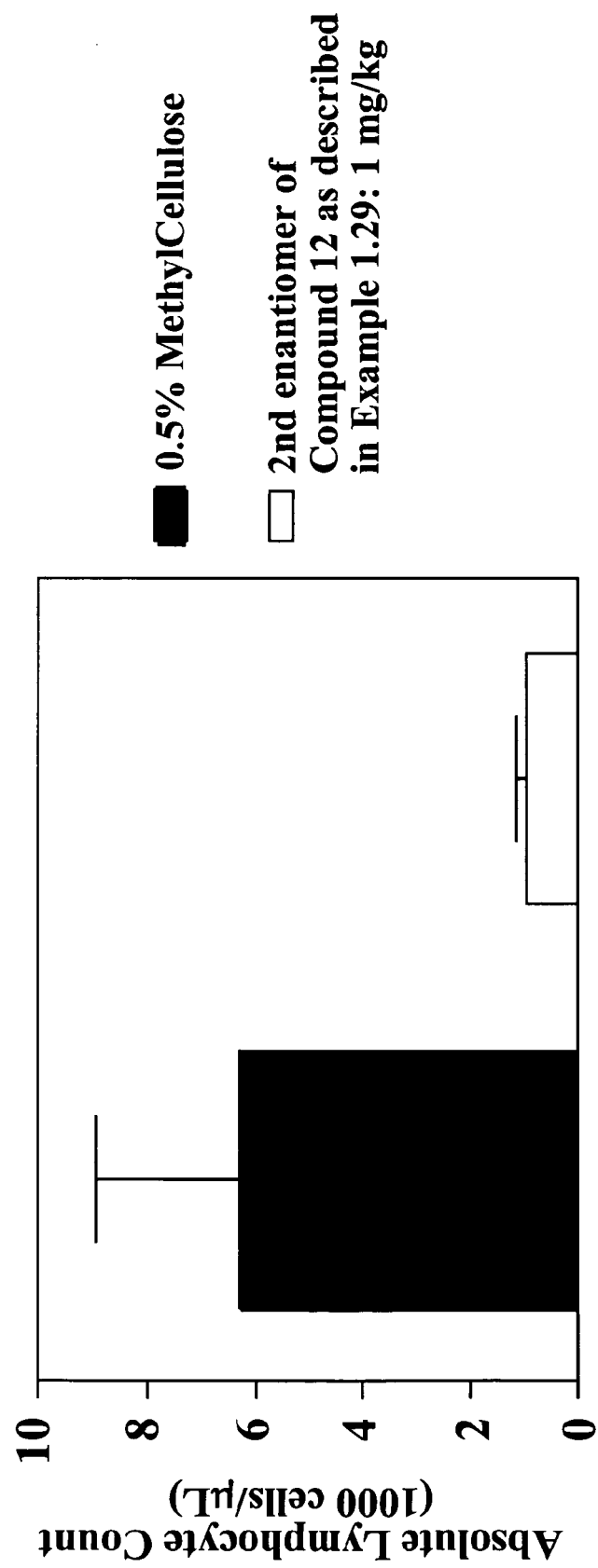
FIG. 8 shows the results of an experiment which measured the ability of the $2^{nd}$ enantiomer of compound 12 (isolated after resolution of compound 12 by HPLC with a retention time of 13.9 min per the conditions reported in Example 1.29) to lower the absolute count of peripheral lymphocytes in rats compared to vehicle.

A compound of the invention can be shown to induce peripheral lymphocyte lowering (PLL).
A. Mouse PLL Assay.
Animals: Male BALB/c mice (Charles River Laboratories, Wilmington, Mass.) were housed four per cage and maintained in a humidity-controlled (40 to 60%) and temperature-controlled (68 to 72° F.) facility on a 12 h:12 h light/dark cycle (lights on at 6:30 am) with free access to food (Harlan Teklad, Orange, Calif., Rodent Diet 8604) and water. Mice were allowed one week of habituation to the animal facility before testing.
PLL Assay: Mice were given an oral dose of Compound 5, Compound 7 or dosing vehicle (0.5% methylcellulose) in a total volume of 10 mL/kg. Peripheral blood samples were collected at 5 hours post-dose. The mice were anesthetized with isoflurane and blood was collected via cardiac puncture. A complete cell count (CBC), including lymphocyte count, was obtained using a CELL-DYN® 3700 (Abbott Laboratories, Abbott Park, Ill.) instrument. Results are presented in FIGS. 1 and 2, in which peripheral blood lymphocyte (PBL) count is shown for the 5 hour group. Reduction of the PBL count by the test compound in comparison with vehicle is indicative of the test compound exhibiting activity or inducing peripheral lymphocyte lowering. It is apparent from inspection of FIGS. 1 and 2 that Compound 5 and Compound 7 exhibited activity for inducing PBL lowering (lymphopenia) in the mouse.
PLL Assay: Mice were given a 1.00 mg/kg oral dose of the $2^{nd}$ enantiomer of compound 12 (isolated after resolution of compound 12 by HPLC, with a retention time of 13.9 min per the conditions reported in Example 1.29) or dosing vehicle (0.5% methylcellulose in sterile water) in a total volume of 10 mL/kg. Peripheral blood samples were collected at 5 hours post-dose. The mice were anesthetized with isoflurane and blood was collected via cardiac puncture. A complete cell count (CBC), including lymphocyte count, was obtained using a CELL-DYN® 3700 (Abbott Laboratories, Abbott Park, Ill.) instrument. Results are presented in FIG. 7, in which peripheral blood lymphocyte (PBL) count is shown for the 5 hour group. Reduction of the PBL count by the test compound in comparison with vehicle is indicative of the test compound exhibiting activity or inducing peripheral lymphocyte lowering. It is apparent from inspection of FIG. 7 that the $2^{nd}$ enantiomer of compound 12 (isolated after resolution of compound 12 by HPLC, with a retention time of 13.9 min per the conditions reported in Example 1.29) exhibited activity for inducing PBL lowering (lymphopenia) in the mouse.
B. Rat PLL Assay.
Animals: Male Sprague-Dawley rats (7 weeks of age at start of study) (Charles River Laboratories) were housed two per cage and maintained in a humidity-controlled (40-60%) and temperature-controlled (68-72° F.) facility on a 12 h:12 h light/dark cycle (lights on at 6:30 am) with free access to food (Harlan Teklad, Orange, Calif., Rodent Diet 8604) and water. Rats were allowed one week of habituation to the animal facility before testing.
PLL Assay: Rats were given a 1.00 mg/kg oral dose of the $2^{nd}$ enantiomer of compound 12 (isolated after resolution of compound 12 by HPLC, with a retention time of 13.9 min per the conditions reported in Example 1.29) or dosing vehicle (0.5% methylcellulose in sterile water) in a total volume of 1.00 mL/kg. Peripheral blood samples were collected at 5 hours post-dose. Blood was collected via indwelling catheter. A complete cell count (CBC), including lymphocyte count, was obtained using a CELL-DYN® 3700 (Abbott Laboratories, Abbott Park, Ill.) instrument. Results are presented in FIG. 8, in which peripheral blood lymphocyte (PBL) count is shown for the 5 hour group. Reduction of the PBL count by the test compound in comparison with vehicle is indicative of the test compound exhibiting activity or inducing peripheral lymphocyte lowering. It is apparent from inspection of FIG. 8 that the $2^{nd}$ enantiomer of compound 12 (isolated after resolution of compound 12 by HPLC, with a retention time of 13.9 min per the conditions reported in Example 1.29) exhibited activity for inducing PBL lowering (lymphopenia) in the rat.

Example 5

Effect of Compounds on Experimental Autoimmune Encephalomyelitis (EAE)

A compound of the invention can be shown to have therapeutic efficacy in multiple sclerosis by showing it to have therapeutic efficacy in experimental autoimmune encephalomyelitis (EAE), an animal model for multiple sclerosis. In certain exemplary well-established models, EAE is induced in rodents by injection of myelin oligodendrocyte glycoprotein (MOG) peptide, by injection of myelin basic protein (MBP) or by injection of proteolipid protein (PLP) peptide.
A. MOG-Induced EAE in Mice.
Animals: Female C57BL/6 mice (8 to 10 weeks of age at start of study) (Jackson Laboratory, Bar Harbor, Me.) were housed four per cage and maintained in a humidity-controlled (40-60%) and temperature-controlled (68-72° F.) facility on a 12 h:12 h light/dark cycle (lights on at 6:30 am) with free access to food (Harlan Teklad, Orange, Calif., Rodent Diet 8604) and water. Mice were allowed one week of habituation to the animal facility before testing.
Induction of EAE: Mice were immunized subcutaneously, 50 µL per hind flank, with a total of 100 µg $MOG_{35-55}$ peptide emulsified 1:1 with Complete Freund's adjuvant containing 4 mg/mL heat-killed *Mycobacterium tuberculosis*. Mice also received 200 ng pertussis toxin intraperitoneally on the day of immunization and 48 h later.

Clinical scoring: Severity of disease symptoms was scored as follows (in increasing order of severity): 0=normal; 1=limp tail OR hind limb weakness; 2=limp tail AND limb weakness/weakness of 2 or more limbs; 3=severe limb weakness or single limb paralysis; 4=paralysis of 2 or more limbs; 5=death.

Figure 10:
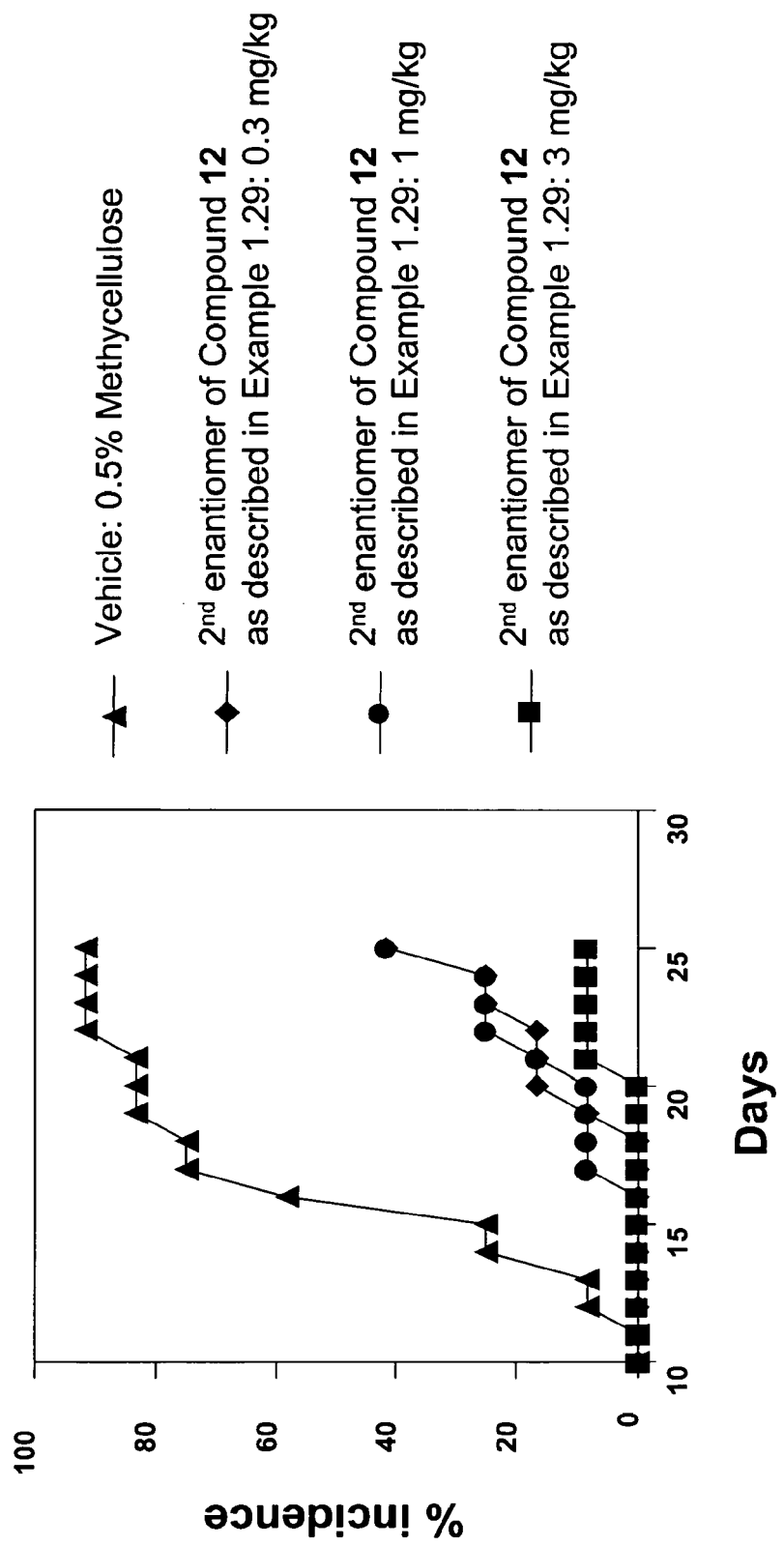
FIG. 10 shows the results of an experiment which measured the ability of three different doses of the $2^{nd}$ enantiomer of compound 12 (isolated after resolution of compound 12 by HPLC, with a retention time of 13.9 min per the conditions reported in Example 1.29) to have efficacy in experimental autoimmune encephalomyelitis (EAE) compared to vehicle.

Drug treatment: Mice were dosed orally, with vehicle or the $2^{nd}$ enantiomer of compound 12 (isolated after resolution of compound 12 by HPLC, with a retention time of 13.9 min per the conditions reported in Example 1.29), once a day from day 3 until day 21. Dosing volume is 5 mL/kg. The $2^{nd}$ enantiomer of compound 12 (isolated after resolution of compound 12 by HPLC, with a retention time of 13.9 min per the conditions reported in Example 1.29) was dosed at 0.3 mg/kg, 1 mg/kg and 3 mg/kg. Mice were weighed daily. Mice were monitored daily from day 7 onward for disease symptoms. After the last dose on day 21, disease progression was monitored daily for 2 more weeks. Reduction of the severity of disease symptoms by the $2^{nd}$ enantiomer of compound 12 (isolated after resolution of compound 12 by HPLC, with a retention time of 13.9 min per the conditions reported in Example 1.29) in comparison with vehicle was indicative of the test compound exhibiting therapeutic efficacy in EAE. It is apparent from inspection of FIG. 10 that the $2^{nd}$ enantiomer of compound 12 (isolated after resolution of compound 12 by HPLC, with a retention time of 13.9 min per the conditions reported in Example 1.29) exhibited activity in the mouse EAE assay.

B. PLP-Induced EAE in Mice.

Animals: Female SJL/J mice (8 to 10 weeks of age at start of study) (Jackson Laboratory, Bar Harbor, Me.) are housed four per cage and maintained in a humidity-controlled (40-60%) and temperature-controlled (68-72° F.) facility on a 12 h:12 h light/dark cycle (lights on at 6:30 am) with free access to food (Harlan-Teklad Western Res, Orange, Calif., Rodent Diet 8604) and water. Mice are allowed one week of habituation to the animal facility before testing.

Induction of EAE: Mice are immunized subcutaneously with 100 μg $PLP_{139-151}$ peptide emulsified 1:1 with Complete Freund's adjuvant containing 4 mg/mL heat-killed *Mycobacterium tuberculosis*. Mice also receive 200 ng pertussis toxin intravenously on the day of immunization.

Clinical scoring: Severity of disease symptoms is scored as follows (in increasing order of severity): 0=normal; 1=limp tail OR hind limb weakness; 2=limp tail AND limb weakness/weakness of 2 or more limbs; 3=severe limb weakness or single limb paralysis; 4=paralysis of 2 or more limbs; 5=death.

Drug treatment: Mice are dosed orally, with vehicle or a test compound, once a day from day 3 until day 21. Dosing volume is 5 ml/kg. The test compound is dosed at, e.g., 1 mg/kg, 3 mg/kg, 10 mg/kg or 30 mg/kg. Mice are weighed daily. Mice are monitored daily from day 7 onward for disease symptoms. After the last dose on day 21, disease progression is monitored daily for two more weeks.

C. MBP-Induced EAE in Rats.

Animals: Male Lewis rats (325-375 g at start of study) (Harlan, San Diego, Calif.) are housed two per cage and maintained in a humidity-controlled (30-70%) and temperature-controlled (20-22° C.) facility on a 12 h:12 h light/dark cycle (lights on at 6:30 A.M.) with free access to food (Harlan-Teklad Western Res., Orange, Calif., Rodent Diet 8604) and water. Rats are allowed one week of habituation to the animal facility before testing. During the study, rats are weighed daily prior to clinical scoring at 11 am.

Induction of EAE: Myelin basic protein (MBP; guinea pig) is dissolved in sterile saline at a concentration of 1 mg/ml, and then emulsified 1:1 with Complete Freund's adjuvant (1 mg/ml). 50 μL, of this emulsion is administered by intraplantar (ipl) injection into both hind paws of each rat, for a total injected volume of 100 μL per rat and a total dose of 50 μg of MBP per rat.

Clinical scoring: Severity of disease symptoms is scored daily after body weighing and before drug dosing. Severity of disease symptoms is scored as follows (in increasing order of severity): 0=normal; 1=tail OR limb weakness; 2=tail AND limb weakness; 3=severe hind limb weakness or single limb paralysis; 4=loss of tail tone and paralysis of 2 or more limbs; 5=death.

Drug treatment: Rats are dosed orally, with vehicle or a test compound, 1 hour prior to MBP injection on day 0 and daily thereafter, after clinical scoring, for the duration of the study. Dosing volume is 5 mL/kg. The test compound is dosed at, e.g., 1 mg/kg, 3 mg/kg, 10 mg/kg or 30 mg/kg. Reduction of the severity of disease symptoms by the test compound in comparison with vehicle is indicative of the test compound exhibiting therapeutic efficacy in EAE.

Example 6

Effect of Compounds on Type I Diabetes

A compound of the invention can be shown to have therapeutic efficacy in type I diabetes using an animal model for type I diabetes, such as cyclophosphamide-induced type I diabetes in mice.

Animals: Baseline blood glucose measurements are taken from 9-10 week old female NOD/Ltj mice (Jackson Laboratory, Bar Harbor, Me.) to ensure that they are normoglycemic (blood glucose is 80-120 mg/dL) prior to initiation of the experiment. Blood glucose is measured from tail bleeds using a OneTouch® Ultra® meter and test strips (LifeScan, Milpitas, Calif.).

Cyclophosphamide induction of type I diabetes: On day 0 and day 14, normoglycemic NOD mice are injected intraperitoneally with 4 mg cyclophosphamide monohydrate (200 mg/kg) dissolved in 0.9% saline. If mice are diabetic (blood glucose is >250 mg/dL), they are not given a booster dose of cyclophosphamide on day 14.

Drug Treatment: Mice are dosed orally, with vehicle or test compound, once a day from day 0 until day 25. Compounds are suspended in 0.5% methyl cellulose vehicle using a sonicator to ensure uniform suspension. Mice are weighed twice weekly and are dosed according to weight. Dosing volume is 5 mL/kg. The test compound is dosed at, e.g., 1 mg/kg, 3 mg/kg, 10 mg/kg or 30 mg/kg. Blood glucose is measured twice weekly. After dosing is completed at day 25, the mice continue to be monitored and blood glucose measurements are taken once a week for 3 weeks. Promotion of normoglycemia by the test compound in comparison with vehicle is indicative of the test compound exhibiting therapeutic efficacy in type I diabetes.

Example 7

Allograft Survival

A compound of the invention can be shown to have therapeutic efficacy in prolonging allograft survival by showing it to have therapeutic efficacy in prolonging, e.g., survival of a skin allograft in an animal model.

Animals: Female Balbc/J mice (6 to 7 weeks of age at start of study) (Jackson Laboratory, Bar Harbor, Me.) are housed four per cage and maintained in a humidity-controlled (40-60%) and temperature-controlled (68-72° F.) facility on a 12 h:12 h light/dark cycle (lights on at 6:30 am) with free access to food (Harlan Teldad, Orange, Calif., Rodent Diet 8604) and water. Female C57BL/6 mice (8 to 10 weeks of age at start of study) (Jackson Laboratory, Bar Harbor, Me.) are similarly housed and maintained. Mice are allowed one week of habituation to the animal facility before testing.

Skin allograft: Balbc/J and C57BL/6 mice are used as donors and recipients, respectively, in a model of skin allograft transplantation. Donor Balbc/J mice are anesthetized, and 0.5 cm-diameter full thickness areas of abdominal skin are surgically removed. Skin grafts harvested from the Balbc/J mice are sutured onto the dorsum of anesthetized recipient C57BL/6 mice. Sutured allografts are covered with Vaseline gauze and Bolster dressing for 7 days. The allografted mice are divided into 8 groups of 8 mice each.

Clinical scoring: Skin allografts are inspected and digital images recorded daily until rejection, which is defined as the first day on which more than 80% of the graft is necrotic. Histological analysis of the rejected graft is carried out on hematoxylin and eosin (H&E)-stained sections. In an optional related study, on post-transplantation day 5 isolated lymphocytes from peripheral lymph nodes and spleen are counted and characterized for activation markers (e.g., T-cell activation markers) by flow cytometry. Also on day 5, grafts are removed from transplanted recipients, cut into small fragments, digested with collagenase and sedimented over Ficoll-Paque (Pharmacia Biotech, Uppsala, Sweden) to isolate graft-infiltrating lymphocytes, which are counted and characterized for activation markers (e.g., T-cell activation markers) by flow cytometry. Histological analysis of the graft on day 5 can be carried out on hematoxylin and eosin (H&E)-stained sections.

Drug treatment: Mice are dosed orally, with vehicle or test compound, once a day from the day of transplantation until the end of the study, e.g. until day 14, 21 or 28. Dosing volume is 5 mL/kg. The test compound is dosed at, e.g., 1 mg/kg, 3 mg/kg, 10 mg/kg or 30 mg/kg. Delay of time of rejection of the skin allograft by the test compound in comparison with vehicle is indicative of the test compound exhibiting therapeutic efficacy in prolonging skin allograft survival.

Example 8

Effect of Compounds on Colitis

A compound of the invention can be shown to have therapeutic efficacy in colitis using an animal model for colitis. Suitable animal models are known in the art (Boismenu et al., *J. Leukoc. Biol.*, 67:267-278, 2000). A first exemplary animal model for colitis is trinitrobenzenesulfonic acid (TNBS)-induced colitis, which presents clinical and histopathological findings that resemble those in Crohn's disease (Neurath et al., *J. Exp. Med.*, 182:1281-1290, 1995; Boismenu et al., *J. Leukoc. Biol.*, 67:267-278, 2000). A second exemplary animal model for colitis is dextran sulfate sodium (DSS)-induced colitis, which presents clinical and histopathological findings that resemble those in ulcerative colitis (Okayasu et al., *Gastroenterology*, 98:694-702, 1990; Boismenu et al., *J. Leukoc. Biol.*, 67:267-278, 2000). Compounds can be commercially tested for efficacy in at least DSS-induced colitis and TNBS-induced colitis, e.g. by the Jackson Laboratory (Bar Harbor, Me.).

A. Mouse Model for Colitis.

Animals: Male BALB/c mice (6 weeks of age at start of study) (Jackson Laboratory, Bar Harbor, Me.) are housed four per cage and maintained in a humidity-controlled (40-60%) and temperature-controlled (68-72° F.) facility on a 12 h:12 h light/dark cycle (lights on at 6:30 am) with free access to food (Harlan Teklad, Orange Calif., Rodent Diet 8604) and water. Mice are allowed one week of habituation to the animal facility before testing.

TNBS induction of colitis: Mice are weighed for baseline body weights and fasted later that day beginning at 6:15 pm just prior to lights-out (day 0). Body weights are taken again the following morning (day 1) at approximately 7:30 am. Mice are anesthetized with isoflurane prior to induction of colitis. Colitis is induced in the mice by intracolonic injection of about 150 mg/kg TNBS in 50% ethanol (in a volume of 150 µL) using an intubation needle (22 g, 1.5 in) inserted completely into the anus with the mouse held by the tail in a vertical position. The mouse is held vertically for 30 additional seconds to allow thorough absorption and minimize leakage, after which the mouse is returned to its cage. Mice are then fed, following the preceding approximately 14 hour of fasting. Each morning thereafter, the mice are weighed. In control experiments, mice receive 50% ethanol alone using the same protocol.

Drug treatment: Drug treatment begins on day 2. Mice are dosed orally, with vehicle or a test compound, once a day from day 2 until the conclusion of the experiment on, e.g., day 7, 14 or 21. Dosing volume is 5 mL/kg. The test compound is dosed at, e.g., 1 mg/kg, 3 mg/kg, 10 mg/kg or 30 mg/kg.

Clinical scoring: Upon conclusion of the experiment, colons are extracted and measured. Mice are euthanized with $CO_2$ and colon is removed from anus to cecum. Excised colon is measured for entire length, length from anus to end of inflamed area and length of inflamed (affected) area. After measurements, colon is cleared of excrement by flushing with saline and then cut open to clear more thoroughly. Colon is then weighed and preserved in neutral buffered formalin (NBF; 10% formalin, pH 6.7-7.0). The colon tissue is embedded in paraffin and processed for hematoxylin and eosin (H & E)-stained sections. Severity of disease symptoms is scored histologically from the stained sections as follows: 0=no evidence of inflammation; 1=low level of leukocyte infiltration with infiltration seen in <10% of high-power fields AND no structural changes; 2=moderate leukocyte infiltration with infiltration seen in 10% to 25% of high-power fields AND crypt elongation AND bowel wall thickening that does not extend beyond the mucosal layer AND no ulcerations; 3=high level of leukocyte infiltration seen in 25% to 50% of high-power fields AND crypt elongation AND infiltration beyond the mucosal layer AND thickening of the bowel wall AND superficial ulcerations; 4=marked degree of transmural leukocyte infiltration seen in >50% of high-power fields AND elongated and distorted crypts AND bowel wall thickening AND extensive ulcerations. Reduction of the severity of the disease symptoms by the test compound in comparison with vehicle is indicative of the test compound exhibiting therapeutic efficacy in colitis.

B. Rat Model for Colitis.

Animals: Male Wistar rats (175-200 g at start of study) (Charles River Laboratories, Wilmington, Mass.) are housed two per cage and maintained in a humidity-controlled (40-60%) and temperature-controlled (68-72° F.) facility on a 12 h:12 h light/dark cycle (lights on at 6:30 am) with free access to food (Harlan Teklad, Orange Calif., Rodent Diet 8604) and water. Rats are allowed one week of habituation to the animal facility before testing.

TNBS induction of colitis: Rats are weighed for baseline body weights and fasted later that day beginning at 6:15 pm just prior to lights-out (day 0). Body weights are taken again the following morning (day 1) at approximately 7:30 am. Rats are anesthetized with isoflurane prior to induction of colitis. Colitis is induced in the rats by intracolonic injection of about 60 mg/kg TNBS in 50% ethanol (in a volume of 500 µL) using a fabricated intubation needle (7.5 Fr umbilical catheter and 14 g hub) inserted 8 cm into the anus with the rat held by the tail in a vertical position. The rat is held vertically for 30 additional s to allow thorough absorption and minimize leakage, after which the rat is returned to its cage. Rats are then fed, following the preceding approximately 14 h of fasting. Each morning thereafter, the rats are weighed. In control experiments, rats receive 50% ethanol alone using the same protocol.

Drug treatment: Drug treatment begins on day 2. Rats are dosed orally, with vehicle or test compound, once a day from day 2 until the conclusion of the experiment on, e.g., day 7, 14 or 21. Dosing volume is 5 mL/kg. Test compound is dosed at, e.g., 1 mg/kg, 3 mg/kg, 10 mg/kg or 30 mg/kg.

Clinical scoring: Upon conclusion of the experiment, colons are extracted and measured. Rats are euthanized with $CO_2$ and colon is removed from anus to cecum. Excised colon is measured for entire length, length from anus to end of inflamed area, and length of inflamed (affected) area. After measurements, colon is cleared of excrement by flushing with saline and then cut open to clear more thoroughly. Colon is then weighed and preserved in neutral buffered formalin (NBF; 10% formalin, pH 6.7-7.0). The colon tissue is embedded in paraffin and processed for hematoxylin and eosin (H & E)-stained sections. Severity of disease symptoms is scored histologically from the stained sections as follows: 0=no evidence of inflammation; 1=low level of leukocyte infiltration with infiltration seen in <10% of high-power fields AND no structural changes; 2=moderate leukocyte infiltration with infiltration seen in 10% to 25% of high-power fields AND crypt elongation AND bowel wall thickening that does not extend beyond the mucosal layer AND no ulcerations; 3=high level of leukocyte infiltration seen in 25% to 50% of high-power fields AND crypt elongation AND infiltration beyond the mucosal layer AND thickening of the bowel wall AND superficial ulcerations; 4=marked degree of transmural leukocyte infiltration seen in >50% of high-power fields AND elongated and distorted crypts AND bowel wall thickening AND extensive ulcerations. Reduction of the severity of the disease symptoms by the test compound in comparison with vehicle is indicative of the test compound exhibiting therapeutic efficacy in colitis.

Example 9

Effects of Compounds on Cardiac Telemetry in the Rat

Animals: Male Sprague-Dawley rats (250-300 g at time of surgery) were implanted by Charles River Laboratories (Wilmington, Mass.) with cardiac transmitting devices (Data Sciences PhysioTel C50-PXT) into the peritoneal space, with a pressure-sensing catheter inserted into the descending aorta. Rats are allowed at least one week to recover. Rats were housed in individual cages and maintained in a humidity-controlled (30-70%) and temperature-controlled (20-22° C.) facility on a 12 h:12 h light/dark cycle (lights on at 7:00 am) with free access to food (Harlan-Teklad, Orange, Calif., Rodent Diet 8604) and water. Rats were allowed one week of habituation to the animal facility before testing.

Measurement of cardiovascular parameters: The implanted transmitting devices transmitted continuous measurements of blood pressure (systolic, diastolic, mean arterial, pulse), heart rate, body temperature, and motor activity in freely moving conscious animals. These data were transmitted via radiofrequency to a computer which binned the data into 1 min averages using DataSciences ART software. Telemetry recording occurred over a 21-h period, starting at noon and continuing until 9:00 am the following day. A maximum of eight rats were tested at a time, and the same eight rats were utilized for all treatment groups in a within-subject design.

Drug treatment: Rats were injected orally with vehicle (PEG400) and the $2^{nd}$ enantiomer of compound 12 (isolated after resolution of compound 12 by HPLC, with a retention time of 13.9 min per the conditions reported in Example 1.29) at 1:00 pm. A full study (vehicle+3 doses) required four separate testing sessions, which occur on Mondays-Tuesdays and Thursdays-Fridays. During each of the testing sessions, the eight rats were divided into four treatment groups such that each group comprised N=2 for any given session. Rats were re-tested in subsequent testing sessions in a crossover design such that by the end of the four sessions, all animals had received all treatments in a pseudo-random order, and each group comprised N=8.

Figure 11:
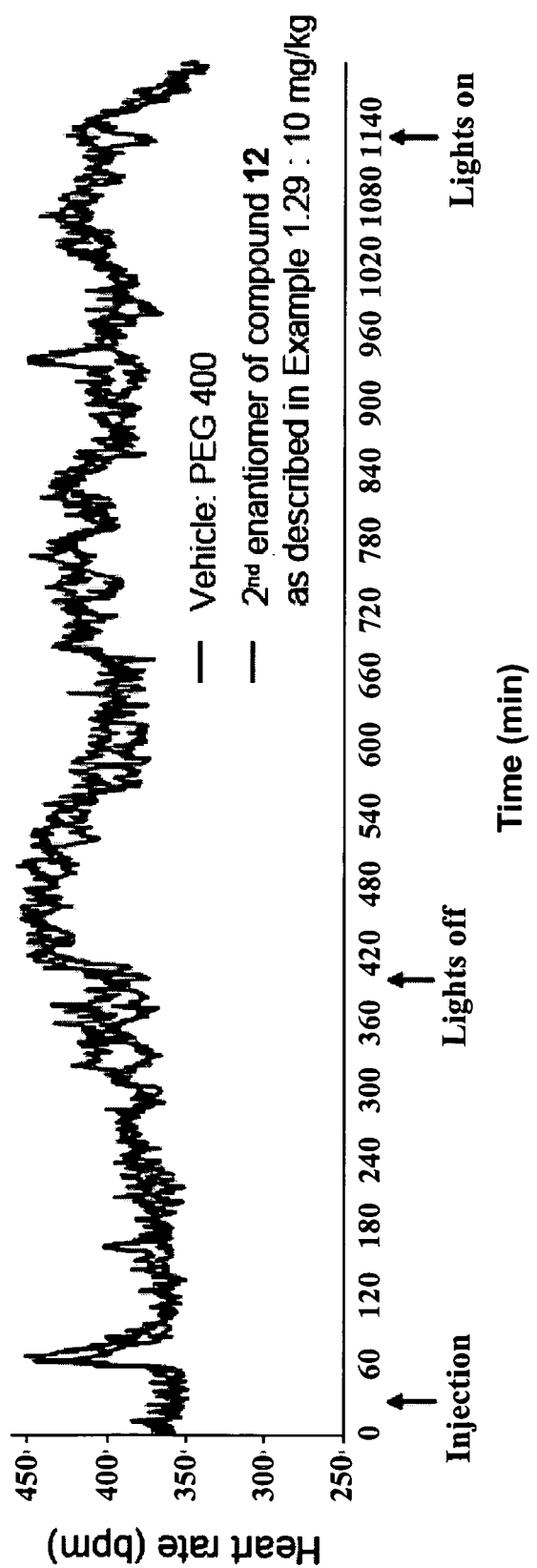
FIG. 11 shows the results of an experiment wherein no or substantially no reduction of heart rate was exhibited in response to the treatment of rats with the $2^{nd}$ enantiomer of compound 12 (isolated after resolution of compound 12 by HPLC with a retention time of 13.9 min per the conditions reported in Example 1.29) in comparison with vehicle.

Exemplary bradycardia assay: It was expressly contemplated that the rats could be used to show that a compound of the invention had no or substantially no activity for bradycardia. By way of illustration and not limitation, the rats were administered vehicle (PEG 400) and the $2^{nd}$ enantiomer of compound 12 (isolated after resolution of compound 12 by HPLC, with a retention time of 13.9 min per the conditions reported in Example 1.29) and heart rate was then measured over a 120 min period. Results are presented in FIG. 11. It is apparent from inspection of FIG. 11 that no or substantially no reduction of heart rate was exhibited in response to the treatment of rats with the $2^{nd}$ enantiomer of compound 12 (isolated after resolution of compound 12 by HPLC, with a retention time of 13.9 min per the conditions reported in Example 1.29) in comparison with vehicle. No or substantially no reduction of heart rate was indicative of the $2^{nd}$ enantiomer of compound 12 (isolated after resolution of compound 12 by HPLC, with a retention time of 13.9 min per the conditions reported in Example 1.29) exhibiting no or substantially no activity for bradycardia.

Example 10

Effect of Compounds on Arthritis

Female Lewis rats were used in this study. Acclimated animals were anesthetized with isoflurane and given the first collagen injection (day 0). On day 6, they were anesthetized again for the second collagen injection. Collagen was prepared by making a 4 mg/mL solution in 0.01 N acetic acid. Equal volumes of collagen and incomplete Freund's adjuvant were emulsified by hand mixing until a bead of this material held its form when placed in water. Each animal received 300 µL of the mixture each time, spread over 3 subcutaneous sites on the back.

Figure 9:
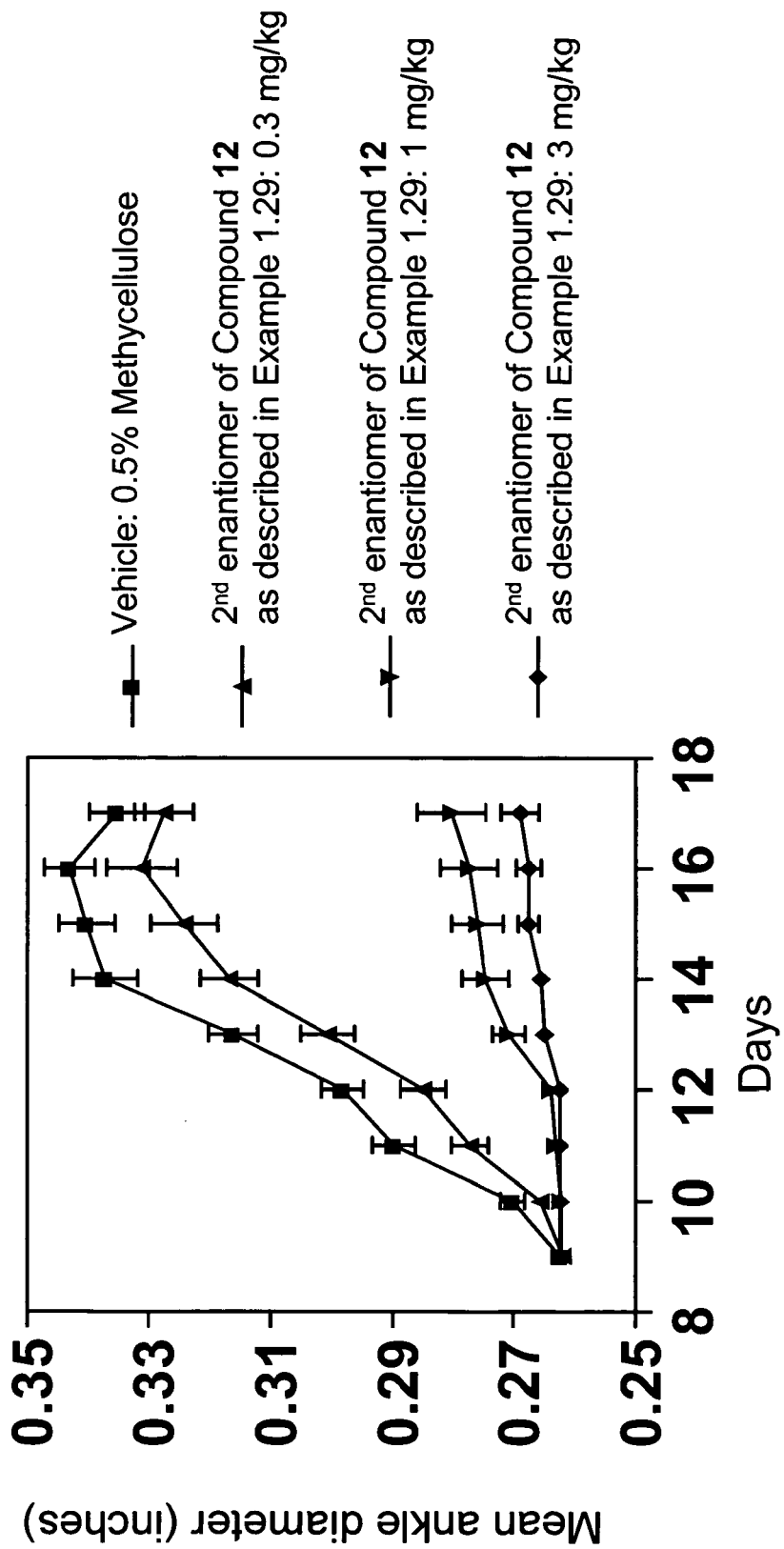
FIG. 9 shows the results of an experiment which measured the ability of three different doses of the $2^{nd}$ enantiomer of compound 12 (isolated after resolution of compound 12 by HPLC with a retention time of 13.9 min per the conditions reported in Example 1.29) to reduce the mean ankle diameter in rats compared to vehicle.

Treatment (p.o., q.d., 5 mL/kg dosing volume) began on day 0 and continued through day 16 with vehicle or compounds given at 24 h intervals. Rats were weighed on days 0, 3, 6 and 9 through 17 and caliper measurements of the ankles taken on days 9 through 17. The 2$^{nd}$ enantiomer of compound 12 (isolated after resolution of compound 12 by HPLC, with a retention time of 13.9 min per the conditions reported in Example 1.29) was dosed at 0.3, 1 and 3 mg/kg. Results are presented in FIG. 9. It is apparent from inspection of FIG. 9 that the 2$^{nd}$ enantiomer of compound 12 (isolated after resolution of compound 12 by HPLC, with a retention time of 13.9 min per the conditions reported in Example 1.29) exhibited activity for reducing mean ankle diameter in the rat.

Example 11

Powder X-Ray Diffraction (PXRD)

Powder X-ray Diffraction (PXRD) data were collected on an X'Pert PRO MPD powder diffractometer (PANalytical, Inc.) with a Cu source set at 45 kV and 40 mA, a Ni-filter to remove Cu Kβ radiation, and an X'Celerator detector. The instrument was calibrated by the vendor using a silicon powder standard NIST # 640c. The calibration was found to be correct when it was tested with NIST #675 low-angle diffraction standard. Samples were prepared for PXRD scanning by placing several milligrams of gently ground compound onto a sample holder and smoothing as flat as possible by pressing weigh paper down on the sample with a flat object. The samples were analyzed using a spinning-sample stage. Scans cover the range of 5 to 40° 2θ. A continuous scan mode is used with a step size of 0.0167° 2θ. Diffraction data were viewed and analyzed with the X'Pert Data Viewer Software, version 1.0a and X'Pert HighScore Software, version 1.0b Example 12

Differential Scanning calorimetry (DSC)

Differential Scanning calorimetry (DSC) was performed on a TA instruments, Inc. DSC Q2000 at 10° C./min. from ~25 to ~210° C. The instrument was calibrated at this scan rate by the vendor for temperature and energy using the melting point and enthalpy of fusion of an indium standard. Samples were prepared by piercing a sample-pan lid with a thumb tack or other sharp tool and taring this lid along with a sample-pan bottom on a Mettler Toldeo MX5 balance. The sample was placed in the bottom of the tared sample pan. The sample-pan lid fitted snuggly in the sample-pan bottom. The sample and pan were reweighed to get the sample weight. Thermal events (onset temperature, enthalpy of fusion, etc.) were calculated using the Universal Analysis 2000 software, version 4.1D, Build 4.1.0.16.

Example 13

Thermal Gravimetric Analysis (TGA)

Thermal Gravimetric Analysis (TGA) was performed on the TA Instruments, Inc. TGA Q500. The instrument was calibrated by the vendor at 10° C./min. for temperature using the curie point of a ferromagnetic standard. The balance was calibrated with a standard weight. Sample scans were performed at 10° C./min. from ~25 to ~250° C. Sample was placed into an open sample pan, previously tared on the TGA balance. Thermal events such as weight-loss were calculated using the Universal Analysis 2000 software, version 4.1D, Build 4.1.0.16.

Example 14

Vapor Sorption Analysis

Hygroscopicity was measured using a dynamic moisture-sorption analyzer, VTI Corporation, SGA-100. The sample was placed as-is in a tared sample holder on the VTI balance. A drying step was run at 40° C. and 1% RH for 20 minutes. The isotherm conditions were 25° C. with steps of 20% RH from 10% RH up to 90% RH and back to 10% RH. Weight was checked every 5 minutes. Consecutive % weight change of <0.01% or 2 hours, whichever occurred first, was required before continuing to the next step.

Those skilled in the art will recognize that various modifications, additions, substitutions and variations to the illustrative examples set forth herein can be made without departing from the spirit of the invention and are, therefore, considered within, the scope of the invention. All documents referenced above, including, but not limited to, printed publications and provisional and regular patent applications, are incorporated herein by reference in their entirety.

What is claimed is:

1. A compound selected from compounds of Formula (Ia) and pharmaceutically acceptable salts, solvates and hydrates thereof:

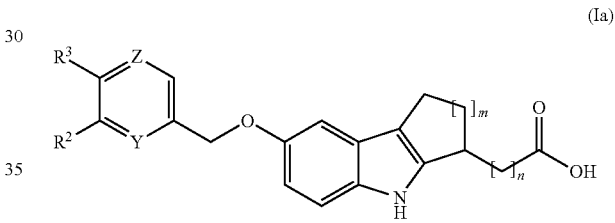

(Ia)

wherein:
 m is 1;
 n is 1 or 2;
 Y is N or CR$^1$;
 Z is N or CR$^4$;
 R$^1$, R$^2$, and R$^4$ are each independently selected from the group consisting of H, C$_1$-C$_6$ alkoxy, C$_1$-C$_6$ alkyl, C$_1$-C$_6$ alkylamino, C$_1$-C$_6$ alkylsulfonyl, C$_1$-C$_6$ alkylthio, carboxamide, cyano, C$_3$-C$_7$ cycloalkoxy, C$_3$-C$_7$ cycloalkyl, C$_1$-C$_6$ haloalkoxy, C$_1$-C$_6$ haloalkyl, halogen, heteroaryl and heterocyclyl, wherein said C$_1$-C$_6$ alkyl and C$_1$-C$_6$ alkoxy are each optionally substituted with one or two substituents selected from C$_3$-C$_7$ cycloalkyl and halogen; and
 R$^3$ is C$_3$-C$_7$ cycloalkyl.

2. The compound according to claim 1, wherein n is 1.
3. The compound according to claim 1, wherein n is 2.
4. The compound according to claim 1, wherein Y is N.
5. The compound according to claim 1, wherein Y is CR$^1$.
6. The compound according to claim 5, wherein R$^1$ is H or C$_1$-C$_6$ haloalkyl.
7. The compound according to claim 5, wherein R$^1$ is H or trifluoromethyl.
8. The compound according to claim 1, wherein R$^2$ is selected from the group consisting of H, cyano, C$_1$-C$_6$ haloalkoxy and C$_1$-C$_6$ haloalkyl.
9. The compound according to claim 1, wherein R$^2$ is selected from the group consisting of H, cyano, trifluoromethoxy and trifluoromethyl.

10. The compound according to claim 1, wherein $R^3$ is selected from the group consisting of cyclobutyl, cyclohexyl, cyclopentyl, and cyclopropyl.

11. The compound according to claim 1, wherein Z is N.

12. The compound according to claim 1, wherein Z is $CR^4$.

13. The compound according to claim 12, wherein $R^4$ is selected from the group consisting of H, cyano, $C_1$-$C_6$ haloalkoxy and $C_1$-$C_6$ haloalkyl.

14. The compound according to claim 12, wherein $R^4$ is selected from the group consisting of H, cyano, trifluoromethoxy and trifluoromethyl.

15. The compound according to claim 1, wherein $R^1$, $R^2$, and $R^4$ are each independently selected from the group consisting of H, $C_1$-$C_6$ alkoxy, $C_1$-$C_6$ alkyl, $C_1$-$C_6$ alkylamino, $C_1$-$C_6$ alkylsulfonyl, $C_1$-$C_6$ alkylthio, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl and heterocyclyl, wherein said $C_1$-$C_6$ alkyl and $C_1$-$C_6$ alkoxy are each optionally substituted with one $C_3$-$C_7$ cycloalkyl group.

16. The compound according to claim 15, wherein $R^3$ is selected from the group consisting of cyclobutyl, cyclohexyl, cyclopentyl, and cyclopropyl.

17. The compound according to claim 15, wherein $R^4$ is selected from the group consisting of H, cyano and $C_1$-$C_6$ haloalkyl.

18. The compound according to claim 15, wherein $R^4$ is selected from the group consisting of H, cyano and trifluoromethyl.

19. The compound according to claim 1, selected from compounds of Formula (Ik) and pharmaceutically acceptable salts, solvates and hydrates thereof:

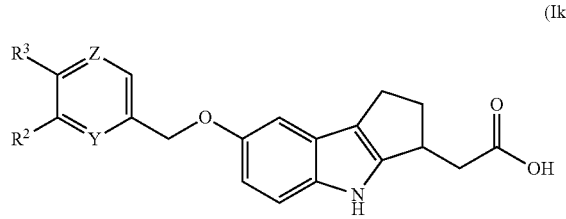

(Ik)

wherein:
Y is N or $CR^1$;
Z is N or $CR^4$;
$R^1$ is H or $C_1$-$C_6$ haloalkyl;
$R^2$ is selected from the group consisting of H, cyano, $C_1$-$C_6$ haloalkoxy and $C_1$-$C_6$ haloalkyl;
$R^3$ is $C_3$-$C_7$ cycloalkyl; and
$R^4$ is selected from the group consisting of H, cyano, $C_1$-$C_6$ haloalkoxy and $C_1$-$C_6$ haloalkyl.

20. The compound according to claim 1, selected from compounds of Formula (Ik) and pharmaceutically acceptable salts, solvates and hydrates thereof:

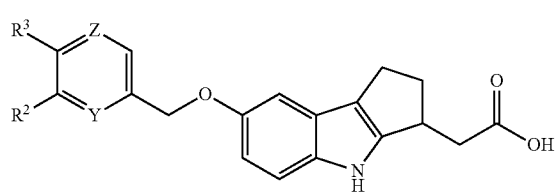

(Ik)

wherein:
Y is N or $CR^1$;
Z is N or $CR^4$;
$R^1$ is H or $C_1$-$C_6$ haloalkyl;
$R^2$ is selected from the group consisting of H, cyano, $C_1$-$C_6$ haloalkoxy and $C_1$-$C_6$ haloalkyl;
$R^3$ is $C_3$-$C_7$ cycloalkyl; and
$R^4$ is selected from the group consisting of H, cyano and $C_1$-$C_6$ haloalkyl.

21. The compound according to claim 1, selected from compounds of Formula (Ik) and pharmaceutically acceptable salts, solvates and hydrates thereof:

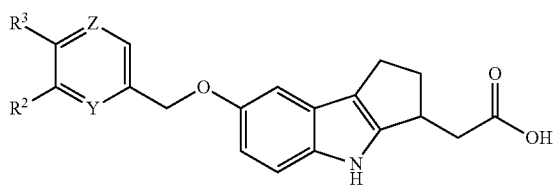

(Ik)

wherein:
Y is N or $CR^1$;
Z is N or $CR^4$;
$R^1$ is H or trifluoromethyl;
$R^2$ is selected from the group consisting of H, cyano, trifluoromethoxy and trifluoromethyl;
$R^3$ is selected from the group consisting of cyclobutyl, cyclohexyl, cyclopentyl, and cyclopropyl; and
$R^4$ is selected from the group consisting of H, cyano, trifluoromethoxy and trifluoromethyl.

22. The compound according to claim 1, selected from compounds of Formula (Ik) and pharmaceutically acceptable salts, solvates and hydrates thereof:

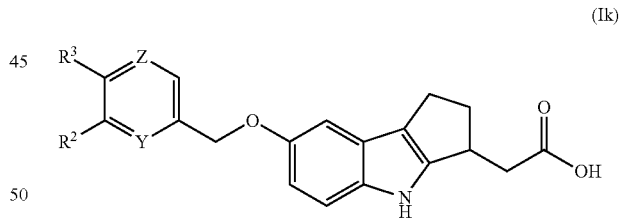

(Ik)

wherein:
Y is N or $CR^1$;
Z is N or $CR^4$;
$R^1$ is H or trifluoromethyl;
$R^2$ is selected from the group consisting of H, cyano, trifluoromethoxy and trifluoromethyl;
$R^3$ is selected from the group consisting of cyclobutyl, cyclohexyl, cyclopentyl, and cyclopropyl; and
$R^4$ is selected from the group consisting of H, cyano and trifluoromethyl.

23. The compound according to claim 1, selected from compounds of Formula (Im) and pharmaceutically acceptable salts, solvates and hydrates thereof:

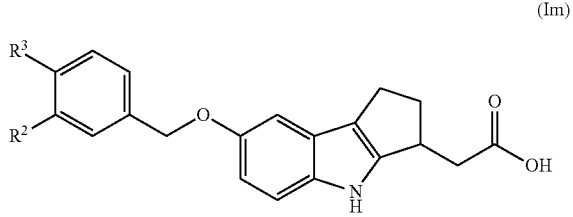

(Im)

wherein:
R² is selected from the group consisting of H, cyano, C₁-C₆ haloalkoxy and C₁-C₆ haloalkyl; and
R³ is selected from the group consisting of C₃-C₇ cycloalkyl.

24. The compound according to claim 1, selected from compounds of Formula (Im) and pharmaceutically acceptable salts, solvates and hydrates thereof:

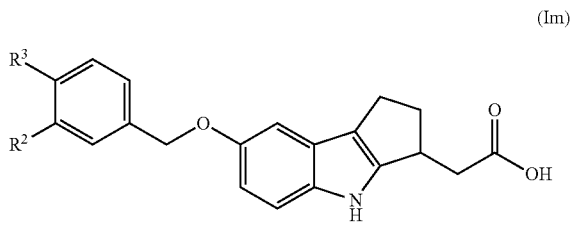

(Im)

wherein:
R² is selected from the group consisting of H, cyano, trifluoromethoxy and trifluoromethyl; and
R³ is selected from the group consisting of cyclobutyl, cyclohexyl, cyclopentyl, and cyclopropyl.

25. The compound according to claim 1, selected from the following compounds and pharmaceutically acceptable salts, solvates and hydrates thereof:
2-(7-(4-cyclohexyl-3-(trifluoromethyl)benzyloxy)-1,2,3,4-tetrahydrocyclopenta[b]indol-3-yl)pacetic acid;
(R)-2-(7-(4-cyclopentyl-3-(trifluoromethyl)benzyloxy)-1,2,3,4-tetrahydrocyclopenta[b]indol-3-yl)acetic acid;
(S)-2-(7-(4-cyclopentyl-3-(trifluoromethyl)benzyloxy)-1,2,3,4-tetrahydrocyclopenta[b]indol-3-yl)acetic acid;
2-(7-(4-cyclopentyl-3-(trifluoromethyebenzyloxy)-1,2,3,4-tetrahydrocyclopenta[b]indol-3-yl) acetic acid;
2-(7-(3-cyano-4-cyclohexylbenzyloxy)-1,2,3,4-tetrahydrocyclopenta[b]indol-3yl)acetic acid;
2-(7-((6-cyclopentyl-5-(trifluoromethyl)pyridin-3-yl)methoxy)-1,2,3,4-tetrahydrocyclopenta[b]indol-3-yl) acetic acid;
2-(7-(4-cyclobutyl-3-(trifluoromethyl)benzyloxy)-1,2,3,4-tetrahydrocyclopenta[b]indol-3-yl)acetic acid; and
2-(7-(4-cyclopropyl-3-(trifluoromethyl)benzyloxy)-1,2,3,4-tetrahydrocyclopenta[b]indol-3-yl)acetic acid.

26. The compound according to claim 1, selected from the following compound and pharmaceutically acceptable salts, solvates and hydrates thereof:
2-(7-(4-cyclohexyl-3-(trifluoromethyl)benzyloxy)-1,2,3,4-tetrahydrocyclopenta[b]indol-3-yl)acetic acid.

27. The compound according to claim 1, selected from the following compound and pharmaceutically acceptable salts, solvates and hydrates thereof:
(R)-2-(7-(4-cyclopentyl-3-(trifluoromethyl)benzyloxy)-1,2,3,4-tetrahydrocyclopenta[b]indol-3-yl)acetic acid.

28. The compound according to claim 1, selected from the following compound and pharmaceutically acceptable salts, solvates and hydrates thereof:
(S)-2-(7-(4-cyclopentyl-3-(trifluoromethyl)benzyloxy)-1,2,3,4-tetrahydrocyclopenta[b]indol-3-yl)acetic acid.

29. The compound according to claim 1, selected from the following compound and pharmaceutically acceptable salts, solvates and hydrates thereof:
2-(7-(3-cyano-4-cyclohexylbenzyloxy)-1,2,3,4-tetrahydrocyclopenta[b]indol-3-yl)acetic acid.

30. The compound according to claim 1, selected from the following compound and pharmaceutically acceptable salts, solvates and hydrates thereof:
2-(7-((6-cyclopentyl-5-(trifluoromethyl)pyridin-3-yl)methoxy)-1,2,3,4-tetrahydrocyclopenta[b]indol-3-yl) acetic acid.

31. A salt according to claim 1 selected from the following salt and pharmaceutically acceptable solvates and hydrates thereof:
Calcium salt of (R)-2-(7-(4-cyclopentyl-3-(trifluoromethyl)benzyloxy)-1,2,3,4-tetrahydrocyclopenta[b]indol-3-yl)acetic acid.

32. A salt according to claim 1 selected from the following salt and pharmaceutically acceptable solvates and hydrates thereof:
L-Arginine salt of (R)-2-(7-(4-cyclopentyl-3-(trifluoromethyl)benzyloxy)-1,2,3,4-tetrahydrocyclopenta[b]indol-3-yl)acetic acid.

33. A hydrate according to claim 1 selected from the following hydrate:
D-Lysine salt of (S)-2-(7-(4-cyclopentyl-3-(trifluoromethyl)benzyloxy)-1,2,3,4-tetrahydrocyclopenta[b]indol-3-yl)acetic acid hydrate.

34. A solvate according to claim 1 selected from the following solvate:
(R)-1-Phenethylamine salt of (S)-2-(7-(4-cyclopentyl-3-(trifluoromethyl)benzyloxy)-1,2,3,4-tetrahydrocyclopenta[b]indol-3-yl)acetic acid acetonitrile solvate.

35. A pharmaceutical composition comprising a compound according to claim 1 and a pharmaceutically acceptable carrier.

36. The compound according to claim 1, selected from the following compound and pharmaceutically acceptable salts, solvates and hydrates thereof:
2-(7-(4-cyclopentyl-3-(trifluoromethyl)benzyloxy)-1,2,3,4-tetrahydrocyclopenta[b]indol-3-yl)acetic acid.

37. The compound according to claim 1, selected from the following compound and pharmaceutically acceptable salts, solvates and hydrates thereof:
2-(7-(4-cyclobutyl-3-(trifluoromethyl)benzyloxy)-1,2,3,4-tetrahydrocyclopenta[b]indol-3-yl)acetic acid.

38. The compound according to claim 1, selected from the following compound and pharmaceutically acceptable salts, solvates and hydrates thereof:
2-(7-(4-cyclopropyl-3-(trifluoromethyl)benzyloxy)-1,2,3,4-tetrahydrocyclopenta[b]indol-3-yl)acetic acid.

39. A pharmaceutical composition comprising a compound according to claim 1, selected from the following compound and pharmaceutically acceptable salts, solvates and hydrates thereof:
2-(7-(4-cyclohexyl-3-(trifluoromethyl)benzyloxy)-1,2,3,4-tetrahydrocyclopenta[b]indol-3-yl)acetic acid;
and a pharmaceutically acceptable carrier.

40. A pharmaceutical composition comprising a compound according to claim 1, selected from the following compound and pharmaceutically acceptable salts, solvates and hydrates thereof:

(R)-2-(7-(4-cyclopentyl-3-(trifluoromethyl)benzyloxy)-1,2,3,4-tetrahydrocyclopenta[b]indol-3-yl)acetic acid
and a pharmaceutically acceptable carrier.

41. A pharmaceutical composition comprising a compound according to claim 1, selected from the following compound and pharmaceutically acceptable salts, solvates and hydrates thereof:
(S)-2-(7-(4-cyclopentyl-3-(trifluoromethyl)benzyloxy)-1,2,3,4-tetrahydrocyclopenta[b]indol-3-yl)acetic acid;
and a pharmaceutically acceptable carrier.

42. A pharmaceutical composition comprising a compound according to claim 1, selected from the following compound and pharmaceutically acceptable salts, solvates and hydrates thereof:
2-(7-(3-cyano-4-cyclohexylbenzyloxy)-1,2,3,4-tetrahydrocyclopenta[b]indol-3-yl)acetic acid;
and a pharmaceutically acceptable carrier.

43. A pharmaceutical composition comprising a compound according to claim 1, selected from the following compound and pharmaceutically acceptable salts, solvates and hydrates thereof:
2-(7-((6-cyclopentyl-5-(trifluoromethyl)pyridin-3-yl)methoxy)-1,2,3,4-tetrahydrocyclopenta[b]indol-3-yl)acetic acid;
and a pharmaceutically acceptable carrier.

44. A pharmaceutical composition comprising a salt according to claim 1, selected from the following salt and pharmaceutically acceptable solvates and hydrates thereof:
Calcium salt of (R)-2-(7-(4-cyclopentyl-3-(trifluoromethyl)benzyloxy)-1,2,3,4-tetrahydrocyclopenta[b]indol-3-yl)acetic acid
and a pharmaceutically acceptable carrier.

45. A pharmaceutical composition comprising a salt according to claim 1, selected from the following salt and pharmaceutically acceptable solvates and hydrates thereof:
L-Arginine salt of (R)-2-(7-(4-cyclopentyl-3-(trifluoromethyl)benzyloxy)-1,2,3,4-tetrahydrocyclopenta[b]indol-3-yl)acetic acid
and a pharmaceutically acceptable carrier.

46. A pharmaceutical composition comprising a hydrate according to claim 1, selected from the following hydrate:
D-Lysine salt of (S)-2-(7-(4-cyclopentyl-3-(trifluoromethyl)benzyloxy)-1,2,3,4-tetrahydrocyclopenta[b]indol-3-yl)acetic acid hydrate
and a pharmaceutically acceptable carrier.

47. A pharmaceutical composition comprising a solvate according to claim 1 selected from the following solvate:
(R)-1-Phenethylamine salt of (S)-2-(7-(4-cyclopentyl-3-(trifluoromethyl)benzyloxy)-1,2,3,4-tetrahydrocyclopenta[b]indol-3-yl)acetic acid acetonitrile solvate
and a pharmaceutically acceptable carrier.

48. A pharmaceutical composition comprising a compound according to claim 1, selected from the following compound and pharmaceutically acceptable salts, solvates and hydrates thereof:
2-(7-(4-cyclopentyl-3-(trifluoromethyl)benzyloxy)-1,2,3,4-tetrahydrocyclopenta[b]indol-3-yl)acetic acid
and a pharmaceutically acceptable carrier.

49. A pharmaceutical composition comprising a compound according to claim 1, selected from the following compound and pharmaceutically acceptable salts, solvates and hydrates thereof:
2-(7-(4-cyclobutyl-3-(trifluoromethyl)benzyloxy)-1,2,3,4-tetrahydrocyclopenta[b]indol-3-yl)acetic acid
and a pharmaceutically acceptable carrier.

50. A pharmaceutical composition comprising a compound according to claim 1, selected from the following compound and pharmaceutically acceptable salts, solvates and hydrates thereof:
2-(7-(4-cyclopropyl-3-(trifluoromethyl)benzyloxy)-1,2,3,4-tetrahydrocyclopenta[b]indol-3-yl)acetic acid;
and a pharmaceutically acceptable carrier.

51. A pharmaceutical composition comprising a compound according to claim 1, selected from compounds of Formula (Ik) and pharmaceutically acceptable salts, solvates and hydrates thereof:

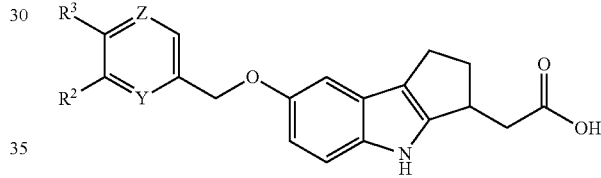

(Ik)

wherein:
Y is N or $CR^1$;
Z is N or $CR^4$;
$R^1$ is H or $C_1$-$C_6$ haloalkyl;
$R^2$ is selected from the group consisting of H, cyano, $C_1$-$C_6$ haloalkoxy and $C_1$-$C_6$ haloalkyl;
$R^3$ is $C_3$-$C_7$ cycloalkyl; and
$R^4$ is selected from the group consisting of H, cyano, $C_1$-$C_6$ haloalkoxy and $C_1$-$C_6$ haloalkyl;
and a pharmaceutically acceptable carrier.

* * * * *

UNITED STATES PATENT AND TRADEMARK OFFICE
CERTIFICATE OF CORRECTION

PATENT NO. : 8,580,841 B2
APPLICATION NO. : 13/055333
DATED : November 12, 2013
INVENTOR(S) : Robert M. Jones et al.

Page 1 of 1

It is certified that error appears in the above-identified patent and that said Letters Patent is hereby corrected as shown below:

Title Page, item [56]

List of References (Other Publications)

Page 3, Col. 1, Line 15, delete "Arteriosler Thomb." and insert --Arterioscler Thromb.--;

Page 3, Col. 1, Line 46, delete "Phsiol.," and insert --Physiol.,--;

Page 3, Col. 2, Line 70, delete "Ophthamol." and insert --Ophthalmol.--;

Claims

Col. 95, Claim 25, line 41, delete "pacetic" and insert --acetic--;

Col. 95, Claim 25, line 47, delete "trifluoromethyebenzyloxy" and insert --trifluoromethyl)benzyloxy--;

Col. 95, Claim 25, line 50, delete "3yl)" and insert --3-yl)--.

Signed and Sealed this
Thirtieth Day of September, 2014

Michelle K. Lee
*Deputy Director of the United States Patent and Trademark Office*